(12) United States Patent
Fima et al.

(10) Patent No.: US 12,203,113 B2
(45) Date of Patent: *Jan. 21, 2025

(54) LONG-ACTING COAGULATION FACTORS AND METHODS OF PRODUCING SAME

(71) Applicant: OPKO BIOLOGICS LTD., Kiryat Gat (IL)

(72) Inventors: Udi Eyal Fima, Dvira (IL); Gili Hart, Shoham (IL)

(73) Assignee: OPKO BIOLOGICS LTD., Kiryat Gat (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/379,504

(22) Filed: Jul. 19, 2021

(65) Prior Publication Data
US 2022/0170005 A1 Jun. 2, 2022

Related U.S. Application Data

(60) Division of application No. 16/865,086, filed on May 1, 2020, now Pat. No. 11,066,658, which is a division of application No. 16/160,000, filed on Oct. 15, 2018, now Pat. No. 10,640,758, which is a division of application No. 14/948,890, filed on Nov. 23, 2015, now Pat. No. 10,119,132, which is a division of application No. 13/932,839, filed on Jul. 1, 2013, now Pat. No. 9,249,407, which is a continuation-in-part of application No. 13/759,860, filed on Feb. 5, 2013, now Pat. No. 9,458,444, which is a continuation-in-part of application No. 13/372,540, filed on Feb. 14, 2012, now Pat. No. 8,759,292, which is a continuation-in-part of application No. 12/826,754, filed on Jun. 30, 2010, now Pat. No. 8,476,234.

(60) Provisional application No. 61/224,366, filed on Jul. 9, 2009.

(51) Int. Cl.
| | |
|---|---|
| A61K 39/395 | (2006.01) |
| C07K 14/505 | (2006.01) |
| C07K 14/59 | (2006.01) |
| C07K 14/745 | (2006.01) |
| C07K 16/46 | (2006.01) |
| C07K 19/00 | (2006.01) |
| C12N 9/64 | (2006.01) |
| C12N 9/96 | (2006.01) |
| A61K 38/00 | (2006.01) |
| A61K 38/48 | (2006.01) |

(52) U.S. Cl.
CPC .......... *C12N 9/6437* (2013.01); *C07K 14/505* (2013.01); *C07K 14/59* (2013.01); *C07K 14/745* (2013.01); *C12N 9/644* (2013.01); *C12N 9/96* (2013.01); *C12Y 304/21021* (2013.01); *A61K 38/00* (2013.01); *A61K 38/4846* (2013.01); *A61K 39/395* (2013.01); *C07K 16/46* (2013.01); *C07K 2319/31* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | MacConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,400,316 A | 8/1983 | Katsuragi et al. |
| 4,666,828 A | 5/1987 | Gusella |
| 4,683,202 A | 7/1987 | Mullis |
| 4,801,531 A | 1/1989 | Frossard |
| 4,853,332 A | 8/1989 | Mark et al. |
| 4,873,316 A | 10/1989 | Meade et al. |
| 4,879,219 A | 11/1989 | Wands et al. |
| 4,911,691 A | 3/1990 | Aniuk et al. |
| 5,011,771 A | 4/1991 | Bellet et al. |
| 5,118,666 A | 6/1992 | Habener |
| 5,177,193 A | 1/1993 | Boime et al. |

(Continued)

FOREIGN PATENT DOCUMENTS

| | | |
|---|---|---|
| CA | 2641342 | 8/2007 |
| CN | 1528787 A | 9/2004 |

(Continued)

OTHER PUBLICATIONS

U.S. Appl. No. 60/764,761, filed Feb. 3, 2006, Fares et al.

(Continued)

*Primary Examiner* — Elizabeth C. Kemmerer
*Assistant Examiner* — Regina M DeBerry
(74) *Attorney, Agent, or Firm* — Mark S. Cohen; PEARL COHEN ZEDEK LATZER BARATZ LLP

(57) ABSTRACT

Polypeptides comprising at least one carboxy-terminal peptide (CTP) of chorionic gonadotrophin attached to the carboxy terminus but not to the amino terminus of a coagulation factor and polynucleotides encoding the same are disclosed. Pharmaceutical compositions comprising the polypeptides and polynucleotides of the invention and methods of using and producing same are also disclosed.

19 Claims, 43 Drawing Sheets

Specification includes a Sequence Listing.

(56) References Cited

U.S. PATENT DOCUMENTS

| | | |
|---|---|---|
| 5,192,659 A | 3/1993 | Simons |
| 5,272,057 A | 12/1993 | Smulson et al. |
| 5,281,521 A | 1/1994 | Trojanowski et al. |
| 5,338,835 A | 8/1994 | Boime |
| 5,405,945 A | 4/1995 | Boime et al. |
| 5,464,764 A | 11/1995 | Capecchi et al. |
| 5,487,992 A | 1/1996 | Capecchi et al. |
| 5,585,345 A | 12/1996 | Boime |
| 5,597,797 A | 1/1997 | Clark |
| 5,643,575 A | 7/1997 | Martinez et al. |
| 5,681,567 A | 10/1997 | Martinez et al. |
| 5,705,478 A | 1/1998 | Boime |
| 5,712,122 A | 1/1998 | Boime et al. |
| 5,759,818 A | 6/1998 | Boime |
| 5,792,460 A | 8/1998 | Boime |
| 5,824,642 A | 10/1998 | Attie et al. |
| 5,919,455 A | 7/1999 | Greenwald et al. |
| 5,929,028 A | 7/1999 | Skrabanja et al. |
| 5,932,447 A | 8/1999 | Siegall |
| 5,935,924 A | 8/1999 | Bunting et al. |
| 5,958,737 A | 9/1999 | Boime et al. |
| 6,028,177 A | 2/2000 | Boime |
| 6,083,725 A | 7/2000 | Selden et al. |
| 6,103,501 A | 8/2000 | Boime et al. |
| 6,113,906 A | 9/2000 | Greenwald et al. |
| 6,225,449 B1 | 5/2001 | Boime |
| 6,238,890 B1 | 5/2001 | Boime |
| 6,242,580 B1 | 6/2001 | Boime et al. |
| 6,306,654 B1 | 10/2001 | Boime et al. |
| 6,310,183 B1 | 10/2001 | Johannessen et al. |
| 6,340,742 B1 | 1/2002 | Burg et al. |
| 6,514,729 B1 | 2/2003 | Bentzien |
| 6,897,039 B2 | 5/2005 | Graversen et al. |
| 7,081,446 B2 | 7/2006 | Lustbader |
| 7,091,326 B2 | 8/2006 | Lee et al. |
| 7,094,566 B2 | 8/2006 | Medlock et al. |
| 7,141,547 B2 | 11/2006 | Rosen et al. |
| 7,202,215 B2 | 4/2007 | Lustbader |
| 7,217,689 B1 | 5/2007 | Elliot et al. |
| 7,371,372 B2 | 5/2008 | Chaturvedi et al. |
| 7,371,373 B2 | 5/2008 | Shirley et al. |
| 7,425,539 B2 | 9/2008 | Donovan et al. |
| 7,442,684 B2 | 10/2008 | Lustbader et al. |
| 7,459,429 B2 | 12/2008 | Klima et al. |
| 7,459,435 B2 | 12/2008 | Lehmann et al. |
| 7,459,436 B2 | 12/2008 | Lehmann et al. |
| 7,553,940 B2 | 6/2009 | Fares et al. |
| 7,553,941 B2 | 6/2009 | Fares et al. |
| 7,585,837 B2 | 9/2009 | Shechter et al. |
| 7,649,084 B2 | 1/2010 | Ferguson |
| 7,666,835 B2 | 2/2010 | Bloom et al. |
| 7,795,210 B2 | 9/2010 | Defrees et al. |
| 8,008,454 B2 | 8/2011 | Lee et al. |
| 8,048,846 B2 | 11/2011 | Chahal et al. |
| 8,048,848 B2 | 11/2011 | Fares et al. |
| 8,048,849 B2 | 11/2011 | Fares et al. |
| 8,063,015 B2 | 11/2011 | Defrees et al. |
| 8,097,435 B2 | 1/2012 | Fares et al. |
| 8,110,376 B2 | 2/2012 | Fares et al. |
| 8,114,836 B2 | 2/2012 | Fares et al. |
| 8,129,330 B2 | 3/2012 | Martinez et al. |
| 8,304,386 B2 | 11/2012 | Fares et al. |
| 8,426,166 B2 | 4/2013 | Fares et al. |
| 8,450,269 B2 | 5/2013 | Fares et al. |
| 8,465,958 B2 | 6/2013 | Lopez De Leon et al. |
| 8,746,234 B2 | 6/2014 | Samaniego et al. |
| 8,759,292 B2 | 6/2014 | Fima et al. |
| 8,946,155 B2 | 2/2015 | Fares et al. |
| 9,249,407 B2 | 2/2016 | Fima et al. |
| 10,119,132 B2 | 11/2018 | Fima et al. |
| 2001/0007757 A1 | 7/2001 | Boime et al. |
| 2001/0028895 A1 | 10/2001 | Bisgaier et al. |
| 2002/0127652 A1 | 9/2002 | Schambye et al. |
| 2002/0160944 A1 | 10/2002 | Boime et al. |
| 2003/0113871 A1 | 6/2003 | Lee et al. |
| 2003/0143694 A1 | 7/2003 | Lustbader |
| 2003/0216313 A1 | 11/2003 | Lustbader et al. |
| 2004/0009902 A1 | 1/2004 | Boime et al. |
| 2004/0018240 A1 | 1/2004 | Ohmachi et al. |
| 2004/0053370 A1 | 3/2004 | Glaesner et al. |
| 2004/0057996 A1 | 3/2004 | Takada et al. |
| 2004/0115774 A1 | 6/2004 | Kochendoerfer |
| 2004/0138227 A1 | 7/2004 | Nishiyama et al. |
| 2004/0209804 A1 | 10/2004 | Govardhan et al. |
| 2005/0234221 A1 | 10/2005 | Medlock et al. |
| 2006/0073571 A1 | 4/2006 | Saxena et al. |
| 2006/0088595 A1 | 4/2006 | Asakawa et al. |
| 2006/0160177 A1 | 7/2006 | Okkels et al. |
| 2006/0171920 A1 | 8/2006 | Shechter et al. |
| 2007/0184530 A1 | 8/2007 | Fares et al. |
| 2007/0190610 A1 | 8/2007 | Fares et al. |
| 2007/0190611 A1 | 8/2007 | Fares et al. |
| 2007/0298041 A1 | 12/2007 | Tomlinson |
| 2008/0064856 A1 | 3/2008 | Warne et al. |
| 2008/0206270 A1 | 8/2008 | Minev et al. |
| 2008/0221032 A1 | 9/2008 | Turecek et al. |
| 2009/0053185 A1 | 2/2009 | Schulte et al. |
| 2009/0087411 A1 | 4/2009 | Fares et al. |
| 2009/0130060 A1 | 5/2009 | Weimer et al. |
| 2009/0221037 A1 | 9/2009 | Lee et al. |
| 2009/0221485 A1 | 9/2009 | James |
| 2009/0270489 A1 | 10/2009 | Fares et al. |
| 2009/0275084 A1 | 11/2009 | Fares et al. |
| 2009/0286733 A1 | 11/2009 | Fares et al. |
| 2009/0312254 A1 | 12/2009 | Fares et al. |
| 2010/0006156 A1 | 1/2010 | Schilp et al. |
| 2010/0081614 A1 | 4/2010 | Fares et al. |
| 2010/0144617 A1 | 6/2010 | Sinha Roy et al. |
| 2010/0310546 A1 | 12/2010 | Schuster et al. |
| 2010/0317585 A1 | 12/2010 | Fima et al. |
| 2011/0004172 A1 | 1/2011 | Eckstein et al. |
| 2011/0034374 A1 | 2/2011 | Bloom et al. |
| 2011/0065660 A1 | 3/2011 | Baron et al. |
| 2011/0152182 A1 | 6/2011 | Alsina-Fernandez et al. |
| 2011/0166063 A1 | 7/2011 | Bossard et al. |
| 2011/0223151 A1 | 9/2011 | Behrens et al. |
| 2011/0286967 A1 | 11/2011 | Fares et al. |
| 2012/0004286 A1 | 1/2012 | Fares et al. |
| 2012/0015437 A1 | 1/2012 | Fares et al. |
| 2012/0035101 A1 | 2/2012 | Fares et al. |
| 2012/0048878 A1 | 3/2012 | Burger et al. |
| 2012/0087908 A1 | 4/2012 | Bardat et al. |
| 2012/0114651 A1 | 5/2012 | De Wildt et al. |
| 2012/0208759 A1 | 8/2012 | Fima et al. |
| 2012/0264920 A1 | 10/2012 | Wang et al. |
| 2013/0183052 A1 | 7/2013 | Tsukada |
| 2013/0184207 A1 | 7/2013 | Fares et al. |
| 2013/0243747 A1 | 9/2013 | Fima et al. |
| 2013/0295072 A1 | 11/2013 | Fima et al. |
| 2014/0113860 A1 | 4/2014 | Fima et al. |
| 2014/0170728 A1 | 6/2014 | DeFrees et al. |
| 2014/0316112 A1 | 10/2014 | Hershkovitz et al. |
| 2014/0371144 A1 | 12/2014 | Fares et al. |
| 2015/0038413 A1 | 2/2015 | Fares et al. |
| 2015/0072924 A1 | 3/2015 | Fima et al. |
| 2015/0079063 A1 | 3/2015 | Fima et al. |
| 2015/0133636 A1 | 5/2015 | Xenopoulos et al. |
| 2015/0158926 A1 | 6/2015 | Fares et al. |
| 2015/0203558 A1 | 7/2015 | Fares et al. |
| 2015/0216951 A1 | 8/2015 | Bardat et al. |
| 2015/0258208 A1 | 9/2015 | Fima et al. |
| 2015/0295072 A1 | 10/2015 | Rezanezhad Gatabi |
| 2015/0368630 A9 | 12/2015 | Fima et al. |
| 2016/0168588 A1 | 6/2016 | Hershkovitz et al. |

FOREIGN PATENT DOCUMENTS

| | | |
|---|---|---|
| CN | 1528894 A | 3/2006 |
| EP | 0167825 | 1/1986 |
| EP | 0264166 | 4/1988 |
| EP | 0394788 A1 | 10/1990 |
| EP | 01319712 A2 | 6/2003 |
| EP | 2532674 | 12/2012 |
| EP | 2420251 | 3/2013 |

(56) References Cited

FOREIGN PATENT DOCUMENTS

| | | |
|---|---|---|
| JP | H8-509218 | 10/1996 |
| JP | 2002226365 A | 8/2002 |
| JP | 2002255857 A | 9/2002 |
| JP | 2004269516 A | 9/2004 |
| KR | 20030037598 A | 5/2003 |
| WO | WO 1989/10756 | 11/1989 |
| WO | WO 1993/006844 | 4/1993 |
| WO | WO 1994/24148 A1 | 10/1994 |
| WO | WO 2000/23472 A2 | 4/2000 |
| WO | WO 2002/036169 A2 | 5/2002 |
| WO | WO 2002/48194 A1 | 6/2002 |
| WO | WO 2003/038100 A1 | 5/2003 |
| WO | WO 2002/085311 A2 | 10/2003 |
| WO | WO 2004006756 | 1/2004 |
| WO | WO 2004/089280 A2 | 10/2004 |
| WO | WO 2004/111242 | 12/2004 |
| WO | WO 2005/035761 | 4/2005 |
| WO | WO 2005/080544 | 9/2005 |
| WO | WO 2006/018204 | 2/2006 |
| WO | WO 2006/134340 | 12/2006 |
| WO | WO 2007/094985 | 8/2007 |
| WO | WO 2007/149406 A2 | 12/2007 |
| WO | WO 2010/007622 | 1/2010 |
| WO | WO 2010/097077 | 9/2010 |
| WO | WO 2011/004361 A2 | 1/2011 |
| WO | WO 2011/087672 | 7/2011 |
| WO | WO 2012/011752 | 5/2012 |
| WO | WO 2012/167251 | 12/2012 |
| WO | WO 2012/173422 | 12/2012 |
| WO | WO 2013/009627 A2 | 1/2013 |
| WO | WO 2013/018098 | 2/2013 |
| WO | WO 2003/048210 A1 | 6/2013 |
| WO | WO 2013/096386 | 6/2013 |
| WO | WO 2013/121416 | 8/2013 |
| WO | WO 2013/121416 A1 | 8/2013 |
| WO | WO 2013/152351 A2 | 10/2013 |
| WO | WO 2013/157002 | 10/2013 |
| WO | WO 2013/183052 | 12/2013 |
| WO | WO 2014/080401 | 5/2014 |
| WO | WO 2016/092549 | 6/2016 |
| WO | WO 2016/092549 A1 | 6/2016 |
| WO | WO 2016/092550 | 6/2016 |
| WO | WO 2016/203482 | 12/2016 |

OTHER PUBLICATIONS

U.S. Appl. No. 61/224,366, filed Jul. 9, 2009, Fima et al.
U.S. Appl. No. 11/700,910, filed Feb. 1, 2007, Fares et al.
U.S. Appl. No. 11/700,911, filed Feb. 1, 2007, Fares et al.
U.S. Appl. No. 11/702,156, filed Feb. 5, 2007, Fares et al.
U.S. Appl. No. 12/216,989, filed Jul. 14, 2008, Fares et al.
U.S. Appl. No. 12/401,746, filed Mar. 11, 2009, Fares et al.
U.S. Appl. No. 12/401,755, filed Mar. 11, 2009, Fares et al.
U.S. Appl. No. 12/476,916, filed Jun. 2, 2009, Fares et al.
Alberts et al. "Molecular biology of the cell", 5th ed.(Garland Science, 2008). 2002, p. 367.
Ameredes et al. "Growth Hormone Improves Body Mass Recovery with Refeeding after Chronic Undernutrition-Induced Muscle Atrophy in Aging Male Rats" Journal of Nutrition. 129:2264-2270 (1999).
Amirizahdeh et al. "Expression of biologically active recombinant B-domain-deleted human VIII in mammalian cells" Journal of Science, Islamic Republic of Iran. Abstract. 16(2):103-112, (2005).
Anonymous "Corporate Presentation—Lazard Capital Markets Healthcare Conference", Nov. 15, 2011, pp. 1-19; Retrieved from the Internet: URL:http://web.archive.org/web/20110628023057/http://www.prolor-biotech.com/_Uploads/dbsAttachedFiles/prolorInvestorsNov2011.pdf.
Anonymous "Corporate Presentation", Jun. 1, 2011, pp. 1-35; Retrieved from the Internet: URL;http://web.archive.org/web/20110628023057/http://www.prolor-biotech.com/_Uploads/dbsAttachedFiles/prolorPresentationJune2011Investors.pdf.
Anonymous "Prolor and Yeda enter definitive license agreement for Reversible PEGylation technology", Jan. 18, 2011, pp. 1-3; Retrieved from the Internet: URL;http://web.archive.org/web/20110123063420/http://www.news-medical.net/news/20110118/PROLOR-and-Yeda-enter-definitive-license-agreemen-for-Reversible-PEGYlation-technology.aspx.
Anonymous "Prolor Biotech Announces Positive Results of its Obesity/Diabetes Drug Candidate in Preclinical Weight Loss Study", Apr. 17, 2012, pp. 1-2; Retrieved from the Internet: URL;http://web.archive.org/web/20120526154526/uttp://www.prolor-biotech.com/_Uploads/dbsAttachedFiles/NewsPROLORAnnouncesObesityDiabetesStudyResults.pdf.
Anonymous "Prolor Biotech Receives New U.S. Patent Allowance Covering Broad Applications of its CTP Platform for Long Acting Therapeutic Proteins", Jul. 11, 2011, pp. 1-2; Retrieved from the Internet: URL;http://web.archive.org/web/20110725053527/http://www.prolor-biotech.com/_Uploads/dbsAttachedFiles/NewsPROLORAnnouncesAllowanceOfNewCTPPlatformPatentByUSPatentOffice.pdf.
Anson et al. "The gene structure of human anti-haemophilic factor IX", The EMBO Journal (1984) 3(5):1053-1060.
Askoy et al., "A study of the intracellular and secreted forms of the MUC2 mucin from the PC/AA intestinal cell line." Glycobiology 9.7: 739-746 (1999).
Banerji et al. "A lymphocyte-specific cellular enhancer is located downstream of the joining region in immunoglobulin heavy chain genes" Cell 33:729-740 (1983).
Barker et al. "An immunomagnetic-base method for the purification of ovarian cancer cells from patient-derived ascites" (Gynecologic Oncology 82, 57-63, 2001).
Beeley, Glycoprotein and proteoglycan techniques. Elsevier: 69-72 (1985).
Bengtsson et al. "Treatment of adults with growth hormone (GH) deficiency with recombinant human GH" J Clin Endocrinol Metab. Feb. 1993;76(2):309-17.
Berntorp et al. "The pharmacokinetics of clotting factor therapy"; Haemophilia (2003) 9:353-359.
Biller et al. Effects of once-weekly sustained-release growth hormone: a double-blind, placebo-controlled study in adult growth hormone deficiency. The Journal of Clinical Endocrinology & Metabolism. Mar. 16, 2011;96(6):1718-26.
Bitter et al. "Expression and secretion vectors for yeast" (1987) Methods in Enzymol. 153:516-544.
Bjorkman et al. Pharmacokinetics of Coagulation Factors Clinical Relevance for Patients with Haemophilia. Clin Pharmacokinet vol. 40 (11): 815-832 (2001).
Bohl et al. "Improvement of erythropoiesis in b-thalassemic mice by continuous erythropoietin delivery from muscle" Blood 95:2793-2798 (2000).
Boissel et al. "Erythropoietin structure-function relationships" The Journal of Biological Chemistry 268(21):15983-15993 (1993).
Booth et al. "The use of a 'universal' yeast expression vector to produce an antigenic protein of Mycobacterium leprae" Immunol. Lett. 19:65-70 (1988).
Bouloux et al. "First human exposure to FSH-CTP in hypogonadotrophic hypogonadal males" Human Reproduction. Aug. 1, 2001;16(8):1592-7.
Brisson et al. "Expression of a bacterial gene in plants by using a viral vector" Nature, 310:511-514 (1984).
Broglie et al. "Light-Regulated Expression of a Pea Ribulose-1,5-Bisphosphat Carboxylase Small Subunit Gene in Transformed Plant Cells" Science 224:838-843 (1984).
Brunetti-Pierri et al. "Bioengineered factor IX molecules with increased catalytic activity improve the therapeutic index of gene therapy vectors for hemophilia B." Human Gene Therapy 20.5: 479-485 (2009).
Buchwald et al. "Long-term, continuous intravenous heparin administration by an implantable infusion pump in ambulatory patients with recurrent venous thrombosis" Surgery 88:507-516 (1980).
Butler et al., "The beta-subunit of human chorionic gonadotrophin exists as a homodimer." Journal of Molecular Endocrinology 22.2: 185-192 (1999).

(56) References Cited

OTHER PUBLICATIONS

Byrne et al. "Multiplex gene regulation: A two-tiered approach to transgene regulation in transgenic mice" Proc. Natl. Acad. Sci USA 86:5473-5477 (1989).
Calame et al. "Transcriptional Controlling Elements in the Immunoglobulin and T Cell Receptor Loci" Adv. Immunol 43:235-275 (1988).
Carles-Bonnet et al. "H-Lys-Arg-Asn-Lys-Asn-Asn-OH is the minimal active structure of oxyntomodulin" Peptides. Dec. 31, 1996;17(3):557-61.
Cawley et al. "Developing long-acting growth hormone formulations", Clinical Endocrinology (2013) 79, 305-309.
Chan et al. "Plasma Insulin-Like Growth Factor-I and Prostate Cancer Risk: A Prospective Study", Science vol. 279:563-566, Jan. 1998.
Chen et al. "Recombinant carbohydrate variant of human choriogonadotropin beta-subunit (hCG beta) descarboxyl terminus (115-145). Expression and characterization of carboxyl-terminal deletion mutant of hCG beta in the baculovirus system." Journal of Biological Chemistry 266.10: 6246-6251 (1991).
Chen et al., "Glycoengineering Approach to Half-Life Extension of Recombinant Biotherapeutics." Bioconjugate Chemistry 23.8: 1524-1533 (2012).
Chen et al., "Modulating antibody pharmacokinetics using hydrophilic polymers." Expert Opinion on Drug Delivery 8.9: 1221-1236 (2011).
Chihara K. "Clinical aspect of growth hormone deficiency in adults" Nihon Naika Gakkai zasshi. The Journal of the Japanese Society of Internal Medicine. Sep. 10, 2000;89(9):2010; with English Abstract.
Claxton et al., A systematic review of the associations between dose regimens and medication compliance. Clinical Therapeutics 23.8: 1296-1310 (2001).
Cohen et al. "Oxyntomodulin suppresses appetite and reduces food intake in humans", J Clin Endocrinol Metab. Oct. 2003;88(10):4696-701.
Coleman et al., "Dosing frequency and medication adherence in chronic disease." Journal of managed care pharmacy: JMCP 18.7: 527-539 (2012).
Coruzzi et al. "Tissue-specific and light-regulated expression of a pea nuclear gene encoding the small subunit of ribulose-1,5-bisphosphate carboxylase" The EMBO Journal 3:1671-1680 (1984).
Cutfield et al., "Non-compliance with growth hormone treatment in children is common and impairs linear growth." PLoS One 6.1: e16223 (2011).
Dalton et al. "Over-expression of secreted proteins from mammalian cell lines" Protein Science. May 1, 2014:23(5):517-25.
Database Geneseq [Online] Apr. 7, 2005, "Human interferon beta (without signal peptide)." XP002664024 retrieved from EBI accession No. GSP: ADW02285, Database accession No. ADW02285.
Davis CG et al. "Deletion of clustered O-linked carbohydrates does not impair function of low density lipoprotein receptor in transfected fibroblasts" J Biol Chem. 261(6):2828-38, Feb. 25, 1986.
Diederichs et al., "Liposome in kosmetika und arzneimitteln." Pharmazeutische Industrie 56.3: 267-275 (1994).
Diness, et al. Lund-Hansen, and U. Hedner. "Effect of recombinant human FVIIA on warfarin-induced bleeding in rats." Thrombosis research 59.6 (1990): 921-929.
Dong et al. "The prolonged half-lives of new erythropoietin derivatives via peptide addition" Biochemical Research Communications, 339(1):380-385 (Jan. 6, 2006).
Drake et al. "Optimizing GH therapy in adults and children" Endocr Rev. Aug. 2001;22(4):425-50. Review.
Edlund et al. "Cell-Specific Expression of the Rat Insulin Gene: Evidence for Role of Two Distinct 5' Flanking Elements" Science 230:912-916 (1985).
Edmunds et al. "Plasma erythropoietin levels and acquired cystic disease of the kidney in patients receiving regular haemodialysis treatment" Br J Haematol. Jun. 1991;78(2):275-7.
Eschbach et al. "Correction of the Anemia of End-Stage Rental Disease with Recombinant Human Erythropoietin", The New England Journal of Medicine Jan. 8, 1987, vol. 316 No. 2, pp. 73-78.

European Search Report for Application No. 10796803 dated Feb. 28, 2013.
European Search Report for Application No. 12150722.2 Dated Jun. 4, 2012.
European Search Report for Application No. 07749922 dated Oct. 8, 2009.
European Search Report for Application No. 14196333.0 mailed on Mar. 2, 2015.
European Search Report for Application No. 14197286.9 mailed on Mar. 2, 2015.
European Search Report for Application No. 16187710.5 dated Oct. 14, 2016.
European Search Report for Application No. 10796803.4 dated Feb. 28, 2013.
European Search Report for Application No. 12179805 dated Nov. 9, 2012.
European Search Report for Application No. 12179821 dated Nov. 12, 2012.
European Search Report for Application No. 18150731.0 dated Feb. 27, 2018.
European Search Report for Application No. 18198355 dated Mar. 21, 2019.
Extended European Search Report for Application No. 09797630.2, dated Dec. 5, 2011.
Fares "The role of O-linked and N-linked oligosaccharides on the structure-function of glycoprotein hormones: Development of agonists and antagonists", Biochimica et Biophysica Acta (BBA)-General Subjects 1760.4: 560-567 (2006).
Fares et al.g-acting follitropin agonist by fusing the C-terminal sequence of the chorionic gonadotropin beta subunit to the follitropin beta subunit Proc Natl Acad Sci U S A., 89(10):4304-4308, May 15, 1992.
Fares et al. "Designing a long-acting human growth hormone (hGH) by fusing the carboxy-terminal peptide of human chorionic gonadotropin B-subunit to the coding sequence of hGH" Endocrinology 151(9):4410-4417 (2010).
Fares et al. "Growth hormone (GH) retardation of muscle damage due to immobilization in old rats. Possible intervention with a new long-acting recombinant GH" Ann N Y Acad Sci. 786:430-43 (Jun. 15, 1996).
Fares et al. "Designing a Long Acting Erythropoietin by Fusing Three Carboxyl-Terminal Peptides of Human Chorionic Gondotropin [beta] Subunit to the N-Terminal and C-Terminal Coding Sequence", International Journal of Cell Biology, vol. 9, No. 11, Jan. 1, 2011, pp. 2021-2027.
Fares et al., "Development of a long-acting erythropoietin by fusing the carboxyl-terminal peptide of human chorionic gonadotropin B-subunit to the coding sequence of human erythropoietin." Endocrinology 148.10: 5081-5087 (2007).
Fayad et al. "Update of the M. D. Anderson Cancer Center experience with hyper-CVAD and rituximab for the treatment of mantle cell and Burkitt-type lymphomas" Clin Lymphoma Myeloma. Dec. 2007;8 Suppl 2:S57-62.
Final Office Action U.S. Appl. No. 13/372,540, filed Feb. 14, 2012.
Fingl et al., "General Principles." The Pharmacological Basis of Therapeutics (ed. Goodman, LS & Gilman, A,): 1-46 (1975).
Fogarty, Patrick F. "Biological rationale for new drugs in the bleeding disorders pipeline." ASH Education Program Book 2011.1 (2011): 397-404.
Freshney "Culture of animal cells: A manual of basic technique" (Culture of Animal Cells, A Manual of Basic Technique, Alan R. Liss, Inc., 1983, New York, p. 4).
Fuentes-Prior et al. "Structural basis for the anticoagulant activity of the thrombin-thrombomodulin complex" Nature. Mar. 30, 2000; 404 (6777):518-25.
Furuhashi et al. "Fusing the carboxy-terminal peptide of the chorionic gonadotropin (CG)-subunit to the common alpha-submit:: Retention of O-linked glycosylation and enhanced in vivo bioactivity of chimeric human CG" Molecular Endocrinology 9(1):54-63 (1995).
Furuhashi et al. "Processing of O-linked glycosylation in the chimera consisting of alpha-subunit and carboxyl-terminal peptide of the human chorionic gonadotropin beta-subunit is affected by

(56) References Cited

OTHER PUBLICATIONS dimer formation with follicle-stimulating hormone beta-subunit" Endocrine Journal 51(1):53-59 (2004).
Gao et al., "Erythropoietin gene therapy leads to autoimmune anemia in macaques" Blood 103(9):3300-3302 (2004).
Garcia-Campayo et al. "Unmasking a new recognition signal for< i> O</i>-linked glycosylation in the chorionic gonadotropin β subunit" Molecular and Cellular Endocrinology 194.1: 63-70 (2002).
Gardella et al. "Expression of Human Parathyroid Hormone-(1-84) in *Escherichia coli* as a Factor X-cleavable Fusion Protein" J. Biol. Chem. 265:15854-15859 (1990).
Gellerfors et al. "Characterisation of a secreted form of recombinant derived human growth hormone, expressed in *Escherichia coli* cells", J Pharm Biomed Anal 7(2):173-83 (1989).
Ghosh et al., "Activity and regulation of factor VIIa analogs with increased potency at the endothelial cell surface." Journal of Thrombosis and Haemostasis 5.2: 336-346 (2007).
Gilboa et al., "Transfer And Expression of Cloned Genes Using Retroviral Vectors", Biotechniques, vol. 4:504-512, (1986).
Goodson, in "Medical applications of controlled release." vol. 2: 115-138 (1984).
Guitton et al., "Influence of in vitro non-enzymatic glycosylation on the physicochemical parameters of type I collagen." Collagen and Related Research 4.4: 253-264 (1984).
Gurley et al. "Upstream Sequences Required for Efficient Expression of a Soybean Heat Shock Gene" Mol.Cell.Biol 6:559-565 (1986).
Hacke et al. "Intravenous thrombolysis with recombinant tissue plasminogen activator for acute hemispheric stroke. The European Cooperative Acute Stroke Study (ECASS)" JAMA. 1995;274(13):1017-1025.
Hammerling et al. "In vitro bioassay for human erythropoietin based on proliferative stimulation of an erythroid cell line and analysis of carbohydrate-dependent microheterogeneity" Journal of Pharm. Biomed. Analysis 14(11):1455-1469 (1996).
Havron et al. "OR2, 8 Phase I PK&PD profile of long acting bio-better CTP modified hGH (MOD-4023) in healthy volunteers" Growth Hormone & IGF Research. Jan. 1, 2010;20:24-5.
Heffernan et al., "Effects of oral administration of a synthetic fragment of human growth hormone on lipid metabolism." American Journal of Physiology—Endocrinology and Metabolism 279.3: E501-E507 (2000).
Houdebine, L., "The methods to generate transgenic animals and to control transgene expression" Journal of Biotechnology 98:145-160 (2002).
Huston et al. "Protein engineering of antibody binding sites: Recovery of specific activity in an anti-digoxin single-chain Fv analogue produced in *Escherichia coli*" Proc. Natl. Acad. Sci. USA vol. 85, pp. 5879-5883, Biochemistry, Aug. 1988.
International Preliminary Report on Patentability for Application No. PCT/IL09/00700 dated Jan. 27, 2011.
International Preliminary Report on Patentability for Application No. PCT/US07/02767 dated Aug. 14, 2008.
International Preliminary Report on Patentability for Application No. PCT/IL2010/000532 dated Jan. 19, 2012.
International Preliminary Report on Patentability for Application No. PCT/US07/03014 dated Apr. 2, 2009.
International Preliminary Report on Patentability for Application No. PCT/IL2017/050645 dated Dec. 20, 2018.
International Preliminary Report on Patentability for Application No. PCT/IL2017/050784 dated Jan. 24, 2019.
International Search Report and Written Opinion for PCT Application No. PCT/IL/050645 Mailed Sep. 21, 2017.
International Search Report and Written Opinion for PCT Application No. PCT/IL/050784 Mailed Sep. 22, 2017.
International Search Report and Written Opinion for PCT Application No. PCT/IL09/00700 dated Feb. 4, 2010.
International Search Report and Written Opinion for PCT Application No. PCT/IL10/00532 dated Apr. 11, 2011.
International Search Report and Written Opinion for PCT Application No. PCT/IL13/50107 dated Jul. 10, 2013.
International Search Report and Written Opinion for PCT Application No. PCT/US07/02767 dated Feb. 15, 2008.
International Search Report and Written Opinion for PCT Application No. PCT/US07/03014 dated Sep. 22, 2008.
International Search Report for Application No. PCTIL2014050910 mailed on Jan. 25, 2015.
International Search Report for PCT Application No. PCT/IL 12/50288 mailed Jan. 28, 2013.
Isgaard et al. "Effects of local administration of GH and IGF-1 on longitudinal bone growth in rats" Am J Physiol. Apr. 1986;250(4 Pt 1): E367-72.
Jarrousse et al. "Oxyntomodulin (glucagon-37) and its C-terminal octapeptide inhibit gastric acid secretion", FEBS Lett. Aug. 19, 1985; 188(1): 81-4.
Joshi et al. "Recombinant thyrotropin containing a beta-subunit chimera with the human chorionic gonadotropin-beta carboxyterminus is biologically active, with a prolonged plasma half-life: role of carbohydrate in bioactivity and metabolic clearance" Endocrinology. Sep. 1995; 136(9):3839-48.
Kanda et al. "Genetic Fusion of an a-subunit Gene to the Follicle-Stimulating Hormone and Chorionic Gonadotropin-b Subunit Genes: Production of a Bifunctional Protein", Molecular Endocrinolog, vol. 13, No. 11, p. 1873-1881, Nov. 1999.
Kelly et al. "Outcomes of patients with Burkitt lymphoma older than age 40 treated with intensive chemotherapeutic regimens." Clin Lymphoma Myeloma. Aug. 2009;9(4):307-10.
Kessler et al. "Structure and location of the O-glycosidic carbohydrate units of human chorionic gonadotropin" J Biol Chem. 25;254(16):7909-14 , Aug. 1979.
Kessler et al., "Structures of N-Glycosidic Carbohydrate Units of Human Chorionic Gonadotropin" J Biol Chem. Aug. 25, 1979;254(16):7901-8.
Kicman et al., "Human chorionic gonadotrophin and sport." British Journal of Sports Medicine 25.2 : 73-80 (1991).
Kieffer et al. "Distribution of glucagon receptors on hormone-specific endocrine cells of rat pancreatic islets" Endocrinology. Nov. 1996;137(11):5119-25.
Kontermann, "Half-Life Modulating Strategies—An Introduction." Therapeutic Proteins: Strategies to Modulate Their Plasma Half-Lives : 1-21 (2012).
Kontermann, "Strategies for extended serum half-life of protein therapeutics." Current opinion in Biotechnology 22.6: 868-876 (2011).
Kotler et al., "Effects of growth hormone on abnormal visceral adipose tissue accumulation and dyslipidemia in HIV-infected patients." JAIDS Journal of Acquired Immune Deficiency Syndromes 35.3: 239-252 (2004).
Krantz et al. "Specific binding of erythropoietin to spleen cells infected with the anemia strain of Friend virus" Proc Natl Acad Sci U S A. Dec. 1984;81(23):7574-8.
Langer Robert "New Methods of Drug Delivery" Science 249:1527-1533 (1990).
Larsen et al., "Accumulation of magnetic iron oxide nanoparticles coated with variably sized polyethylene glycol in murine tumors." Nanoscale 4.7: 2352-2361 (2012).
Le et al., "Improved Vancomycin Dosing in Children Using Area Under the Curve Exposure." Pediatr Infect Dis J vol. 32, pp. e155-e163 (2013).
Lentz et al., "Posttranslational modification of the carboxy-terminal region of the. beta. subunit of human chorionic gonadotropin." Biochemistry 23.22: 5330-5337 (1984).
Li et al. "Bioassay of hGH .I. Weight gain of hypophysectomized rats". Abstract, Yaowu Fenxi Zazhi 15(2), 3-7 (1995).
Lippin et al. "Human erythropoietin gene therapy for patients with chronic renal failure" Blood 106(7):2280-2286 (2005).
Littleword, T.J. "Erythropoietin for the treatment of anemia associated with hematological malignancy" Hematol Oncol. Mar. 2001;19(1):19-30.

(56) References Cited

OTHER PUBLICATIONS

Lo et al. "The effects of recombinant human growth hormone on body composition andglucose metabolism in HIV-infected patients with fat accumulation" J Clin Endocrinol Metab. Aug. 2001;86(8):3480-7. PubMed PMID: 11502767.
Lopez-Berenstein, Liposomes in the Therapy of Infectious Disease and Cancer, Lopez-Berestein and Fidler (eds.), Liss, New York, pp. 317-327 (1989).
Lopez-Berestein et al. "Treatment of systemic fungal infections with liposomal amphotericin B." Liposomes in the therapy of infectious diseases and cancer. (1989): 310-327.
Maheshwari et al., "Manipulation of Electrostatic and Saccharide Linker Interactions in the Design of Efficient Glycopolypeptide-Based Cholera Toxin Inhibitors." Macromolecular bioscience 10.1: 68-81 (2010).
Maston et al., "Chorionic gonadotropin beta subunit [*Homo sapiens*]" NCBI Accession No. AAL69705.1 (Apr. 3, 2002).
Matsumoto et al. The measurement of low levels of factor VIII or factor IX in hemophilia A and hemophilia B plasma by clot waveform analysis and thrombin generation assay. Journal of Thrombosis and Haemostasis vol. 4:377-384 (2006).
Matsuo et al. "Thrombolysis by human tissue plasminogen activator and urokinase in rabbits with experimental pulmonary embolus" Nature. Jun. 18, 1981;291(5816):590-1.
Maun et al., "Disulfide locked variants of factor VIIa with a restricted B-strand conformation have enhanced enzymatic activity." Protein Science 14.5: 1171-1180 (2005).
McAlister et al. "NMR analysis of the N-terminal SRCR domain of human CD5: engineering of a glycoprotein for superior characteristics in NMR experiments." Protein Engineering 11.10: 847-853 (1998).
Medlock et al. "Epogen signal peptide", Jan. 6, 2005, XP002685292.
Meulien et al., "Increased biological activity of a recombinant factor IX variant carrying alanine at position+ 1." Protein Engineering 3.7: 629-633 (1990).
Milton et al. The Delineation of a Decapeptide Gonadotropin-releasing Sequence in the Carboxyl-terminal Extension of the Human Gonadotropin releasing Hormone Precursor. The Journal of Biological Chemistry, vol. 261/36:16990-16997 (Dec. 1986).
Morgan et al. "The amino acid sequence of human chorionic gonadotropin. The alpha subunit and beta subunit", J Biol Chem. Jul. 10, 1975;250(13):5247-58.
Muleo et al. Small doses of recombinant factor Vila in acquired deficiencies of vitamin K dependent factors. Blood Coagulation & Fibrinolysis Abstract, 10(8), 521-522 (1999).
Murray et al. "Dose titration and patient selection increases the efficacy of GH replacement in severely GH deficient adults", Clinical Endocrinology (1999) 50, pp. 749-757.
Musto "The role of recombinant erythropoietin for the treatment of anemia in multiple myeloma" Leuk Lymphoma. Apr. 1998;29(3-4):283-91.
Mutter et al. "A New Base-Labile Anchoring Group for Polymer-Supported Peptide Synthesis." Helvetica chimica acta 67.7 (1984): 2009-2016.
Mutter et al. "Evolution versus design: template-directed self-assembly of peptides to artificial proteins (TASP)." CHIMIA International Journal for Chemistry 54.10 (2000): 552-557.
NCBI GenBank Accession No. AAL69702 (Apr. 3, 2002).
Nezu et al. "Treatment of idiopathic pituitary dwarfism with human growth hormone", Journal of Nara Medical Association 40.1(1989): 16-22; with English Abstract.
Ngo et al. "Computational Complexity, Protein Structure Protein Prediction and the Levinthal Paradox" in Birkhauser The Protein Folding Problem And Tertiary Structure Prediction, pp. 433-440 and 492-495 (1994).
Office Action U.S. Appl. No. 12/826,754, filed Jun. 30, 2010.
Office Action U.S. Appl. No. 13/372,540, filed Feb. 14, 2012.
Office Action for Japanese Application No. 2014-523441 dated May 24, 2016.
Ogle et al. "Renal effects of growth hormone. I. Renal function and kidney growth", Pediatr. Nephrol. vol. 6:394-398, 1992.
Oosterhof et al. Regulation of whole body energy homeostasis with growth hormone replacement therapy and endurance exercise Physiol Genomics. Jun. 28, 2011;43(12):739-48. doi: 10.1152/physiolgenomics. 00034.2010. Epub Mar. 29, 2011.
Pedrosa et al., "Selective neoglycosylation increases the structural stability of vicilin, the 7S storage globulin from pea seeds." Archives of Biochemistry and Biophysics 382.2: 203-210 (2000).
Persson et al. "Recombinant coagulation factor VIIa—from molecular to clinical aspects of a versatile haemostatic agent", Thrombosis Research (2010) 125:483-489.
Persson et al., "Rational design of coagulation factor VIIa variants with substantially increased intrinsic activity." Proceedings of the National Academy of Sciences 98.24: 13583-13588 (2001).
Philips A. "The challenge of gene therapy and DNA delivery" J Pharm. Pharmacology 53:1169-1174 (2001).
Pierce et al. "Glycoprotein hormones: structure and function." Annual review of biochemistry 50.1: 465-495 (1981).
Pinkert et al. "An albumin enhancer located 10 kb upstream functions along with its promoter to direct liver-specific expression in transgenic mice" Genes Dev. 1:268-277 (1987).
Polizzotti et al. "Effects of saccharide spacing and chain extension on toxin inhibition by glycopolypeptides of well-defined architecture", Macromolecules 40.20: 7103-7110 (2007).
Poreddy et al., "Exogenous fluorescent tracer agents based on pegylated pyrazine dyes for real-time point-of-care measurement of glomerular filtration rate." Bioorganic & Medicinal Chemistry 20.8: 2490-2497 (2012).
Puett et al. "Structure-Function Relationships of the Luteinizing Hormone Receptor" Annals of the New York Academy of Sciences. Dec. 1, 2005;1061(1):41-54.
Rebois et al., "Hydrodynamic properties of the gonadotropin receptor from a murine Leydig tumor cell line are altered by desensitization." Biochemistry 26.20: 6422-6428 (1987).
Reichel "Sarcosyl-Page: a new electrophoretic method for the separation and immunological detection of PEGylated proteins." Protein Electrophoresis. Humana Press 65-79 (2012).
Riddick et al., "A stepwise increase in recombinant human growth hormone dosing during puberty achieves improved pubertal growth: A national cooperative study report". Journal of Pediatric Endocrinology & Metabolism, 22, 623-628 (200).
Reiter et al. "A multicenter study of the efficacy and safety of sustained release GH in the treatment of naive pediatric patients with GH deficiency" J Clin Endocrinol Metab. 86(10):4700-6 (Oct. 2001).
Response Final Office Action U.S. Appl. No. 13/372,540, filed Feb. 14, 2012.
Rosario PW. "Normal values of serum IGF-1 in adults: results from a Brazilian population" Arquivos Brasileiros de Endocrinologia & Metabologia. 2010;54(5):447-81.
Ronzi et al. Optimisation of a freeze-drying process of high purity Factor VIII and Factor IX concentrates. Chemical Engineering and Processing. vol. 42:751-757 (2003).
Rudman et al. "Effects of human growth hormone in men over 60 years old" N Engl J Med. Jul. 5, 1990;323(1):1-6.
Russell et al. "Local injections of human or rat growth hormone or of purified human somatomedin-C stimulate unilateral tibial epiphyseal growth in hypophysectomized rats" Endocrinology. Jun. 1985;116(6):2563-7.
Sambrook et al. "Molecular cloning: a laboratory manual." Cold Spring Harbor Laboratory Press, Cold Spring Harbor, New York 2 (2001).
Saudek et al. "A preliminary trial of the programmable implantable medication system for insulin delivery" N Engl J Med. 321:574 (1989).
Schein, Catherine H. "The shape of the messenger: Using protein structure information to design novel cytokine-based therapeutics" Abstract; Current Pharmaceutical Design 8(24):2113-2129 (2002).
Scheuttrumpf et al., "Factor IX variants improve gene therapy efficacy for hemophilia B." Blood 105.6: 2316-2323 (2005).
Schneider KH "GMP Requirements for master and working cell bank" Pharmazeutische Industrie. Jan. 1, 2005;67(11):1366-9.

(56) References Cited

OTHER PUBLICATIONS

Schulte "Half-life extension through albumin fusion technologies", Thrombosis Research (2009) 124 Suppl. 2;S6-S8.
Sefton, "Implantable pumps." Critical Reviews in Biomedical Engineering 14.3: 201-240 (1986).
Shechter et al. "Reversible PEGylation of peptide YY3-36 prolongs its inhibition of food intake in mice", FEBS Lett. Apr. 25, 2005;579(11):2439-44.
Sheffield et al. "Effects of genetic fusion of factor IX to albumin on in vivo clearance in mice and rabbits", Blackwell Publishing Ltd, British Journal of Haematology (2004) 126:565-573.
Silverman et al. "A long-acting human growth hormone (Nutropin Depot): Efficacy and safety following two years of treatment in children with growth hormone deficiency" J Pediatr Endocrinol Metab. 15 Suppl 2:715-22. (May 2002).
Smeland et al. "Treatment of Burkitt's/Burkitt-like lymphoma in adolescents and adults: a 20-year experience from the Norwegian Radium Hospital with the use of three successive regimens." Ann Oncol. Jul. 2004; 15(7):1072-8.
Speiser et al. "Optimization of spray-dried and -congealed lipid micropellets and characterization of their surface morphology." Pharm. Res. 8:47-54 (1991).
Srour et al. "Regulation of human factor IX expression using doxycycline-inducible gene expression system" Thromb Haemost 90:398-405 (2003).
Stuart et al. "Polycythemia vera" Am Fam Physician. May 1, 2004;69(9):2139-44.
Studier F.W. et al."Use of T7 RNA Polymerase to Direct Expression of Cloned Genes" Methods in Enzymol. 185:60-89 (1990).
Su et al. "Curcumin Inhibits Human Lung Cell Carcinoma Cancer Tumour Growth in a Murine Xenograft Model" (Phytother. Res. 24:189-191, 2010).
Sugahara et al. "Characterization of the O-glycosylation sites in the chorionic gonadotropin β subunit in vivo using site-directed mutagenesis and gene transfer." Journal of Biological Chemistry 271.34: 20797-20804 (1996).
Supplementary European Search Report for Application No. 16811146 mailed on Jan. 8, 2019.
Supplementary European Search Report for Application No. 12819794.4 mailed on Feb. 24, 2015.
Takamatsu et al. "Expression of bacterial chloramphenicol acetyltransferase gene in tobacco plants mediated by TMV-RNA" EMBO J 6:307-311 (1987).
Takeya et al. "Bovine factor VII. Its purification and complete amino acid sequence". Journal of Biological Chemistry. Oct. 15, 1988;263(29):14868-77.
Tape et al. "Apolipoprotein A-I and apolipoprotein SAA half-lives during acute inflammation and amyloidogenesis", Biochimica et Biophysica Acta (lipid and lipid metabolism) 1043: 295-300, 1990.
Tharakan et al. "Emerging therapies in the treatment of 'diabesity': beyond GLP-1" Trends Pharmacol Sci. Jan. 2011;32(1):8-15.
Treat et al., in "Liposomes in the therapy of infectious diseases and cancer." 353-365 (1989).
Treat, J, Greenspan, AR, and Rahman, A. Liposome Encapsulated Doxorubicin Preliminary Results of Phase I and Phase II Trials. in: G Lopez-Berestein, IJ Fidler (Eds.) Liposomes in the Therapy of Infectious Diseases and Cancer. Alan R. Liss, New York; 1989: 353-365.
Uenalp et al. "Factor VII deficiency associated with valproate treatment" Pediatrics International 50(3):403-405 Abstract (2008).
Venn et al. "Biosynthesis and metabolism in vivo of intervertebral-disc proteoglycans in the mouse." Biochem. J 215: 217-225 (1983).
Verhoef et al. "Recombinant human erythropoietin for the treatment of anemia in the myelodysplastic syndromes: a clinical and erythrokinetic assessment" Ann Hematol. Jan. 1992;64(1):16-21.
Weiss et al. "Noncompliance in Neurologic Patients" Current Treatment Options in Neurology 7:419-425 (2005).
Weissbach and Weissbach, "Methods for Plant Molecular Biology." Selected Methods in Enzymology (USA) Section VIII: 421-463 (1988).
Wells, J.A, "Additivity of Mutational Effects in Proteins" Biochemistry 29:8509-8517 (1990).
White et al. "Mammalian Recombinant Coagulation Proteins: Structure and Function", Transfus. Sci. (1998) 19(2):177-189.
Wildt et al., "The humanization of N-glycosylation pathways in yeast." Nature Reviews Microbiology 3.2: 119-128 (2005).
Wilken et al. "A novel four-amino acid determinant defines conformational freedom within chorionic gonadotropin β-subunits." Biochemistry 46.14: 4417-4424 (2007).
Winoto et al. "A novel, inducible and T cell-specific enhancer located at the 3' end of the T cell receptor alpha locus" EMBO J. 8:729-733 (1989).
Wynne et al. "Subcutaneous oxyntomodulin reduces body weight in overweight and obese subjects a double-blind, randomized, controlled trial." Diabetes 54.8 (2005): 2390-2395.
Yefenof & McConnell "Interferon amplifies complement activation by Burkitt's lymphoma cells" Nature. Feb. 21-27, 1985;313(6004):68.
Yin et al. "Recombinant human growth hormone replacement therapy in HIV-associated wasting and visceral adiposity". Exper. Rev. Anti-Infect. Ther. 3(5):727-736 (2005).
Yong et al., "The molecular design and drug development of recombinant long-acting follicle stimulating hormone". Institute of Molecular Medicine, Huaqiao University, Quanzhou, China and Centre for Reproduction and Genomics, AgResearch, Invermay, Mosgiel, New Zealand. Acta Pharmaceutica Sinica 2012, 47 (4): 421-426.
Zheng et al., "The impact of glycosylation on monoclonal antibody conformation and stability." MAbs. vol. 3. No. 6. Landes Bioscience, pp. 568-576, (Nov.-Dec. 2011).
Zhong et al. "The N-terminal epidermal growth factor-like domain in factor IX and factor X represents an important recognition motif for binding to tissue factor" J. Biol. Chem. (2002) 277(5):3622-31.
Beeley, Laboratory Techniques in Biochemistry and Molecular Biology, vol. 16, Amsterdam, Elsevier Science Publishing Company, pp. 69-72 (1985).
Calo, Doron et al. "Enhancing the Longevity and In Vivo Potency of Therapeutic Proteins: The Power of CTP", Precision Medicine, vol. 2,Oct. 27, 2015, pp. 1-8.
Chevreux, et al., "N-/O-glycosylation analysis of human FVIIa produced in the milk of transgenic rabbits", Glycobiology, vol. 23, 2013, pp. 1531-1546.
European Search Report dated Apr. 23, 2020 from European Application No. 19205364.
Goodson, J. Max, "Dental applications." in: Langer and Wise, Medical Applications of Controlled Release, vol. 2, Chapter 6 (Boca Raton, FL, CRC Press, Inc.), pp. 115-138 (1984).
Hershkovitz et al., "In Vitro and in Vivo Characterization of MOD-4023, a Long-Acting Carboxyl-Terminal Peptide (CTP)-Modified Human Growth Hormone", Molecular Pharmaceutics, vol. 13, No. 2, Feb. 1, 2016, pp. 631-639.
International Search Report and Written Opinion dated Sep. 22, 2020 from International Application No. PCT/IL2020/050769.
Naguib, Rania, et al. "Development and Validation of an IGF-1-Modified Child-Pugh Score to Risk-Stratify Hepatocellular Carcinoma Patients", Egyptian Journal of Obesity, Diabetes and Endocrinology, vol. 1, No. 1, Jan. 1, 2015, pp. 14-20.
Pearlman, et al., "Formulation, Characterization, and Stability of Protein Drugs", vol. 9., Springer Science & Business Media, 1996, pp. 247-274.
Peter, et al. "Pharmacokinetic and pharmacodynamic profile of a new sustained-release GH formulation, LB03002, in children with GH deficiency", European Journal of Endocrinology, 2009, pp. 349-355.
Quade-Lyssy,et al. "Engineered Factor VII, Factor IX, and Factor X Variants for Hemophilia Gene Therapy", Journal of Genetic Syndromes & Gene Therapy, 2012, pp. 1-7.
Wang, et al., "Research Progress in Long-Acting Dosage Form of Recombinant Human Growth Hormone", Chinese Journal of Pediatric, vol. 48, No. 4, Apr. 2010, pp. 317-320.
Yang, et al., "Change and Relative Analysis of Serum Levels of Insulin-Like Growth Factor-I and Bone Metabolization Indexes in

(56) References Cited

OTHER PUBLICATIONS

Idiopathic Short Stature Children", Chinese Journal of Child Health Care, vol. 17, No. 5, Oct. 2009 pp. 528-532. (English Abstract included within paper).

Zhong, et al., "Biological Insights into Therapeutic Protein Modifications throughout Trafficking and Their Biopharmaceutical Applications, "International Journal of Cell Biology, vol. 40, No. 14, Mar. 20, 2013, pp. 1-20.

Calo et al. "Enhancing the longevity and in vivo potency of therapeutic proteins: the power of CTP" Precision Medicine. 2015; 2: e989. doi: 10.14800/pm.989.

Chevreux et al. "N-/O-glycosylation analysis of human FVIIa produced in the milk of transgenic rabbits" Glycobiology. Dec. 1, 2013;23(12):1531-46.

Del Rosario Alemá el al. "Some methods for contamination testing of a master cell bank" Biopharm-Eugene-. Jun. 2000;13(6):48-53.

European Search Report for European Application No. EP21188483.8 dated Mar. 25, 2022.

European Search Report for European Application No. EP23191797.2 dated Jan. 9, 2024.

Fares et al. "Designing a Long Acting Erythropoietin by Fusing Three Carboxyl-Terminal Peptides of Human Chorionic Gonadotropin β Subunit to the N-Terminal and C-Terminal Coding Sequence" International journal of cell biology. 2011:275063.

Package Insert(s) for NovoSeven® HI 1/2/5 mg for intravenous injection, 2013.

Zhong et al. "Biological insights into therapeutic protein modifications throughout trafficking and their biopharmaceutical applications" International journal of cell biology. Apr. 18, 2013;2013, 19 pages.

Aleman, et al., "Some Methods for Contamination Testing of a Master Cell Bank", Biopharm, Cleveland, vol. 13, Issue 6, pp. 48-52, Jun. 2000.

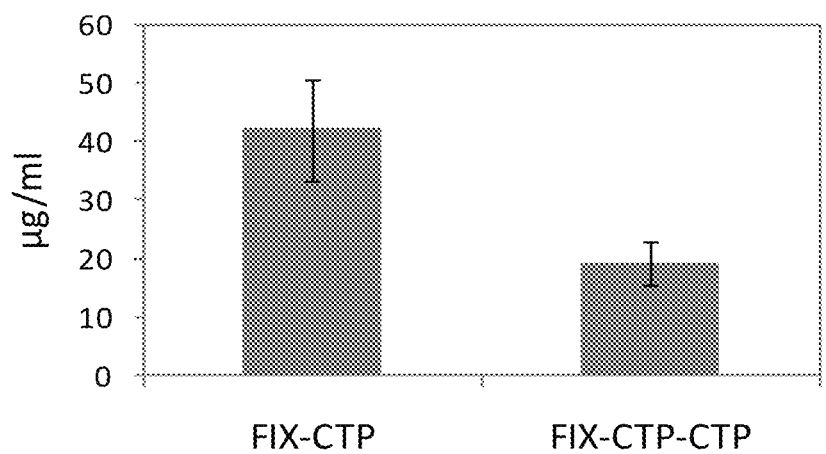
FIGURE 1A
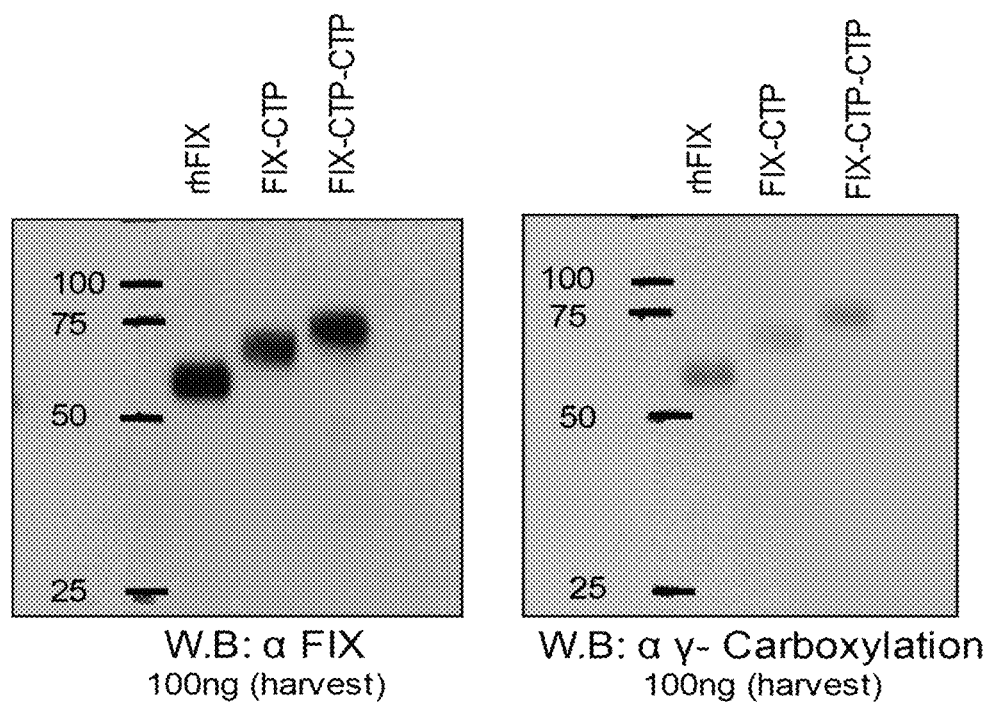
FIGURE 1B
FIGURE 1C

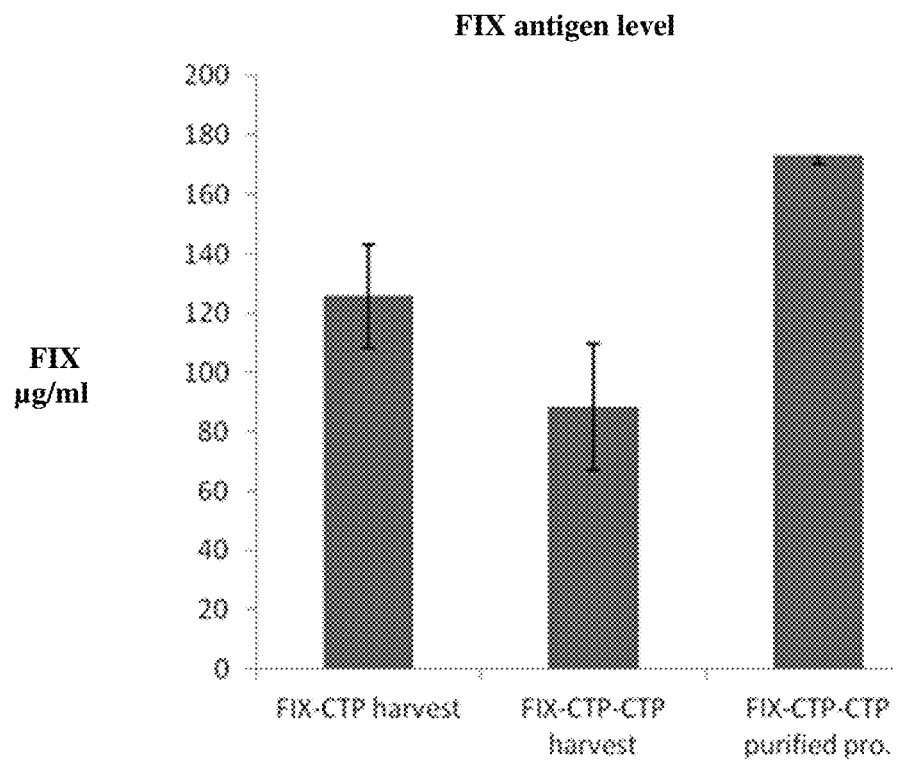
FIGURE 4
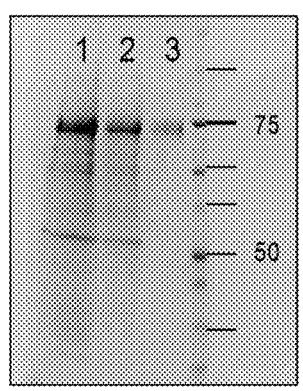 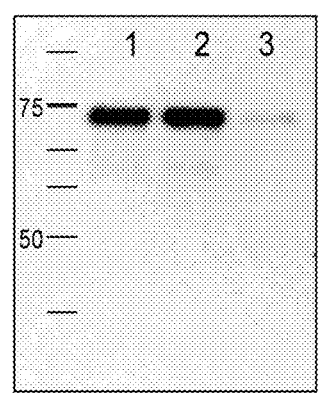 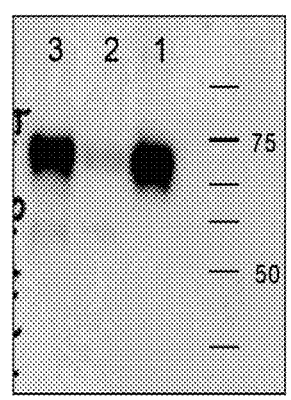
FIGURE 5A　　　　FIGURE 5B　　　　FIGURE 5C
1-FIX-(CTP)$_2$ Harvest
2-Unbound
3-Conc. elution (MOD3012)

|  | First bleeding challenge : Hemoglobin OD value | | |
|---|---|---|---|
|  | FIX-CTP-3 | BeneFIX | FIXKO |
| #1 | 6.84 | 10.26 | 19.92 |
| #2 | 0.72 | 10.14 | 13.32 |
| #3 | 4.68 | 11.16 | 16.38 |
| #4 | N | 9.18 | 7.92 |
| #5 | 7.86 | 7.77 | 9.72 |
| #6 | 4.14 | 9.15 | 14.7 |

First bleeding time (min)

|  | cohort#1 | cohort #3 | FIXKO |
|---|---|---|---|
| #1 | 10 | 10 | 10 |
| #2 | 5.12 | 10 | 8.17 |
| #3 | 10 | 10 | 10 |
| #4 |  | 10 | 10 |
| #5 | 10 | 7 | 10 |
| #6 | 10 | 10 | 10 |

Second bleeding OD value

|    | FIX-CTP₃ | BeneFIX | FIXKO |
|----|----------|---------|-------|
| #1 | 0.324    | 1.368   | 1.32  |
| #2 | 0.358    | 0.516   | 0.43  |
| #3 | 0.006    | 0.548   | 0.6   |
| #4 |          |         | 1.26  |
| #5 | 0.064    | 0.158   | 0.46  |
| #6 | 0.045    | 0.992   | 0.384 |

Second bleeding time (min)

|    | cohort#1 | cohort #3 | FIXKO |
|----|----------|-----------|-------|
| #1 | 4.63     | 10        | 10    |
| #2 | 2.5      | 10        | 8.7   |
| #3 | 1.2      | 10        | 7.13  |
| #4 |          | 5         | 10    |
| #5 | 3.87     | 7.4       | 10    |
| #6 | 1.83     | 10        | 6.5   |

FVII-CTP

FVII-CTP-CTP

FIX-CTP

FIX-CTP-CTP

| Time | PT | aPTT |
|---|---|---|
| 0 | 10.71 | 16.54 |
| 10 | 21.37 | 12.90 |
| 24 | 40.48 | 48.60 |
| 36 | 79.05 | 58.35 |
| 48 | 80.50 | 100.10 |
| 60 | 49.75 | 85.48 |
| 72 | 27.50 | 63.50 |

SEQUENCE LISTING

```
<160> NUMBER OF SEQ ID NOS: 49

<210> SEQ ID NO 1
<211> LENGTH: 32
<212> TYPE: PRT
<213> ORGANISM: Homo sapiens

<400> SEQUENCE: 1

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 2
<211> LENGTH: 28
<212> TYPE: PRT
<213> ORGANISM: Homo sapiens

<400> SEQUENCE: 2

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 3
<211> LENGTH: 12
<212> TYPE: PRT
<213> ORGANISM: Homo sapiens

<400> SEQUENCE: 3
```

Ser Ser Ser Lys Ala Pro Pro Ser Leu Pro
1               5                   10

<210> SEQ ID NO 4
<211> LENGTH: 28
<212> TYPE: PRT
<213> ORGANISM: Homo sapiens

<400> SEQUENCE: 4

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 5
<211> LENGTH: 25
<212> TYPE: DNA
<213> ORGANISM: Artificial Sequence
<220> FEATURE:
<223> OTHER INFORMATION: PCR primer for Factor VII

<400> SEQUENCE: 5
ctcgaggaca tggtctccca ggccc                                             25

<210> SEQ ID NO 6
<211> LENGTH: 24
<212> TYPE: DNA
<213> ORGANISM: Artificial Sequence
<220> FEATURE:
<223> OTHER INFORMATION: PCR primer for Factor VII

<400> SEQUENCE: 6
tctagaatag gtattttttcc acat                                             24

<210> SEQ ID NO 7
<211> LENGTH: 22
<212> TYPE: DNA
<213> ORGANISM: Artificial Sequence
<220> FEATURE:
<223> OTHER INFORMATION: PCR primer for Factor VII

<400> SEQUENCE: 7
tctagaaaaa agaaatgcca gc                                                22

<210> SEQ ID NO 8
<211> LENGTH: 32
<212> TYPE: DNA
<213> ORGANISM: Artificial Sequence
<220> FEATURE:
<223> OTHER INFORMATION: PCR primer for Factor VII

<400> SEQUENCE: 8
gcggccgcat cctcagggaa atggggctcg ca                                     32

<210> SEQ ID NO 9
<211> LENGTH: 444
<212> TYPE: PRT
<213> ORGANISM: Homo sapiens

<400> SEQUENCE: 9

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

```
Leu His Arg Arg Arg Ala Asn Ala Phe Leu Glu Glu Leu Arg Pro
         35                  40                  45

Gly Ser Leu Glu Arg Glu Cys Lys Glu Glu Gln Cys Ser Phe Glu Glu
 50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Ser Pro Cys Gln Asn Gly
                 85                  90                  95

Gly Ser Cys Lys Asp Gln Leu Gln Ser Tyr Ile Cys Phe Cys Leu Pro
                100                 105                 110

Ala Phe Glu Gly Arg Asn Cys Glu Thr His Lys Asp Asp Gln Leu Ile
            115                 120                 125

Cys Val Asn Glu Asn Gly Gly Cys Glu Gln Tyr Cys Ser Asp His Thr
130                 135                 140

Gly Thr Lys Arg Ser Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro
            435                 440
```

<210> SEQ ID NO 10
<211> LENGTH: 448
<212> TYPE: PRT
<213> ORGANISM: Homo sapiens

<400> SEQUENCE: 10

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380
```

```
Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Cys Gly Arg
        435                 440                 445
```

<210> SEQ ID NO 11
<211> LENGTH: 1356
<212> TYPE: DNA
<213> ORGANISM: Homo sapiens

<400> SEQUENCE: 11

```
ctcgaggaca tggtctccca ggccctcagg ctcctctgcc ttctgcttgg gcttcagggc      60
tgcctggctg cagtcttcgt aacccaggag gaagcccacg gcgtcctgca ccggcgccgg     120
cgcgccaacg cgttcctgga ggagctgcgg ccgggctccc tggagaggga gtgcaaggag     180
gagcagtgct ccttcgagga gccccgggag atcttcaagg acgcggagag gacgaagctg     240
ttctggattt cttacagtga tggggaccag tgtgcctcaa gtccatgcca gaatggggcc     300
tcctgcaagg accagctcca gtcctatatc tgcttctgcc tccctgcctt cgagggccgg     360
aactgtgaga cgcacaagga tgaccagctg atctgtgtga acgagaacgg cggctgtgag     420
cagtactgca gtgaccacac gggcaccaag cgctcctgtc ggtgccacga ggggtactct     480
ctgctggcag acggggtgtc ctgcacaccc acagttgaat atccatgtgg aaaaatacct     540
attctagaaa aaagaaatgc cagcaaaccc caaggccgaa ttgtgggggg caaggtgtgc     600
cccaaagggg agtgtccatg caggtcctg ttgttggtga atggagctca gttgtgtggg     660
gggaccctga tcaacaccat ctgggtggtc tccgcggccc actgtttcga caaaatcaag     720
aactggagga acctgatcgc ggtgctgggc gagcacgacc tcagcgagca cgacggggat     780
gagcagagcc ggcgggtggc gcaggtcatc atccccagca cgtacgtccc gggcaccacc     840
aaccacgaca tcgcgctgct ccgcctgcac cagcccgtgg tcctcactga ccatgtggtg     900
cccctctgcc tgcccgaacg gacgttctct gagaggacgc tggccttcgt gcgcttctca     960
ttggtcagcg gctggggcca gctgctggac cgtggcgcca cggccctgga gctcatggtc    1020
ctcaacgtgc cccggctgat gacccaggac tgcctgcagc agtcacggaa ggtgggagac    1080
tccccaaata tcacggagta catgttctgt gccggctact cggatggcag caaggactcc    1140
tgcaagggg acagtggagg cccacatgcc acccactacc ggggcacgtg gtacctgacg    1200
ggcatcgtca gctggggcca gggctgcgca accgtgggcc actttggggt gtacaccagg    1260
gtctcccagt acatcgagtg gctgcaaaag ctcatgcgct cagagccacg cccaggagtc    1320
ctcctgcgag ccccatttcc ctgaggatgc ggccgc                              1356
```

<210> SEQ ID NO 12
<211> LENGTH: 1442
<212> TYPE: DNA
<213> ORGANISM: Artificial Sequence
<220> FEATURE:
<223> OTHER INFORMATION: CTP-modified Factor VII

<400> SEQUENCE: 12

```
ctcgaggaca tggtctccca ggccctcagg ctcctctgcc ttctgcttgg gcttcagggc      60
```

-continued

```
tgcctggctg cagtcttcgt aacccaggag gaagcccacg gcgtcctgca ccggcgccgg     120
cgcgccaacg cgttcctgga ggagctgcgg ccgggctccc tggagaggga gtgcaaggag     180
gagcagtgct ccttcgagga ggcccgggag atcttcaagg acgcggagag gacgaagctg     240
ttctggattt cttacagtga tggggaccag tgtgcctcaa gtccatgcca gaatggggc     300
tcctgcaagg accagctcca gtcctatatc tgcttctgcc tccctgcctt cgagggccgg     360
aactgtgaga cgcacaagga tgaccagctg atctgtgtga cgagaacgg cggctgtgag     420
cagtactgca gtgaccacac gggcaccaag cgctcctgtc ggtgccacga ggggtactct     480
ctgctggcag acggggtgtc ctgcacaccc acagttgaat atccatggg aaaaataccct    540
attctagaaa aagaaatgc cagcaaaccc caaggccgaa ttgtgggggg caaggtgtgc     600
cccaaagggg agtgtccatg gcaggtcctg ttgttggtga atggagctca gttgtgtggg     660
gggaccctga tcaacaccat ctgggtggtc tccgcggccc actgtttcga caaaatcaag     720
aactggagga acctgatcgc ggtgctgggc gagcacgacc tcagcgagca cgacggggat     780
gagcagagcc ggcgggtggc gcaggtcatc atccccagca cgtacgtccc gggcaccacc     840
aaccacgaca tcgcgctgct ccgcctgcac cagcccgtgg tcctcactga ccatgtggtg     900
cccctctgcc tgcccgaacg gacgttctct gagaggacgc tggccttcgt gcgcttctca     960
ttggtcagcg gctggggcca gctgctggac cgtggcgcca cggccctgga gctcatggtc    1020
ctcaacgtgc cccggctgat gacccaggac tgcctgcagc agtcacggaa ggtgggagac    1080
tccccaaata tcacggagta catgttctgt gccggctact cggatggcag caaggactcc    1140
tgcaaggggg acagtggagg cccacatgcc acccactacc ggggcacgtg gtacctgacc    1200
ggcatcgtga gctggggcca gggctgcgcc accgtgggcc acttcggcgt gtacaccagg    1260
gtgtcccagt acatcgagtg gctgcagaaa ctgatgagaa gcgagccag acccggcgtg    1320
ctgctgagag ccccttccc cagcagcagc tccaaggccc ctccccctag cctgcccagc    1380
cctagcagac tgcctgggcc cagcgacacc cccatcctgc cccagtgagg atccgcggcc    1440
gc                                                                      1442
```

<210> SEQ ID NO 13
<211> LENGTH: 472
<212> TYPE: PRT
<213> ORGANISM: Artificial Sequence
<220> FEATURE:
<223> OTHER INFORMATION: CTP-modified Factor VII

<400> SEQUENCE: 13

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110
```

Ala Phe Glu Gly Arg Asn Cys Glu Thr His Lys Asp Asp Gln Leu Ile
            115                 120                 125

Cys Val Asn Glu Asn Gly Gly Cys Glu Gln Tyr Cys Ser Asp His Thr
        130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ser Ser Ser Ser
        435                 440                 445

Lys Ala Pro Pro Pro Ser Leu Pro Ser Pro Ser Arg Leu Pro Gly Pro
450                 455                 460

Ser Asp Thr Pro Ile Leu Pro Gln
465                 470

<210> SEQ ID NO 14
<211> LENGTH: 1535
<212> TYPE: DNA
<213> ORGANISM: Artificial Sequence
<220> FEATURE:
<223> OTHER INFORMATION: CTP-modified Factor VII

<400> SEQUENCE: 14

```
ctcgaggaca tggtctccca ggccctcagg ctcctctgcc ttctgcttgg gcttcagggc    60
tgcctggctg cagtcttcgt aacccaggag gaagcccacg gcgtcctgca ccggcgccgg   120
cgcgccaacg cgttcctgga ggagctgcgg ccgggctccc tggagaggga gtgcaaggag   180
gagcagtgct ccttcgagga ggcccgggag atcttcaagg acgcggagag gacgaagctg   240
ttctggattt cttacagtga tggggaccag tgtgcctcaa gtccatgcca gaatgggggc   300
tcctgcaagg accagctcca gtcctatatc tgcttctgcc tccctgcctt cgagggccgg   360
aactgtgaga cgcacaagga tgaccagctg atctgtgtga cgagaacggc ggctgtgagc   420
cagtactgca gtgaccacac gggcaccaag cgctcctgtc ggtgccacga ggggtactct   480
ctgctggcag acgggtgtc ctgcacaccc acagttgaat atccatgtgg aaaaatacct   540
attctagaaa aaagaaatgc cagcaaaccc caaggccgaa ttgtgggggg caaggtgtgc   600
cccaaagggg agtgtccatg gcaggtcctg ttgttggtga atggagctca gttgtgtggg   660
gggaccctga tcaacaccat ctgggtggtc tccgcggccc actgtttcga caaaatcaag   720
aactggagga acctgatcgc ggtgctgggc gagcacgacc tcagcgagca cgacgggat   780
gagcagagcc ggcgggtggc gcaggtcatc atccccagca cgtacgtccc gggcaccacc   840
aaccacgaca tcgcgctgct ccgcctgcac cagcccgtgg tcctcactga ccatgtggtg   900
cccctctgcc tgcccgaacg gacgttctct gagaggacgc tggccttcgt gcgcttctca   960
ttggtcagcg gctggggcca gctgctggac cgtggcgcca cggccctgga gctcatggtc  1020
ctcaacgtgc ccggctgat gacccaggac tgcctgcagc agtcacggaa ggtgggagac  1080
tccccaaata tcacggagta catgttctgt gccggctact cggatggcag caaggactcc  1140
tgcaaggggg acagtggagg cccacatgcc acccactacc ggggcacgtg gtacctgacc  1200
ggcatcgtga gctggggcca gggctgcgcc accgtgggcc acttcggcgt gtacaccagg  1260
gtgtcccagt acatcgagtg gctgcagaaa ctgatgagaa gcgagcccag accggcgtg  1320
ctgctgagag cccccttccc cagcagcagc tccaaggccc ctcccctag cctgcccagc  1380
cctagcagac tgcctgggcc ctccgacaca ccaatcctgc acagagcag ctcctctaag  1440
gcccctcctc catccctgcc atccccctcc cggctgccag gcccctctga cacccctatc  1500
ctgcctcagt gatgaaggtc tggatccgcg gccgc                             1535
```

<210> SEQ ID NO 15
<211> LENGTH: 500
<212> TYPE: PRT
<213> ORGANISM: Artificial Sequence
<220> FEATURE:
<223> OTHER INFORMATION: CTP-modified Factor VII

<400> SEQUENCE: 15

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

-continued

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Gln Leu Ile
            115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
        210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
        370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ser Ser Ser Ser
            435                 440                 445

Lys Ala Pro Pro Pro Ser Leu Pro Ser Pro Ser Arg Leu Pro Gly Pro
            450                 455                 460

Ser Asp Thr Pro Ile Leu Pro Gln Ser Ser Ser Lys Ala Pro Pro
465                 470                 475                 480

Pro Ser Leu Pro Ser Pro Ser Arg Leu Pro Gly Pro Ser Asp Thr Pro
                485                 490                 495

Ile Leu Pro Gln
            500

<210> SEQ ID NO 16
<211> LENGTH: 1404
<212> TYPE: DNA
<213> ORGANISM: Homo sapiens

<400> SEQUENCE: 16

```
gcgatcgcca tgcagcgcgt gaacatgatc atggcagaat caccaggcct catcaccatt      60
gcctttagg atatctactc agtgctgaat gtacagtttt tcttgatcat gaaaacgcca      120
acaaaattct gaatcggcca agaggtata attcaggtaa attggaagag tttgttcaag      180
ggaaccttga gagaatgt atggaagaaa agtgtagttt tgaagaagca cgagaagttt      240
ttgaaaacac tgaagaaca actgaatttt ggaagcagta tgttgatgga gatcagtgtg      300
agtccaatcc atgtttaaat ggcggcagtt gcaaggatga cattaattcc tatgaatgtt      360
ggtgtccctt tggatttgaa ggaaagaact gtgaattaga tgtaacatgt aacattaaga      420
atggcagatg cgagcagttt tgtaaaaata gtgctgataa caaggtggtt tgctcctgta      480
ctgagggata tcgacttgca gaaaaccaga agtcctgtga accagcagtg ccatttccat      540
gtggaagagt ttctgtttca caacttcta agctcacccg tgctgagact gtttttcctg      600
atgtggacta tgtaaattct actgaagctg aaaccatttt ggataacatc actcaaagca      660
cccaatcatt taatgacttc actcgagttg ttggtggaga agatgccaaa ccaggtcaat      720
tcccttggca ggttgttttg aatggtaaag ttgatgcatt ctgtggaggc tctatcgtta      780
atgaaaaatg gattgtaact gctgcccact gtgttgaaac tggtgttaaa attacagttg      840
tcgcaggtga acataatatt gaggagacag aacatacaga gcaaaagcga atgtgattc      900
gaattattcc tcaccacaac tacaatgcag ctattaataa gtacaaccat gacattgccc      960
ttctggaact ggacgaaccc ttagtgctaa acagctacgt tacacctatt tgcattgctg     1020
acaaggaata cacgaacatc ttcctcaaat ttggatctgg ctatgtaagt ggctggggaa     1080
gagtcttcca caagggagaa tcagctttag ttctccagta ccttagagtt ccacttgttg     1140
accgagccac atgtcttcga tctacaaagt tcaccatcta taacaacatg ttctgtgctg     1200
gcttccatga aggaggtaga gattcatgtc aaggagatag tggggaccc catgttactg     1260
aagtggaagg gaccagtttc ttaactggaa ttattagctg gggtgaagag tgtgcaatga     1320
aaggcaaata tggaatatat accaaggtat cccggtatgt caactggatt aaggaaaaaa     1380
caaagctcac ttgaacgcgg ccgc                                           1404
```

<210> SEQ ID NO 17
<211> LENGTH: 461
<212> TYPE: PRT
<213> ORGANISM: Homo sapiens

<400> SEQUENCE: 17

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80
```

```
Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
450                 455                 460

<210> SEQ ID NO 18
<211> LENGTH: 1502
<212> TYPE: DNA
<213> ORGANISM: Artificial Sequence
<220> FEATURE:
<223> OTHER INFORMATION: CTP-modified Factor IX
```

<400> SEQUENCE: 18

```
gcgatcgcca tgcagcgcgt gaacatgatc atggcagaat caccaggcct catcaccatc    60
tgcctttag gatatctact cagtgctgaa tgtacagttt ttcttgatca tgaaaacgcc    120
aacaaaattc tgaatcggcc aaagaggtat aattcaggta aattggaaga gtttgttcaa   180
gggaaccttg agagagaatg tatggaagaa aagtgtagtt ttgaagaagc acgagaagtt   240
tttgaaaaca ctgaaagaac aactgaattt tggaagcagt atgttgatgg agatcagtgt   300
gagtccaatc catgtttaaa tggcggcagt tgcaaggatg acattaattc ctatgaatgt   360
tggtgtccct ttggatttga aggaaagaac tgtgaattag atgtaacatg taacattaag   420
aatggcagat gcgagcagtt ttgtaaaaat agtgctgata caaggtggt ttgctcctgt    480
actgagggat atcgacttgc agaaaaccag aagtcctgtg aaccagcagt gccatttcca   540
tgtggaagag tttctgtttc acaaacttct aagctcaccc gtgctgagac tgtttttcct   600
gatgtggact atgtaaattc tactgaagct gaaaccattt tggataacat cactcaaagc   660
acccaatcat taatgacctt cactcgagtt gttggtggag aagatgccaa accaggtcaa   720
ttcccttggc aggttgtttt gaatggtaaa gttgatgcat tctgtggagg ctctatcgtt   780
aatgaaaaat ggattgtaac tgctgcccac tgtgttgaaa ctggtgttaa aattacagtt   840
gtcgcaggtg aacataatat tgaggagaca gaacatacag agcaaaagcg aaatgtgatt   900
cgaattattc ctcaccacaa ctacaatgca gctattaata agtacaacca tgacattgcc   960
cttctggaac tggacgaacc cttagtgcta aacagctacg ttacacctat ttgcattgct  1020
gacaaggaat acacgaacat cttcctcaaa tttggatctg gctatgtaag tggctgggga  1080
agagtcttcc acaagggag atcagcttta gttcttcagt accttagagt tccacttgtt  1140
gaccgagcca catgtcttcg atctacaaag ttcaccatct ataacaacat gttctgtgct  1200
ggcttccatg aaggaggtag agattcatgt caaggagata gtgggggacc ccatgttact  1260
gaagtggaag ggaccagttt cttaactgga attattagct ggggtgaaga gtgtgcaatg  1320
aaaggcaaat atgggaatata taccaaggta tcccggtatg tcaactggat taaggaaaaa  1380
acaaagctca ctagctccag cagcaaggcc cctcccccga gcctgccctc cccaagcagg  1440
ctgcctgggc cctccgacac accaatcctg ccacagtgat gaaggtctgg atccgcggcc  1500
gc                                                                  1502
```

<210> SEQ ID NO 19
<211> LENGTH: 489
<212> TYPE: PRT
<213> ORGANISM: Artificial Sequence
<220> FEATURE:
<223> OTHER INFORMATION: CTP-modified Factor IX

<400> SEQUENCE: 19

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80
```

```
Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Ser Ser Ser
    450                 455                 460

Ser Lys Ala Pro Pro Ser Leu Pro Ser Pro Ser Arg Leu Pro Gly
465                 470                 475                 480

Pro Ser Asp Thr Pro Ile Leu Pro Gln
                485
```

<210> SEQ ID NO 20
<211> LENGTH: 1585
<212> TYPE: DNA
<213> ORGANISM: Artificial Sequence
<220> FEATURE:
<223> OTHER INFORMATION: CTP-modified Factor IX

<400> SEQUENCE: 20

```
gcgatcgcca tgcagcgcgt gaacatgatc atggcagaat caccaggcct catcaccatc     60
tgccttttag atatctact cagtgctgaa tgtacagttt ttcttgatca tgaaaacgcc      120
aacaaaattc tgaatcggcc aaagaggtat aattcaggta aattggaaga gtttgttcaa     180
gggaaccttg agagagaatg tatggaagaa agtgtagtt tgaagaagc acgagaagtt       240
tttgaaaaca ctgaaagaac aactgaattt tggaagcagt atgttgatgg agatcagtgt     300
gagtccaatc catgttttaaa tggcggcagt tgcaaggatg acattaattc ctatgaatgt    360
tggtgtccct ttggatttga aggaaagaac tgtgaattag atgtaacatg taacattaag    420
aatggcagat gcgagcagtt ttgtaaaaat agtgctgata caaggtggt ttgctcctgt     480
actgagggat atcgacttgc agaaaaccag aagtcctgtg aaccagcagt gccatttcca    540
tgtggaagag tttctgtttc acaaacttct aagctcaccc gtgctgagac tgttttttcct   600
gatgtggact atgtaaattc tactgaagct gaaaccattt tggataacat cactcaaagc    660
acccaatcat ttaatgactt cactcgagtt gttggtggag aagatgccaa accaggtcaa    720
ttcccttggc aggttgtttt gaatggtaaa gttgatgcat ctgtggagg ctctatcgtt    780
aatgaaaaat ggattgtaac tgctgcccac tgtgttgaaa ctggtgttaa aattacagtt    840
gtcgcaggtg aacataatat tgaggagaca gaacatacag agcaaaagcg aaatgtgatt    900
cgaattattc tcaccacaa ctacaatgca gctattaata agtacaacca tgacattgcc     960
cttctggaac tggacgaacc cttagtgcta aacagctacg ttacacctat ttgcattgct   1020
acaaggaata cacgaacatc ttcctcaaat ttggatctgg ctatgtaagt ggctggggaa   1080
gagtcttcca caagggaga tcagctttag ttcttcagta ccttagagtt ccacttgttg   1140
accgagccac atgtcttcga tctacaaagt tcaccatcta taacaacatg ttctgtgctg   1200
gcttccatga aggaggtaga gattcatgtc aaggagatag tggggaccc catgttactg   1260
aagtggaagg gaccagtttc ttaactggaa ttattagctg gggtgaagag tgtgcaatga   1320
aaggcaaata tggaatatat accaaggtat cccggtatgt caactggatt aaggaaaaaa   1380
caaagctcac tagctccagc agcaaggcc ctcccccgag cctgcccctcc caagcaggc   1440
tgcctgggcc ctccgacaca ccaatcctgc cacagagcag ctcctctaag gcccctcctc   1500
catccctgcc atcccctcc cggctgcctg gcccctctga cacccctatc ctgcctcagt   1560
gatgaaggtc tggatccgcg gccgc                                         1585
```

<210> SEQ ID NO 21
<211> LENGTH: 517
<212> TYPE: PRT
<213> ORGANISM: Artificial Sequence
<220> FEATURE:
<223> OTHER INFORMATION: CTP-modified Factor IX

<400> SEQUENCE: 21

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30
```

```
Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                    85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                    165                 170                 175

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
        210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                    245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
        290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                    325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                    405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
            435                 440                 445
```

```
Arg Tyr Val Asn Trp Ile Lys Glu Lys Thr Lys Leu Thr Ser Ser Ser
    450                 455                 460

Ser Lys Ala Pro Pro Pro Ser Leu Pro Ser Pro Ser Arg Leu Pro Gly
465                 470                 475                 480

Pro Ser Asp Thr Pro Ile Leu Pro Gln Ser Ser Ser Ser Lys Ala Pro
                485                 490                 495

Pro Pro Ser Leu Pro Ser Pro Ser Arg Leu Pro Gly Pro Ser Asp Thr
            500                 505                 510

Pro Ile Leu Pro Gln
        515

<210> SEQ ID NO 22
<211> LENGTH: 2413
<212> TYPE: DNA
<213> ORGANISM: Homo sapiens

<400> SEQUENCE: 22
```

| | | | | | |
|---|---|---|---|---|---|
| tctagagtcg | accccgccat | ggagctgagg | ccctggttgc | tatgggtggt | agcagcaaca | 60 |
| ggaaccttgg | tcctgctagc | agctgatgct | cagggccaga | aggtcttcac | caacacgtgg | 120 |
| gctgtgcgca | tccctggagg | cccagcggtg | gccaacagtg | tggcacggaa | gcatgggttc | 180 |
| ctcaacctgg | ccagatctt | cggggactat | taccacttct | ggcatcgagg | agtgacgaag | 240 |
| cggtccctgt | cgcctcaccg | cccgcggcac | agccggctgc | agaggggagcc | tcaagtacag | 300 |
| tggctggaac | agcaggtggc | aaagcgacgg | actaaacggg | acgtgtacca | ggagcccaca | 360 |
| gaccccaagt | tcctcagca | gtggtacctg | tctggtgtca | ctcagcggga | cctgaatgtg | 420 |
| aaggcggcct | gggcgcaggg | ctacacaggg | cacggcattg | tggtctccat | tctggacgat | 480 |
| ggcatcgaga | gaaccaccc | ggacttggca | ggcaattatg | atcctggggc | cagttttgat | 540 |
| gtcaatgacc | aggaccctga | cccccagcct | cggtacacac | agatgaatga | caacaggcac | 600 |
| ggcacacggt | gtgcggggga | agtggctgcg | gtggccaaca | acgtgtctg | tggtgtaggt | 660 |
| gtggcctaca | acgcccgcat | tggaggggtg | cgcatgctgg | atggcgaggt | gacagatgca | 720 |
| gtggaggcac | gctcgctggg | cctgaacccc | aaccacatcc | acatctacag | tgccagctgg | 780 |
| ggcccccgagg | atgacggcaa | gacagtggat | gggccagccc | gcctcgccga | ggaggccttc | 840 |
| ttccgtgggg | ttagccaggg | ccgagggggg | ctgggctcca | tctttgtctg | ggcctcgggg | 900 |
| aacgggggcc | gggaacatga | cagctgcaac | tgcgacggct | acaccaacag | tatctacacg | 960 |
| ctgtccatca | gcagcgccac | gcagtttggc | aacgtgccgt | ggtacagcga | ggcctgctcg | 1020 |
| tccacactgg | ccacgaccta | cagcagtggc | aaccagaatg | agaagcagat | cgtgacgact | 1080 |
| gacttgcggc | agaagtgcac | ggagtctcac | acgggcacct | cagcctctgc | ccccttagca | 1140 |
| gccggcatca | ttgctctcac | cctggaggcc | aataagaacc | tcacatggcg | ggacatgcaa | 1200 |
| cacctggtgg | tacagacctc | gaagccagcc | cacctcaatg | ccaacgactg | ggccaccaat | 1260 |
| ggtgtgggcc | ggaaagtgag | ccactcatat | ggctacgggc | ttttggacgc | aggcgccatg | 1320 |
| gtggccctgg | cccagaattg | gaccacagtg | gcccccagc | ggaagtgcat | catcgacatc | 1380 |
| ctcaccgagc | caaagacat | cgggaaacgg | ctcgaggtgc | ggaagaccgt | gaccgcgtgc | 1440 |
| ctgggcgagc | caaccacat | cactcggctg | agcacgctc | aggcgcggct | cacctgtcc | 1500 |
| tataatcgcc | gtggcgacct | ggccatccac | ctggtcagcc | ccatgggcac | ccgctccacc | 1560 |
| ctgctggcag | ccaggccaca | tgactactcc | gcagatgggt | taatgactg | ggccttcatg | 1620 |
| acaactcatt | cctgggatga | ggatccctct | ggcgagtggg | tcctagagat | tgaaaacacc | 1680 |

-continued

```
agcgaagcca acaactatgg gacgctgacc aagttcaccc tcgtactcta tggcaccgcc    1740 cctgagggge tgeccgtace tecagaaage agtggetgca agaccctcac gtccagtcag    1800
gcctgtgtgg tgtgcgagga aggcttctcc ctgcaccaga agagctgtgt ccagcactgc    1860
cctccaggct tcgcccccca agtcctcgat acgcactata gcaccgagaa tgacgtggag    1920
accatccggg ccagcgtctg cgccccctgc cacgcctcat gtgccacatg ccaggggccg    1980
gccctgacag actgcctcag ctgccccagc cacgcctcct tggaccctgt ggagcagact    2040
tgctcccggc aaagccagag cagccgagag tccccgccac agcagcagcc acctcggctg    2100
cccccggagg tggaggcggg gcaacggctg cgggcagggc tgctgccctc acacctgcct    2160
gaggtggtgg ccggcctcag ctgcgccttc atcgtgctgg tcttcgtcac tgtcttcctg    2220
gtcctgcagc tgcgctctgg ctttagttt cggggggtga aggtgtacac catgaccgt    2280 ggcctcatct cctacaaggg gctgccccct gaagcctggc aggaggagtg cccgtctgac    2340
tcagaagagg acgagggccg gggcgagagg accgccttta tcaaagacca gagcgccctc    2400
tgaacgcggc cgc                                                        2413
```

<210> SEQ ID NO 23
<211> LENGTH: 794
<212> TYPE: PRT
<213> ORGANISM: Homo sapiens

<400> SEQUENCE: 23

```
Met Glu Leu Arg Pro Trp Leu Leu Trp Val Ala Ala Thr Gly Thr
 1               5                  10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
            35                  40                  45

Ala Arg Lys His Gly Phe Leu Asn Leu Gly Gln Ile Phe Gly Asp Tyr
        50                  55                  60

Tyr His Phe Trp His Arg Gly Val Thr Lys Arg Ser Leu Ser Pro His
 65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240
```

-continued

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
    530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu

```
                660             665             670
Gln Thr Cys Ser Arg Gln Ser Gln Ser Ser Arg Glu Ser Pro Pro Gln
            675                 680                 685

Gln Gln Pro Pro Arg Leu Pro Pro Glu Val Glu Ala Gly Gln Arg Leu
        690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Glu Gly Arg Gly Glu Arg
    770                 775                 780

Thr Ala Phe Ile Lys Asp Gln Ser Ala Leu
785                 790

<210> SEQ ID NO 24
<211> LENGTH: 1621
<212> TYPE: DNA
<213> ORGANISM: Artificial Sequence
<220> FEATURE:
<223> OTHER INFORMATION: CTP-modified Factor VII

<400> SEQUENCE: 24
ctcgaggaca tggtctccca ggccctcagg ctcctctgcc ttctgcttgg gcttcagggc      60
tgcctggctg cagtcttcgt aacccaggag gaagcccacg gcgtcctgca ccggcgccgg     120
cgcgccaacg cgttcctgga ggagctgcgg ccgggctccc tggagaggga gtgcaaggag     180
gagcagtgct ccttcgagga ggcccgggag atcttcaagg acgcggagag gacgaagctg     240
ttctggattt cttacagtga tggggaccag tgtgcctcaa gtccatgcca gaatgggggc     300
tcctgcaagg accagctcca gtcctatatc tgcttctgcc tccctgcctt cgagggccgg     360
aactgtgaga gcacaagga tgaccagctg atctgtgtga cgagaacgg cggctgtgag     420 cagtactgca gtgaccacac gggcaccaag cgctcctgtc ggtgccacga ggggtactct     480
ctgctggcag acggggtgtc ctgcacaccc acagttgaat atccatgtgg aaaaatacct     540
attctagaaa aagaaatgc cagcaaaccc caaggccgaa ttgtgggggg caaggtgtgc     600
cccaaagggg agtgtccatg gcaggtcctg ttgttggtga atggagctca gttgtgtggg     660
gggaccctga tcaacaccat ctgggtggtc tccgcggccc actgtttcga caaaatcaag     720
aactggagga acctgatcgc ggtgctgggc gagcacgacc tcagcgagca cgacggggat     780
gagcagagcc ggcgggtggc gcaggtcatc atccccagca cgtacgtccc gggcaccacc     840
aaccacgaca tcgcgctgct ccgcctgcac cagcccgtgg tcctcactga ccatgtggtg     900
cccctctgcc tgcccgaacg gacgttctct gagaggacgc tggccttcgt gcgcttctca     960
ttggtcagcg gctggggcca gctgctggac cgtggcgcca cggccctgga gctcatggtc    1020
ctcaacgtgc ccggctgat gacccaggac tgcctgcagc agtcacggaa ggtgggagac    1080
tccccaaata tcacggagta catgttctgt gccggctact cggatggcag caaggactcc    1140 tgcaagggg acagtggagg cccacatgcc acccactacc ggggcacgtg gtacctgacc    1200
ggcatcgtga gctggggcca gggctgcgcc accgtgggcc acttcggcgt gtacaccagg    1260
gtgtcccagt acatcgagtg gctgcagaaa ctgatgagaa gcgagcccag accggcgtg    1320
```

```
ctgctgagag ccccttccc cagcagcagc tccaaggccc ctcccctag cctgcccagc   1380 cctagcagac tgcctgggcc cagtgacacc cctatcctgc ctcagtccag ctccagcaag   1440
gccccacccc ctagcctgcc ttctccttct cggctgcctg gccccagcga tactccaatt   1500
ctgccccagt cctccagcag taaggctccc cctccatctc tgccatcccc cagcagactg   1560
ccaggccctt ctgatacacc catcctccca cagtgatgag gatccgcggc cgcttaatta   1620
a                                                                   1621
```

<210> SEQ ID NO 25
<211> LENGTH: 528
<212> TYPE: PRT
<213> ORGANISM: Artificial Sequence
<220> FEATURE:
<223> OTHER INFORMATION: CTP-modified Factor VII

<400> SEQUENCE: 25

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
                20                  25                  30

Leu His Arg Arg Arg Arg Ala Asn Ala Phe Leu Glu Glu Leu Arg Pro
            35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
        210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
        290                 295                 300
```

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
        340                 345                 350

Arg Lys Val Gly Asp Ser Pro Asn Ile Thr Glu Tyr Met Phe Cys Ala
    355                 360                 365

Gly Tyr Ser Asp Gly Ser Lys Asp Ser Cys Lys Gly Asp Ser Gly Gly
370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415

Arg Val Ser Gln Tyr Ile Glu Trp Leu Gln Lys Leu Met Arg Ser Glu
        420                 425                 430

Pro Arg Pro Gly Val Leu Leu Arg Ala Pro Phe Pro Ser Ser Ser Ser
    435                 440                 445

Lys Ala Pro Pro Pro Ser Leu Pro Ser Pro Ser Arg Leu Pro Gly Pro
450                 455                 460

Ser Asp Thr Pro Ile Leu Pro Gln Ser Ser Ser Lys Ala Pro Pro
465                 470                 475                 480

Pro Ser Leu Pro Ser Pro Ser Arg Leu Pro Gly Pro Ser Asp Thr Pro
            485                 490                 495

Ile Leu Pro Gln Ser Ser Ser Ser Lys Ala Pro Pro Ser Leu Pro
        500                 505                 510

Ser Pro Ser Arg Leu Pro Gly Pro Ser Asp Thr Pro Ile Leu Pro Gln
    515                 520                 525

<210> SEQ ID NO 26
<211> LENGTH: 1607
<212> TYPE: DNA
<213> ORGANISM: Artificial Sequence
<220> FEATURE:
<223> OTHER INFORMATION: CTP-modified Factor VII

<400> SEQUENCE: 26
ctcgaggaca tggtctccca ggccctcagg ctcctctgcc ttctgcttgg gcttcagggc      60
tgcctggctg cagtcttcgt aacccaggag gaagcccacg gcgtcctgca ccggcgccgg     120
cgcgccaacg cgttcctgga ggagctgcgg ccgggctccc tggagaggga gtgcaaggag     180
gagcagtgct ccttcgagga ggcccgggag atcttcaagg acgcggagag gacgaagctg     240
ttctggattt cttacagtga tggggaccag tgtgcctcaa gtccatgcca gaatgggggc     300
tcctgcaagg accagctcca gtcctatatc tgcttctgcc tccctgcctt cgagggccgg     360
aactgtgaga cgcacaagga tgaccagctg atctgtgtga acgagaacgg cggctgtgag     420
cagtactgca gtgaccacac gggcaccaag cgctcctgtc ggtgccacga ggggtactct     480
ctgctggcag acggggtgtc ctgcacaccc acagttgaat atccatgtgg aaaaatacct     540
attctagaaa aagaaatgc cagcaaaccc caaggccgaa ttgtgggggg caaggtgtgc     600
cccaaagggg agtgtccatg gcaggtcctg ttgttggtga atggagctca gttgtgtggg     660
gggaccctga tcaacaccat ctgggtggtc tccgcggccc actgtttcga caaaatcaag     720
aactggagga acctgatcgc ggtgctgggc gagcacgacc tcagcgagca cgacgggat     780

-continued

```
gagcagagcc ggcgggtggc gcaggtcatc atccccagca cgtacgtccc gggcaccacc    840
aaccacgaca tcgcgctgct ccgcctgcac cagcccgtgg tcctcactga ccatgtggtg    900
cccctctgcc tgcccgaacg gacgttctct gagaggacgc tggccttcgt gcgcttctca    960
ttggtcagcg gctggggcca gctgctggac cgtggcgcca cggccctgga gctcatggtc   1020
ctcaacgtgc ccggctgat gacccaggac tgcctgcagc agtcacggaa ggtgggagac   1080
tccccaaata tcacggagta catgttctgt gccggctact cggatggcag caaggactcc   1140 tgcaagggg acagtggagg cccacatgcc acccactacc ggggcacgtg gtacctgacc   1200
ggcatcgtga gctggggcca gggctgcgcc accgtgggcc acttcggcgt gtacaccagg   1260
gtgtcccagt acatcgagtg gctgcagaaa ctgatgagaa gcgagcccag acccggcgtg   1320
ctgctgagag ccccttccc cagcagcagc tccaaggccc tcccctag cctgcccagc   1380 cctagcagac tgcctgggcc cagtgacacc cctatcctgc tcagtccag ctccagcaag   1440 gccccacccc ctagcctgcc ttctccttct cggctgcctg ccccagcga tactccaatt   1500 ctgccccagt cctccagcag taaggctccc cctccatctc tgccatcccc cagcagactg   1560
ccaggccctt ctgatacacc catcctccca cagtgatgag gatccgc           1607
```

<210> SEQ ID NO 27
<211> LENGTH: 532
<212> TYPE: PRT
<213> ORGANISM: Artificial Sequence
<220> FEATURE:
<223> OTHER INFORMATION: CTP-modified Factor VII

<400> SEQUENCE: 27

```
Leu Glu Asp Met Val Ser Gln Ala Leu Arg Leu Leu Cys Leu Leu Leu
 1               5                  10                  15

Gly Leu Gln Gly Cys Leu Ala Ala Val Phe Val Thr Gln Glu Glu Ala
            20                  25                  30

His Gly Val Leu His Arg Arg Arg Ala Asn Ala Phe Leu Glu Glu
        35                  40                  45

Leu Arg Pro Gly Ser Leu Glu Arg Glu Cys Lys Glu Glu Gln Cys Ser
    50                  55                  60

Phe Glu Glu Ala Arg Glu Ile Phe Lys Asp Ala Glu Arg Thr Lys Leu
65                  70                  75                  80

Phe Trp Ile Ser Tyr Ser Asp Gly Asp Gln Cys Ala Ser Ser Pro Cys
                85                  90                  95

Gln Asn Gly Gly Ser Cys Lys Asp Gln Leu Gln Ser Tyr Ile Cys Phe
            100                 105                 110

Cys Leu Pro Ala Phe Glu Gly Arg Asn Cys Glu Thr His Lys Asp Asp
        115                 120                 125

Gln Leu Ile Cys Val Asn Glu Asn Gly Gly Cys Glu Gln Tyr Cys Ser
    130                 135                 140

Asp His Thr Gly Thr Lys Arg Ser Cys Arg Cys His Glu Gly Tyr Ser
145                 150                 155                 160

Leu Leu Ala Asp Gly Val Ser Cys Thr Pro Thr Val Glu Tyr Pro Cys
                165                 170                 175

Gly Lys Ile Pro Ile Leu Glu Lys Arg Asn Ala Ser Lys Pro Gln Gly
            180                 185                 190

Arg Ile Val Gly Gly Lys Val Cys Pro Lys Gly Glu Cys Pro Trp Gln
        195                 200                 205

Val Leu Leu Leu Val Asn Gly Ala Gln Leu Cys Gly Gly Thr Leu Ile
    210                 215                 220
```

-continued

```
Asn Thr Ile Trp Val Val Ser Ala Ala His Cys Phe Asp Lys Ile Lys
225                 230                 235                 240

Asn Trp Arg Asn Leu Ile Ala Val Leu Gly Glu His Asp Leu Ser Glu
            245                 250                 255

His Asp Gly Asp Glu Gln Ser Arg Arg Val Ala Gln Val Ile Ile Pro
        260                 265                 270

Ser Thr Tyr Val Pro Gly Thr Thr Asn His Asp Ile Ala Leu Leu Arg
    275                 280                 285

Leu His Gln Pro Val Val Leu Thr Asp His Val Val Pro Leu Cys Leu
290                 295                 300

Pro Glu Arg Thr Phe Ser Glu Arg Thr Leu Ala Phe Val Arg Phe Ser
305                 310                 315                 320

Leu Val Ser Gly Trp Gly Gln Leu Leu Asp Arg Gly Ala Thr Ala Leu
                325                 330                 335

Glu Leu Met Val Leu Asn Val Pro Arg Leu Met Thr Gln Asp Cys Leu
            340                 345                 350

Gln Gln Ser Arg Lys Val Gly Asp Ser Pro Asn Ile Thr Glu Tyr Met
        355                 360                 365

Phe Cys Ala Gly Tyr Ser Asp Gly Ser Lys Asp Ser Cys Lys Gly Asp
    370                 375                 380

Ser Gly Gly Pro His Ala Thr His Tyr Arg Gly Thr Trp Tyr Leu Thr
385                 390                 395                 400

Gly Ile Val Ser Trp Gly Gln Gly Cys Ala Thr Val Gly His Phe Gly
                405                 410                 415

Val Tyr Thr Arg Val Ser Gln Tyr Ile Glu Trp Leu Gln Lys Leu Met
            420                 425                 430

Arg Ser Glu Pro Arg Pro Gly Val Leu Leu Arg Ala Pro Phe Pro Ser
        435                 440                 445

Ser Ser Ser Lys Ala Pro Pro Pro Ser Leu Pro Ser Pro Ser Arg Leu
    450                 455                 460

Pro Gly Pro Ser Asp Thr Pro Ile Leu Pro Gln Ser Ser Ser Ser Lys
465                 470                 475                 480

Ala Pro Pro Pro Ser Leu Pro Ser Pro Ser Arg Leu Pro Gly Pro Ser
                485                 490                 495

Asp Thr Pro Ile Leu Pro Gln Ser Ser Ser Ser Lys Ala Pro Pro Pro
            500                 505                 510

Ser Leu Pro Ser Pro Ser Arg Leu Pro Gly Pro Ser Asp Thr Pro Ile
        515                 520                 525

Leu Pro Gln Gly
    530
```

<210> SEQ ID NO 28
<211> LENGTH: 1775
<212> TYPE: DNA
<213> ORGANISM: Artificial Sequence
<220> FEATURE:
<223> OTHER INFORMATION: CTP-modified Factor VII

<400> SEQUENCE: 28

```
ctcgaggaca tggtctccca ggccctcagg ctcctctgcc ttctgcttgg gcttcagggc    60
tgcctggctg cagtcttcgt aacccaggag gaagcccacg gcgtcctgca ccggcgccgg   120
cgcgccaacg cgttcctgga ggagctgcgc ccgggctccc tgagagggga gtgcaaggag   180
gagcagtgct ccttcgagga ggcccgggag atcttcaaga cgcggagag gacgaagctg   240
```

-continued

```
ttctggattt cttacagtga tggggaccag tgtgcctcaa gtccatgcca gaatgggggc    300
tcctgcaagg accagctcca gtcctatatc tgcttctgcc tccctgcctt cgagggccgg    360
aactgtgaga cgcacaagga tgaccagctg atctgtgtga cgagaacggg cggctgtgag    420
cagtactgca gtgaccacac gggcaccaag cgctcctgtc ggtgccacga ggggtactct    480
ctgctggcag acggggtgtc ctgcacaccc acagttgaat atccatgtgg aaaaatacct    540
attctagaaa aaagaaatgc cagcaaaccc caaggccgaa ttgtgggggg caaggtgtgc    600
cccaaagggg agtgtccatg gcaggtcctg ttgttggtga atggagctca gttgtgtggg    660
gggaccctga tcaacaccat ctgggtggtc tccgcggccc actgtttcga caaaatcaag    720
aactggagga acctgatcgc ggtgctgggc gagcacgacc tcagcgagca cgacggggat    780
gagcagagcc ggcgggtggc gcaggtcatc atccccagca cgtacgtccc gggcaccacc    840
aaccacgaca tcgcgctgct ccgcctgcac cagcccgtgg tcctcactga ccatgtggtg    900
cccctctgcc tgcccgaacg gacgttctct gagaggacgc tggccttcgt gcgcttctca    960
ttggtcagcg gctgggggcca gctgctggac cgtggcgcca cggccctgga gctcatggtc   1020
ctcaacgtgc cccggctgat gacccaggac tgcctgcagc agtcacggaa ggtgggagac   1080
tcccaaata tcacggagta catgttctgt gccggctact cggatggcag caaggactcc   1140
tgcaaggggg acagtggagg cccacatgcc acccactacc ggggcacgtg gtacctgacc   1200
ggcatcgtga gctggggcca gggctgcgcc accgtgggcc acttcggcgt gtacaccagg   1260
gtgtcccagt acatcgagtg gctgcagaaa ctgatgagaa gcgagccag acccggcgtg   1320
ctgctgagag cccccttccc cagcagcagc tccaaggccc ctccccctag cctgcccagc   1380
cctagcagac tgcctgggcc ctctgacacc ctatcctgc tcagtccag ctcctctaag    1440
gctccaccac cttccctgcc tagcccttca agactgccag gccctagcga tacaccaatt   1500
ctgccccagt cctccagcag caaggctccc ccacctagcc tgccttctcc atcaaggctg   1560
cctggcccat ccgataccccc aatttttgcct cagagcagct ctagcaaggc cctccccccc   1620
agtctgccct ctccaagcag actccctggc ccttcagaca ctccaatcct cccacagtcc   1680
tctagctcta aagctccacc tcccagcctg cccagcccta gtagactccc cggaccttct   1740
gatacccca tcttgcccca gtgatgagga tccgc                                1775
```

<210> SEQ ID NO 29
<211> LENGTH: 589
<212> TYPE: PRT
<213> ORGANISM: Artificial Sequence
<220> FEATURE:
<223> OTHER INFORMATION: CTP-modified Factor VII

<400> SEQUENCE: 29

```
Leu Glu Asp Met Val Ser Gln Ala Leu Arg Leu Leu Cys Leu Leu Leu
1               5                   10                  15

Gly Leu Gln Gly Cys Leu Ala Ala Val Phe Val Thr Gln Glu Glu Ala
            20                  25                  30

His Gly Val Leu His Arg Arg Arg Arg Ala Asn Ala Phe Leu Glu Glu
        35                  40                  45

Leu Arg Pro Gly Ser Leu Glu Arg Glu Cys Lys Glu Glu Gln Cys Ser
    50                  55                  60

Phe Glu Glu Ala Arg Glu Ile Phe Lys Asp Ala Glu Arg Thr Lys Leu
65                  70                  75                  80

Phe Trp Ile Ser Tyr Ser Asp Gly Asp Gln Cys Ala Ser Ser Pro Cys
                85                  90                  95
```

-continued

```
Gln Asn Gly Gly Ser Cys Lys Asp Gln Leu Gln Ser Tyr Ile Cys Phe
                100                 105                 110
Cys Leu Pro Ala Phe Glu Gly Arg Asn Cys Glu Thr His Lys Asp Asp
            115                 120                 125
Gln Leu Ile Cys Val Asn Glu Asn Gly Gly Cys Glu Gln Tyr Cys Ser
        130                 135                 140
Asp His Thr Gly Thr Lys Arg Ser Cys Arg Cys His Glu Gly Tyr Ser
145                 150                 155                 160
Leu Leu Ala Asp Gly Val Ser Cys Thr Pro Thr Val Glu Tyr Pro Cys
                165                 170                 175
Gly Lys Ile Pro Ile Leu Glu Lys Arg Asn Ala Ser Lys Pro Gln Gly
            180                 185                 190
Arg Ile Val Gly Gly Lys Val Cys Pro Lys Gly Glu Cys Pro Trp Gln
        195                 200                 205
Val Leu Leu Leu Val Asn Gly Ala Gln Leu Cys Gly Gly Thr Leu Ile
    210                 215                 220
Asn Thr Ile Trp Val Val Ser Ala Ala His Cys Phe Asp Lys Ile Lys
225                 230                 235                 240
Asn Trp Arg Asn Leu Ile Ala Val Leu Gly Glu His Asp Leu Ser Glu
                245                 250                 255
His Asp Gly Asp Glu Gln Ser Arg Arg Val Ala Gln Val Ile Ile Pro
            260                 265                 270
Ser Thr Tyr Val Pro Gly Thr Thr Asn His Asp Ile Ala Leu Leu Arg
        275                 280                 285
Leu His Gln Pro Val Val Leu Thr Asp His Val Val Pro Leu Cys Leu
    290                 295                 300
Pro Glu Arg Thr Phe Ser Glu Arg Thr Leu Ala Phe Val Arg Phe Ser
305                 310                 315                 320
Leu Val Ser Gly Trp Gly Gln Leu Leu Asp Arg Gly Ala Thr Ala Leu
                325                 330                 335
Glu Leu Met Val Leu Asn Val Pro Arg Leu Met Thr Gln Asp Cys Leu
            340                 345                 350
Gln Gln Ser Arg Lys Val Gly Asp Ser Pro Asn Ile Thr Glu Tyr Met
        355                 360                 365
Phe Cys Ala Gly Tyr Ser Asp Gly Ser Lys Asp Ser Cys Lys Gly Asp
    370                 375                 380
Ser Gly Gly Pro His Ala Thr His Tyr Arg Gly Thr Trp Tyr Leu Thr
385                 390                 395                 400
Gly Ile Val Ser Trp Gly Gln Gly Cys Ala Thr Val Gly His Phe Gly
                405                 410                 415
Val Tyr Thr Arg Val Ser Gln Tyr Ile Glu Trp Leu Gln Lys Leu Met
            420                 425                 430
Arg Ser Glu Pro Arg Pro Gly Val Leu Leu Arg Ala Pro Phe Pro Ser
        435                 440                 445
Ser Ser Ser Lys Ala Pro Pro Pro Ser Leu Pro Ser Pro Ser Arg Leu
    450                 455                 460
Pro Gly Pro Ser Asp Thr Pro Ile Leu Pro Gln Ser Ser Ser Ser Lys
465                 470                 475                 480
Ala Pro Pro Pro Ser Leu Pro Ser Ser Arg Leu Pro Gly Pro Ser
                485                 490                 495
Asp Thr Pro Ile Leu Pro Gln Ser Ser Ser Ser Lys Ala Pro Pro Pro
            500                 505                 510
```

```
Ser Leu Pro Ser Pro Ser Arg Leu Pro Gly Pro Ser Asp Thr Pro Ile
        515                 520                 525
Leu Pro Gln Ser Ser Ser Lys Ala Pro Pro Ser Leu Pro Ser
    530                 535                 540
Pro Ser Arg Leu Pro Gly Pro Ser Asp Thr Pro Ile Leu Pro Gln Ser
545                 550                 555                 560
Ser Ser Ser Lys Ala Pro Pro Ser Leu Pro Ser Pro Ser Arg Leu
            565                 570                 575
Pro Gly Pro Ser Asp Thr Pro Ile Leu Pro Gln Gly Ser
        580                 585
```

<210> SEQ ID NO 30
<211> LENGTH: 1673
<212> TYPE: DNA
<213> ORGANISM: Artificial Sequence
<220> FEATURE:
<223> OTHER INFORMATION: CTP-modified Factor IX

<400> SEQUENCE: 30

| | | | | | |
|---|---|---|---|---|---|
| tctagagtcg | accccgccat | gcagcgcgtg | aacatgatca | tggcagaatc | accaggcctc | 60 |
| atcaccatct | gccttttagg | atatctactc | agtgctgaat | gtacagtttt | tcttgatcat | 120 |
| gaaaacgcca | acaaaattct | gaatcggcca | agaggtata | attcaggtaa | attggaagag | 180 |
| tttgttcaag | gaaccttga | gagaatgt | atggaagaaa | agtgtagttt | tgaagaagca | 240 |
| cgagaagttt | ttgaaaacac | tgaaagaaca | actgaatttt | ggaagcagta | tgttgatgga | 300 |
| gatcagtgtg | agtccaatcc | atgtttaaat | ggcggcagtt | gcaaggatga | cattaattcc | 360 |
| tatgaatgtt | ggtgtccctt | tggatttgaa | ggaaagaact | gtgaattaga | tgtaacatgt | 420 |
| aacattaaga | atggcagatg | cgagcagttt | tgtaaaaata | gtgctgataa | caaggtggtt | 480 |
| tgctcctgta | ctgagggata | tcgacttgca | gaaaaccaga | agtcctgtga | accagcagtg | 540 |
| ccatttccat | gtggaagagt | ttctgtttca | caaacttcta | agctcacccg | tgctgaggca | 600 |
| gttttcctg | atgtggacta | tgtaaattct | actgaagctg | aaaccatttt | ggataacatc | 660 |
| actcaaagca | cccaatcatt | taatgacttc | actcgagttg | ttggtggaga | agatgccaaa | 720 |
| ccaggtcaat | tcccttggca | ggttgttttg | aatggtaaag | ttgatgcatt | ctgtggaggc | 780 |
| tctatcgtta | tgaaaaatg | gattgtaact | gctgccact | gtgttgaaac | tggtgttaaa | 840 |
| attacagttg | tcgcaggtga | acataatatt | gaggagacag | aacatacaga | gcaaaagcga | 900 |
| aatgtgattc | gaattattcc | tcaccacaac | tacaatgcag | ctattaataa | gtacaaccat | 960 |
| gacattgccc | ttctggaact | ggacgaaccc | ttagtgctaa | acagctacgt | tacacctat | 1020 |
| tgcattgctg | acaaggaata | cacgaacatc | ttcctcaaat | ttggatctgg | ctatgtaagt | 1080 |
| ggctgggggaa | gagtcttcca | caaagggaga | tcagctttag | ttcttcagta | ccttagagtt | 1140 |
| ccacttgttg | accgagccac | atgtcttcga | tctacaaagt | tcaccatcta | taacaacatg | 1200 |
| ttctgtgctg | gcttccatga | aggaggtaga | gattcatgtc | aaggagatag | tgggggaccc | 1260 |
| catgttactg | aagtggaagg | gaccagtttc | ttaactggaa | ttattagctg | ggtgaagag | 1320 |
| tgtgcaatga | aagcaaata | tggaatatat | accaaggtat | cccggtatgt | caactggatt | 1380 |
| aaggaaaaaa | caaagctcac | tagctccagc | agcaaggccc | ctcccccgag | cctgccctcc | 1440 |
| ccaagcaggc | tgcctgggcc | cagtgacacc | ctatcctgc | ctcagtccag | ctccagcaag | 1500 |
| gccccacccc | ctagcctgcc | ttctccttct | cggctgcctg | gccccagcga | tactccaatt | 1560 |
| ctgccccagt | cctccagcag | taaggctccc | cctccatctc | tgccatcccc | cagcagactg | 1620 | ccaggcccttt ctgatacacc catcctccca cagtgatgag gatccgcggc cgc        1673

<210> SEQ ID NO 31
<211> LENGTH: 545
<212> TYPE: PRT
<213> ORGANISM: Artificial Sequence
<220> FEATURE:
<223> OTHER INFORMATION: CTP-modified Factor IX

<400> SEQUENCE: 31

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
```

```
                 355                 360                 365
Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Ser Ser Ser
    450                 455                 460

Ser Lys Ala Pro Pro Pro Ser Leu Pro Ser Pro Ser Arg Leu Pro Gly
465                 470                 475                 480

Pro Ser Asp Thr Pro Ile Leu Pro Gln Ser Ser Ser Ser Lys Ala Pro
                485                 490                 495

Pro Pro Ser Leu Pro Ser Pro Ser Arg Leu Pro Gly Pro Ser Asp Thr
            500                 505                 510

Pro Ile Leu Pro Gln Ser Ser Ser Ser Lys Ala Pro Pro Pro Ser Leu
        515                 520                 525

Pro Ser Pro Ser Arg Leu Pro Gly Pro Ser Asp Thr Pro Ile Leu Pro
    530                 535                 540

Gln
545
```

<210> SEQ ID NO 32
<211> LENGTH: 1757
<212> TYPE: DNA
<213> ORGANISM: Artificial Sequence
<220> FEATURE:
<223> OTHER INFORMATION: CTP-modified Factor IX

<400> SEQUENCE: 32

```
tctagagtcg accccgccat gcagcgcgtg aacatgatca tggcagaatc accaggcctc        60
atcaccatct gccttttagg atatctactc agtgctgaat gtacagtttt tcttgatcat       120
gaaaacgcca acaaaattct gaatcggcca agagggtata attcaggtaa attggaagag       180
tttgttcaag gaaccttga gagagaatgt atggaagaaa agtgtagttt tgaagaagca       240
cgagaagttt ttgaaaacac tgaaagaaca actgaatttt ggaagcagta tgttgatgga       300
gatcagtgtg agtccaatcc atgtttaaat ggcggcagtt gcaaggatga cattaattcc       360
tatgaatgtt ggtgtccctt tggatttgaa ggaaagaact gtgaattaga tgtaacatgt       420
aacattaaga atggcagatg cgagcagttt tgtaaaaata gtgctgataa caaggtggtt       480
tgctcctgta ctgagggata tcgacttgca gaaaaccaga gtcctgtga accagcagtg       540
ccatttccat gtggaagagt ttctgtttca caaacttcta agctcacccg tgctgaggca       600
gttttttcctg atgtggacta tgtaaattct actgaagctg aaaccatttt ggataacatc       660
actcaaagca cccaatcatt taatgacttc actcgagttt tggtggaga agatgccaaa       720
ccaggtcaat tcccttggca ggttgttttg aatggtaaag ttgatgcatt ctgtggaggc       780
tctatcgtta atgaaaaatg gattgtaact gctgcccact gtgttgaaac tggtgttaaa       840
attacagttg tcgcaggtga acataatatt gaggagacaa acatacaga gcaaaagcga       900
aatgtgattc gaattattcc tcaccacaac tacaatgcag ctattaataa gtacaaccat       960
```

```
gacattgccc ttctggaact ggacgaaccc ttagtgctaa acagctacgt tacacctatt    1020
tgcattgctg acaaggaata cacgaacatc ttcctcaaat ttggatctgg ctatgtaagt    1080
ggctggggaa gagtcttcca caaagggaga tcagctttag ttcttcagta ccttagagtt    1140
ccacttgttg accgagccac atgtcttcga tctacaaagt tcaccatcta acaacatg     1200 ttctgtgctg gcttccatga aggaggtaga gattcatgtc aaggagatag tgggggaccc    1260
catgttactg aagtggaagg gaccagtttc ttaactggaa ttattagctg gggtgaagag    1320
tgtgcaatga aaggcaaata tggaatatat accaaggtat cccggtatgt caactggatt    1380
aaggaaaaaa caaagctcac tagctccagc agcaaggccc ctcccccgag cctgccctcc    1440
ccaagcaggc tgcctgggcc tctgacaccc ctatcctgc ctcagtccag ctcctctaag     1500
gccccaccac cttccctgcc tagcccttca agactgccag ccctagcga tacaccaatt    1560 ctgccccagt cctccagcag caaggctccc ccacctagcc tgccttctcc atcaaggctg    1620
cctggcccat ccgataccc aattttgcct cagagcagct ctagcaaggc acctccccc     1680 agtctgccct ctccaagcag actccctggc ccttcagaca ctcccattct gccacagtga   1740
tgaggatccg cggccgc                                                   1757

<210> SEQ ID NO 33
<211> LENGTH: 583
<212> TYPE: PRT
<213> ORGANISM: Artificial Sequence
<220> FEATURE:
<223> OTHER INFORMATION: CTP-modified Factor IX

<400> SEQUENCE: 33

Ser Arg Val Asp Pro Ala Met Gln Arg Val Asn Met Ile Met Ala Glu
1               5                   10                  15

Ser Pro Gly Leu Ile Thr Ile Cys Leu Leu Gly Tyr Leu Leu Ser Ala
                20                  25                  30

Glu Cys Thr Val Phe Leu Asp His Glu Asn Ala Asn Lys Ile Leu Asn
            35                  40                  45

Arg Pro Lys Arg Tyr Asn Ser Gly Lys Leu Glu Glu Phe Val Gln Gly
        50                  55                  60

Asn Leu Glu Arg Glu Cys Met Glu Glu Lys Cys Ser Phe Glu Glu Ala
65                  70                  75                  80

Arg Glu Val Phe Glu Asn Thr Glu Arg Thr Thr Glu Phe Trp Lys Gln
                85                  90                  95

Tyr Val Asp Gly Asp Gln Cys Glu Ser Asn Pro Cys Leu Asn Gly Gly
                100                 105                 110

Ser Cys Lys Asp Asp Ile Asn Ser Tyr Glu Cys Trp Cys Pro Phe Gly
            115                 120                 125

Phe Glu Gly Lys Asn Cys Glu Leu Asp Val Thr Cys Asn Ile Lys Asn
        130                 135                 140

Gly Arg Cys Glu Gln Phe Cys Lys Asn Ser Ala Asp Asn Lys Val Val
145                 150                 155                 160

Cys Ser Cys Thr Glu Gly Tyr Arg Leu Ala Glu Asn Gln Lys Ser Cys
                165                 170                 175

Glu Pro Ala Val Pro Phe Pro Cys Gly Arg Val Ser Val Ser Gln Thr
            180                 185                 190

Ser Lys Leu Thr Arg Ala Glu Ala Val Phe Pro Asp Val Asp Tyr Val
        195                 200                 205

Asn Ser Thr Glu Ala Glu Thr Ile Leu Asp Asn Ile Thr Gln Ser Thr
```

```
            210                 215                 220
Gln Ser Phe Asn Asp Phe Thr Arg Val Val Gly Gly Glu Asp Ala Lys
225                 230                 235                 240

Pro Gly Gln Phe Pro Trp Gln Val Val Leu Asn Gly Lys Val Asp Ala
                245                 250                 255

Phe Cys Gly Gly Ser Ile Val Asn Glu Lys Trp Ile Val Thr Ala Ala
                260                 265                 270

His Cys Val Glu Thr Gly Val Lys Ile Thr Val Val Ala Gly Glu His
                275                 280                 285

Asn Ile Glu Glu Thr Glu His Thr Glu Gln Lys Arg Asn Val Ile Arg
290                 295                 300

Ile Ile Pro His His Asn Tyr Asn Ala Ala Ile Asn Lys Tyr Asn His
305                 310                 315                 320

Asp Ile Ala Leu Leu Glu Leu Asp Glu Pro Leu Val Leu Asn Ser Tyr
                325                 330                 335

Val Thr Pro Ile Cys Ile Ala Asp Lys Glu Tyr Thr Asn Ile Phe Leu
                340                 345                 350

Lys Phe Gly Ser Gly Tyr Val Ser Gly Trp Gly Arg Val Phe His Lys
                355                 360                 365

Gly Arg Ser Ala Leu Val Leu Gln Tyr Leu Arg Val Pro Leu Val Asp
370                 375                 380

Arg Ala Thr Cys Leu Arg Ser Thr Lys Phe Thr Ile Tyr Asn Asn Met
385                 390                 395                 400

Phe Cys Ala Gly Phe His Glu Gly Gly Arg Asp Ser Cys Gln Gly Asp
                405                 410                 415

Ser Gly Gly Pro His Val Thr Glu Val Glu Gly Thr Ser Phe Leu Thr
                420                 425                 430

Gly Ile Ile Ser Trp Gly Glu Glu Cys Ala Met Lys Gly Lys Tyr Gly
                435                 440                 445

Ile Tyr Thr Lys Val Ser Arg Tyr Val Asn Trp Ile Lys Glu Lys Thr
                450                 455                 460

Lys Leu Thr Ser Ser Ser Lys Ala Pro Pro Pro Ser Leu Pro Ser
465                 470                 475                 480

Pro Ser Arg Leu Pro Gly Pro Ser Asp Thr Pro Ile Leu Pro Gln Ser
                485                 490                 495

Ser Ser Ser Lys Ala Pro Pro Pro Ser Leu Pro Ser Pro Ser Arg Leu
                500                 505                 510

Pro Gly Pro Ser Asp Thr Pro Ile Leu Pro Gln Ser Ser Ser Ser Lys
                515                 520                 525

Ala Pro Pro Pro Ser Leu Pro Ser Pro Ser Arg Leu Pro Gly Pro Ser
                530                 535                 540

Asp Thr Pro Ile Leu Pro Gln Ser Ser Ser Ser Lys Ala Pro Pro Pro
545                 550                 555                 560

Ser Leu Pro Ser Pro Ser Arg Leu Pro Gly Pro Ser Asp Thr Pro Ile
                565                 570                 575

Leu Pro Gln Gly Ser Ala Ala
            580

<210> SEQ ID NO 34
<211> LENGTH: 1840
<212> TYPE: DNA
<213> ORGANISM: Artificial Sequence
<220> FEATURE:
<223> OTHER INFORMATION: CTP-modified Factor IX
```

<400> SEQUENCE: 34

```
ctagagtcga ccccgccatg cagcgcgtga acatgatcat ggcagaatca ccaggcctca    60
tcaccatctg cctttagga tatctactca gtgctgaatg tacagttttt cttgatcatg    120
aaaacgccaa caaaattctg aatcggccaa agaggtataa ttcaggtaaa ttggaagagt    180
ttgttcaagg gaaccttgag agagaatgta tggaagaaaa gtgtagtttt gaagaagcac    240
gagaagtttt tgaaaacact gaaagaacaa ctgaattttg gaagcagtat gttgatggag    300
atcagtgtga gtccaatcca tgtttaaatg gcggcagttg caaggatgac attaattcct    360
atgaatgttg gtgtccctt ggatttgaag gaaagaactg tgaattagat gtaacatgta    420
acattaagaa tggcagatgc gagcagtttt gtaaaaatag tgctgataac aaggtggttt    480
gctcctgtac tgagggatat cgacttgcag aaaaccagaa gtcctgtgaa ccagcagtgc    540
catttccatg tggaagagtt tctgtttcac aaacttctaa gctcaccgt gctgaggcag    600
ttttcctga tgtggactat gtaaattcta ctgaagctga accatttgg ataacatca    660
ctcaaagcac ccaatcattt aatgacttca ctcgagttgt tggtggagaa gatgccaaac    720
caggtcaatt cccttggcag gttgttttga atggtaaagt tgatgcattc tgtgggggct    780
ctatcgttaa tgaaaaatgg attgtaactg ctgcccactg tgttgaaact ggtgttaaaa    840
ttacagttgt cgcaggtgaa cataatattg aggagacaga acatacagag caaaagcgaa    900
atgtgattcg aattattcct caccacaact acaatgcagc tattaataag tacaaccatg    960
acattgccct tctggaactg gacgaacccct tagtgctaaa cagctacgtt acacctattt   1020
gcattgctga caaggaatac acgaacatct tcctcaaatt tggatctggc tatgtaagtg   1080
gctgggaag agtcttccac aaagggagat cagctttagt tcttcagtac cttagagttc   1140
cacttgttga ccgagccaca tgtcttcgat ctacaaagtt caccatctat aacaacatgt   1200
tctgtgctgg cttccatgaa ggaggtagag attcatgtca aggagatagt gggggacccc   1260
atgttactga agtggaaggg accagtttct taactggaat tattagctgg ggtgaagagt   1320
gtgcaatgaa aggcaaatat ggaatatata ccaaggtatc ccggtatgtc aactggatta   1380
aggaaaaaac aaagctcact agctccagca gcaaggcccc tccccgagc tgccctccc   1440
caagcaggct gcctgggccc tctgacaccc ctatcctgcc tcagtccagc tcctctaagg   1500
ctccaccacc ttccctgcct agccttcaa gactgcagg ccctagcgat acaccattc   1560
tgccccagtc ctccagcagc aaggctcccc cacctagcct gccttctcca tcaaggctgc   1620
ctggcccatc cgatacccca ttttgcctc agagcagctc tagcaaggca cctccccca   1680
gtctgccctc tccaagcaga ctccctggcc cttcagacac tccaatcctc ccacagtcct   1740
ctagctctaa agctccacct cccagcctgc cagccctag tagactcccc ggaccttctg   1800
ataccccat cttgccccag tgatgaggat ccgcggccgc                           1840
```

<210> SEQ ID NO 35
<211> LENGTH: 610
<212> TYPE: PRT
<213> ORGANISM: Artificial Sequence
<220> FEATURE:
<223> OTHER INFORMATION: CTP-modified Factor IX

<400> SEQUENCE: 35

```
Arg Val Asp Pro Ala Met Gln Arg Val Asn Met Ile Met Ala Glu Ser
1               5                   10                  15

Pro Gly Leu Ile Thr Ile Cys Leu Leu Gly Tyr Leu Leu Ser Ala Glu
                20                  25                  30
```

```
Cys Thr Val Phe Leu Asp His Glu Asn Ala Asn Lys Ile Leu Asn Arg
            35                  40                  45

Pro Lys Arg Tyr Asn Ser Gly Lys Leu Glu Glu Phe Val Gln Gly Asn
 50                  55                  60

Leu Glu Arg Glu Cys Met Glu Glu Lys Cys Ser Phe Glu Glu Ala Arg
 65                  70                  75                  80

Glu Val Phe Glu Asn Thr Glu Arg Thr Thr Glu Phe Trp Lys Gln Tyr
                    85                  90                  95

Val Asp Gly Asp Gln Cys Glu Ser Asn Pro Cys Leu Asn Gly Gly Ser
                100                 105                 110

Cys Lys Asp Asp Ile Asn Ser Tyr Glu Cys Trp Cys Pro Phe Gly Phe
            115                 120                 125

Glu Gly Lys Asn Cys Glu Leu Asp Val Thr Cys Asn Ile Lys Asn Gly
            130                 135                 140

Arg Cys Glu Gln Phe Cys Lys Asn Ser Ala Asp Asn Lys Val Val Cys
145                 150                 155                 160

Ser Cys Thr Glu Gly Tyr Arg Leu Ala Glu Asn Gln Lys Ser Cys Glu
                165                 170                 175

Pro Ala Val Pro Phe Pro Cys Gly Arg Val Ser Val Ser Gln Thr Ser
                180                 185                 190

Lys Leu Thr Arg Ala Glu Ala Val Phe Pro Asp Val Asp Tyr Val Asn
                195                 200                 205

Ser Thr Glu Ala Glu Thr Ile Leu Asp Asn Ile Thr Gln Ser Thr Gln
                210                 215                 220

Ser Phe Asn Asp Phe Thr Arg Val Val Gly Gly Glu Asp Ala Lys Pro
225                 230                 235                 240

Gly Gln Phe Pro Trp Gln Val Val Leu Asn Gly Lys Val Asp Ala Phe
                245                 250                 255

Cys Gly Gly Ser Ile Val Asn Glu Lys Trp Ile Val Thr Ala Ala His
                260                 265                 270

Cys Val Glu Thr Gly Val Lys Ile Thr Val Val Ala Gly Glu His Asn
            275                 280                 285

Ile Glu Glu Thr Glu His Thr Glu Gln Lys Arg Asn Val Ile Arg Ile
            290                 295                 300

Ile Pro His His Asn Tyr Asn Ala Ala Ile Asn Lys Tyr Asn His Asp
305                 310                 315                 320

Ile Ala Leu Leu Glu Leu Asp Glu Pro Leu Val Leu Asn Ser Tyr Val
                325                 330                 335

Thr Pro Ile Cys Ile Ala Asp Lys Glu Tyr Thr Asn Ile Phe Leu Lys
            340                 345                 350

Phe Gly Ser Gly Tyr Val Ser Gly Trp Gly Arg Val Phe His Lys Gly
            355                 360                 365

Arg Ser Ala Leu Val Leu Gln Tyr Leu Arg Val Pro Leu Val Asp Arg
370                 375                 380

Ala Thr Cys Leu Arg Ser Thr Lys Phe Thr Ile Tyr Asn Asn Met Phe
385                 390                 395                 400

Cys Ala Gly Phe His Glu Gly Gly Arg Asp Ser Cys Gln Gly Asp Ser
                405                 410                 415

Gly Gly Pro His Val Thr Glu Val Glu Gly Thr Ser Phe Leu Thr Gly
                420                 425                 430

Ile Ile Ser Trp Gly Glu Glu Cys Ala Met Lys Gly Lys Tyr Gly Ile
            435                 440                 445
```

```
Tyr Thr Lys Val Ser Arg Tyr Val Asn Trp Ile Lys Glu Lys Thr Lys
    450                 455                 460

Leu Thr Ser Ser Ser Lys Ala Pro Pro Ser Leu Pro Ser Pro
465                 470                 475                 480

Ser Arg Leu Pro Gly Pro Ser Asp Thr Pro Ile Leu Pro Gln Ser Ser
                485                 490                 495

Ser Ser Lys Ala Pro Pro Ser Leu Pro Ser Pro Ser Arg Leu Pro
            500                 505                 510

Gly Pro Ser Asp Thr Pro Ile Leu Pro Gln Ser Ser Ser Lys Ala
            515                 520                 525

Pro Pro Ser Leu Pro Ser Pro Ser Arg Leu Pro Gly Pro Ser Asp
    530                 535                 540

Thr Pro Ile Leu Pro Gln Ser Ser Ser Lys Ala Pro Pro Ser
545                 550                 555                 560

Leu Pro Ser Pro Ser Arg Leu Pro Gly Pro Ser Asp Thr Pro Ile Leu
                565                 570                 575

Pro Gln Ser Ser Ser Lys Ala Pro Pro Ser Leu Pro Ser Pro
            580                 585                 590

Ser Arg Leu Pro Gly Pro Ser Asp Thr Pro Ile Leu Pro Gln Gly Ser
            595                 600                 605

Ala Ala
    610

<210> SEQ ID NO 36
<211> LENGTH: 20
<212> TYPE: DNA
<213> ORGANISM: Artificial Sequence
<220> FEATURE:
<223> OTHER INFORMATION: Primer 101 for FIX-(CTP)2

<400> SEQUENCE: 36
gtttagtgaa ccgtcagaat                                              20

<210> SEQ ID NO 37
<211> LENGTH: 20
<212> TYPE: DNA
<213> ORGANISM: Artificial Sequence
<220> FEATURE:
<223> OTHER INFORMATION: Primer 103-R for FIX-(CTP)2

<400> SEQUENCE: 37
ttgaggaaga tgttcgtgta                                              20

<210> SEQ ID NO 38
<211> LENGTH: 20
<212> TYPE: DNA
<213> ORGANISM: Artificial Sequence
<220> FEATURE:
<223> OTHER INFORMATION: Primer 98 for FIX-(CTP)2

<400> SEQUENCE: 38
attacagttg tcgcaggtga                                              20

<210> SEQ ID NO 39
<211> LENGTH: 30
<212> TYPE: DNA
<213> ORGANISM: Artificial Sequence
<220> FEATURE:
<223> OTHER INFORMATION: Primer 99-Rfor FIX-(CTP)2

<400> SEQUENCE: 39
```
gctggagcta gtgagctttg ttttttcctt                                        30

<210> SEQ ID NO 40
<211> LENGTH: 25
<212> TYPE: DNA
<213> ORGANISM: Artificial Sequence
<220> FEATURE:
<223> OTHER INFORMATION: Primer 100 for FIX-(CTP)2

<400> SEQUENCE: 40
gctcactagc tccagcagca aggcc                                             25

<210> SEQ ID NO 41
<211> LENGTH: 23
<212> TYPE: DNA
<213> ORGANISM: Artificial Sequence
<220> FEATURE:
<223> OTHER INFORMATION: Primer 27-R for FIX-(CTP)2

<400> SEQUENCE: 41
ttttcactgc attctagttg tgg                                               23

<210> SEQ ID NO 42
<211> LENGTH: 20
<212> TYPE: DNA
<213> ORGANISM: Artificial Sequence
<220> FEATURE:
<223> OTHER INFORMATION: Primer 75

<400> SEQUENCE: 42
ctcccagttc aattacagct                                                   20

<210> SEQ ID NO 43
<211> LENGTH: 27
<212> TYPE: DNA
<213> ORGANISM: Artificial Sequence
<220> FEATURE:
<223> OTHER INFORMATION: Primer 122r

<400> SEQUENCE: 43
ggaaaaactg cctcagcacg ggtgagc                                           27

<210> SEQ ID NO 44
<211> LENGTH: 32
<212> TYPE: DNA
<213> ORGANISM: Artificial Sequence
<220> FEATURE:
<223> OTHER INFORMATION: Primer 123

<400> SEQUENCE: 44
gtgctgaggc agtttttcct gatgtggact at                                     32

<210> SEQ ID NO 45
<211> LENGTH: 18
<212> TYPE: DNA
<213> ORGANISM: Artificial Sequence
<220> FEATURE:
<223> OTHER INFORMATION: Primer 124r

<400> SEQUENCE: 45
caacacagtg ggcagcag                                                     18

<210> SEQ ID NO 46
<211> LENGTH: 490
<212> TYPE: PRT
<213> ORGANISM: Artificial Sequence

```
<220> FEATURE:
<223> OTHER INFORMATION: CTP Modified FVII

<400> SEQUENCE: 46

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
370                 375                 380

Glu Trp Leu Gln Lys Leu Met Arg Ser Glu Pro Arg Pro Gly Val Leu
385                 390                 395                 400
```

Leu Arg Ala Pro Phe Pro Ser Ser Ser Lys Ala Pro Pro Ser
            405                 410                 415

Leu Pro Ser Pro Ser Arg Leu Pro Gly Pro Ser Asp Thr Pro Ile Leu
            420                 425                 430

Pro Gln Ser Ser Ser Ser Lys Ala Pro Pro Ser Leu Pro Ser Pro
            435                 440                 445

Ser Arg Leu Pro Gly Pro Ser Asp Thr Pro Ile Leu Pro Gln Ser Ser
450                 455                 460

Ser Ser Lys Ala Pro Pro Ser Leu Pro Ser Pro Ser Arg Leu Pro
465                 470                 475                 480

Gly Pro Ser Asp Thr Pro Ile Leu Pro Gln
            485                 490

<210> SEQ ID NO 47
<211> LENGTH: 38
<212> TYPE: PRT
<213> ORGANISM: Artificial Sequence
<220> FEATURE:
<223> OTHER INFORMATION: FVII signal peptide

<400> SEQUENCE: 47

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg
        35

<210> SEQ ID NO 48
<211> LENGTH: 499
<212> TYPE: PRT
<213> ORGANISM: Artificial Sequence
<220> FEATURE:
<223> OTHER INFORMATION: Mature engineered coagulation factor lacking
      the N-terminal propeptide

<400> SEQUENCE: 48

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

```
Ala Glu Thr Ile Leu Asp Asn Ile Thr Gln Ser Thr Gln Ser Phe Asn
            165                 170                 175

Asp Phe Thr Arg Val Val Gly Gly Glu Asp Ala Lys Pro Gly Gln Phe
        180                 185                 190

Pro Trp Gln Val Val Leu Asn Gly Lys Val Asp Ala Phe Cys Gly Gly
    195                 200                 205

Ser Ile Val Asn Glu Lys Trp Ile Val Thr Ala Ala His Cys Val Glu
210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Ser
                405                 410                 415

Ser Ser Ser Lys Ala Pro Pro Ser Leu Pro Ser Pro Ser Arg Leu
            420                 425                 430

Pro Gly Pro Ser Asp Thr Pro Ile Leu Pro Gln Ser Ser Ser Ser Lys
    435                 440                 445

Ala Pro Pro Pro Ser Leu Pro Ser Pro Ser Arg Leu Pro Gly Pro Ser
        450                 455                 460

Asp Thr Pro Ile Leu Pro Gln Ser Ser Ser Ser Lys Ala Pro Pro Pro
465                 470                 475                 480

Ser Leu Pro Ser Pro Ser Arg Leu Pro Gly Pro Ser Asp Thr Pro Ile
                485                 490                 495

Leu Pro Gln

<210> SEQ ID NO 49
<211> LENGTH: 46
<212> TYPE: PRT
<213> ORGANISM: Artificial Sequence
<220> FEATURE:
<223> OTHER INFORMATION: N-terminal propeptide of Factor IX-CTP-CTP-CTP

<400> SEQUENCE: 49

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
```

-continued

```
            20                  25                  30
Asp His Glu Asn Ala Asn Lys Ile Leu Asn Arg Pro Lys Arg
        35                  40                  45
```

LONG-ACTING COAGULATION FACTORS AND METHODS OF PRODUCING SAME

CROSS REFERENCE TO RELATED APPLICATIONS

This application is a divisional of U.S. patent application Ser. No. 16/865,086, filed May 1, 2020, which is a divisional of U.S. patent application Ser. No. 16/160,000, filed Oct. 15, 2018, which is a divisional of U.S. patent application Ser. No. 14/948,890, filed Nov. 23, 2015, which is a divisional of U.S. patent application Ser. No. 13/932,839, filed Jul. 1, 2013, which is a continuation-in-part of U.S. patent application Ser. No. 13/759,860, filed Feb. 5, 2013, which is a continuation-in-part of U.S. patent application Ser. No. 13/372,540, filed Feb. 14, 2012, which is a continuation-in-part of U.S. patent application Ser. No. 12/826,754, filed Jun. 30, 2010, which claims the benefit of U.S. Provisional Application Ser. No. 61/224,366, filed Jul. 9, 2009.

FIELD OF INVENTION

Polypeptides comprising at least one carboxy-terminal peptide (CTP) of chorionic gonadotrophin attached to the carboxy terminus of a coagulation factor and polynucleotides encoding the same are disclosed. Pharmaceutical compositions comprising the polypeptides and polynucleotides of the invention and methods of using and producing same are also disclosed.

BACKGROUND OF THE INVENTION

The development of coagulation factor replacement therapy has transformed the lives of many individuals with hemophilia. Hemophilia is a group of hereditary genetic disorders that impair the body's ability to control blood clotting or coagulation. Patients with hemophilia do not produce adequate amounts of Factor VIII or Factor IX proteins, which are necessary for effective blood clotting. In severe hemophiliacs even a minor injury can result in blood loss that continues for days or weeks, and complete healing may not occur, leading to the potential for debilitating permanent damage to joints and other organs, and premature death.

One type of hemophilia, Hemophilia B, is an X-linked bleeding disorder caused by a mutation in the Factor IX (FIX) gene, resulting in a deficiency of the procoagulant activity of FIX. Hemophilia B patients have spontaneous soft tissue hemorrhages and recurrent hemarthroses that often lead to a crippling arthopathy. Current treatment for these patients includes an intravenous administration of recombinant FIX. However issues of cost and relatively rapid clearance of FIX from the circulation make developing a long-acting FIX a challenging task.

Commercial availability of FVIII and FIX has led to improved control of life-threatening bleedings episodes. Many patients receive prophylactic therapy, which reduces the risk of bleeding and its associated complications. However, a significant proportion of patients (10-30%) develop inhibitory antibodies to exogenously administered FVIII and FIX. Administration of FVIIa, which is a bypassing product, can induce homeostasis and provide an effective treatment for patients with inhibitory Abs.

Recombinant FVIIa (NovoSeven®) is commercially available and was approved in 1996 for treatment of bleeding episodes in hemophilia patients with inhibitors. However, rFVIIa is rapidly cleared with a terminal half-life of 2.5 hours. As a result, patients generally require multiple, frequent infusions (2-3 doses given in 2-3 hour intervals) to achieve adequate homeostasis following a mild to moderate bleed. Consequently, there is much interest in developing a long-acting form of FVIIa that would prolong the duration of haemostatic activity following a single dose and allow much less frequent dosing. A long-acting FVIIa would also increase the feasibility of long-term prophylactic therapy.

Various technologies are being developed for prolonging the half-life of FVIIa. However, there remains a need to achieve a prolonged half-life of this protein while preserving its biological activity and ensuring that the modifications do not induce significant immunogenicity. The present invention addresses this need by attaching gonadotrophin carboxy terminal peptides (CTPs) to FVIIa, thereby modifying it to prolong its half-life and biological activity.

SUMMARY OF THE INVENTION

In one embodiment, the present invention relates to a CTP-modified Factor VII (FVII) polypeptide consisting of a FVII polypeptide and three to five gonadotropin carboxy terminal peptides (CTPs) attached to the carboxy terminus of said CTP-modified FVII polypeptide.

In another embodiment, the present invention relates to a method of extending the biological half-life, improving the area under the curve (AUC), reducing the dosing frequency, or reducing the clearance rate of a Factor VII (FVII) polypeptide, comprising the step of attaching three to five chorionic gonadotrophin carboxy terminal peptides (CTPs) to the carboxy terminus of said FVII polypeptide, thereby extending the biological half-life of said FVII polypeptide.

In one embodiment, the present invention relates to a method of producing a CTP-modified Factor VII (FVII) polypeptide, comprising the step of attaching three to five chorionic gonatodrophin carboxy terminal peptides (CTPs) to the carboxy terminus of said FVII polypeptide, thereby producing a CTP-modified FVII polypeptide.

In another embodiment, the present invention relates to a method of preventing a blood clotting or coagulation disorder in a subject, the method comprising the step of administering to the subject a CTP-modified coagulation factor, comprising three to five chorionic gonadotrophin carboxy terminal peptides (CTPs) attached to the carboxy terminus of said FVII polypeptide, thereby preventing hemophilia in said subject.

In another embodiment, the present invention relates to a method of treating a blood clotting or coagulation disorder in a subject, the method comprising the step of administering to the subject a CTP-modified coagulation factor, comprising three to five chorionic gonadotrophin carboxy terminal peptides (CTPs) attached to the carboxy terminus of said coagulation factor, thereby preventing hemophilia in said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 1A. Shows a bar graph showing harvests limited, diluted, transfected, and selected cells with FIX-CTP and FIX-CTP-CTP variants in the presence of 5 μg/ml of Vitamin K3. The level of FIX was quantified using Human FIX ELISA kit (Affinity Biologicals; Cat. No. FIX-AG RUO), and the calculated protein concentration (μg/ml) is the average of two independent runs.

FIG. 1B. Shows SDS-PAGE gel micrographs of FIX Ab recognition and depicts recognition of anti-FIX antibody in Western-blot; Lane 1 in FIG. 1B was loaded with a sample containing recombinant FIX; Lane 2 in FIG. 1B was loaded with a sample containing FIX-CTP harvests. Lane 3 in FIG. 1B was loaded with a sample containing FIX-(CTP)$_2$ harvest.

FIG. 1C. Shows SDS-PAGE gel micrographs of FIX Ab recognition. FIG. 1C depicts recognition of anti-γ carboxylation antibody in Western-blot. Lane 1 in FIG. 1C was loaded with a sample containing recombinant FIX. Lane 2 in FIG. 1C was loaded with a sample containing FIX-CTP harvests. Lane 3 in FIG. 1C was loaded with a sample containing FIX-(CTP)$_2$ harvest.

FIG. 4. Shows a bar graph showing harvests of FIX-CTP and FIX-CTP-CTP harvests and FIX-CTP-CTP purified protein FIX antigen level as determined using Human FIX ELISA kit (Affinity Biologicals; cat. No. FIX-AG RUO). The calculated protein concentration (μg/ml) is the average of two independent runs.

FIG. 5A. Shows SDS-PAGE gel micrographs of FIX Ab recognition and depicts a coomassie blue staining. Lane 1 was loaded with a sample containing FIX-(CTP)$_2$. Lane 2 was loaded with a sample containing unbound FIX-(CTP)$_2$. Lane 3 was loaded with a sample containing a concentrated elution of FIX-(CTP)$_2$.

FIG. 5B. Shows SDS-PAGE gel micrographs of FIX Ab recognition and depicts recognition of anti-FIX antibody in Western-blot. Lane 1 was loaded with a sample containing FIX-(CTP)$_2$. Lane 2 was loaded with a sample containing unbound FIX-(CTP)$_2$. Lane 3 was loaded with a sample containing a concentrated elution of FIX-(CTP)$_2$.

FIG. 5C. Shows SDS-PAGE gel micrographs of FIX Ab recognition and depicts recognition of anti-γ carboxylation antibody in Western-blot. Lane 1 was loaded with a sample containing FIX-(CTP)$_2$. Lane 2 was loaded with a sample containing unbound FIX-(CTP)$_2$. Lane 3 was loaded with a sample containing a concentrated elution of FIX-(CTP)$_2$.

DETAILED DESCRIPTION OF THE INVENTION

Figure 2:
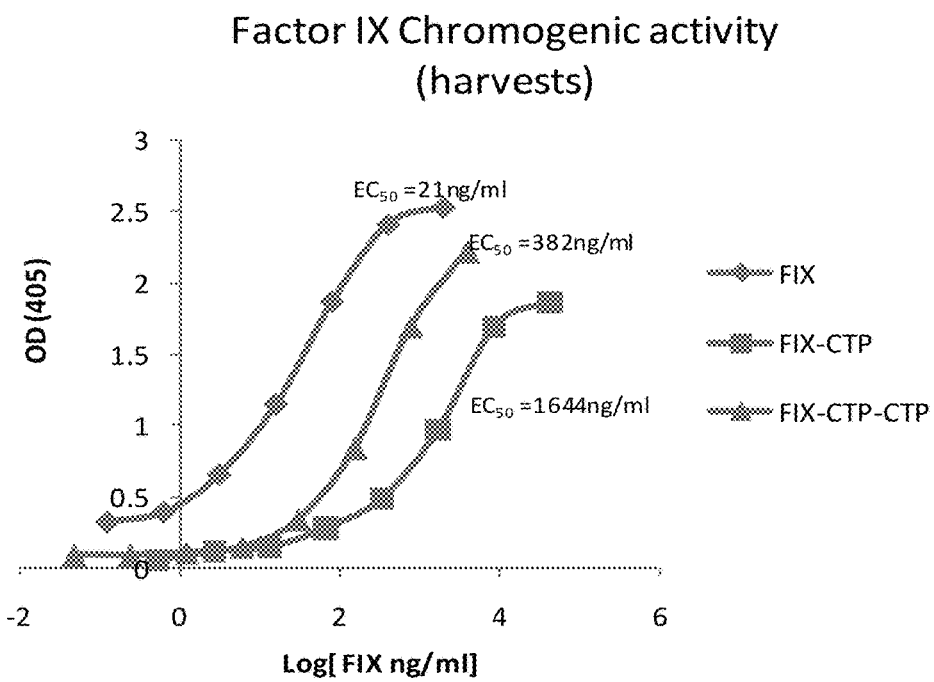
FIG. 2. Shows a graph showing FIX-CTP and FIX-(CTP)$_2$ harvests comparative chromogenic activity (measured by a the EC$_{50}$. concentration) compared to rhFIX (American Diagnostics).

In one embodiment, the present invention provides long-acting coagulation factors and methods of producing and using same. In another embodiment, long-acting coagulation factors comprise a carboxy terminal peptide (CTP, also referred to as CTP unit). In another embodiment, long-acting polypeptides which comprise a coagulation factor further comprise a carboxy terminal peptide (CTP) of human Chorionic Gonadotropin (hCG). In another embodiment, CTP acts as a protectant against the degradation of a coagulation factor. In another embodiment, CTP extends the $C_{max}$ of a coagulation factor. In another embodiment, CTP extends the $T_{max}$ of a coagulation factor. In another embodiment, CTP extends the circulatory half-life of a coagulation factor. In some embodiments, CTP enhances the potency of a coagulation factor.

In another embodiment, provided herein is a method of extending the biological half-life of a coagulation factor, comprising the step of attaching one to ten CTPs to the carboxy terminus of the coagulation factor, thereby extending the biological half-life of the coagulation factor. In another embodiment, provided herein is a method of extending the biological half-life of a coagulation factor, comprising the step of attaching one to five CTPs to the carboxy terminus of the coagulation factor, thereby extending the biological half-life of the coagulation factor. In another embodiment, the present invention provides a method for extending the circulatory half-life of a coagulation factor. In another embodiment, the present invention provides a method for increasing the half-life of a coagulation factor. In another embodiment, the present invention provides a method for extending the half-life of a coagulation factor.

Coagulation Factor VII (FVII) is a 444 amino acid glycoprotein (50 KDa) secreted by hepatocytes into the bloodstream as an inactive pro-enzyme. Upon tissue injury and exposure to circulating blood, FVII forms a complex with Tissue Factor (TF) which is a true receptor protein to FVII and is expressed by various cells localized in the deeper layers of the vessel wall. The formation of this FVII-TF complex leads to activation of FVII. Activated FVII (FVIIa) initiates the extrinsic coagulation pathway by activating Factor IX and Factor X.

FVII belong to a group of Vitamin K-dependent glycoproteins associated with the coagulation system. Besides FVII, this group consists of Factor IX, Factor X, Protein C and prothrombin. These proteins have similar domain organizations and are synthesized as precursors with an N-terminal propeptide followed by a mature amino acid sequence. The propeptide contains a docking site for gammacarboxylase which converts glutamic acids (Glu) into gamma carboxy glutamic acids (Gla). This domain is followed by two epidermal growth factor-like (EGF) domains, a connecting region (CR) and a C-terminal serine protease domain. Prior to secretion, FVII propeptide is cleaved forming a 406 amino acid single chain zymogen FVII glycoprotein. After secretion, the protein can be activated into a disulfide-linked two chain heterodimer, FVIIa, by cleavage in the CR. The plasma concentration of FVII is 10 nM and approximately 1% circulates in the active form in healthy individuals. Factor IX (FIX) is a 415 Amino acid (55 KDa) glycoprotein; it belongs to a group of vitamin K dependent glycoproteins associated with the coagulation system. FIX has a similar domain organization as factor FVII, Factor X, Protein C and prothrombin that are synthesized as precursors with an N-terminal propeptide followed by a mature amino acid sequence.

FIX is secreted as a single chain molecule that undergoes complex post-transcriptional modifications, many of which are critical to its biochemical and pharmacokinetic properties. Among all the post-transcriptional modifications, 12 glutamic acid residues near the amino terminus of FIX that are gamma carboxylated by the vitamin K-dependent gamma carboxylase are the most crucial ones. Carboxylation is required for the interaction of FIX with the phospholipid surfaces and for optimal FIX activity. The amino terminus propeptide serves as a recognition site for the gamma carboxylase and thus, following gamma carboxylation, it is cleaved off by the Golgi apparatus serine protease known as Paired basic Amino acid Cleave Enzyme (PACE/Furin). Four additional post-transcriptional modifications might occur at the Golgi apparatus: sulfation of tyrosine 155, phosphorylation of serine 158, O-glycosylation on Ser 63 and on 61 and finally, N-glycosylation on Asn 157 and 16, but were shown not to be necessary for proper activity of FIX.

FIX circulates in the plasma (average concentration of 5 µg/ml) as a single chain inactive zymogen. Upon proteolytic cleavage at two peptide bonds: Arg 145 and Arg 180 by either one or two physiological activators, FVIIa-TF complex or FIXa, the activation peptide is removed, converting FIX to a fully active enzyme consisting of a light and heavy chain held together by a single disulfide bond. The N-terminal light chain contains the non-catalytic gamma carboxyglutamic acid (Gla) and two epidermal growth factor-like domains, while the C-terminal heavy chain contains the trypsin-like catalytic domain of the molecule. FIXa alone is characterized by poor catalytic activity. However when complexed with FVIII, its proteolytic activity increase by 4-5 orders of magnitude towards its natural substrate FX.

In another embodiment, provided herein is a method of extending the biological half-life or a method of improving the area under the curve (AUC) of a coagulation factor, comprising the step of attaching one to ten CTPs to the carboxy terminus of the coagulation factor, thereby extending the biological half-life or improving the AUC of the coagulation factor. In another embodiment, provided herein is a method of extending the biological half-life or a method of improving the area under the curve (AUC) of a coagulation factor, comprising the step of attaching one to five CTPs to the carboxy terminus of the coagulation factor, thereby extending the biological half-life or improving the AUC of the coagulation factor. In another embodiment, provided herein is a method of extending the biological half-life or a method of improving the area under the curve (AUC) of FIX, comprising the step of attaching one to five CTPs to the carboxy terminus of the FIX, thereby extending the biological half-life or improving the AUC of the FIX. In another embodiment, provided herein is a method of extending the biological half-life or a method of improving the area under the curve (AUC) of FVII or FVIIa, comprising the step of attaching one to five CTPs to the carboxy terminus of FVII or FVIIa, thereby extending the biological half-life or improving the AUC of FVII or FVIIa.

In another embodiment, the present invention provides a method of extending the biological half-life of a Factor IX (FIX) polypeptide, comprising the step of attaching three chorionic gonadotrophin carboxy terminal peptides (CTPs) to the carboxy terminus of said FIX polypeptide, thereby extending the biological half-life of said FIX polypeptide. In another embodiment, the present invention further provides a method of extending the biological half-life of a Factor VIIa (FVIIa) polypeptide, comprising the step of attaching up to five chorionic gonadotrophin carboxy terminal peptides (CTPs) to the carboxy terminus of said FVIIa polypeptide, thereby extending the biological half-life of said FVIIa polypeptide. In one embodiment, three chorionic gonadotrophin carboxy terminal peptides (CTPs) are attached to the carboxy terminus of said FVIIa polypeptide. In another embodiment, four chorionic gonadotrophin carboxy terminal peptides (CTPs) are attached to the carboxy terminus of said FVIIa polypeptide. In another embodiment, five chorionic gonadotrophin carboxy terminal peptides (CTPs) are attached to the carboxy terminus of said FVIIa polypeptide.

In another embodiment, the present invention provides a method of improving the area under the curve (AUC) of a Factor IX (FIX) polypeptide, comprising the step of attaching three chorionic gonadotrophin carboxy terminal peptides (CTPs) to the carboxy terminus of said FIX polypeptide, thereby improving the AUC of said FIX polypeptide. In another embodiment, the present invention provides a method of improving the area under the curve (AUC) of a Factor VIIa (FVIIa) polypeptide, comprising the step of attaching up to five chorionic gonadotrophin carboxy terminal peptides (CTPs) to the carboxy terminus of said FVIIa polypeptide, thereby improving the AUC of said FVIIa polypeptide. In one embodiment, three chorionic gonadotrophin carboxy terminal peptides (CTPs) are attached to the carboxy terminus of said FVIIa polypeptide. In another embodiment, four chorionic gonadotrophin carboxy terminal peptides (CTPs) are attached to the carboxy terminus of said FVIIa polypeptide. In another embodiment, five chorionic gonadotrophin carboxy terminal peptides (CTPs) are attached to the carboxy terminus of said FVIIa polypeptide.

In another embodiment, a coagulation factor of the invention is a protein. In another embodiment, a coagulation factor of the invention is a peptide. In another embodiment, a coagulation factor of the invention is a polypeptide. In another embodiment, the coagulation factor is an enzyme. In another embodiment, the coagulation factor is a serine protease. In another embodiment, the coagulation factor is a glycoprotein. In another embodiment, the coagulation factor is a transglutaminase. In another embodiment, the coagulation factor is an inactive zymogen. In another embodiment, the coagulation factor is any coagulation factor known to one of skill in the art.

In another embodiment, the coagulation factor is Factor VIII (FVIII). In another embodiment, the coagulation factor is Factor V (FV). In another embodiment, the coagulation factor is Factor XIII (FXIII). In another embodiment, the coagulation factor is Factor X (FX). In another embodiment, the coagulation factor is fibrin.

In another embodiment, the coagulation factor is Factor VIIa (FVIIa). In another embodiment, the coagulation factor is Factor VII (FVII). In another embodiment, the coagulation factor is Factor IX (FIX). In another embodiment, the coagulation factor is Factor X (FX). In another embodiment, the coagulation factor is Factor XIa (FXIa). In another embodiment, the coagulation factor is Factor XII (FXII). In another embodiment, the coagulation factor is Factor Xa (FXa). In another embodiment, the coagulation factor is Factor Va (FVa). In another embodiment, the coagulation factor is prothrombin. In another embodiment, the coagulation factor is thrombin. In another embodiment, the coagulation factor is Factor XI (FXI). In another embodiment, the coagulation factor is Von Willebrand factor (vWF). In another embodiment, the coagulation factor is Factor VIIIa (FVIIIa). In another embodiment, the coagulation factor is B-deleted Domain FVIII (FVIIIBDD). In another embodiment, the coagulation factor is B domain-deleted FVIII (FVIIIBDD). In another embodiment, the coagulation factor is Beta domain-deleted FVIII (FVIIIBDD). In another embodiment, the coagulation factor is Factor IXa (FIXa). In another embodiment, the coagulation factor is prekallikrein. In another embodiment, the coagulation factor is kallikrein. In another embodiment, the coagulation factor is Factor XIIa (FXIIa). In another embodiment, the coagulation factor is Fibrinogen. In another embodiment, the coagulation factor is thrombomodulin. In another embodiment, the coagulation factor is Factor II (FII).

In another embodiment, the coagulation factor is a glycoprotein. In another embodiment, the coagulation factor is a vitamin K-dependent glycoprotein. In another embodiment, the coagulation factor is a vitamin K-independent glycoprotein.

In another embodiment, the coagulation factor is a recombinant protein. In another embodiment, the coagulation factor is a recombinant glycoprotein. In another embodiment, the coagulation factor is a recombinant glycoprotein FV. In another embodiment, the coagulation factor is a recombinant FVI. In another embodiment, the coagulation factor is a recombinant FVII. In another embodiment, the coagulation factor is a recombinant FVIII. In another embodiment, the coagulation factor is a recombinant FIX. In another embodiment, the coagulation factor is a recombinant FX. In another embodiment, the coagulation factor is a recombinant FXI. In another embodiment, the coagulation factor is a recombinant FXII. In another embodiment, the coagulation factor is a recombinant FvW. In another embodiment, the coagulation factor is a recombinant FII. In another embodiment, the coagulation factor is a recombinant FIXa. In another embodiment, the coagulation factor is a recombinant FXIa. In another embodiment, the coagulation factor is a recombinant fibrin. In another embodiment, the coagulation factor is a recombinant FVIIa. In another embodiment, the coagulation factor is a recombinant FXa. In another embodiment, the coagulation factor is a recombinant FVa. In another embodiment, the coagulation factor is a recombinant prothrombin. In another embodiment, the coagulation factor is a recombinant thrombin. In another embodiment, the coagulation factor is a recombinant FVIIIa. In another embodiment, the coagulation factor is a recombinant prekallikrein. In another embodiment, the coagulation factor is a recombinant kallikrein. In another embodiment, the coagulation factor is a recombinant FXIIa. In another embodiment, the coagulation factor is any known recombinant coagulation factor. In another embodiment, the coagulation factor comprising a signal peptide is any known recombinant coagulation factor.

In another embodiment, a coagulation factor comprises 1-10 CTP repeats attached to the C-terminus and no CTPs attached to the N-terminus. In another embodiment, a coagulation factor comprises at least one CTP attached to the C-terminus and no CTPs attached to the N-terminus. In another embodiment, a coagulation factor comprising 1-10 CTP repeats attached to the C-terminus and no CTPs attached to the N-terminus is an engineered coagulation factor. In another embodiment, a coagulation factor comprising at least one CTP attached to the C-terminus and no CTPs attached to the N-terminus is an engineered coagulation factor. In another embodiment, a coagulation factor comprising 1-10 CTP repeats attached to the C-terminus and no CTPs attached to the N-terminus is a conjugated coagulation factor. In another embodiment, a coagulation factor comprising at least one CTP attached to the C-terminus and no CTPs attached to the N-terminus is a conjugated coagulation factor.

In one embodiment, the present invention provides a CTP-modified Factor IX (FIX) polypeptide consisting of a FIX polypeptide and three gonadotropin carboxy terminal peptides (CTPs) attached to the carboxy terminus of said CTP-modified FIX polypeptide.

In another embodiment, the present invention further provides a CTP-modified Factor VIIa (FVIIa) polypeptide consisting of a FVIIa polypeptide and five gonadotropin carboxy terminal peptides (CTPs) attached to the carboxy terminus of said FVIIa.

In another embodiment, the coagulation factor is a coagulation factor comprising a domain organization similar or identical to the domain organization of FIX, FVII, Factor X. Protein C, or prothrombin. In another embodiment, the coagulation factor is synthesized as a precursor with an N-terminal propeptide. In another embodiment, the coagulation factor as used herein is in an inactive pro-enzyme form. In another embodiment, the coagulation factor is produced in hepatocytes. In another embodiment, the coagulation factor comprises a docking site for gammacarboxylase which converts glutamic acids (Glu) into gamma carboxy glutamic acids (Gla). In another embodiment, the coagulation factor as used herein is a commercially available coagulation factor.

In one embodiment, the nucleic acid sequence encoding Factor VII comprises the following nucleic acid sequence:

(SEQ ID NO: 11)
ctcgaggacatggtctcccaggccctcaggctcctctgccttctgcttg ggcttcagggctgcctggctgcagtcttcgtaacccaggaggaagccca cggcgtcctgcaccggcgccggcgcgccaacgcgttcctggaggagctg cggccgggctccctggagagggagtgcaaggaggagcagtgctccttcg aggaggcccgggagatcttcaaggacgcggagaggacgaagctgttctg gatttcttacagtgatggggaccagtgtgcctcaagtccatgccagaat gggggctcctgcaaggaccagctccagtcctatatctgcttctgcctcc ctgccttcgagggccggaactgtgagacgcacaaggatgaccagctgat ctgtgtgaacgagaacggcggctgtgagcagtactgcagtgaccacacg ggcaccaagcgctcctgtcggtgccacgaggggtactctctgctggcag acggggtgtcctgcacacccacagttgaatatccatgtggaaaaatacc tattctagaaaaaagaaatgccagcaaacccccaaggccgaattgtgggg ggcaaggtgtgccccaaagggggagtgtccatggcaggtcctgttgttgg tgaatggagctcagttgtgtggggggaccctgatcaacaccatctgggt ggtctccgcggcccactgtttcgacaaaatcaagaactggaggaacctg atcgcggtgctgggcgagcacgacctcagcgagcacgacggggatgagc agagccggcgggtggcgcaggtcatcatccccagcacgtacgtcccggg caccaccaaccacgacatcgcgctgctccgcctgcaccagcccgtggtc ctcactgaccatgtggtgcccctctgcctgcccgaacggacgttctctg agaggacgctggccttcgtgcgcttctcattggtcagcggctggggcca gctgctggaccgtggcgccacggccctggagctcatggtcctcaacgtg ccccggctgatgacccaggactgcctgcagcagtcacggaaggtgggag actccccaaatatcacggagtacatgttctgtgccggctactcggatgg cagcaaggactcctgcaaggggacagtggaggcccacatgccacccac taccggggcacgtggtacctgacgggcatcgtcagctggggccagggct gcgcaaccgtgggccactttgggtgtacaccagggtctcccagtacat cgagtggctgcaaaagctcatgcgctcagagccacgcccaggagtcctc ctgcgagcccatttccctgaggatgcggccgc.

In another embodiment, the amino acid sequence of Factor VII comprises the following amino acid sequence:

(SEQ ID NO: 9)
MVSQALRLLCLLLGLQGCLAAVFVTQEEAHGVLHRRRRANAFLEELRPG

SLERECKEEQCSFEEAREIFKDAERTKLFWISYSDGDQCASSPCQNGGS

CKDQLQSYICFCLPAFEGRNCETHKDDQLICVNENGGCEQYCSDHTGTK

RSCRCHEGYSLLADGVSCTPTVEYPCGKIPILEKRNASKPQGRIVGGKV

CPKGECPWQVLLLVNGAQLCGGTLINTIWVVSAAHCFDKIKNWRNLIAV

LGEHDLSEHDGDEQSRRVAQVIIPSTYVPGTTNHDIALLRLHQPVVLTD

HWPLCLPERTFSERTLAFVRFSLVSGWGQLLDRGATALELMVLNVPRLM

TQDCLQQSRKVGDSPNITEYMFCAGYSDGSKDSCKGDSGGPHATHYRGT

WYLTGIVSWGQGCATVGHFGVYTRVSQYIEWLQKLMRSEPRPGVLLRAP

FP.

In another embodiment, the amino acid sequence of Factor VII comprises the following amino acid sequence:

(SEQ ID NO: 10)
MVSQALRLLCLLLGLQGCLAAVFVTQEEAHGVLHRRRRANAFLEELRPG

SLERECKEEQCSFEEAREIFKDAERTKLFWISYSDGDQCASSPCQNGGS

CKDQLQSYICFCLPAFEGRNCETHKDDQLICVNENGGCEQYCSDHTGTK

RSCRCHEGYSLLADGVSCTPTVEYPCGKIPILEKRNASKPQGRIVGGKV

CPKGECPWQVLLLVNGAQLCGGTLINTIWVVSAAHCFDKIKNWRNLIAV

LGEHDLSEHDGDEQSRRVAQVIIPSTYVPGTTNHDIALLRLHQPVVLTD

HVVPLCLPERTFSERTLAFVRFSLVSGWGQLLDRGATALELMVLNVPRL

MTQDCLQQSRKVGDSPNITEYMFCAGYSDGSKDSCKGDSGGPHATHYRG

TWYLTGIVSWGQGCATVGHFGVYTRVSQYIEWLQKLMRSEPRPGVLLRA

PFP*GCGR.

In another embodiment, the nucleic acid sequence encoding Factor VII-CTP (attached to the carboxy terminus) comprises the following nucleic acid sequence:

(SEQ ID NO: 12)
ctcgaggacatggtctcccaggccctcaggctcctctgccttctgcttg ggcttcagggctgcctggctgcagtcttcgtaacccaggaggaagccca cggcgtcctgcaccggcgccggcgcgccaacgcgttcctggaggagctg cggccgggctccctggagagggagtgcaaggaggagcagtgctccttcg aggaggcccgggagatcttcaaggacgcggagaggacgaagctgttctg gatttcttacagtgatggggaccagtgtgcctcaagtccatgccagaat gggggctcctgcaaggaccagctccagtcctatatctgcttctgcctcc ctgccttcgagggccggaactgtgagacgcacaaggatgaccagctgat ctgtgtgaacgagaacggcggctgtgagcagtactgcagtgaccacacg ggcaccaagcgctcctgtcggtgccacgaggggtactctctgctggcag acggggtgtcctgcacacccacagttgaatatccatgtggaaaaatacc tattctagaaaaagaaatgccagcaaacccaaggccgaattgtggggg ggcaaggtgtgcccaagggagtgtccatggcaggtcctgttgttgg tgaatggagctcagttgtgtgggggaccctgatcaacaccatctgggt ggtctccgcggcccactgtttcgacaaaatcaagaactggaggaacctg atcgcggtgctgggcgagcacgacctcagcgagcacgacggggatgagc agagccggcgggtggcgcaggtcatcatcccagcacgtacgtcccggg caccaccaaccacgacatcgcgctgctccgcctgcaccagcccgtggtc ctcactgaccatgtggtgcccctctgcctgcccgaacggacgttctctg agaggacgctggccttcgtgcgcttctcattggtcagcggctggggcca gctgctggaccgtggcgccacggccctggagctcatggtcctcaacgtg ccccggctgatgacccaggactgcctgcagcagtcacggaaggtgggag actccccaaatatcacggagtacatgttctgtgccggctactcggatgg cagcaaggactcctgcaaggggggacagtggaggcccacatgccacccac taccggggcacgtggtacctgaccggcatcgtgagctggggccagggct gcgccaccgtgggccacttcggcgtgtacacccagggtgtcccagtacat cgagtggctgcagaaactgatgagaagcgagcccagaccggcgtgctg ctgagagcccccttccccagcagcagctccaaggcccctcccctagcc tgcccagccctagcagactgcctgggcccagcgacacccccatcctgcc ccagtgaggatccgcggccgc.

In another embodiment, the amino acid sequence of Factor VII-CTP (attached to the carboxy terminus) comprises the following amino acid sequence:

(SEQ ID NO. 13)
MVSQALRLLCLLLGLQGCLAAVFVTQEEAHGVLHRRRRANAFLEELRPG

SLERECKEEQCSFEEAREIFKDAERTKLFWISYSDGDQCASSPCQNGGS

CKDQLQSYICFCLPAFEGRNCETHKDDQLICVNENGGCEQYCSDHTGTK

RSCRCHEGYSLLADGVSCTPTVEYPCGKIPILEKRNASKPQGRIVGGKV

CPKGECPWQVLLLVNGAQLCGGTLINTIWVVSAAHCFDKIKNWRNLIAV

LGEHDLSEHDGDEQSRRVAQVIIPSTYVPGTTNHDIALLRLHQPVVLTD

HVVPLCLPERTFSERTLAFVRFSLVSGWGQLLDRGATALELMVLNVPRL

MTQDCLQQSRKVGDSPNITEYMFCAGYSDGSKDSCKGDSGGPHATHYRG

TWYLTGIVSWGQGCATVGHFGVYTRVSQYIEWLQKLMRSEPRPGVLLRA

PFPSSSSKAPPPSLPSPSRLPGPSDTPILPQ*.

In another embodiment, the nucleic acid sequence encoding Factor VII-CTP-CTP (attached to the carboxy terminus) comprises the following nucleic acid sequence:

(SEQ ID NO: 14)
ctcgaggacatggtctcccaggccctcaggctcctctgccttctgcttgg gcttcagggctgcctggctgcagtcttcgtaacccaggaggaagcccacg gcgtcctgcaccggcgccggcgcgccaacgcgttcctggaggagctgcgg ccgggctccctggagagggagtgcaaggaggagcagtgctccttcgagga ggcccgggagatcttcaaggacgcggagaggacgaagctgttctggattt cttacagtgatggggaccagtgtgcctcaagtccatgccagaatggggc tcctgcaaggaccagctccagtcctatatctgcttctgcctccctgcctt cgagggccggaactgtgagacgcacaaggatgaccagctgatctgtgtga acgagaacggcggctgtgagcagtactgcagtgaccacacgggcaccaag cgctcctgtcggtgccacgaggggtactctctgctggcagacggggtgtc ctgcacacccacagttgaatatccatgtggaaaaatacctattctagaaa aagaaatgccagcaaacccaaggccgaattgtgggggcaaggtgtgc cccaaggggagtgtccatggcaggtcctgttgttggtgaatggagctca

```
gttgtgtgggggggaccctgatcaacaccatctgggtggtctccgcggccc
actgtttcgacaaaatcaagaactggaggaacctgatcgcggtgctgggc
gagcacgacctcagcgagcacgacggggatgagcagagccggcgggtggc
gcaggtcatcatccccagcacgtacgtcccgggcaccaccaaccacgaca
tcgcgctgctccgcctgcaccagccgtggtcctcactgaccatggtg
cccctctgcctgcccgaacggacgttctctgagaggacgctggccttcgt
gcgcttctcattggtcagcggctggggccagctgctggaccgtggcgcca
cggccctggagctcatggtcctcaacgtgccccggctgatgacccaggac
tgcctgcagcagtcacggaaggtgggagactccccaaatatcacggagta
catgttctgtgccggctactcggatggcagcaaggactcctgcaagggg
acagtggaggcccacatgccacccactaccggggcacgtggtacctgacc
ggcatcgtgagctgggccagggctgcgccaccgtgggccacttcggcgt
gtacaccagggtgtcccagtacatcgagtggctgcagaaactgatgagaa
gcgagcccagacccggcgtgctgctgagagccccttccccagcagcagc
tccaaggcccctccccctagcctgcccagcctagcagactgcctgggcc
ctccgacacaccaatcctgccacagagcagctcctctaaggcccctcctc
catccctgccatccccctcccggctgccaggcccctctgacacccctatc
ctgcctcagtgatgaaggtctggatccgcggccgc.
```

In another embodiment, the amino acid sequence of Factor VII-CTP-CTP (attached to the carboxy terminus) comprises the following amino acid sequence:

(SEQ ID NO 15)
MVSQALRLLCLLLGLQGCLAAVFVTQEEAHGVLHRRRRANAFLEELRPG
SLERECKEEQCSFEEAREIFKDAERTKLFWISYSDGDQCASSPCQNGGS
CKDQLQSYICFCLPAFEGRNCETHKDDQLICVNENGGCEQYCSDHTGTK
RSCRCHEGYSLLADGVSCTPTVEYPCGKIPILEKRNASKPQGRIVGGKV
CPKGECPWQVLLLVNGAQLCGGTLINTIWVVSAAHCFDKIKNWRNLIAV
LGEHDLSEHDGDEQSRRVAQVIIPSTYVPGTTNHDIALLRLHQPVVLTD
HVVPLCLPERTFSERTLAFVRFSLVSGWGQLLDRGATALELMVLNVPRL
MTQDCLQQSRKVGDSPNITEYMFCAGYSDGSKDSCKGDSGGPHATHYRG
TWYLTGIVSWGQGCATVGHFGVYTRVSQYIEWLQKLMRSEPRPGVLLRA
PFPSSSSKAPPPSLPSPSRLPGPSDTPILPQSSSSKAPPPSLPSPSRLP
GPSDTPILPQ**.

In another embodiment, the nucleic acid sequence encoding Factor VII-CTP-CTP-CTP (attached to the carboxy terminus) comprises the following nucleic acid sequence:

```
(SEQ ID NO: 24)
ctcgaggacatggtctcccaggccctcaggctcctctgccttctgcttg
ggcttcagggctgcctggctgcagtcttcgtaacccaggaggaagccca
cggcgtcctgcaccggcgccggcgcgccaacgcgttcctggaggagctg
cggccggctccctggagagggagtgcaaggaggagcagtgctccttcg
aggaggcccgggagatcttcaaggacgcggagaggacgaagctgttctg
gatttcttacagtgatgagggccggaactgtgagacgcacaaggatgac
cagctgatctgtgtgaacgagaacggcggctgtgagcagtactgcagtg
accacacgggcaccaagcgctcctgtcggtgccacgaggggtactctct
gctggcagacggggtgtcctgcacacccacagttgaatatccatgtgga
aaaatacctattctagaaaaaagaaatgccagcaaaccccaaggccgaa
ttgtggggggcaaggtgtgccccaaaggggagtgtccatggcaggtcct
gttgttggtaatggagctcagttgtgtgggggggaccctgatcaacacc
atctgggtggtctccgcggccactgtttcgacaaaatcaagaactgga
ggaacctgatcgcggtgctgggcgagcacgacctcagcgagcacgacgg
ggatgagcagagccggcgggtggcgcaggtcatcatccccagcacgtac
gtcccgggcaccaccaaccacgacatcgcgctgctccgcctgcaccagc
ccgtggtcctcactgaccatgtggtgcccctctgcctgcccgaacggac
gttctctgagaggacgctggccttcgtgcgcttctcattggtcagcggc
tggggccagctgctggaccgtggcgccacgcccctggagctcatggtcc
tcaacgtgccccggctgatgacccaggactgcctgcagcagtcacggaa
ggtgggagactccccaaatatcacggagtacatgttctgtgccggctac
tcggatggcagcaaggactcctgcaagggggacagtggaggcccacatg
ccacccactaccggggcacgtggtacctgaccggcatcgtgagctgggg
ccagggctgcgccaccgtgggccacttcggcgtgtacaccagggtgtcc
cagtacatcgagtggctgcagaaactgatgagaagcgagcccagacccg
gcgtgctgctgagagccccttccccagcagcagctccaaggcccctcc
ccctagcctgcccagccctagcagactgcctgggcccagtgacaccct
atcctgcctcagtccagctccagcaaggcccccacccccctagcctgcctt
ctccttctcggctgcctggccccagcgatactccaattctgccccagtc
ctccagcagtaaggctccccctccatctctgccatccccagcagactg
ccaggcccttctgatacacccatcctcccacagtgatgaggatccgcgg
ccgcttaattaa.
```

In another embodiment, the amino acid sequence of Factor VII-CTP-CTP-CTP (attached to the carboxy terminus) comprises the following amino acid sequence (SEQ ID NO: 25)
MVSQALRLLCLLLGLQGCLAAVFVTQEEAHGVLHRRRRANAFLEELRPG
SLERECKEEQCSFEEAREIFKDAERTKLFWISYSDGDQCASSPCQNGGS
CKDQLQSYICFCLPAFEGRNCETHKDDQLICVNENGGCEQYCSDHTGTK
RSCRCHEGYSLLADGVSCTPTVEYPCGKIPILEKRNASKPQGRIVGGKV
CPKGECPWQVLLLVNGAQLCGGTLINTIWVVSAAHCFDKIKNWRNLIAV
LGEHDLSEHDGDEQSRRVAQVIIPSTYVPGTTNHDIALLRLHQPVVLTD
HVVPLCLPERTFSERTLAFVRFSLVSGWGQLLDRGATALELMVLNVPRL
MTQDCLQQSRKVGDSPNITEYMFCAGYSDGSKDSCKGDSGGPHATHYRG
TWYLTGIVSWGQGCATVGHFGVYTRVSQYIEWLQKLMRSEPRPGVLLRA
PFPSSSSKAPPPSLPSPSRLPGPSDTPILPQSSSSKAPPPSLPSPSRLP -continued

GPSDTPILPQSSSSKAPPPSLPSPSRLPGPSDTPILPQ**.

In another embodiment, the amino acid sequence of Factor VII-CTP-CTP-CTP without the signal peptide is set forth in SEQ ID NO: 46.

In another embodiment, the signal peptide of Factor VII-CTP-CTP-CTP is set forth in SEQ ID NO: 47.

In another embodiment, the nucleic acid sequence encoding Factor VII-(CTP)$_4$ (attached to the carboxy terminus) comprises the following nucleic acid sequence:

(SEQ ID NO: 26)
ctcgaggacatggtctcccaggccctcaggctcctctgccttctgcttg ggcttcagggctgcctggctgcagtcttcgtaacccaggaggaagccca cggcgtcctgcaccggcgccggcgcgccaacgcgttcctggaggagctg cggccgggctccctggagagggagtgcaaggaggagcagtgctccttcg aggaggcccgggagatcttcaaggacgcggagaggacgaagctgttctg gatttcttacagtgatggggaccagtgtgcctcaagtccatgccagaat gggggctcctgcaaggaccagctccagtcctatatctgcttctgcctcc ctgccttcgagggccggaactgtgagacgcacaaggatgaccagctgat ctgtgtgaacgagaacggcggctgtgagcagtactgcagtgaccacacg ggcaccaagcgctcctgtcggtgccacgaggggtactctctgctggcag acggggtgtcctgcacacccacagttgaatatccatgtggaaaaatacc tattctagaaaaaagaaatgccagcaaaccccaaggccgaattgtgggg ggcaaggtgtgccccaaggggagtgtccatggcaggtcctgttgttgg tgaatggagctcagttgtgtgggggaccctgatcaacaccatctgggt ggtctccgcggccactgtttcgacaaaatcaagaactggaggaacctg atcgcggtgctgggcgagcacgacctcagcgagcacgacggggatgagc agagccggcgggtggcgcaggtcatcatcccagcacgtacgtcccggg caccaccaaccacgacatcgcgctgctccgcctgcaccagcccgtggtc ctcactgaccatgtggtgcccctctgcctgcccgaacggacgttctctg agaggacgctggccttcgtgcgcttctcattggtcagcggctggggcca gctgctggaccgtggcgccacggccctggagctcatggtcctcaacgtg ccccggctgatgacccaggactgcctgcagcagtcacggaaggtgggag actcccaaatatcacggagtacatgttctgtgccggctactcggatgg cagcaaggactcctgcaaggggacagtggaggcccacatgccacccac taccggggcacgtggtacctgaccggcatcgtgagctggggccagggct gcgccaccgtgggccacttcggcgtgtacaccagggtgtcccagtacat cgagtggctgcagaaactgatgagaagcgagcccagaccggcgtgctg ctgagagccccttccccagcagcagctccaaggcccctccccctagcc tgcccagccctagcagactgcctgggcccagtgacacccctatcctgcc tcagtccagctccagcaaggcccaccccctagcctgccttctccttct cggctgcctggccccagcgatactccaattctgccccagtcctccagca gtaaggctccccctccatctctgccatccccagcagactgccaggccc ttctgatacacccatcctcccacagtgatgaggatccgc.

In another embodiment, the amino acid sequence of Factor VII-(CTP)$_4$ (attached to the carboxy terminus) comprises the following amino acid sequence:

(SEQ ID NO: 27)
LEDMVSQALRLLCLLLGLQGCLAAVFVTQEEAHGVLHRRRRANAFLEEL

RPGSLERECKEEQCSFEEAREIFKDAERTKLFWISYSDGDQCASSPCQN

GGSCKDQLQSYICFCLPAFEGRNCETHKDDQLICVNENGGCEQYCSDHT

GTKRSCRCHEGYSLLADGVSCTPTVEYPCGKIPILEKRNASKPQGRIVG

GKVCPKGECPWQVLLLVNGAQLCGGTLINTIWVVSAAHCFDKIKNWRNL

IAVLGEHDLSEHDGDEQSRRVAQVIIPSTYVPGTTNHDIALLRLHQPVV

LTDHVVPLCLPERTFSERTLAFVRFSLVSGWGQLLDRGATALELMVLNV

PRLMTQDCLQQSRKVGDSPNITEYMFCAGYSDGSKDSCKGDSGGPHATH

YRGTWYLTGIVSWGQGCATVGHFGVYTRVSQYIEWLQKLMRSEPRPGVL

LRAPFPSSSSKAPPPSLPSPSRLPGPSDTPILPQSSSSKAPPPSLPSPS

RLPGPSDTPILPQSSSSKAPPPSLPSPSRLPGPSDTPILPQ**G.

In another embodiment, the nucleic acid sequence encoding Factor VII-(CTP)$_5$ (attached to the carboxy terminus) comprises the following nucleic acid sequence:

(SEQ ID NO: 28)
ctcgaggacatggtctcccaggccctcaggctcctctgccttctgcttg ggcttcagggctgcctggctgcagtcttcgtaacccaggaggaagccca cggcgtcctgcaccggcgccggcgcgccaacgcgttcctggaggagctg cggccgggctccctggagagggagtgcaaggaggagcagtgctccttcg aggaggcccgggagatcttcaaggacgcggagaggacgaagctgttctg gatttcttacagtgatggggaccagtgtgcctcaagtccatgccagaat gggggctcctgcaaggaccagctccagtcctatatctgcttctgcctcc ctgccttcgagggccggaactgtgagacgcacaaggatgaccagctgat ctgtgtgaacgagaacggcggctgtgagcagtactgcagtgaccacacg ggcaccaagcgctcctgtcggtgccacgaggggtactctctgctggcag acggggtgtcctgcacacccacagttgaatatccatgtggaaaaatacc tattctagaaaaaagaaatgccagcaaaccccaaggccgaattgtgggg ggcaaggtgtgccccaaggggagtgtccatggcaggtcctgttgttgg tgaatggagctcagttgtgtgggggaccctgatcaacaccatctgggt ggtctccgcggccactgtttcgacaaaatcaagaactggaggaacctg atcgcggtgctgggcgagcacgacctcagcgagcacgacggggatgagc agagccggcgggtggcgcaggtcatcatcccagcacgtacgtcccggg caccaccaaccacgacatcgcgctgctccgcctgcaccagcccgtggtc ctcactgaccatgtggtgcccctctgcctgcccgaacggacgttctctg agaggacgctggccttcgtgcgcttctcattggtcagcggctggggcca gctgctggaccgtggcgccacggccctggagctcatggtcctcaacgtg ccccggctgatgacccaggactgcctgcagcagtcacggaaggtgggag actcccaaatatcacggagtacatgttctgtgccggctactcggatgg -continued

```
cagcaaggactcctgcaaggggga cagtggaggcccacatgccaccac
tttccggggcacgtggtacctgaccggcatcgtgagctgggg ccagggc
tgcgccaccgtgggccacttcggcgtgtacaccagggtgtcccagtaca
tcgagtggctgcagaaactgatgagaagcgagcccagacccggcgtgct
gctgagagccccttccccagcagcagctccaaggccctcccc ctagc
ctgcccagcctagcagactgcctgggccctctgacacccctatcctgc
ctcagtccagctcctctaaggctccaccacttccctgcctagccttc
aagactgccaggccctagcgataccaattctgccccagtcctccagc
agcaaggctcccccacctagcctgccttctccatcaaggctgcctggcc
catccgataccccaattttgcctcagagcagctctagcaaggcacctcc
ccccagtctgccctctccaagcagactccctggcccttcagacactcca
atcctcccacagtcctctagctctaaagctccacctcccagcctgccca
gccctagtagactccccggaccttctgatacccccatcttgccccagtg
atgaggatccgc.
```

In another embodiment, the amino acid sequence of Factor VII-(CTP)$_5$ (attached to the carboxy terminus) comprises the following amino acid sequence:

(SEQ ID NO: 29)
LEDMVSQALRLLCLLLGLQGCLAAVFVTQEEAHGVLHRRRRANAFLEEL

RPGSLERECKEEQCSFEEAREIFKDAERTKLFWISYSDGDQCASSPCQN

GGSCKDQLQSYICFCLPAFEGRNCETHKDDQLICVNENGGCEQYCSDHT

GTKRSCRCHEGYSLLADGVSCTPTVEYPCGKIPILEKRNASKPQGRIVG

GKVCPKGECPWQVLLLVNGAQLCGGTLINTIWVVSAAHCFDKIKNWRNL

IAVLGEHDLSEHDGDEQSRRVAQVIIPSTYVPGTTNHDIALLRLHQPVV

LTDHVVPECLPERTFSERTLAFVRFSLVSGWGQLLDRGATALELMVLNV

PRLMTQDCLQQSRKVGDSPNITEYMFCAGYSDGSKDSCKGDSGGPHATH

YRGTWYLTGIVSWGQGCATVGHFGVYTRVSQYIEWLQKLMRSEPRPGVL

LRAPFPSSSKAPPPSLPSPSRLPGPSDTPILPQSSSSKAPPPSLPSPS

RLPGPSDTPILPQSSSSKAPPPSLPSPSRLPGPSDTPILPQSSSSKAPP

PSLPSPSRLPGPSDTPILPQSSSvSKAPPPSLPSPSRLPGPSDTPILPQ

**GS.

In another embodiment, the nucleic acid sequence encoding Factor IX comprises the following nucleic acid sequence:

(SEQ ID NO: 16)
```
gcgatcgccatgcagcgcgtgaacatgatcatggcagaatcaccaggcc
tcatcaccattgccttttaggatatctactcagtgctgaatgtacagtt
tttcttgatcatgaaaacgccaacaaaattctgaatcggccaaagaggt
ataattcaggtaaattggaagagtttgttcaagggaaccttgagagaga
atgtatggaagaaaagtgtagttttgaagaagcacgagaagtttttgaa
aacactgaaagaacaactgaattttggaagcagtatgttgatggagatc
agtgtgagtccaatccatgtttaaatggcggcagttgcaaggatgacat
```

```
taattcctatgaatgttggtgtccctttggatttgaaggaaagaactgt
gaattagatgtaacatgtaacattaagaatggcagatgcgagcagtttt
gtaaaatagtgctgataacaaggtggtttgctcctgtactgagggata
tcgacttgcagaaaaccagaagtcctgtgaaccagcagtgccatttcca
tgtggaagagtttctgttt cacaaacttctaagctcaccgtgctgaga
ctgttttttcctgatgtggactatgtaaattctactgaagctgaaaccat
tttggataacatcactcaaagcacccaatcatttaatgacttcactcga
gttgttggtggagaagatgccaaaccaggtcaattcccttggcaggttg
ttttgaatggtaaagttgatgcattctgtggaggctctatcgttaatga
aaaatggattgtaactgctgcccactgtgttgaaactggtgttaaaatt
acagttgtcgcaggtgaacataatattgaggagacagaacatacagagc
aaaagcgaaatgtgattcgaattattcctcaccacaactacaatgcagc
tattaataagtacaaccatgacattgcccttctggaactggacgaaccc
ttagtgctaaacagctacgttacacctatttgcattgctgacaaggaat
acacgaacatcttcctcaaatttggatctggctatgtaagtggctgggg
aagagtcttccacaaagggagatcagctttagttctccagtaccttaga
gttccacttgttgaccgagccacatgtcttcgatctacaaagttcacca
tctataacaacatgttctgtgctggcttccatgaaggaggtagagattc
atgtcaaggagatagtgggggacccatgttactgaagtggaagggacc
agtttcttaactggaattattagctgggtgaagagtgtgcaatgaaag
gcaaatatggaatatataccaaggtatcccggtatgtcaactggattaa
ggaaaaaacaaagctcacttgaacgcggccgc.
```

In another embodiment, the amino acid sequence of Factor IX comprises the following amino acid sequence:

(SEQ ID NO: 17)
MQRVNMIMAESPGLITICLLGYLLSAECTVFLDHENANKILNRPKYNS

GKLEEFVQGNLERECMEEKCSFEEAREVFENTERTTEFWKQYVDGDQCE

SNPCLNGGSCKDDINSYECWCPFGFEGKNCELDVTCNIKNGRCEQFCKN

SADNKVVCSCTEGYRLAENQKSCEPAVPFPCGRVSVSQTSKLTRAETVF

PDVDYVNSTEAETILDNITQSTQSFNDFTRVVGGEDAKPGQFPWQVVLN

GKVDAFCGGSIVNEKWIVTAAHCVETGVKITVVAGEHNIEETEHTEQKR

NVIRIIPHHNYNAAFNKYNHDIALLELDEPLVLNSYVTPICIADKEYTN

IFLKFGSGYVSGWGRVFHKGRSALVLQYLRVPLVDRATCLRSTKFTIYN

NMFCAGFHEGGRDSCQGDSGGPHVTEVEGTSFLTGIISWGEECAMKGKY

GIYTKVSRYVNWIKEKTKLT*.

In another embodiment, the nucleic acid sequence encoding Factor IX-CTP (attached to the carboxy terminus) comprises the following nucleic acid sequence:

(SEQ ID NO: 18)
gcgatcgccatgcagcgcgtgaacatgatcatggcagaatcaccaggcc tcatcaccatctgccttttaggatatctactcagtgctgaatgtacagt -continued ttttcttgatcatgaaaacgccaacaaaattctgaatcggccaaagagg tataattcaggtaaattggaagagtttgttcaagggaaccttgagagag aatgtatggaagaaaagtgtagttttgaagaagcacgagaagtttttga aaacactgaaagaacaactgaattttggaagcagtatgttgatggagat cagtgtgagtccaatccatgtttaaatggcggcagttgcaaggatgaca ttaattcctatgaatgttggtgtccctttggatttgaaggaaagaactg tgaattagatgtaacatgtaacattaagaatggcagatgcgagcagttt tgtaaaaatagtgctgataacaaggtggtttgctcctgtactgagggat atcgacttgcagaaaccagaagtcctgtgaaccagcagtgccatttcc atgtggaagagtttctgtttcacaaacttctaagctcacccgtgctgag actgttttcctgatgtggactatgtaaattctactgaagctgaaacca ttttggataacatcactcaaagcacccaatcatttaatgacttcactcg agttgttggtggagaagatgccaaaccaggtcaattcccttggcaggtt gttttgaatggtaaagttgatgcattctgtggaggctctatcgttaatg aaaaatggattgtaactgctgcccactgtgttgaaactggtgttaaaat tacagttgtcgcaggtaacataatattgaggagacagaacatacagag caaaagcgaaatgtgattcgaattattcctcaccacaactacaatgcag ctattaataagtacaaccatgacattgcccttctggaactggacgaacc cttagtgctaaacagctacgttacacctatttgcattgctgacaaggaa tacacgaacatcttcctcaaatttggatctggctatgtaagtggctggg gaagagtcttccacaaagggagatcagctttagttcttcagtaccttag agttccacttgttgaccgagccacatgtcttcgatctacaaagttcacc atctataacaacatgttctgtgctggcttccatgaaggaggtagagatt catgtcaaggagatagtgggggaccccatgttactgaagtggaagggac cagtttcttaactggaattattagctggggtgaagagtgtgcaatgaaa ggcaaatatggaatatataccaaggtatcccggtatgtcaactggatta aggaaaaaacaaagctcactagctccagcagcaaggcccctcccccgag cctgccctccccaagcaggctgcctgggccctccgacacaccaatcctg ccacagtgatgaaggtctggatccgcggccgc.

In another embodiment, the amino acid sequence of Factor IX-CTP (attached to the carboxy terminus) comprises the following amino acid sequence:

(SEQ ID NO: 19)
MQRVNMIMAESPGLITICLLGYLLSAECTVFLDHENANKILNRPKRYNS

GKLEEFVQGNLERECMEEKCSFEEAREVFENTERTTEFWKQYVDGDQCE

SNPCLNGGSCKDDINSYECWCPFGFEGKNCELDVTCNIKNGRCEQFCKN

SADNKVVCSCTEGYRLAENQKSCEPAVPFPCGRVSVSQTSKLTRAETVF

PDVDYVNSTEAETILDNITQSTQSFNDFTRVVGGEDAKPGQFPWQVVLN

GKVDAFCGGSIVNEKWIVTAAHCVETGVKITVVAGEHNIEETEHTEQKR

NVIRIIPHHNYNAAINKYNHDIALLELDEPLVLNSYVTPICIADKEYTN

IFLKFGSGYVSGWGRVFHKGRSALVLQYLRVPLVDRATCLRSTKFTIYN

NMFCAGFHEGGRDSCQGDSGGPHVTEVEGTSFLTGIISWGEECAMKGKY

GIYTKVSRYVNWIKEKTKLTSSSSKAPPPSLPSPSRLPGPSDTPILP

Q**.

In another embodiment, the nucleic acid sequence encoding Factor IX-CTP-CTP (attached to the carboxy terminus) comprises the following nucleic acid sequence:

(SEQ ID NO: 20)
gcgatcgccatgcagcgcgtgaacatgatcatggcagaatcaccaggcc tcatcaccatctgccttttaggatatctactcagtgctgaatgtacagt ttttcttgatcatgaaaacgccaacaaaattctgaatcggccaaagagg tataattcaggtaaattggaagagtttgttcaagggaaccttgagagag aatgtatggaagaaaagtgtagttttgaagaagcacgagaagtttttga aaacactgaaagaacaactgaattttggaagcagtatgttgatggagat cagtgtgagtccaatccatgtttaaatggcggcagttgcaaggatgaca ttaattcctatgaatgttggtgtccctttggatttgaaggaaagaactg tgaattagatgtaacatgtaacattaagaatggcagatgcgagcagttt tgtaaaaatagtgctgataacaaggtggtttgctcctgtactgagggat atcgacttgcagaaaccagaagtcctgtgaaccagcagtgccatttcc atgtggaagagtttctgtttcacaaacttctaagctcacccgtgctgag actgttttcctgatgtggactatgtaaattctactgaagctgaaacca ttttggataacatcactcaaagcacccaatcatttaatgacttcactcg agttgttggtggagaagatgccaaaccaggtcaattcccttggcaggtt gttttgaatggtaaagttgatgcattctgtggaggctctatcgttaatg aaaaatggattgtaactgctgcccactgtgttgaaactggtgttaaaat tacagttgtcgcaggtaacataatattgaggagacagaacatacagag caaaagcgaaatgtgattcgaattattcctcaccacaactacaatgcag ctattaataagtacaaccatgacattgcccttctggaactggacgaacc cttagtgctaaacagctacgttacacctatttgcattgctacaaggaat acacgaacatcttcctcaaatttggatctggctatgtaagtggctgggg aagagtcttccacaaagggagatcagctttagttcttcagtaccttaga gttccacttgttgaccgagccacatgtcttcgatctacaaagttcacca tctataacaacatgttctgtgctggcttccatgaaggaggtagagattc atgtcaaggagatagtgggggaccccatgttactgaagtggaagggacc agtttcttaactggaattattagctggggtgaagagtgtgcaatgaaag gcaaatatggaatatataccaaggtatcccggtatgtcaactggattaa ggaaaaaacaaagctcactagctccagcagcaaggcccctcccccgagc ctgccctccccaagcaggctgcctgggccctccgacacaccaatcctgc cacagagcagctcctctaaggcccctcctccatccctgccatcccctc ccggctgcctggccctctgacacccctatcctgcctcagtgatgaagg tctggatccgcggccgc.

In another embodiment, the amino acid sequence of Factor IX-CTP-CTP (attached to the carboxy terminus) comprises the following amino acid sequence:

(SEQ ID NO: 21)
MQRVNMIMAESPGLITICLLGYLLSAECTVFLDHENANKILNRPKRYNS

GKLEEFVQGNLERECMEEKCSFEEAREVFENTERTTEFWKQYVDGDQCE

SNPCLNGGSCKDDINSYECWCPFGFEGKNCELDVTCNIKNGRCEQFCKN

SADNKVVCSCTEGYRLAENQKSCEPAVPFPCGRVSVSQTSKLTRAETVF

PDVDYVNSTEAETILDNFTQSTQSFNDFTRVVGGEDAKPGQFPWQVVLN

GKVDAFCGGSIVNEKWIVTAAHCVETGVKITVVAGEHNIEETEHTEQKR

NVIRIIPHHNYNAAINKYNHDIALLELDEPLVLNSYVTPICIADKEYTN

IFLKFGSGYVSGWGRVFHKGRSALVLQYLRVPLVDRATCLRSTKFTIYN

NMFCAGFHEGGRDSCQGDSGGPHVTEVEGTSFLTGIISWGEECAMKGKY

GIYTKVSRYVNWIKEKTKLTSSSSKAPPPSLPSPSRLPGPSDTPILPQS

SSSKAPPPSLPSPSRLPGPSDTPILPQ**.

In another embodiment, the nucleic acid sequence encoding Factor IX-(CTP)₃ (attached to the carboxy terminus) comprises the following nucleic acid sequence:

(SEQ ID NO: 30)
tctagagtcgacccgccatgcagcgcgtgaacatgatcatggcagaat caccaggcctcatcaccatctgcctttaggatatctactcagtgctga atgtacagtttttcttgatcatgaaaacgccaacaaaattctgaatcgg ccaaagaggtataattcaggtaaattggaagagtttgttcaagggaacc ttgagagagaatgtatggaagaaaagtgtagttttgaagaagcacgaga agtttttgaaaacactgaaagaacaactgaattttggaagcagtatgtt gatggagatcagtgtgagtccaatccatgtttaaatggcggcagttgca aggatgacattaattcctatgaatgttggtgtccctttggatttgaagg aaagaactgtgaattagatgtaacatgtaacattaagaatggcagatgc gagcagtttttgtaaaaatagtgctgataacaaggtggtttgctcctgta ctgagggatatcgacttgcagaaaaccagaagtcctgtgaaccagcagt gccatttccatgtggaagagtttctgtttcacaaacttctaagctcacc cgtgctgaggcagttttcctgatgtggactatgtaaattctactgaag ctgaaaccatttggataacatcactcaaagcacccaatcatttaatga cttcactcgagttgttggtggagaagatgccaaaccaggtcaattccct tggcaggttgttttgaatggtaaagttgatgcattctgtggaggctcta tcgttaatgaaaaatggattgtaactgctgcccactgtgttgaaactgg tgttaaaattacagttgtcgcaggtgaacataatattgaggagacaaa catacagagcaaaagcgaaatgtgattcgaattattcctcaccacaact acaatgcagctattaataagtacaaccatgacattgcccttctggaact ggacgaacccttagtgctaaacagctacgttacacctatttgcattgct gacaaggaatacacgaacatcttcctcaaatttggatctggctatgtaa gtggctggggaagagtcttccacaaagggagatcagctttagttcttca gtaccttagagttccacttgttgaccgagccacatgtcttcgatctaca aagttcaccatctataacaacatgttctgtgctggcttccatgaaggag gtagagattcatgtcaaggagatagtgggggacccccatgttactgaagt ggaagggaccagtttcttaactggaattattagctggggtgaagagtgt gcaatgaaaggcaaatatggaatatataccaaggtatcccggtatgtca actggattaaggaaaaaacaaagctcactagctccagcagcaaggcccc tcccccgagcctgccctccccaagcaggctgcctgggcccagtgacacc cctatcctgcctcagtccagctccagcaaggccccaccccctagcctgc cttctccttctcggctgcctggcccccagcgatactccaattctgcccca gtcctccagcagtaaggctccccctccatctctgccatcccccagcaga ctgccaggcccttctgatacacccatcctcccacagtgatgaggatccg cggccgc.

In another embodiment, the amino acid sequence of Factor IX-(CTP)₃ (attached to the carboxy terminus) comprises the following amino acid sequence:

(SEQ ID NO: 31)
MQRVNMIMAESPGLITICLLGYLLSAECTVFLDHENANKILNRPKRYNS

GKLEEFVQGNLERECMEEKCSFEEAREVFENTERTTEFWKQYVDGDQCE

SNPCLNGGSCKDDINSYECWCPFGFEGKNCELDVTCNIKNGRCEQFCKN

SADNKVVCSCTEGYRLAENQKSCEPAVPFPCGRVSVSQTSKLTRAEAVF

PDVDYVNSTEAETILDNITQSTQSFNDFTRVVGGEDAKPGQFPWQVVLN

GKVDAFCGGSIVNEKWIVTAAHCVETGVKITVVAGEHNIEETEHTEQKR

NVIRIIPHHNYNAAINKYNHDIALLELDEPLVLNSYVTPICIADKEYTN

IFLKFGSGYVSGWGRVFHKGRSALVLQYLRVPLVDRATCLRSTKFTIYN

NMFCAGFHEGGRDSCQGDSGGPHVTEVEGTSFLTGIISWGEECAMKGKY

GIYTKVSRYVNWIKEKTKLTSSSSKAPPPSLPSPSRLPGPSDTPILPQS

SSSKAPPPSLPSPSRLPGPSDTPILPQSSSSKAPPPSLPSPSRLPGPSD

TPILPQ**.

In one embodiment, following expression and secretion, the N-terminal propeptide is cleaved from the precursor engineered CTP-modified coagulation factor FIX-CTP-CTP-CTP resulting in the mature engineered coagulation factor. For example, in SEQ ID NO: 31 presented above, amino acids 1-46 MQRVNMIMAESPGLITICLLGYLL-SAECTVFLDHENANKILNRPKR (SEQ ID NO: 49) represent an N-terminal propeptide of Factor IX-CTP-CTP-CTP, and amino acids 47-545 YNSGKLEEFVQGNLERECMEEKCSFEEAREVFEN-TERTTEFWKQYVDGDQCESNPCL NGGSCKDDIN-SYECWCPFGFEGKNCELDVTCNIKNGRCEQFCKN-SADNKVVCSCTE GYRLAENQKSCEPAVPFPCGRVSVSQTSKLTRA-EAVFPDVDYVNSTEAETILDNITQS TQSFND-FTRVVGGEDAKPGQFPWQVVLNGKVDAFCGG-SIVNEKWIVTAAHCVETGV KITVVAGEHNIEETEHTEQKRNVIRIIPHHNYNAAIN-KYNHDIALLELDEPLVLNSYVT PICIADKEYTNI-FLKFGSGYVSGWGRVFHKGR-SALVLQYLRVPLVDRATCLRSTKFTI YNNMFCAGFHEGGRDSCQGDSGGPHVTEVEG- TSFLTGIISWGEECAMKGKYGIYTK VSRYVNWIKEKTKLTSSSSKAPPPSLPSPSRLPGPSDT-PILPQSSSSKAPPPSLPSPSRLP GPSDTPIL-PQSSSSKAPPPSLPSPSRLPGPSDTPILPQ (SEQ ID NO: 48) represent the mature engineered coagulation factor lacking the N-terminal propeptide. In one embodiment, the amino acid sequence of Factor IX-CTP-CTP-CTP without the N-terminal propeptide is set forth in SEQ ID NO: 48. In another embodiment, the N-terminal propeptide of Factor IX-CTP-CTP-CTP is set forth in SEQ ID NO: 49.

In another embodiment, the nucleic acid sequence encoding Factor IX-(CTP)$_4$ (attached to the carboxy terminus) comprises the following nucleic acid sequence:

(SEQ ID NO: 32)
tctagagtcgaccccgccatgcagcgcgtgaacatgatcatggcagaat caccaggcctcatcaccatctgccttttaggatatctactcagtgctga atgtacagttttcttgatcatgaaaacgccaacaaaattctgaatcgg ccaaagaggtataattcaggtaaattggaagagtttgttcaagggaacc ttgagagagaatgtatggaagaaaagtgtagttttgaagaagcacgaga agttttgaaaacactgaaagaacaactgaattttggaagcagtatgtt gatggagatcagtgtgagtccaatccatgtttaaatggcggcagttgca aggatgacattaattcctatgaatgttggtgtcccttggatttgaagg aaagaactgtgaattagatgtaacatgtaacattaagaatggcagatgc gagcagttttgtaaaaatagtgctgataacaaggtggtttgctcctgta ctgagggatatcgacttgcagaaaaccagaagtcctgtgaaccagcagt gccatttccatgtgaagagtttctgtttcacaaacttctaagctcacc cgtgctgaggcagttttcctgatgtggactatgtaaattctactgaag ctgaaaccattttggataacatcactcaaagcacccaatcatttaatga cttcactcgagttgttggtggagaagatgccaaaccaggtcaattccct tggcaggttgttttgaatggtaaagttgatgcattctgtggaggctcta tcgttaatgaaaaatggattgtaactgctgcccactgtgttgaaactgg tgttaaaattacagttgtcgcaggtgaacataatattgaggagacgaa catccagagcaaaagcgaaatgtgattcgaattattcctcaccacaact acaatgcagctattaataagtacaaccatgacattgcccttctggaact ggacgaaccctagtgctaaacagctacgttacacctatttgcattgct gacaaggaatacacgaacatcttcctcaaatttggatctggctatgtaa gtggctggggaagagtcttccacaaagggagatcagctttagttcttca gtacttagagttccacttgttgaccgagccacatgtcttcgatctaca aagttcaccatctataacaacatgttctgtgctggcttccatgaaggag gtagagattcatgtcaaggagatagtgggggaccccatgttactgaagt ggaagggaccagtttcttaactggaattattagctggggtgaagagtgt gcaatgaaaggcaaatatggaatatataccaaggtatcccggtatgtca actggattaaggaaaaaacaaagctcactagctccagcagcaaggcccc tccccgagcctgccctccccaagcaggctgcctgggccctctgacacc cctatcctgcctcagtccagctcctctaaggcccaccacttccctgc -continued
ctagcccttcaagactgccaggccctagcgatacaccaattctgcccca gtcctccagcagcaaggctcccccacctagcctgccttctccatcaagg ctgcctggcccatccgataccccaattttgcctcagagcagctctagca aggcacctcccccagtctgccctctccaagcagactccctggcccttc agacactcccattctgccacagtgatgaggatccgcggccgc.

In another embodiment, the amino acid sequence of Factor IX-(CTP)$_4$ (attached to the carboxy terminus) comprises the following amino acid sequence:

(SEQ ID NO: 33)
SRVDPAMQRVNMIMAESPGLITICLLGYLLSAECTVFLDHENANKILNR

PKRYNSGKLEEFVQGNLERECMEEKCSFEEAREVFENTERTTEFWKQYV

DGDQCESNPCLNGGSCKDDINSYECWCPFGFEGKNCELDVTCNIKMGRC

EQFCKNSADNKVVCSCTEGYRLAENQKSCEPAVPFPCGRVSVSQTSKLT

RAEAVFPDVDYVNSTEAETILDNITQSTQSFNDFTRVVGGEDAKPGQFP

WQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIA

DKEYTNIFLKFGSGYVSGWGRVFHKGRSALVLQYLRVPLVDRATCLRST

KFTIYNNMFCAGFHEGGRDSCQGDSGGPHVTEVEGTSFLTGIISWGEEC

AMKGKYGIYTKVSRYVNWIKEKTKLTSSSSKAPPPSLPSPSRILGPSDT

PILPQSSSSKAPPPSLPSPSRLPGPSDTPILPQSSSSKAPPPSLPSPSR

LPGPSDTPILPQSSSSKAPPPSLPSPSRLGPSDTPILPQ**GSAA.

In another embodiment, the nucleic acid sequence encoding Factor IX-(CTP)$_5$ (attached to the carboxy terminus) comprises the following nucleic acid sequence:

(SEQ ID NO: 34)
ctagagtcgacccgccatgcagcgcgtgaacatgatcatggcagaatc accaggcctcatcaccatctgccttttaggatatctactcagtgctgaa tgtacagttttcttgatcatgaaaacgccaacaaaattctgaatcggc caaagaggtataattcaggtaaattggaagagtttgttcaagggaacct tgagagagaatgtatggaagaaaagtgtagttttgaagaagcacgagaa gttttgaaaacactgaaagaacaactgaattttggaagcagtatgttg atggagatcagtgtgagtccaatccatgtttaaatggcggcagttgcaa ggatgacattaattcctatgaatgttggtgtcccttggatttgaagga agaactgtgaattagatgtaacatgtaacattaagaatggcagatgcg agcagttttgtaaaaatagtgctgataacaaggtggtttgctcctgtac tgagggatatcgacttgcagaaaaccagaagtcctgtgaaccagcagtg ccatttccatgtgaagagtttctgtttcacaaacttctaagctcaccc gtgctgaggcagttttcctgatgtggactatgtaaattctactgaagc tgaaaccattttggataacatcactcaaagcacccaatcatttaatgac ttcactcgagttgttggtggagaagatgccaaaccaggtcaattccctt ggcaggttgttttgaatggtaaagttgatgcattctgtggaggctctat cgttaatgaaaaatggattgtaactgctgcccactgtgttgaaactggt -continued

```
gttaaaattacagttgtcgcaggtgaacataatattgaggagacagaac
atacagagcaaaagcgaaatgtgattcgaattattcctcaccacaacta
caatgcagctattaataagtacaaccatgacattgcccttctggaactg
gacgaacccttagtgctaaacagctacgttacacctatttgcattgctg
acaaggaatacacgaacatcttcctcaaatttggatctggctatgtaag
tggctggggaagagtcttccacaaaggggagatcagctttagttcttcag
taccttagagttccacttgttgaccgagccacatgtcttcgatctacaa
agttcaccatctataacaacatgttctgtgctggcttccatgaaggagg
tagagattcatgtcaaggagatagtgggggacccccatgttactgaagtg
gaagggaccagtttcttaactggaattattagctggggtgaagagtgtg
caatgaaaggcaaatatggaatatataccaaggtatcccggtatgtcaa
ctggattaaggaaaaaacaaagctcactagctccagcagcaaggcccct
cccccgagcctgccctcccaagcaggctgcctgggccctctgacaccc
ctatcctgcctcagtccagctcctctaaggctccaccaccttccctgcc
tagcccttcaagactgccaggccctagcgataccaattctgcccag
tcctccagcagcaaggctcccccacctagcctgccttctccatcaaggc
tgcctggcccatccgataccccaattttgcctcagagcagctctagcaa
ggcacctcccccagtctgccctctccaagcagactccctggccttca
gacactccaatcctcccacagtcctctagctctaaagctccacctccca
gcctgcccagccctagtagactccccggaccttctgataccccatctt
gccccagtgatgaggatccgcggccgc.
```

In another embodiment, the amino acid sequence of Factor IX-(CTP). (attached to the carboxy terminus) comprises the following amino acid sequence:

```
                                      (SEQ ID NO: 35)
RVDPAMQRVNMIMAESPGLITICLLGYLLSAECTVFLDHENANKILNRP
KRYNSGRLEEFVQGNLERECMEEKCSFEEAREVFENTERTTEFWKQYVD
GDQCESNPCLNGGSCKDDINSYECWCPFGFEGKNCELDVTCNIKNGRCE
QFCKNSADNKVVCSCTEGYRLAENQKSCEPAVPFPCGRVSVSQTSKLTR
AEAVFPDVDYVNSTEAETILDNITQSTQSFNDFTRVVGGEDAKPGQFPW
QVVLNGKVDAFCGGSIVNEKWIVTAAHCVETGVKITVVAGEHNIEETEH
TEQKRNVIRIIPHHNYNAAINKYNHDIALLELDEPLVLNSYVTPICIAD
KEYTNIFLKFGSGYVSGWGRVFHKGRSALVLQYLRVPLVDRATCLRSTK
FTIYNNMFCAGFHEGGRDSCQGDSGGPHVTEVEGTSFLTGIISWGEECA
MKGKYGIYTKVSRYVNWIKEKTKLTSSSSKAPPPSLPSPSRLPGPSDTP
ILPQSSSSKAPPPSLPSPSRLPGPSDTPILPQSSSSKAPPPSLPSPSRL
PGPSDTPILPQSSSSKAPPPSLPSPSRLPGPSDTPILPQSSSSKAPPPS
LPSPSRLPGPSDTPILPQ**GSAA.
```

In another embodiment, furin is added to a cell expressing the coagulation factor-CTP of the invention. In another embodiment, furin increases the production efficiency of a coagulation factor-CTP of the invention in a cell. In another embodiment, furin is co-transfected with the vector comprising the coding sequence of the coagulation factor-CTP of the invention. In another embodiment, furin is encoded by a separate vector. In another embodiment, furin and a coagulation factor-CTP are encoded by one vector. In another embodiment, the coding sequence of furin is inserted into pCI-DHFR. In another embodiment, the coding sequence of furin is engineered in pCI-dhfr/smaI+NotI, Furin/AsisI F.I.+NotI.

In another embodiment, the nucleic acid sequence encoding furin comprises the following nucleic acid sequence:

```
                                      (SEQ ID NO: 22)
tctagagtcgaccccgccatggagctgagggccctggttgctatgggtgg
tagcagcaacaggaaccttggtcctgctagcagctgatgctcagggcca
gaaggtcttcaccaacacgtgggctgtgcgcatccctggagcccagcg
gtggccaacagtgtggcacggaagcatgggttcctcaacctgggccaga
tcttcggggactattaccacttctggcatcgaggagtgacgaagcggtc
cctgtcgcctcaccgcccgcggcacagccggctgcagagggagcctcaa
gtacagtggctggaacagcaggtggcaaagcgacggactaaacgggacg
tgtaccaggagcccacagaccccaagtttcctcagcagtggtacctgtc
tggtgtcactcagcgggacctgaatgtgaaggcggcctgggcgcagggc
tacacagggcacggcattgtggtctccattctggacgatggcatcgaga
gaaccacccggacttggcaggcaattatgatcctggggccagttttga
tgtcaatgaccaggaccctgaccccagcctcggtacacacagatgaat
gacaacaggcacggcacacggtgtgcggggaagtggctgcggtggcca
acaacggtgtctgtggtgtaggtgtggcctacaacgcccgcattggagg
ggtgcgcatgctggatggcgaggtgacagatgcagtggaggcacgctcg
ctgggcctgaaccccaaccacatccacatctacagtgccagctggggcc
ccgaggatgacggcaagacagtggatgggccagcccgcctcgccgagga
ggccttcttccgtggggttagccagggccgaggggggctgggctccatc
tttgtctgggcctcggggaacggggggcgggaacatgacagctgcaact
gcgacggctacaccaacagtatctacacgctgtccatcagcagcgccac
gcagtttggcaacgtgccgtggtacagcgaggcctgctcgtccacactg
gccacgacctacagcagtggcaaccagaatgagaagcagatcgtgacga
ctgacttgcggcagaagtgcacggagtctcacacgggcacctcagcctc
tgccccttagcagccggcatcattgctctcaccctggaggccaataag
aacctcacatggcgggacatgcaacacctggtgtacagacctcgaagc
cagcccacctcaatgccaacgactgggccaccaatggtgtgggccggaa
agtgagccactcatatggctacgggcttttggacgcaggcgccatggtg
gccctggcccagaattggaccacagtggcccccagcggaagtgcatca
tcgacatcctcaccgagcccaaagacatcgggaaacggctcgaggtgcg
gaagaccgtgaccgcgtgcctgggcgagcccaaccacatcactcggctg
gagcacgctcaggcgggctcaccctgtcctataatcgccgtggcgacc
tggccatccacctggtcagccccatgggcacccgctccaccctgctggc
agccaggccacatgactactccgcagatgggtttaatgactgggccttc
```

```
-continued
atgacaactcattcctgggatgaggatccctctggcgagtgggtcctag agattgaaaacaccagcgaagccaacaactatgggacgctgaccaagtt caccctcgtactctatggcaccgccctgaggggctgcccgtacctcca gaaagcagtggctgcaagaccctcacgtccagtcaggcctgtgtggtgt gcgaggaaggcttctccctgcaccagaagagctgtgtccagcactgccc tccaggcttcgcccccaagtcctcgatacgcactatagcaccgagaat gacgtggagaccatccgggccagcgtctgcgcccctgccacgcctcat gtgccacatgccaggggccggccctgacagactgcctcagctgcccag ccacgcctccttggaccctgtggagcagacttgctccggcaaagccag agcagccgagagtccccgccacagcagcagccacctcggctgccccgg aggtggaggcggggcaacggctgcgggcagggctgctgccctcacacct gcctgaggtggtggccggcctcagctgcgccttcatcgtgctggtcttc gtcactgtcttcctggtcctgcagctgcgctctggctttagtttcggg gggtgaaggtgtacaccatggaccgtggcctcatctcctacaaggggct gccccctgaagcctggcaggaggagtgcccgtctgactcagaagaggac gagggccggggcgagaggaccgcctttatcaaagaccagagcgccctct gaacgcggccgc.
```

In another embodiment, the amino acid sequence of furin comprises the following amino acid sequence:

(SEQ IP NO: 23)
MELRPWLLWVVAATGTLVLLAADAQGQKVFTNTWAVRIPGGPAVANSVA

RKHGFLNLGQIFGDYYHFWHRGVTKRSLSPHRPRHSRLQREPQVQWLEQ

QVAKRRTKRDVYQEPTDPKFPQQWYLSGVTQRDLNVKAAWAQGYTGHGI

VVSILDDGIEKNHPDLAGNYDPGASFDVNDQDPDPQPRYTQMNDNRHGT

RCAGEVAAVANNGVCGVGVAYNARIGGVRMLDGEVTDAVEARSLGLNPN

HIHIYSASWGPEDDGKTVDGPARLAEEAFFRGVSQGRGGLGSIFVWASG

NGGREHDSCNCDGYTNSIYTLSISSATQFGNVPWYSEACSSTLATTYSS

GNQNEKQIVTTDLRQKCTESHTGTSASAPLAAGIIALTLEANKNLTWRD

MQHLVVQTSKPAHLNANDWATNGVGRKVSHSYGYGLLDAGAMVALAQNW

TTVAPQRKCIIDILTEPKDIGKRLEVRKTVTACLGEPNFHTRLEHAQAR

LTLSYNRRGDLAIHLVSPMGTRSTLLAARPHDYSADGFNDWAFMTTHSW

DEDPSGEWVLEIENTSEANNYGTLTKFTLVLYGTAPEGLPVPPESSGCK

TLTSSQACVVCEEGFSLHQKSCVQHCPPGFAPQVLDTHYSTENDVETIR

ASVCAPCHASCATCQGPALTDCLSCPSHASLDPVEQTCSRQSQSSRESP

PQQQPPRLPPEVEAGQRLRAGLLPSHLPEVVAGLSCAFIVLVFVTVFLV

LQLRSGFSFRGVKVYTMDRGLISYKGLPPEAWQEECPSDSEEDEGRGER

TAFIKDQSAL*.

In one embodiment, the term coagulation factor further includes a homologue of a known coagulation factor. In one embodiment, the homologue has a coagulating activity. In some embodiments, homology according to the present invention also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three dimensional structure of the coagulation factor. In another embodiment, the deletion, insertion, or substitution does not alter the function of interest of the coagulation factor, which in one embodiment, is binding to a particular binding partner.

In another embodiment, the invention includes a homologue of a coagulation factor. In another embodiment, the invention includes a homologue of a coagulation factor having a coagulation activity. In another embodiment, the invention includes a homologue of a coagulation factor having functional binding. In another embodiment, the invention includes homologues of a coagulation factor as described herein having a coagulation activity. In another embodiment, the invention includes homologues of a coagulation factor as described herein having functional binding. In another embodiment, homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a coagulation factor as determined using BlastP software of the National Center of Biotechnology Information (NCBI) using default parameters.

In another embodiment, the invention includes homologues of furin. In another embodiment, the invention includes homologues of furin maintaining a function of interest, which in one embodiment is cleaving of a precursor protein. In another embodiment, homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a furin as determined using BlastP software of the National Center of Biotechnology Information (NCBI) using default parameters.

In another embodiment, provided herein is a polypeptide comprising a coagulation factor and one to ten gonadotrophin carboxy terminal peptides (CTPs) attached to the carboxy terminus of the coagulation factor. In another embodiment, provided herein is a polypeptide comprising a coagulation factor and one to three gonadotrophin carboxy terminal peptides (CTPs) attached to the carboxy terminus of the coagulation factor. In another embodiment, provided herein is a polypeptide comprising a coagulation factor and one to five gonadotrophin carboxy terminal peptides (CTPs) attached to the carboxy terminus of the coagulation factor. In another embodiment, provided herein is a polypeptide comprising a coagulation factor having at least one CTP on its carboxy terminus.

In another embodiment, provided herein is a polypeptide consisting of a coagulation factor and one to five gonadotrophin carboxy terminal peptides (CTPs) attached to the carboxy terminus of the coagulation factor.

In another embodiment, provided herein is a polypeptide consisting essentially of a coagulation factor and one to five CTPs attached to the carboxy terminus of the coagulation factor.

It is to be understood that the compositions and methods of the present invention comprising the elements or steps as described herein may, in another embodiment, consist of those elements or steps, or in another embodiment, consist essentially of those elements or steps. In some embodiments, the term "comprise" refers to the inclusion of the indicated active agent, such as the CTP-modified coagulation factor, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides a polypeptide comprising a coagulation factor and two gonadotrophin carboxy terminal peptides (CTPs) attached to the carboxy terminus of the coagulation factor. In another embodiment, provided herein is a polypeptide comprising a coagulation factor and two to three CTPs attached to the carboxy terminus of the coagulation factor. In another embodiment, provided herein is a polypeptide comprising a coagulation factor and two to four CTPs attached to the carboxy terminus of the coagulation factor. In another embodiment, provided herein is a polypeptide comprising a coagulation factor and two to five CTPs attached to the carboxy terminus of the coagulation factor. In another embodiment, provided herein is a polypeptide comprising a coagulation factor and two to six CTPs attached to the carboxy terminus of the coagulation factor. In another embodiment, provided herein is a polypeptide comprising a coagulation factor and two to seven CTPs attached to the carboxy terminus of the coagulation factor. In another embodiment, provided herein is a polypeptide comprising a coagulation factor and two to eight CTPs attached to the carboxy terminus of the coagulation factor. In another embodiment, provided herein is a polypeptide comprising a coagulation factor and two to nine CTPs attached to the carboxy terminus of the coagulation factor. In another embodiment, provided herein is a polypeptide comprising a coagulation factor and two to ten CTPs attached to the carboxy terminus of the coagulation factor.

In one embodiment, the present invention provides a polypeptide comprising a coagulation factor and three gonadotrophin carboxy terminal peptides (CTPs) attached to the carboxy terminus of the coagulation factor. In another embodiment, provided herein is a polypeptide comprising a coagulation factor and three to four CTPs attached to the carboxy terminus of the coagulation factor. In another embodiment, provided herein is a polypeptide comprising a coagulation factor and three to five CTPs attached to the carboxy terminus of the coagulation factor. In another embodiment, provided herein is a polypeptide comprising a coagulation factor and three to six CTPs attached to the carboxy terminus of the coagulation factor. In another embodiment, provided herein is a polypeptide comprising a coagulation factor and three to seven CTPs attached to the carboxy terminus of the coagulation factor. In another embodiment, provided herein is a polypeptide comprising a coagulation factor and three to eight CTPs attached to the carboxy terminus of the coagulation factor. In another embodiment, provided herein is a polypeptide comprising a coagulation factor and three to nine CTPs attached to the carboxy terminus of the coagulation factor. In another embodiment, provided herein is a polypeptide comprising a coagulation factor and three to ten CTPs attached to the carboxy terminus of the coagulation factor.

In one embodiment, the present invention provides a polypeptide comprising a coagulation factor and four gonadotrophin carboxy terminal peptides (CTPs) attached to the carboxy terminus of the coagulation factor. In another embodiment, provided herein is a polypeptide comprising a coagulation factor and four to five CTPs attached to the carboxy terminus of the coagulation factor. In another embodiment, provided herein is a polypeptide comprising a coagulation factor and four to six CTPs attached to the carboxy terminus of the coagulation factor. In another embodiment, provided herein is a polypeptide comprising a coagulation factor and four to seven CTPs attached to the carboxy terminus of the coagulation factor. In another embodiment, provided herein is a polypeptide comprising a coagulation factor and four to eight CTPs attached to the carboxy terminus of the coagulation factor. In another embodiment, provided herein is a polypeptide comprising a coagulation factor and four to nine CTPs attached to the carboxy terminus of the coagulation factor. In another embodiment, provided herein is a polypeptide comprising a coagulation factor and four to ten CTPs attached to the carboxy terminus of the coagulation factor.

In one embodiment, the present invention provides a polypeptide comprising a coagulation factor and five gonadotrophin carboxy terminal peptides (CTPs) attached to the carboxy terminus of the coagulation factor. In another embodiment, provided herein is a polypeptide comprising a coagulation factor and five to six CTPs attached to the carboxy terminus of the coagulation factor. In another embodiment, provided herein is a polypeptide comprising a coagulation factor and five to seven CTPs attached to the carboxy terminus of the coagulation factor. In another embodiment, provided herein is a polypeptide comprising a coagulation factor and five to eight CTPs attached to the carboxy terminus of the coagulation factor. In another embodiment, provided herein is a polypeptide comprising a coagulation factor and five to nine CTPs attached to the carboxy terminus of the coagulation factor. In another embodiment, provided herein is a polypeptide comprising a coagulation factor and five to ten CTPs attached to the carboxy terminus of the coagulation factor.

In one embodiment, the present invention provides a polypeptide consisting of a coagulation factor and two gonadotrophin carboxy terminal peptides (CTPs) attached to the carboxy terminus of the coagulation factor. In another embodiment, provided herein is a polypeptide consisting of a coagulation factor and two to three CTPs attached to the carboxy terminus of the coagulation factor. In another embodiment, provided herein is a polypeptide consisting of a coagulation factor and two to four CTPs attached to the carboxy terminus of the coagulation factor. In another embodiment, provided herein is a polypeptide consisting of a coagulation factor and two to five CTPs attached to the carboxy terminus of the coagulation factor. In another embodiment, provided herein is a polypeptide consisting of a coagulation factor and two to six CTPs attached to the carboxy terminus of the coagulation factor. In another embodiment, provided herein is a polypeptide consisting of a coagulation factor and two to seven CTPs attached to the carboxy terminus of the coagulation factor. In another embodiment, provided herein is a polypeptide consisting of a coagulation factor and two to eight CTPs attached to the carboxy terminus of the coagulation factor. In another embodiment, provided herein is a polypeptide consisting of a coagulation factor and two to nine CTPs attached to the carboxy terminus of the coagulation factor. In another embodiment, provided herein is a polypeptide consisting of a coagulation factor and two to ten CTPs attached to the carboxy terminus of the coagulation factor.

In one embodiment, the present invention provides a polypeptide consisting of a coagulation factor and three gonadotrophin carboxy terminal peptides (CTPs) attached to the carboxy terminus of the coagulation factor. In another embodiment, provided herein is a polypeptide consisting of a coagulation factor and three to four CTPs attached to the carboxy terminus of the coagulation factor. In another embodiment, provided herein is a polypeptide consisting of a coagulation factor and three to five CTPs attached to the carboxy terminus of the coagulation factor. In another embodiment, provided herein is a polypeptide consisting of a coagulation factor and three to six CTPs attached to the carboxy terminus of the coagulation factor. In another embodiment, provided herein is a polypeptide consisting of a coagulation factor and three to seven CTPs attached to the carboxy terminus of the coagulation factor. In another embodiment, provided herein is a polypeptide consisting of a coagulation factor and three to eight CTPs attached to the carboxy terminus of the coagulation factor. In another embodiment, provided herein is a polypeptide consisting of a coagulation factor and three to nine CTPs attached to the carboxy terminus of the coagulation factor. In another embodiment, provided herein is a polypeptide consisting of a coagulation factor and three to ten CTPs attached to the carboxy terminus of the coagulation factor.

In one embodiment, the present invention provides a polypeptide consisting of a coagulation factor and four gonadotrophin carboxy terminal peptides (CTPs) attached to the carboxy terminus of the coagulation factor. In another embodiment, provided herein is a polypeptide consisting of a coagulation factor and four to five CTPs attached to the carboxy terminus of the coagulation factor. In another embodiment, provided herein is a polypeptide consisting of a coagulation factor and four to six CTPs attached to the carboxy terminus of the coagulation factor. In another embodiment, provided herein is a polypeptide consisting of a coagulation factor and four to seven CTPs attached to the carboxy terminus of the coagulation factor. In another embodiment, provided herein is a polypeptide consisting of a coagulation factor and four to eight CTPs attached to the carboxy terminus of the coagulation factor. In another embodiment, provided herein is a polypeptide consisting of a coagulation factor and four to nine CTPs attached to the carboxy terminus of the coagulation factor. In another embodiment, provided herein is a polypeptide consisting of a coagulation factor and four to ten CTPs attached to the carboxy terminus of the coagulation factor.

In one embodiment, the present invention provides a polypeptide consisting of a coagulation factor and five gonadotrophin carboxy terminal peptides (CTPs) attached to the carboxy terminus of the coagulation factor. In another embodiment, provided herein is a polypeptide consisting of a coagulation factor and five to six CTPs attached to the carboxy terminus of the coagulation factor. In another embodiment, provided herein is a polypeptide consisting of a coagulation factor and five to seven CTPs attached to the carboxy terminus of the coagulation factor. In another embodiment, provided herein is a polypeptide consisting of a coagulation factor and five to eight CTPs attached to the carboxy terminus of the coagulation factor. In another embodiment, provided herein is a polypeptide consisting of a coagulation factor and five to nine CTPs attached to the carboxy terminus of the coagulation factor. In another embodiment, provided herein is a polypeptide consisting of a coagulation factor and five to ten CTPs attached to the carboxy terminus of the coagulation factor.

In one embodiment, the present invention provides a polypeptide consisting essentially of a coagulation factor and two gonadotrophin carboxy terminal peptides (CTPs) attached to the carboxy terminus of the coagulation factor. In another embodiment, provided herein is a polypeptide consisting essentially of a coagulation factor and two to three CTPs attached to the carboxy terminus of the coagulation factor. In another embodiment, provided herein is a polypeptide consisting essentially of a coagulation factor and two to four CTPs attached to the carboxy terminus of the coagulation factor. In another embodiment, provided herein is a polypeptide consisting essentially of a coagulation factor and two to five CTPs attached to the carboxy terminus of the coagulation factor. In another embodiment, provided herein is a polypeptide consisting essentially of a coagulation factor and two to six CTPs attached to the carboxy terminus of the coagulation factor. In another embodiment, provided herein is a polypeptide consisting essentially of a coagulation factor and two to seven CTPs attached to the carboxy terminus of the coagulation factor. In another embodiment, provided herein is a polypeptide consisting essentially of a coagulation factor and two to eight CTPs attached to the carboxy terminus of the coagulation factor. In another embodiment, provided herein is a polypeptide consisting essentially of a coagulation factor and two to nine CTPs attached to the carboxy terminus of the coagulation factor. In another embodiment, provided herein is a polypeptide consisting essentially of a coagulation factor and two to ten CTPs attached to the carboxy terminus of the coagulation factor.

In one embodiment, the present invention provides a polypeptide consisting essentially of a coagulation factor and three gonadotrophin carboxy terminal peptides (CTPs) attached to the carboxy terminus of the coagulation factor. In another embodiment, provided herein is a polypeptide consisting essentially of a coagulation factor and three to four CTPs attached to the carboxy terminus of the coagulation factor. In another embodiment, provided herein is a polypeptide consisting essentially of a coagulation factor and three to five CTPs attached to the carboxy terminus of the coagulation factor. In another embodiment, provided herein is a polypeptide consisting essentially of a coagulation factor and three to six CTPs attached to the carboxy terminus of the coagulation factor. In another embodiment, provided herein is a polypeptide consisting essentially of a coagulation factor and three to seven CTPs attached to the carboxy terminus of the coagulation factor. In another embodiment, provided herein is a polypeptide consisting essentially of a coagulation factor and three to eight CTPs attached to the carboxy terminus of the coagulation factor. In another embodiment, provided herein is a polypeptide consisting essentially of a coagulation factor and three to nine CTPs attached to the carboxy terminus of the coagulation factor. In another embodiment, provided herein is a polypeptide consisting essentially of a coagulation factor and three to ten CTPs attached to the carboxy terminus of the coagulation factor.

In one embodiment, the present invention provides a polypeptide consisting essentially of a coagulation factor and four gonadotrophin carboxy terminal peptides (CTPs) attached to the carboxy terminus of the coagulation factor. In another embodiment, provided herein is a polypeptide consisting essentially of a coagulation factor and four to five CTPs attached to the carboxy terminus of the coagulation factor. In another embodiment, provided herein is a polypeptide consisting essentially of a coagulation factor and four to six CTPs attached to the carboxy terminus of the coagulation factor. In another embodiment, provided herein is a polypeptide consisting essentially of a coagulation factor and four to seven CTPs attached to the carboxy terminus of the coagulation factor. In another embodiment, provided herein is a polypeptide consisting essentially of a coagulation factor and four to eight CTPs attached to the carboxy terminus of the coagulation factor. In another embodiment, provided herein is a polypeptide consisting essentially of a coagulation factor and four to nine CTPs attached to the carboxy terminus of the coagulation factor. In another embodiment, provided herein is a polypeptide consisting essentially of a coagulation factor and four to ten CTPs attached to the carboxy terminus of the coagulation factor.

In one embodiment, the present invention provides a polypeptide consisting essentially of a coagulation factor and five gonadotrophin carboxy terminal peptides (CTPs) attached to the carboxy terminus of the coagulation factor. In another embodiment, provided herein is a polypeptide consisting essentially of a coagulation factor and five to six CTPs attached to the carboxy terminus of the coagulation factor. In another embodiment, provided herein is a polypeptide consisting essentially of a coagulation factor and five to seven CTPs attached to the carboxy terminus of the coagulation factor. In another embodiment, provided herein is a polypeptide consisting essentially of a coagulation factor and five to eight CTPs attached to the carboxy terminus of the coagulation factor. In another embodiment, provided herein is a polypeptide consisting essentially of a coagulation factor and five to nine CTPs attached to the carboxy terminus of the coagulation factor. In another embodiment, provided herein is a polypeptide consisting essentially of a coagulation factor and five to ten CTPs attached to the carboxy terminus of the coagulation factor.

In another embodiment, provided herein is a polypeptide comprising, consisting essentially of, or consisting of a coagulation factor having no CTPs on its amino terminus. In another embodiment, provided herein is a polypeptide comprising, consisting essentially of, or consisting of a coagulation factor lacking a CTP on its amino terminus. In another embodiment, provided herein is a polypeptide comprising, consisting essentially of, or consisting of a coagulation factor having at least one CTP on its carboxy terminus and no CTPs on its amino terminus. In another embodiment, provided herein is a polypeptide comprising, consisting essentially of, or consisting of a coagulation factor having the number of CTPs on its carboxy terminus as described herein and no CTPs on its amino terminus.

In another embodiment, the present invention provides a polynucleotide encoding a polypeptide as described hereinabove.

In another embodiment, the present invention further provides a composition comprising an expression vector comprising a polynucleotide encoding a CTP-modified polypeptide consisting of a Factor IX (FIX) polypeptide and three gonadotropin carboxy terminal peptides (CTPs) attached to the carboxy terminus of said FIX polypeptide.

In another embodiment, the present invention further provides a polynucleotide encoding a CTP-modified polypeptide consisting of a Factor VIIa (FVIIa) polypeptide and three gonadotropin carboxy terminal peptides (CTPs) attached to the carboxy terminus of said FVIIa polypeptide.

In one embodiment, the present invention provides a recombinant coagulation factor as described hereinabove. In one embodiment, the present invention provides an engineered coagulation factor as described hereinabove. In one embodiment, the engineered coagulation factor as described hereinabove is referred to as a CTP-modified coagulation factor.

In one embodiment, the CTPs that are attached to the carboxy terminus of the coagulation factor are attached in tandem to the carboxy terminus.

In one embodiment, an engineered coagulation factor as described herein has equivalent or improved biological activity compared to the non-CTP-modified coagulation factor. In another embodiment, an engineered coagulation factor as described herein has equivalent or improved pharmacological measurements compared to the non-CTP-modified coagulation factor. In another embodiment, an engineered coagulation factor as described herein has equivalent or improved pharmacokinetics compared to the non-CTP-modified coagulation factor. In another embodiment, an engineered coagulation factor as described herein has equivalent or improved pharmacodynamics compared to the non-CTP-modified coagulation factor.

In one embodiment, the present invention provides a cell comprising an expression vector comprising a polynucleotide encoding a CTP-modified polypeptide consisting of a Factor VII (FVII) polypeptide and three to five gonadotropin carboxy terminal peptides (CTPs) attached to the carboxy terminus of said FVII polypeptide. In another embodiment, the present invention provides a cell comprising an expression vector comprising a polynucleotide encoding a CTP-modified polypeptide consisting of a Factor VII (FVII) polypeptide and three gonadotropin carboxy terminal peptides (CTPs) attached to the carboxy terminus of said FVII polypeptide. In another embodiment, the present invention provides a cell comprising an expression vector comprising a polynucleotide encoding a CTP-modified polypeptide consisting of a Factor VII (FVII) polypeptide and five gonadotropin carboxy terminal peptides (CTPs) attached to the carboxy terminus of said FVII polypeptide.

In one embodiment, the term "three to five" when referring to gonadotropin carboxy terminal peptides (CTPs), refers to attaching three, four, or five CTPs to the carboxy terminal of a coagulation factor polypeptide provided herein In one embodiment, the present invention provides a composition comprising an expression vector comprising a polynucleotide encoding a CTP-modified polypeptide consisting of a Factor VII (FVII) polypeptide and three to five gonadotropin carboxy terminal peptides (CTPs) attached to the carboxy terminus of said FVII polypeptide. In another embodiment, the present invention provides a composition comprising an expression vector comprising a polynucleotide encoding a CTP-modified polypeptide consisting of a Factor VII (FVII) polypeptide and three gonadotropin carboxy terminal peptides (CTPs) attached to the carboxy terminus of said FVII polypeptide. In another embodiment, the present invention provides a composition comprising an expression vector comprising a polynucleotide encoding a CTP-modified polypeptide consisting of a Factor VII (FVII) polypeptide and five gonadotropin carboxy terminal peptides (CTPs) attached to the carboxy terminus of said FVII polypeptide.

In one embodiment, the present invention provides a method of extending the biological half-life of a Factor VII (FVII) polypeptide, comprising the step of attaching three to five chorionic gonadotrophin carboxy terminal peptides (CTPs) to the carboxy terminus of said FVII polypeptide, thereby extending the biological half-life of said FVII polypeptide. In another embodiment, the present invention provides a method of extending the biological half-life of a Factor VII (FVII) polypeptide, comprising the step of attaching three chorionic gonadotrophin carboxy terminal peptides (CTPs) to the carboxy terminus of said FVII polypeptide, thereby extending the biological half-life of said FVII polypeptide. In another embodiment, the present invention provides a method of extending the biological half-life of a Factor VII (FVII) polypeptide, comprising the step of attaching five chorionic gonadotrophin carboxy terminal peptides (CTPs) to the carboxy terminus of said FVII polypeptide, thereby extending the biological half-life of said FVI polypeptide.

In another embodiment, the present invention provides a method of improving the area under the curve (AUC) of a Factor VII (FVII) polypeptide, comprising the step of attaching three to five chorionic gonadotrophin carboxy terminal peptides (CTPs) to the carboxy terminus of said FVII polypeptide, thereby improving the AUC of said FVII polypeptide. In another embodiment, the present invention provides a method of improving the area under the curve (AUC) of a Factor VII (FVII) polypeptide, comprising the step of attaching three chorionic gonadotrophin carboxy terminal peptides (CTPs) to the carboxy terminus of said FVII polypeptide, thereby improving the AUC of said FVII polypeptide. In another embodiment, the present invention provides a method of improving the area under the curve (AUC) of a Factor VII (FVII) polypeptide, comprising the step of attaching five chorionic gonadotrophin carboxy terminal peptides (CTPs) to the carboxy terminus of said FVII polypeptide, thereby improving the AUC of said FVII polypeptide.

In one embodiment, the present invention provides a method of reducing the dosing frequency of a Factor VII (FVI) polypeptide, comprising the step of attaching three to five chorionic gonadotrophin carboxy terminal peptides (CTPs) to the carboxy terminus of said FVII polypeptide, thereby reducing the dosing frequency of said FVII polypeptide. In another embodiment, the present invention provides a method of reducing the dosing frequency of a Factor VII (FVII) polypeptide, comprising the step of attaching three chorionic gonadotrophin carboxy terminal peptides (CTPs) to the carboxy terminus of said FVI polypeptide, thereby reducing the dosing frequency of said FVII polypeptide. In another embodiment, the present invention provides a method of reducing the dosing frequency of a Factor VII (FVII) polypeptide, comprising the step of attaching five chorionic gonadotrophin carboxy terminal peptides (CTPs) to the carboxy terminus of said FVII polypeptide, thereby reducing the dosing frequency of said FVII polypeptide.

In one embodiment, the present invention provides a method of reducing the clearance rate of a Factor VII (FVII) polypeptide, comprising the step of attaching three to five chorionic gonadotrophin carboxy terminal peptides (CTPs) to the carboxy terminus of said FVII polypeptide, thereby reducing the clearance rate of said FVII polypeptide. In another embodiment, the present invention provides a method of reducing the clearance rate of a Factor VII (FVII) polypeptide, comprising the step of attaching three chorionic gonadotrophin carboxy terminal peptides (CTPs) to the carboxy terminus of said FVII polypeptide, thereby reducing the clearance rate of said FVII polypeptide. In another embodiment, the present invention provides a method of reducing the clearance rate of a Factor VII (FVII) polypeptide, comprising the step of attaching five chorionic gonadotrophin carboxy terminal peptides (CTPs) to the carboxy terminus of said FVII polypeptide, thereby reducing the clearance rate of said FVII polypeptide.

In one embodiment, the present invention provides a method of producing a CTP-modified Factor VII (FVII) polypeptide, comprising the step of attaching three to five chorionic gonadotrophin carboxy terminal peptides (CTPs) to the carboxy terminus of said FVII polypeptide, thereby producing a CTP-modified FVII polypeptide. In another embodiment, the present invention provides a method of producing a CTP-modified Factor VII (FVII) polypeptide, comprising the step of attaching three chorionic gonadotrophin carboxy terminal peptides (CTPs) to the carboxy terminus of said FVII polypeptide, thereby producing a CTP-modified FVII polypeptide. In another embodiment, the present invention provides a method of producing a CTP-modified Factor VII (FVII) polypeptide, comprising the step of attaching five chorionic gonadotrophin carboxy terminal peptides (CTPs) to the carboxy terminus of said FVII polypeptide, thereby producing a CTP-modified FVII polypeptide.

In another embodiment, the present invention provides a method of treating hemophilia in a subject comprising administering a CTP-modified Factor VII (FVII) polypeptide comprising a FVII polypeptide and three to five chorionic gonadotrophin carboxy terminal peptides (CTPs) attached to the carboxy terminus of said FVII polypeptide to said subject, thereby treating hemophilia in said subject. In another embodiment, the present invention provides a method of treating hemophilia in a subject comprising administering a CTP-modified Factor VII (FVII) polypeptide comprising a FVII polypeptide and three chorionic gonadotrophin carboxy terminal peptides (CTPs) attached to the carboxy terminus of said FVII polypeptide to said subject, thereby treating hemophilia in said subject. In another embodiment, the present invention provides a method of treating hemophilia in a subject comprising administering a CTP-modified Factor VII (FVII) polypeptide comprising a FVII polypeptide and five chorionic gonadotrophin carboxy terminal peptides (CTPs) attached to the carboxy terminus of said FVII polypeptide to said subject, thereby treating hemophilia in said subject.

In another embodiment, the methods provided herein further comprise the step of attaching four chorionic gonadotrophin carboxy terminal peptides (CTPs) to the carboxy terminus of said FVII polypeptide.

In one embodiment, the present invention provides a method of treating hemophilia in a subject comprising administering a CTP-modified coagulation factor of the present invention. In another embodiment, the present invention provides a method of treating hemophilia in a subject comprising administering a CTP-modified Factor IX of the present invention. In one embodiment, hemophilia is hemophilia B. In one embodiment, hemophilia B is known as factor IX deficiency or Christmas disease. In one embodiment, the hemophilia is severe hemophilia, which in one embodiment, describes hemophilia in which the coagulation factor levels are 0-1%. In another embodiment, the hemophilia is moderate hemophilia, which in one embodiment, describes hemophilia in which the coagulation factor levels are 1-5%. In another embodiment, the hemophilia is mild hemophilia, which in one embodiment, describes hemophilia in which the coagulation factor levels are 5-50%.

In another embodiment, the present invention provides a method of treating hemophilia in a subject comprising administering a CTP-modified Factor IX (FIX) polypeptide comprising a FIX polypeptide and three to five chorionic gonadotrophin carboxy terminal peptides (CTPs) attached to the carboxy terminus of said FIX polypeptide to said subject, thereby treating hemophilia in said subject. In another embodiment, the present invention provides a method of treating hemophilia in a subject comprising administering a CTP-modified Factor IX (FIX) polypeptide comprising a FIX polypeptide and three chorionic gonadotrophin carboxy terminal peptides (CTPs) attached to the carboxy terminus of said FIX polypeptide to said subject, thereby treating hemophilia in said subject. In another embodiment, the present invention provides a method of treating hemophilia in a subject comprising administering a CTP-modified Factor IX (FIX) polypeptide comprising a FIX polypeptide and five chorionic gonadotrophin carboxy terminal peptides (CTPs) attached to the carboxy terminus of said FIX polypeptide to said subject, thereby treating hemophilia in said subject. In another embodiment, the present invention provides a method of treating hemophilia in a subject comprising administering a CTP-modified Factor VIIa (FVIIa) polypeptide comprising a FVIIa polypeptide and three to five chorionic gonadotrophin carboxy terminal peptides (CTPs) attached to the carboxy terminus of said FVIIa polypeptide to said subject, thereby treating hemophilia in said subject.

In another embodiment, the present invention provides a method of treating hemophilia in a subject comprising administering one or more CTP-modified coagulation factors as described herein to said subject. Thus, in one embodiment, the present invention provides a method of treating hemophilia in a subject comprising administering a CTP-modified Factor IX (FIX) polypeptide comprising a FIX polypeptide and three chorionic gonadotrophin carboxy terminal peptides (CTPs) attached to the carboxy terminus of said FIX polypeptide and a CTP-modified Factor VIIa (FVIIa) polypeptide comprising a FVIIa polypeptide and three to five chorionic gonadotrophin carboxy terminal peptides (CTPs) attached to the carboxy terminus of said FVIIa polypeptide to said subject, thereby treating hemophilia in said subject. In one embodiment, the CTP-modified FIX and the CTP-modified FVIIa are administered in the same composition at the same time. In another embodiment, the CTP-modified FIX and the CTP-modified FVIIa are administered in separate compositions at the same time. In another embodiment, the CTP-modified FIX and the CTP-modified FVIIa are administered in separate compositions at separate times.

In other embodiments, the engineered coagulation factor is for the treatment of hemophilia B patients. In one embodiment, coagulation Factor IX comprising 3 CTPs in tandem in its carboxy terminus is for the treatment of hemophilia B patients. In one embodiment, coagulation Factor IX comprising 4 CTPs in tandem in its carboxy terminus is for the treatment of hemophilia B patients. In one embodiment, coagulation Factor IX comprising 5 CTPs in tandem in its carboxy terminus is for the treatment of hemophilia B patients. In another embodiment, coagulation Factor IX comprising 2 CTPs in tandem in its carboxy terminus is for the treatment of hemophilia B patients. In another embodiment, coagulation Factor IX comprising 1 CTP repeat in its carboxy terminus is for the treatment of hemophilia B patients. In other embodiments, the engineered coagulation factor can reduce the number of infusions required for a patient, reduce the required doses for a patient, or a combination thereof.

In one embodiment, coagulation Factor IX comprising 3 CTPs in tandem in its carboxy terminus exhibits an improved PK profile while maintaining its coagulation activity vs. FIX-CTP-CTP harvest, FIX-CTP harvest or rhFIX. In one embodiment, the elimination half-life of rFIX-CTP3 is 2.5- to 4-fold longer than rFIX in rats and in FIX-deficient mice. In one embodiment, the administration of rFIX-CTP3 significantly prolonged the procoagulatory effect in FIX-deficient mice for at least 76 hr after dosing. In one embodiment, the administration of rFIX-CTP3 produced a higher activity peak than rFIX in FIX-deficient mice. In another embodiment, coagulation Factor IX comprising 2 CTPs in tandem in its carboxy terminus exhibits an improved PK profile while maintaining its coagulation activity vs. FIX-CTP harvest or rhFIX. In another embodiment, coagulation Factor IX comprising 2 CTPs in tandem in its carboxy terminus exhibits 3-fold increase in half-life and 4.5-fold higher AUC compared to rhFIX.

Figure 36:
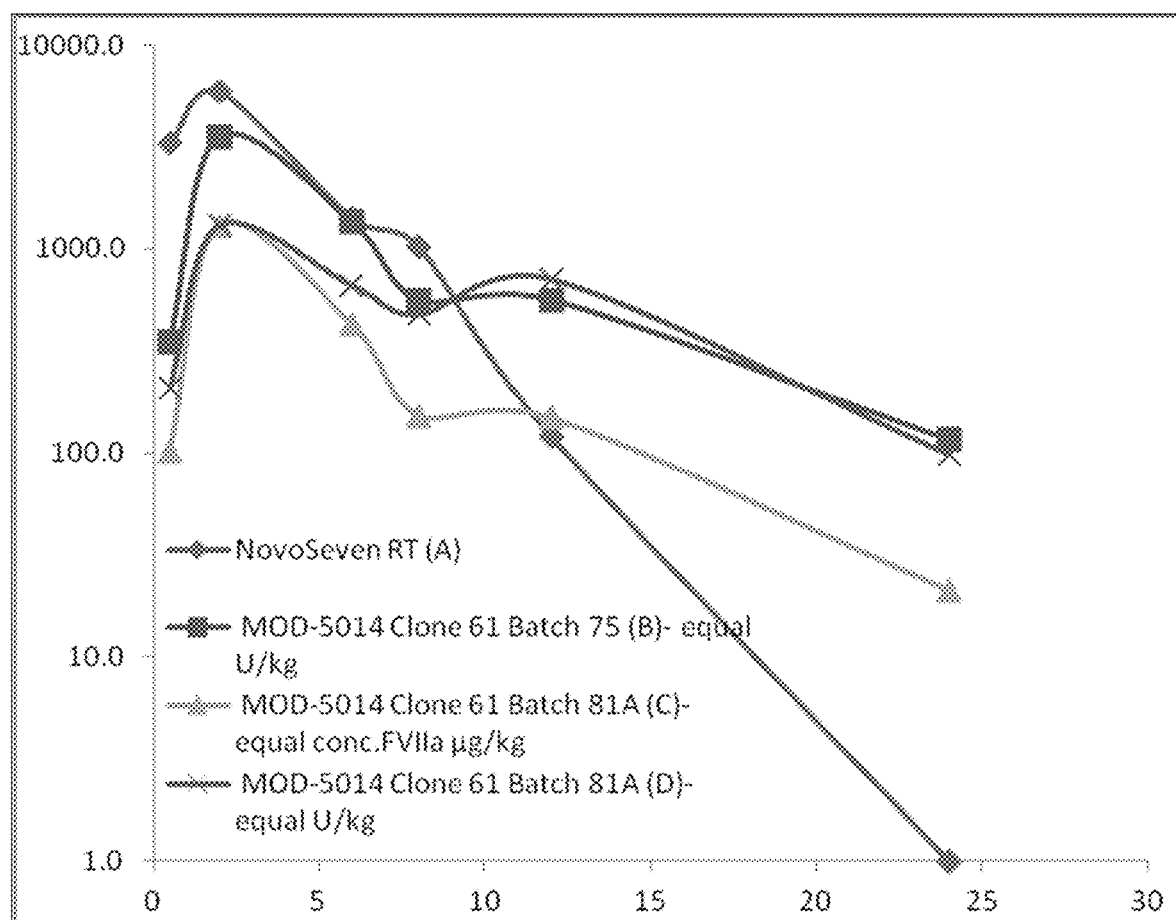
FIG. 36. Shows the PK profile of MOD-5014 (Clone 61 #75, #81) vs. NovoSeven® following single SC administration.

In one embodiment, coagulation Factor VII comprising 3 CTPs in tandem in its carboxy terminus exhibits an improved PK profile while maintaining its coagulation activity vs. NovoSeven® (see Table 59 and FIG. 36).

In another embodiment, the terms "CTP peptide," "carboxy terminal peptide" and "CTP sequence" are used interchangeably herein. In another embodiment, the carboxy terminal peptide is a full-length CTP. Each possibility represents a separate embodiment of the invention.

In another embodiment, a signal peptide is attached to the amino terminus of the CTP, as described in U.S. Pat. No. 7,553,940, which is incorporated by reference herein in its entirety.

In other embodiments, the term engineered coagulation factor refers to the amino acid sequence of a matured coagulation factor. In other embodiments, the term engineered coagulation factor refers to the amino acid sequence of the coagulation factor including its signal sequence or signal peptide.

In another embodiment, "signal sequence" and "signal peptide" are used interchangeably herein. In another embodiment, "sequence" when in reference to a polynucleotide molecule can refer to a coding portion. Each possibility represents a separate embodiment of the present invention.

In another embodiment, an engineered coagulation factor comprising at least one CTP as described herein has enhanced in vivo biological activity compared the same coagulation factor without at least one CTP. In one embodiment, the enhanced biological activity stems from the longer half-life of the engineered coagulation factor while maintaining at least some biological activity. In another embodiment, the enhanced biological activity stems from enhanced biological activity resulting from the CTP modification. In another embodiment, the enhanced biological activity stems from both a longer half-life and from enhanced functionality of the CTP-modified coagulation factor.

In some embodiments, at least one CTP sequence at the carboxy terminal end of the coagulation factor provides enhanced protection against degradation of a coagulation factor. In some embodiments, at least one CTP sequence at the carboxy terminal end of the coagulation factor provides enhanced protection against clearance. In some embodiments, at least one CTP sequence at the carboxy terminal end of the coagulation factor provides prolonged clearance time. In some embodiments, at least one CTP sequence at the carboxy terminal end of the coagulation factor enhances its Cmax. In some embodiments, at least one CTP sequence at the carboxy terminal end of the coagulation factor enhances its Tmax. In some embodiments, at least one CTP sequence at the carboxy terminal end of the coagulation factor prolongs its T½.

In another embodiment, a conjugated coagulation factor of this invention is used in the same manner as an unmodified conjugated coagulation factor. In another embodiment, a conjugated coagulation factor of this invention has an increased circulating half-life and plasma residence time, decreased clearance, and increased clinical activity in vivo. In another embodiment, due to the improved properties of the conjugated coagulation factor as described herein, this conjugate is administered less frequently than the unmodified form of the same coagulation factor.

In another embodiment, decreased frequency of administration will result in improved treatment strategy, which in one embodiment, will lead to improved patient compliance leading to improved treatment outcomes, as well as improved patient quality of life. In another embodiment, compared to conventional conjugates of coagulation factors, it has been found that conjugates having the molecular weight and linker structure of the conjugates of this invention have an improved potency, improved stability, elevated AUC levels, and enhanced circulating half-life.

In another embodiment, the present invention further provides a pharmaceutical composition comprising a CTP-modified Factor IX (FIX) polypeptide consisting of a FIX polypeptide and three gonadotropin carboxy terminal peptides (CTPs) attached to the carboxy terminus of said CTP-modified FIX polypeptide.

In another embodiment, the present invention further provides a pharmaceutical composition comprising a CTP-modified Factor VIIa (FVIIa) polypeptide consisting of a FVIIa polypeptide and three gonadotropin carboxy terminal peptides (CTPs) attached to the carboxy terminus of said FVIIa.

In another embodiment, the present invention further provides a pharmaceutical composition comprising a CTP-modified Factor VIIa (FVIIa) polypeptide consisting of a FVIIa polypeptide and four gonadotropin carboxy terminal peptides (CTPs) attached to the carboxy terminus of said FVIIa.

In another embodiment, the present invention further provides a pharmaceutical composition comprising a CTP-modified Factor VIIa (FVIIa) polypeptide consisting of a FVIIa polypeptide and five gonadotropin carboxy terminal peptides (CTPs) attached to the carboxy terminus of said FVIIa.

In another embodiment, provided herein is a composition comprising a conjugated coagulation factor as described herein. In another embodiment, provided herein is a pharmaceutical composition comprising the conjugated coagulation factor as described herein. In another embodiment, provided herein is a pharmaceutical composition comprising a therapeutically effective amount of the conjugated coagulation factor as described herein. In one embodiment, a therapeutically effective amount of a conjugated coagulation factor is determined according to factors such as the specific condition being treated, the condition of the patient being treated, as well as the other ingredients in the composition.

In another embodiment, a conjugated coagulation factor as described herein is useful in the treatment of subjects afflicted with a coagulation or clotting disorder. In another embodiment, the coagulation or clotting disorder is Hemophilia. In another embodiment, a conjugated coagulation factor as described herein is useful in the prophylactic therapy of Hemophilia thus reducing the risk of bleeding and associated complications. In another embodiment, a conjugated coagulation factor as described herein is useful in the treatment of subjects afflicted with Hemophilia while reducing the risk of developing inhibitory antibodies to exogenously administered coagulation factors. In another embodiment, a conjugated coagulation factor as described herein is useful in the treatment of subjects afflicted with Hemophilia thus inducing homeostasis.

In one embodiment, a CTP-modified coagulation factor of the present invention has therapeutic uses. In another embodiment, a CTP-modified coagulation factor of the present invention has prophylactic uses.

In another embodiment, a conjugated coagulation factor as described herein is useful in the treatment of subjects experiencing excessive bleeding or bruising or having a prolonged Prothrombin Time (PT) or Partial Thromboplastin Time (PT). In another embodiment, a conjugated coagulation factor as described herein is useful in the treatment of subjects having an acquired condition that is causing bleeding, such as vitamin K deficiency or liver disease. In another embodiment, a conjugated coagulation factor as described herein is useful in the treatment of subjects having deficiencies in coagulation factors that are acquired (due to other diseases) or inherited, mild or severe, permanent or temporary. In another embodiment, a conjugated coagulation factor as described herein is useful in the treatment of subjects afflicted with hemophilia A. In another embodiment, a conjugated coagulation factor as described herein is useful in the treatment of subjects afflicted with hemophilia B. In another embodiment, a conjugated coagulation factor as described herein is useful in the treatment of subjects having acquired deficiencies due to chronic diseases, such as liver disease or cancer; to an acute condition such as disseminated intravascular coagulation (DIC), which uses up clotting factors at a rapid rate; or to a deficiency in vitamin K or treatment with a vitamin K antagonist like warfarin (the production of factors II, VII, IX, and X require vitamin K). In another embodiment, a conjugated coagulation factor as described herein is useful in the treatment of subjects afflicted with a disease in which causes clotting imbalances such as but not limited to: a liver disease, uremia, a cancer, a bone marrow disorder, an exposure to snake venom, a vitamin K deficiency, an anticoagulation therapy, an accidental ingestion of the anticoagulant warfarin, multiple blood transfusions (stored units of blood lose some of their clotting factors), or a combination thereof. In another embodiment, the present invention provides a method of treating deep vein thrombosis in a subject comprising administering a CTP-modified coagulation factor of the present invention. In another embodiment, the present invention provides a method of preventing uncontrolled bleeding in a subject with hemophilia comprising administering a CTP-modified coagulation factor of the present invention. In another embodiment, the present invention provides a method of preventing bleeding episodes in a subject with hemophilia comprising administering a CTP-modified coagulation factor of the present invention. In another embodiment, the present invention provides a method of controlling bleeding episodes in a subject with hemophilia B (congenital factor IX deficiency).

In another embodiment, the compositions and methods of the present invention are for the treatment of bleeding episodes in hemophilia A or B patients with inhibitors to FVIII or FIX and in patients with acquired hemophilia; prevention of bleeding in surgical interventions or invasive procedures in hemophilia A or B patients with inhibitors to FVIII or FIX and in patients with acquired hemophilia, treatment of bleeding episodes in patients with congenital FVII deficiency and prevention of bleeding in surgical interventions or invasive procedures in patients with congenital FVI deficiency. Acquired hemophilia is a spontaneous autoimmune disorder in which patients with previously normal hemostasis develop autoantibodies against clotting factors, most frequently FVIII. The development of autoantibodies against FVIII leads to FVIII deficiency, which results in insufficient generation of thrombin by factor IXa and the factor VIIIa complex through the intrinsic pathway of the coagulation cascade. The following conditions may be associated with acquired hemophilia A: idiopathic, pregnancy, autoimmune disorders, inflammatory bowel disease, ulcerative colitis, dermatologic disorders (eg, psoriasis, pemphigus), respiratory diseases (eg, asthma, chronic obstructive pulmonary disease), allergic drug reactions, diabetes, acute hepatitis B infection, acute hepatitis C infection, malignancies-solid tumors (prostate, lung, colon, pancreas, stomach, bile duct, head and neck, cervix, breast, melanoma, kidney), hematologic malignancies. It will be appreciated by the skilled artisan that autoimmune disorders may include rheumatoid arthritis, systemic lupus erythematosus, multiple sclerosis, temporal arteritis, sjögren syndrome, autoimmune hemolytic anemia, goodpasture syndrome, mvasthenia gravis, graves' disease, autoimmune hypothyroidism. It will be appreciated by the skilled artisan that allergic reactions may occur from a subject being administered penicillin and its derivatives, sulfamides, phenytoin, chloramphenicol, methyldopa, depot thioxanthene, interferon alfa, fludarabine, bacille calmette-guérin (BCG) vaccination, desvenlafaxine. It will be appreciated by the skilled artisan that hematologic malignancies may include chronic lymphocytic leukemia, non-Hodgkin lymphoma, multiple myeloma, waldenstrom macroglobulinemia, myelodysplastic syndrome, myelofibrosis, and erythroleukemia. Hence, and in one embodiment, provided herein is a method for treating acquired hemophilia in a subject, comprising administering to the subject any of the compositions provided herein.

In another embodiment, the compositions and methods of the present invention are for the treatment or prevention of muscle bleeds. In another embodiment, the compositions and methods of the present invention are for the treatment or prevention of joint bleeds. In another embodiment, the compositions and methods of the present invention provide therapeutic or prophylactic treatment of epistaxis and gum bleeding, mucous membrane bleeding, bleeding into the central nervous system. In another embodiment, the compositions and methods of the present invention provide therapeutic or prophylactic treatment of gastrointestinal or cerebral bleeding. In another embodiment, the compositions and methods of the present invention provide therapeutic or prophylactic treatment of low frequency mild bleeds. In another embodiment, the compositions and methods of the present invention provide therapeutic or prophylactic treatment of low frequency moderate bleeds. In another embodiment, the compositions and methods of the present invention provide therapeutic or prophylactic treatment of high frequency mild bleeds. In another embodiment, the compositions and methods of the present invention provide therapeutic or prophylactic treatment of high frequency moderate bleeds.

In one embodiment, the compositions and methods of the present invention provide therapeutic or prophylactic treatment of asymptomatic hemophilia. In another embodiment, the compositions and methods of the present invention provide therapeutic or prophylactic treatment of mild to moderate hemophilia. In another embodiment, the compositions and methods of the present invention provide therapeutic or prophylactic treatment of severe hemophilia.

In one embodiment, the compositions and methods of the present invention provide therapeutic or prophylactic treatment of hemorrhage, which in one embodiment, is uncontrollable hemorrhage, and, in another embodiment, intracerebral hemorrhage. In another embodiment, the compositions and methods of the present invention provide therapeutic or prophylactic treatment of neonatal coagulopathies; severe hepatic disease; high-risk surgical procedures; traumatic blood loss; bone marrow transplantation; thrombocytopenias and platelet function disorders; urgent reversal of oral anticoagulation; congenital deficiencies of factors V, VII, X, and XI; or von Willebrand disease, in one embodiment, von Willebrand disease with inhibitors to von Willebrand factor.

In one embodiment, a CTP-modified coagulation factor of the present invention is for the treatment of hemophilia or a related disease as described herein in a subject. In one embodiment, the subject is human. In another embodiment, the subject is a human child. In another embodiment, the subject is a domesticated animal. In another embodiment, the subject is a mammal. In another embodiment, the subject is a farm animal. In another embodiment, the subject is a monkey. In another embodiment, the subject is a horse. In another embodiment, the subject is a cow. In another embodiment, the subject is a mouse. In another embodiment, the subject is a rat. In another embodiment, the subject is canine. In another embodiment, the subject is feline. In another embodiment, the subject is bovine, ovine, porcine, equine, murine, or cervine. In one embodiment, the subject is male. In another embodiment, the subject is female. In one embodiment, the subject is a child, in another embodiment, an adolescent, in another embodiment, an adult or, in another embodiment, an elderly subject. In another embodiment, the subject is a pediatric subject, in another embodiment, a geriatric subject.

In another embodiment, a [(CTP)n>1-coagulation factor] as described herein comprises a full length coagulation factor or an active fragment thereof connected via a peptide bond on its carboxy terminus to at least one CTP unit with no CTPs on its amino terminus. In another embodiment, a [(CTP)n>1-coagulation factor] as described herein comprises a coagulation factor or an active fragment thereof connected via a peptide bond to at least one CTP unit which is connected to an additional CTP unit via a peptide bond with no CTPs on its amino terminus. In another embodiment, one nucleic acid molecule encodes an engineered coagulation factor comprising at least one CTP attached to its C-terminus and no CTPs on its amino terminus.

In another embodiment, the CTP is attached to the coagulation factor via a linker. In another embodiment, the linker which connects the CTP sequence to the coagulation factor is a covalent bond. In another embodiment, the linker which connects the CTP sequence to the coagulation factor is a peptide bond. In another embodiment, the linker which connects the CTP sequence to the coagulation factor is a substituted peptide bond. In another embodiment, the CTP sequence comprises: DPRFQDSSSSKAPPPSLPSPSRLPGPSDTPIL (SEQ ID NO: 1). In another embodiment, the CTP sequence comprises: SSSSKAPPPSLPSPSRLPGPSDTPILPQ (SEQ ID NO: 2). In another embodiment, the CTP sequence comprises an amino acid sequence selected from the sequences set forth in SEQ ID NO: 1 and SEQ ID NO: 2.

In another embodiment, the carboxy terminal peptide (CTP) peptide of the present invention comprises the amino acid sequence from amino acid 112 to position 145 of human chorionic gonadotrophin, as set forth in SEQ ID NO: 1. In another embodiment, the CTP sequence of the present invention comprises the amino acid sequence from amino acid 118 to position 145 of human chorionic gonadotropin, as set forth in SEQ ID NO: 2. In another embodiment, the CTP sequence also commences from any position between positions 112-118 and terminates at position 145 of human chorionic gonadotrophin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotrophin CTP which differs from the native CTP by 1-5 conservative amino acid substitutions as described in U.S. Pat. No. 5,712,122, which is incorporated herein by reference. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions.

In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof. In another embodiment, the CTP peptide amino acid sequence of the present invention is at least 98% homologous to the native CTP amino acid sequence or a peptide thereof.

In another embodiment, the polynucleotide encoding the CTP peptide of the present invention is at least 70% homologous to the native human CTP DNA sequence or a peptide thereof. In another embodiment, the polynucleotide encoding the CTP peptide of the present invention is at least 80% homologous to the native human CTP DNA sequence or a peptide thereof. In another embodiment, the polynucleotide encoding the CTP peptide of the present invention is at least 90)% homologous to the native CTP DNA sequence or a peptide thereof. In another embodiment, the polynucleotide encoding the CTP peptide of the present invention is at least 95% homologous to the native CTP DNA sequence or a peptide thereof. In another embodiment, the polynucleotide encoding the CTP peptide of the present invention is at least 98% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, 2 of the chorionic gonadotrophin CTP amino acid sequences are truncated. In another embodiment, 3 of the chorionic gonadotrophin CTP amino acid sequences are truncated. In another embodiment, 4 of the chorionic gonadotrophin CTP amino acid sequences are truncated. In another embodiment, 5 of the chorionic gonadotrophin CTP amino acid sequences are truncated. In another embodiment, 2 or more of the chorionic gonadotrophin CTP amino acid sequences are truncated. In another embodiment, all of the chorionic gonadotrophin CTP amino acid sequences are truncated. In one embodiment, the truncated CTP comprises the first 10 amino acids of SEQ ID NO: 3. In another embodiment, SEQ ID NO: 3 comprises the following amino acid (AA) sequence: SSSSKAPPPSLP.

In one embodiment, the truncated CTP comprises the first 10 amino acids of SEQ ID NO: 4. In another embodiment. SEQ ID NO: 4 comprises the following amino acid (AA) sequence: SSSSKAPPPSLPSPSRLPGPSDTPILPQ.

In one embodiment, the truncated CTP comprises the first 11 amino acids of SEQ ID NO: 4. In one embodiment, the truncated CTP comprises the first 12 amino acids of SEQ ID NO: 4. In one embodiment, the truncated CTP comprises the first 8 amino acids of SEQ ID NO: 4 or SEQ ID NO: 3. In one embodiment, the truncated CTP comprises the first 13 amino acids of SEQ ID NO: 4. In one embodiment, the truncated CTP comprises the first 14 amino acids of SEQ ID NO: 4. In one embodiment, the truncated CTP comprises the first 6 amino acids of SEQ ID NO; 4 or SEQ ID NO; 3. In one embodiment, the truncated CTP comprises the first 5 amino acids of SEQ ID NO: 4 or SEQ ID NO: 3.

In one embodiment, at least one of the chorionic gonadotrophin CTP amino acid sequences is glycosylated. In another embodiment, both of the chorionic gonadotrophin CTP amino acid sequences are glycosylated. In another embodiment, 2 of the chorionic gonadotrophin CTP amino acid sequences are glycosylated. In another embodiment, 3 of the chorionic gonadotrophin CTP amino acid sequences are glycosylated. In another embodiment, 4 of the chorionic gonadotrophin CTP amino acid sequences are glycosylated. In another embodiment, 5 of the chorionic gonadotrophin CTP amino acid sequences are glycosylated. In another embodiment, 2 or more of the chorionic gonadotrophin CTP amino acid sequences are glycosylated. In another embodiment, all of the chorionic gonadotrophin CTP amino acid sequences are glycosylated.

In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites. In one embodiment, one or more of the chorionic gonadotrophin CTP amino acid sequences is fully glycosylated. In another embodiment, one or more of the chorionic gonadotrophin CTP amino acid sequences is partially glycosylated. In one embodiment, partially glycosylated indicates that one of the CTP glycosylation sites is glycosylated. In another embodiment, two of the CTP glycosylation sites are glycosylated. In another embodiment, three of the CTP glycosylation sites are glycosylated.

In some embodiments, the CTP sequence modification is advantageous in permitting the usage of lower dosages. In some embodiments, the CTP sequences modification is advantageous in permitting fewer dosages. In some embodiments, the CTP sequences modification is advantageous in permitting a safe, long-acting effect.

In some embodiments, "polypeptide", "engineered coagulation factor", or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides comprising a coagulation factor even more stable while in a body or more capable of penetrating into cells.

In some embodiments, modifications include, but are limited to C terminus modification, polypeptide bond modification, including, but not limited to, CH2-NH, CH2-S. CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2. F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated to bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and in one embodiment at several (2-3 bonds) at the same time.

In some embodiments, natural aromatic amino acids of the polypeptide such as Trp, Tyr and Phe, are substituted for synthetic non-natural acid such as Phenylglycine. TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid sequence" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acids.

In some embodiments, the polypeptides of the present invention are utilized in therapeutics which requires the polypeptides comprising a coagulation factor to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the engineered coagulation factor of the present invention is utilized in a linear form, although it will be appreciated by one skilled in the art that in cases where cyclicization does not severely interfere with engineered coagulation factors characteristics, cyclic forms of the engineered coagulation factors can also be utilized.

In some embodiments, the engineered coagulation factors of the present invention are biochemically synthesized such as by using standard solid phase techniques. In some embodiments, these biochemical methods include exclusive solid phase synthesis, partial solid phase synthesis, fragment condensation, or classical solution synthesis.

In some embodiments, recombinant protein techniques are used to generate the engineered coagulation factors of the present invention. In some embodiments, recombinant protein techniques are used for the generation of relatively long polypeptides (e.g., longer than 18-25 amino acids). In some embodiments, recombinant protein techniques are used for the generation of large amounts of the engineered coagulation factors of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463, which are incorporated herein by reference in their entirety.

In another embodiment, the invention provides a polynucleotide molecule comprising the coding portion of a gene encoding a polypeptide comprising a coagulation factor and gonadotrophin carboxy terminal peptides attached to the carboxy terminus of the coagulation factor, as described hereinabove. In another embodiment, the invention provides a polynucleotide molecule consisting of the coding portion of a gene encoding a polypeptide comprising a coagulation factor and gonadotrophin carboxy terminal peptides attached to the carboxy terminus of the coagulation factor, as described hereinabove. In another embodiment, the invention provides a polynucleotide molecule consisting essentially of the coding portion of a gene encoding a polypeptide comprising a coagulation factor and gonadotrophin carboxy terminal peptides attached to the carboxy terminus of the coagulation factor, as described hereinabove.

In another embodiment, the invention provides a polynucleotide encoding a polypeptide comprising a coagulation factor and three gonadotrophin carboxy terminal peptides attached to the carboxy terminus of the coagulation factor, as described hereinabove. In another embodiment, the invention provides a polynucleotide encoding a polypeptide consisting of a coagulation factor and three gonadotrophin carboxy terminal peptides attached to the carboxy terminus of the coagulation factor, as described hereinabove. In another embodiment, the invention provides a polynucleotide encoding a polypeptide consisting essentially of a coagulation factor and three gonadotrophin carboxy terminal peptides attached to the carboxy terminus of the coagulation factor, as described hereinabove. In one embodiment, the polynucleotide is a polynucleotide sequence. In one embodiment, the polynucleotide is a polynucleotide molecule.

In another embodiment, the invention provides an expression vector comprising a polynucleotide molecule as described herein. In another embodiment, the present invention provides an expression vector comprising a polynucleotide encoding a CTP-modified polypeptide consisting of a Factor IX (FIX) polypeptide and three gonadotropin carboxy terminal peptides (CTPs) attached to the carboxy terminus of said FIX polypeptide. In another embodiment, the present invention provides an expression vector comprising a polynucleotide encoding a CTP-modified polypeptide consisting of a Factor VIIa (FVIIa) polypeptide and three to five gonadotropin carboxy terminal peptides (CTPs) attached to the carboxy terminus of said FVIIa polypeptide.

In another embodiment, the invention provides a cell comprising the expression vector as described herein. In another embodiment, the present invention provides a cell comprising an expression vector comprising a polynucleotide encoding a CTP-modified polypeptide consisting of a Factor IX (FIX) polypeptide and three gonadotropin carboxy terminal peptides (CTPs) attached to the carboxy terminus of said FIX polypeptide. In another embodiment, the present invention provides a cell comprising an expression vector comprising a polynucleotide encoding a CTP-modified polypeptide consisting of a Factor VIIa (FVIIa) polypeptide and three gonadotropin carboxy terminal peptides (CTPs) attached to the carboxy terminus of said FVIIa polypeptide.

In another embodiment, the invention provides a composition comprising the expression vector as described herein. In another embodiment, the present invention provides a composition comprising an expression vector comprising a polynucleotide encoding a CTP-modified polypeptide consisting of a Factor IX (FIX) polypeptide and three gonadotropin carboxy terminal peptides (CTPs) attached to the carboxy terminus of said FIX polypeptide. In another embodiment, the present invention provides a composition comprising an expression vector comprising a polynucleotide encoding a CTP-modified polypeptide consisting of a Factor VIIa (FVIIa) polypeptide and three gonadotropin carboxy terminal peptides (CTPs) attached to the carboxy terminus of said FVIIa polypeptide.

In another embodiment, the invention provides a composition comprising the cell as described herein. In another embodiment, the cell is a eukaryotic cell. In another embodiment, the cell is a prokaryotic cell.

In another embodiment, the present invention provides a method of producing a CTP-modified coagulation factor, comprising the step of attaching one to ten chorionic gonadotrophin carboxy terminal peptides (CTPs) to the carboxy terminus of said coagulation factor, thereby producing a CTP-modified coagulation factor. In another embodiment, the present invention provides a method of producing a CTP-modified coagulation factor, comprising the step of attaching one to ten polynucleotide sequences encoding a chorionic gonadotrophin carboxy terminal peptide (CTP) to the carboxy terminus of a polynucleotide sequence encoding said coagulation factor, thereby producing a CTP-modified coagulation factor. In another embodiment, the present invention provides a method of producing a CTP-modified Factor IX (FIX) polypeptide, comprising the step of attaching three chorionic gonadotrophin carboxy terminal peptides (CTPs) to the carboxy terminus of said FIX polypeptide, thereby producing a CTP-modified FIX polypeptide. In another embodiment, the present invention provides a method of producing a CTP-modified Factor VIIa (FVIIa) polypeptide, comprising the step of attaching three chorionic gonadotrophin carboxy terminal peptides (CTPs) to the carboxy terminus of said FVIIa polypeptide, thereby producing a CTP-modified FVIIa polypeptide.

In another embodiment, the engineered coagulation factors of the present invention are synthesized using a polynucleotide molecule encoding a polypeptide of the present invention. In some embodiments, the polynucleotide molecule encoding the engineered coagulation factors of the present invention is ligated into an expression vector, comprising a transcriptional control of a cis-regulatory sequence (e.g., promoter sequence). In some embodiments, the cis-regulatory sequence is suitable for directing constitutive expression of an engineered coagulation factor of the present invention. In some embodiments, the cis-regulatory sequence is suitable for directing tissue-specific expression of the engineered coagulation factors of the present invention. In some embodiments, the cis-regulatory sequence is suitable for directing inducible expression of the engineered coagulation factors of the present invention.

In some embodiment, tissue-specific promoters suitable for use with the present invention include sequences which are functional in one or more specific cell populations. Examples include, but are not limited to, promoters such as albumin that is liver-specific [Pinkert et al., (1987) Genes Dev. 1:268-277], lymphoid-specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264.166). Inducible promoters suitable for use with the present invention include, for example, the tetracycline-inducible promoter (Srour, M. A., et al., 2003. Thromb. Haemost. 90: 398405).

In one embodiment, the phrase "a polynucleotide molecule" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, a "complementary polynucleotide sequence" refers to a sequence, which results from reverse transcription of messenger RNA using a reverse transcriptase or any other RNA-dependent DNA polymerase. In one embodiment, the sequence can be subsequently amplified in vivo or in vitro using a DNA polymerase.

In one embodiment, a "genomic polynucleotide sequence" refers to a sequence derived (isolated) from a chromosome and thus it represents a contiguous portion of a chromosome.

In one embodiment, a "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing therebetween. In one embodiment, the intronic sequences can be of any source, including of other genes, and typically will include conserved splicing signal sequences. In one embodiment, intronic sequences include cis-acting expression regulatory elements.

In one embodiment, following expression and secretion, the signal peptides are cleaved from the precursor engineered coagulation factors resulting in the mature engineered coagulation factors. For example, in SEQ ID NO: 25 presented above, amino acids 1-38 MVSQALRLLCLLLGLQGCLAAVFVTQEE-AHGVLHRRRR (SEQ ID NO: 47) represent the signal peptide of Factor VII-CTP-CTP-CTP, and amino acids 39-528 ANAFLEELRPGSLERECKEEQCSFEEAREIFK-DAERTKLFWISYSDGDQCASSPCQNG GSCKDQLQSYICFCL-PAFEGRNCETHKDDQLICVNENGGCEQYCSD-HTGTKRSCRCH EGYSLLADGVSCTPTVEYPCGKIPI- LEKRNASKPQGRIVGGKVCPKGECPWQVLLLV NGAQLCGGTLINTIWVVSAAHCFDKIKNWRNLIA- VLGEHDLSEHDGDEQSRRVAQVI IPSTYVPGTTNH- DIALLRLHQPVVLTDHVVPLCLPERTFSERT- LAFVRFSLVSGWGQL LDRGATALELMVLNVPRLMTQDCLQQSRKVGD- SPNITEYMFCAGYSDGSKDSCKGD SGGPHATHY- RGTWYLTGIVSWGQGCATVGHFGVYTRVSQYIEW- LQKLMRSEPRPG VLLRAPFPSSSSKAPPPSLPSPSRLPGPSDTPIL- PQSSSSKAPPPSLPSPSRLPGPSDTPILP QSSSSKAPPPSLPSPSRLPGPSDTPILPQ (SEQ ID NO: 46) represent the mature engineered coagulation factor lacking the signal peptide. In one embodiment, the amino acid sequence of Factor VII-CTP-CTP-CTP without the signal peptide is set forth in SEQ ID NO: 46. In another embodiment, the signal peptide of Factor VII-CTP-CTP-CTP is set forth in SEQ ID NO: 47.

In some embodiments, polynucleotides of the present invention are prepared using PCR techniques, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention which encode the engineered coagulation factors are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the coagulation factors of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the coagulation factors of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion proteins are engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447, which is incorporated by reference herein in its entirety. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used in the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the coagulation factors of the present invention since they offer advantages such as lateral infection and targeting specificity. In one embodiment, lateral infection is inherent in the life cycle of, for example, a retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992, incorporated herein by reference, for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the engineered coagulation factors of the present invention can also be expressed from a nucleic acid construct administered to the individual employing any suitable mode of administration, described hereinabove (i.e., in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, transformed cells are cultured under effective conditions, which allow for the expression of high amounts of recombinant engineered coagulation factors. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, the determination of culturing conditions are within the expertise of one of ordinary skill in the art.

In some embodiments, depending on the vector and host system used for production, resultant engineered coagulation factors of the present invention either remain within the recombinant cell, are secreted into the fermentation medium, are secreted into a space between two cellular membranes, such as the periplasmic space in *E. coli*; or are retained on the outer surface of a cell or viral membrane.

In one embodiment, following a predetermined time in culture, recovery of the recombinant engineered coagulation factor is effected.

In one embodiment, the phrase "recovering the recombinant engineered coagulation factor" used herein refers to collecting the whole fermentation medium containing the polypeptide and need not imply additional steps of separation or purification.

In one embodiment, engineered coagulation factors of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the engineered coagulation factor of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the engineered coagulation factor and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988), and Gardella et al., J. Biol. Chem. 265:15854-15859 (1990)].

In one embodiment, the engineered coagulation factor of the present invention is retrieved in "substantially pure" form.

In one embodiment, the phrase "substantially pure" refers to a purity that allows for the effective use of the protein in the applications described herein.

In one embodiment, the engineered coagulation factor of the present invention can also be synthesized using in vitro expression systems. In one embodiment, in vitro synthesis methods are well known in the art and the components of the system are commercially available.

In some embodiments, the recombinant engineered coagulation factors are synthesized and purified; their therapeutic efficacy can be assayed either in vivo or in vitro. In one embodiment, the binding activities of the recombinant engineered coagulation factors of the present invention can be ascertained using various assays as known to one of skill in the art.

In another embodiment, the engineered coagulation factor of the present invention can be provided to the individual per se. In one embodiment, the engineered coagulation factor of the present invention can be provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the polypeptide sequence of interest, which is accountable for the biological effect.

In another embodiment, any of the compositions of the present invention will comprise at least one CTP sequence bound only to the carboxy terminus of an engineered coagulation factor of interest, in any form. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied. e.g., in order to cope with the needs of a patient subpopulation to be treated or the needs of the single patient which different needs can be due to a particular disease, severity of a disease, age, sex, or body weight as can be readily made by a person skilled in the art.

In another embodiment, the phrases "physiologically acceptable carrier" and "pharmaceutically acceptable carrier" which are interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979)).

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, PA, latest edition, which is incorporated herein by reference.

Various embodiments of dosage ranges are contemplated by this invention. The dosage of the engineered coagulation factor of the present invention, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In one embodiment, the dosage of the CTP-modified coagulation factor is 1-5 mg/day. In one embodiment, the dosage of the CTP-modified coagulation factor is 1-3 mg/day. In another embodiment, the dosage of the CTP-modified coagulation factor is 2 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the coagulation factor dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

In another embodiment, a polypeptide comprising a coagulation factor and at least one CTP unit is formulated in an intranasal dosage form. In another embodiment, a polypeptide comprising a coagulation factor and at least one CTP unit is formulated in an injectable dosage form. In another embodiment, a polypeptide comprising a coagulation factor and at least one CTP unit is administered to a subject in a dose ranging from 0.0001 mg to 0.6 mg. In another embodiment, a polypeptide comprising a coagulation factor and at least one CTP unit is administered to a subject in a dose ranging from 0.001 mg to 0.005 mg. In another embodiment, a polypeptide comprising a coagulation factor and at least one CTP unit is administered to a subject in a dose ranging from 0.005 mg to 0.01 mg. In another embodiment, a polypeptide comprising a coagulation factor and at least one CTP unit is administered to a subject in a dose ranging from 0.01 mg to 0.3 mg. In another embodiment, a polypeptide comprising a coagulation factor and at least one CTP unit is administered to a subject in a dose in a dose ranging from 0.2 mg to 0.6 mg. In another embodiment, the coagulation factor is free of CTPs on its amino terminus.

In another embodiment, a polypeptide comprising a coagulation factor and at least one CTP unit is administered to a subject in a dose ranging from 1-100 micrograms. In another embodiment, a polypeptide comprising a coagulation factor and at least one CTP unit is administered to a subject in a dose ranging from 10-80 micrograms. In another embodiment, a polypeptide comprising a coagulation factor and at least one CTP unit is administered to a subject in a dose ranging from 20-60 micrograms. In another embodiment, a polypeptide comprising a coagulation factor and at least one CTP unit is administered to a subject in a dose ranging from 10-50 micrograms. In another embodiment, a polypeptide comprising a coagulation factor and at least one CTP unit is administered to a subject in a dose ranging from 40-80 micrograms. In another embodiment, a polypeptide comprising a coagulation factor and at least one CTP unit is administered to a subject in a dose ranging from 10-30 micrograms. In another embodiment, a polypeptide comprising a coagulation factor and at least one CTP unit is administered to a subject in a dose ranging from 30-60 micrograms.

In another embodiment, a polypeptide comprising a coagulation factor and at least one CTP unit is administered to a subject in a dose ranging from 0.2 mg to 2 mg. In another embodiment, a polypeptide comprising a coagulation factor and at least one CTP unit is administered to a subject in a dose ranging from 2 mg to 6 mg. In another embodiment, a polypeptide comprising a coagulation factor and at least one CTP unit is administered to a subject in a dose ranging from 4 mg to 10 mg. In another embodiment, a polypeptide comprising a coagulation factor and at least one CTP unit is administered to a subject in a dose ranging from 5 mg and 15 mg.

In one embodiment, the dosage of the CTP-modified FIX comprises 50% of the amount of FIX administered in the recommended dosage of recombinant FIX (e.g., Benefix®, Wyeth or Mononine®, CSL Behring) to patients over the same period of time. In one embodiment, the dosage of the CTP-modified FVIIa comprises 50% of the amount of FVIIa administered in the recommended dosage of recombinant FVIIa (e.g., NovoSeven®) to patients over the same period of time. In one embodiment, the dosage of the CTP-modified FVII comprises 50% of the amount of FVII administered in the recommended dosage of recombinant FVII to patients over the same period of time. For example, if NovoSeven® is given at a dose of 90 mcg/kg every two hours to a patient pre- or post-operatively (i.e., 7.65 mg every two hours or 45.9 mg in six doses over a 12 hour period, for an 85 kg patient), a CTP-modified coagulation factor of the present invention may be given at a dose that is 50% of the patient's 12-hour dose of recombinant FVIIa (i.e., at a dose of 23 mg given once over a 12-hour period).

In another embodiment, the dosage of CTP-modified coagulation factor is such that it contains 45% of the amount of the coagulation factor than that administered using the non-CTP-modified coagulation factor. In another embodiment, the dosage of CTP-modified coagulation factor is such that it contains 10% of the amount of the coagulation factor than that administered using the non-CTP-modified coagulation factor. In another embodiment, the dosage of CTP-modified coagulation factor is such that it contains 25% of the amount of the coagulation factor than that administered using the non-CTP-modified coagulation factor. In another embodiment, the dosage of CTP-modified coagulation factor is such that it contains 35% of the amount of the coagulation factor than that administered using the non-CTP-modified coagulation factor. In another embodiment, the dosage of CTP-modified coagulation factor is such that it contains 75% of the amount of the coagulation factor than that administered using the non-CTP-modified coagulation factor. In another embodiment, the dosage of CTP-modified coagulation factor is such that it contains 100% of the amount of the coagulation factor than that administered using the non-CTP-modified coagulation factor. However, even if the dosage contains the same amount of coagulation factor (e.g. FIX) as non-CTP-modified coagulation factor, it is still advantageous to subjects in that it will be administered less frequently because of its increased half-life compared to recombinant coagulation factors.

In another embodiment, a therapeutically effective amount of a conjugated coagulation factor is between 50-500 IU per kg body weight administered once a day to once a week for FIX or 10 µg/Kg-500 µg/Kg for FVIIa. In another embodiment, a therapeutically effective amount of a conjugated coagulation factor is 150-250 IU per kg body weight, administered once a day. In another embodiment, a pharmaceutical composition comprising a conjugated coagulation factor is formulated at a strength effective for administration by various means to a human patient.

In one embodiment, FIX is administered in an amount effective to bring circulating Factor IX activity to 20-30 IU/dL in a subject. In another embodiment, FIX is administered in an amount effective to bring circulating Factor IX activity to 25-50 IU/dL in a subject. In another embodiment, FIX is administered in an amount effective to bring circulating Factor IX activity to 50-100 IU/dL in a subject. In another embodiment, FIX is administered in an amount effective to bring circulating Factor IX activity to 100-200 IU/dL in a subject. In another embodiment, FIX is administered in an amount effective to bring circulating Factor IX activity to 10-50 IU/dL in a subject. In another embodiment, FIX is administered in an amount effective to bring circulating Factor IX activity to 20-100 IU/dL in a subject.

In one embodiment, the CTP-modified coagulation factor is administered to a subject on a weekly basis. In another embodiment, the CTP-modified coagulation factor is administered to a subject twice a week. In another embodiment, the CTP-modified coagulation factor is administered to a subject on a fortnightly (once every two weeks) basis. In another embodiment, the CTP-modified coagulation factor is administered to a subject twice a month. In another embodiment, the CTP-modified coagulation factor is administered to a subject once a month. In another embodiment, the CTP-modified coagulation factor is administered to a subject on a daily basis. In another embodiment, the CTP-modified coagulation factor is administered to a subject every two days.

In another embodiment, a polypeptide comprising a coagulation factor and at least one CTP unit is administered to a subject once every three days. In another embodiment, a polypeptide comprising a coagulation factor and at least one CTP unit is administered to a subject once every four days. In another embodiment, a polypeptide comprising a coagulation factor and at least one CTP unit is administered to a subject once every five days. In another embodiment, a polypeptide comprising a coagulation factor and at least one CTP unit is administered to a subject once every six days. In another embodiment, a polypeptide comprising a coagulation factor and at least one CTP unit is administered to a subject once every 7-14 days. In another embodiment, a polypeptide comprising a coagulation factor and at least one CTP unit is administered to a subject once every 10-20 days. In another embodiment, a polypeptide comprising a coagulation factor and at least one CTP unit is administered to a subject once every 5-15 days. In another embodiment, a polypeptide comprising a coagulation factor and at least one CTP unit is administered to a subject once every 15-30 days.

In another embodiment, the methods of the invention include increasing the compliance in the use of coagulation factor therapy, comprising providing to a subject in need thereof, a polypeptide comprising a coagulation factor and at least one chorionic gonadotrophin carboxy terminal peptide (CTP) attached to the carboxy terminus of the coagulation factor, thereby increasing compliance in the use of coagulation factor therapy.

In another embodiment, the methods of the invention include increasing the compliance of patients afflicted with chronic illnesses that are in need of a coagulation factor therapy. In another embodiment, the methods of the invention enable reduction in the dosing frequency of a coagulation factor by modifying the coagulation factor with CTPs as described hereinabove.

In another embodiment, the present invention provides a method of reducing the dosing frequency of a Factor IX (FIX) polypeptide, comprising the step of attaching three chorionic gonadotrophin carboxy terminal peptides (CTPs) to the carboxy terminus of said FIX polypeptide, thereby reducing the dosing frequency of said FIX polypeptide. In another embodiment, the present invention provides a method of reducing the dosing frequency of a Factor VIIa (FVIIa) polypeptide, comprising the step of attaching three chorionic gonadotrophin carboxy terminal peptides (CTPs) to the carboxy terminus of said FVIIa polypeptide, thereby reducing the dosing frequency of said FVIIa polypeptide.

In another embodiment, the term compliance comprises adherence. In another embodiment, the methods of the invention include increasing the compliance of patients in need of a coagulation factor therapy by reducing the frequency of administration of the coagulation factor. In another embodiment, reduction in the frequency of administration of the coagulation factor is achieved due to the CTP modifications which render the CTP-modified coagulation factor more stable. In another embodiment, reduction in the frequency of administration of the coagulation factor is achieved as a result of increasing T½ of the coagulation factor. In another embodiment, reduction in the frequency of administration of the coagulation factor is achieved as a result of increasing the clearance time or reducing the clearance rate of the coagulation factor.

In another embodiment, the present invention provides a method of reducing the clearance rate of a Factor IX (FIX) polypeptide, comprising the step of attaching three chorionic gonadotrophin carboxy terminal peptides (CTPs) to the carboxy terminus of said FIX polypeptide, thereby reducing the clearance rate of said FIX polypeptide. In another embodiment, the present invention provides a method of reducing the clearance rate of a Factor VIIa (FVIIa) polypeptide, comprising the step of attaching three chorionic gonadotrophin carboxy terminal peptides (CTPs) to the carboxy terminus of said FVIIa polypeptide, thereby reducing the clearance rate of said FVIIa polypeptide.

In another embodiment, reduction in the frequency of administration of the coagulation factor is achieved as a result of increasing the AUC measure of the coagulation factor.

In another embodiment, provided herein is a method of reducing the dosing frequency of a coagulation factor, comprising the step of attaching one to ten CTPs to the carboxy terminus of the coagulation factor, thereby reducing a dosing frequency of the coagulation factor. In another embodiment, provided herein is a method of reducing the dosing frequency of a coagulation factor, comprising the step of attaching one to five CTPs to the carboxy terminus of the coagulation factor, thereby reducing a dosing frequency of the coagulation factor. In another embodiment, provided herein is a method of reducing the dosing frequency of a coagulation factor, comprising the step of attaching three CTPs to the carboxy terminus of the coagulation factor, thereby reducing a dosing frequency of the coagulation factor. In another embodiment, provided herein is a method of reducing the dosing frequency of a coagulation factor, comprising the step of attaching three to five CTPs to the carboxy terminus of the coagulation factor, thereby reducing a dosing frequency of the coagulation factor.

In another embodiment, provided herein is a method of increasing compliance in the use of coagulation factor therapy, comprising providing to a subject in need thereof, a polypeptide comprising a coagulation factor and one to ten chorionic gonadotrophin carboxy terminal peptides attached to the carboxy terminus of a coagulation factor, thereby increasing compliance in the use of coagulation factor therapy. In another embodiment, provided herein is a method of increasing compliance in the use of coagulation factor therapy, comprising providing to a subject in need thereof, a polypeptide comprising a coagulation factor and one to five chorionic gonadotrophin carboxy terminal peptides attached to the carboxy terminus of a coagulation factor, thereby increasing compliance in the use of coagulation factor therapy. In another embodiment, provided herein is a method of increasing compliance in the use of coagulation factor therapy, comprising providing to a subject in need thereof, a polypeptide comprising a coagulation factor and three chorionic gonadotrophin carboxy terminal peptides attached to the carboxy terminus of a coagulation factor, thereby increasing compliance in the use of coagulation factor therapy. In another embodiment, provided herein is a method of increasing compliance in the use of coagulation factor therapy, comprising providing to a subject in need thereof, a polypeptide comprising a coagulation factor and three to five chorionic gonadotrophin carboxy terminal peptides attached to the carboxy terminus of a coagulation factor, thereby increasing compliance in the use of coagulation factor therapy.

In another embodiment, provided herein is a method of preventing or treating a blood clotting or coagulation disorder in a subject, comprising providing to said subject a polypeptide comprising a coagulation factor and one to ten chorionic gonadotrophin carboxy terminal peptides attached to the carboxy terminus of a coagulation factor, thereby treating a blood clotting or coagulation disorder in said subject. In another embodiment, provided herein is a method of preventing or treating a blood clotting or coagulation disorder in a subject, comprising providing to a subject in need thereof, a polypeptide comprising a coagulation factor and one to five chorionic gonadotrophin carboxy terminal peptides attached to the carboxy terminus of a coagulation factor, thereby preventing or treating a blood clotting or coagulation disorder in said subject. In another embodiment, provided herein is a method of preventing or treating a blood clotting or coagulation disorder in a subject, comprising providing to a subject in need thereof, a polypeptide comprising a coagulation factor and three chorionic gonadotrophin carboxy terminal peptides attached to the carboxy terminus of a coagulation factor, thereby preventing or treating a blood clotting or coagulation disorder in said subject. In another embodiment, provided herein is a method of preventing or treating a blood clotting or coagulation disorder in a subject, comprising providing to a subject in need thereof, a polypeptide comprising a coagulation factor and three to five chorionic gonadotrophin carboxy terminal peptides attached to the carboxy terminus of a coagulation factor, thereby preventing or treating a blood clotting or coagulation disorder in said subject.

In another embodiment, provided herein is a method of preventing hemophilia in a subject, comprising providing to said subject a polypeptide comprising a coagulation factor and one to ten chorionic gonadotrophin carboxy terminal peptides attached to the carboxy terminus of a coagulation factor, thereby preventing hemophilia in said subject. In another embodiment, provided herein is a method of preventing hemophilia in a subject, comprising providing to a subject in need thereof, a polypeptide comprising a coagulation factor and one to five chorionic gonadotrophin carboxy terminal peptides attached to the carboxy terminus of a coagulation factor, thereby preventing hemophilia in said subject. In another embodiment, provided herein is a method of preventing hemophilia in a subject, comprising providing to a subject in need thereof, a polypeptide comprising a coagulation factor and three chorionic gonadotrophin carboxy terminal peptides attached to the carboxy terminus of a coagulation factor, thereby preventing hemophilia in said subject. In another embodiment, provided herein is a method of preventing hemophilia in a subject, comprising providing to a subject in need thereof, a polypeptide comprising a coagulation factor and three to five chorionic gonadotrophin carboxy terminal peptides attached to the carboxy terminus of a coagulation factor, thereby preventing hemophilia in said subject.

In another embodiment, the present invention shows that the compositions provided herein are surprisingly more effectively absorbed into the bloodstream after SC administration (see Examples 7-9 herein). To be able to administer FVIIa subcutaneously serves as an advantage as it can be used for prophylactic applications. Subcutaneous injections are also much easier for patients to self-inject, and are advantage when the patients are very young and their veins are small and difficult to find.

In another embodiment, provided herein is a method of treating hemophilia in a subject, comprising providing to said subject a polypeptide comprising a coagulation factor and one to ten chorionic gonadotrophin carboxy terminal peptides attached to the carboxy terminus of a coagulation factor, thereby treating hemophilia in said subject. In another embodiment, provided herein is a method of treating hemophilia in a subject, comprising providing to a subject in need thereof, a polypeptide comprising a coagulation factor and one to five chorionic gonadotrophin carboxy terminal peptides attached to the carboxy terminus of a coagulation factor, thereby treating hemophilia in said subject. In another embodiment, provided herein is a method of treating hemophilia in a subject, comprising providing to a subject in need thereof, a polypeptide comprising a coagulation factor and three chorionic gonadotrophin carboxy terminal peptides attached to the carboxy terminus of a coagulation factor, thereby treating hemophilia in said subject. In another embodiment, provided herein is a method of treating hemophilia in a subject, comprising providing to a subject in need thereof, a polypeptide comprising a coagulation factor and three to five chorionic gonadotrophin carboxy terminal peptides attached to the carboxy terminus of a coagulation factor, thereby treating hemophilia in said subject.

Oral administration, in one embodiment, comprises a unit dosage form comprising tablets, capsules, lozenges, chewable tablets, suspensions, emulsions and the like. Such unit dosage forms comprise a safe and effective amount of the desired coagulation factor of the invention, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of the desired compound or compounds, or in another embodiment, from about 0.01% to about 10%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.001% to about 10.0% w/v of a subject compound, more preferably from about 00.1% to about 2.0, which is used for systemic delivery of the compounds by the intranasal route.

In another embodiment, a polypeptide comprising a coagulation factor and at least one CTP unit is injected into the muscle (intramuscular injection). In another embodiment, a polypeptide comprising a coagulation factor and at least one CTP unit is injected below the skin (subcutaneous injection). In another embodiment, a polypeptide comprising a coagulation factor and at least one CTP unit is injected into the muscle. In another embodiment, a polypeptide comprising a coagulation factor and at least one CTP unit is injected into the skin. In another embodiment, a coagulation factor as described herein is administered via systemic administration. In another embodiment, a coagulation factor as described herein is administered by intravenous injection. In another embodiment, administration can be parenteral, pulmonary, oral, topical, intradermal, intramuscular, intraperitoneal, intravenous, subcutaneous, intranasal, transnasal, intraocular, ophthalmic, epidural, buccal, rectal, transmucosal, intestinal or parenteral delivery, including intramedullary injections as well as intrathecal or direct intraventricular administration.

In another embodiment, the preparation is administered in a local rather than systemic manner, for example, via injection of the preparation directly into a specific region of a patient's body.

In one embodiment, the route of administration may be enteral. In another embodiment, the route may be conjunctival, transdermal, intradermal, intra-arterial, vaginal, rectal, intratumoral, parcanceral, transmucosal, intramuscular, intravascular, intraventricular, intracranial, intra-nasal, sublingual, or a combination thereof.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in a conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables of the invention are formulated in aqueous solutions. In one embodiment, injectables of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oil or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; J. E. Diederichs and al., Pharm./nd. 56 (1994) 267-275).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target. i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80. Pluronic F68, bile acid salts), protease inhibitors, surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also prepared, placed in an appropriate container, and labeled for treatment of an indicated condition.

In another embodiment, a coagulation factor as described herein is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized coagulation factor as described in sterile water for injection. In another embodiment, a pharmaceutical composition comprises a lyophilized coagulation factor as described in sterile PBS for injection. In another embodiment, a pharmaceutical composition comprises a lyophilized coagulation factor as described in sterile 0.9% NaCl for injection.

In another embodiment, the pharmaceutical composition comprises a coagulation factor as described herein and complex carriers such as human serum albumin, polyols, sugars, and anionic surface active stabilizing agents. In another embodiment, the pharmaceutical composition comprises a coagulation factor as described herein and lactobionic acid and an acetate/glycine buffer. In another embodiment, the pharmaceutical composition comprises a coagulation factor as described herein and amino acids, such as arginine or glutamate that increase the solubility of interferon compositions in water. In another embodiment, the pharmaceutical composition comprises a lyophilized coagulation factor as described herein and glycine or human serum albumin (HSA), a buffer (eg. acetate) and an isotonic agent (e.g NaCl). In another embodiment, the pharmaceutical composition comprises a lyophilized coagulation factor as described herein and phosphate buffer, glycine and HSA.

In another embodiment, the pharmaceutical composition comprising a coagulation factor as described herein is stabilized when placed in buffered solutions having a pH between about 4 and 7.2. In another embodiment, the pharmaceutical composition comprising a coagulation factor is in a buffered solution having a pH between about 4 and 8.5. In another embodiment, the pharmaceutical composition comprising a coagulation factor is in a buffered solution having a pH between about 6 and 7. In another embodiment, the pharmaceutical composition comprising a coagulation factor is in a buffered solution having a pH of about 6.5. In another embodiment, the pharmaceutical composition comprising a coagulation factor as described herein is stabilized with an amino acid as a stabilizing agent and in some cases a salt (if the amino acid does not contain a charged side chain).

In another embodiment, the pharmaceutical composition comprising a coagulation factor as described herein is a liquid composition comprising a stabilizing agent at between about 0.3% and 5% by weight which is an amino acid.

In another embodiment, the pharmaceutical composition comprising a coagulation factor as described herein provides dosing accuracy and product safety. In another embodiment, the pharmaceutical composition comprising a coagulation factor as described herein provides a biologically active, stable liquid formulation for use in injectable applications. In another embodiment, the pharmaceutical composition comprises a non-lyophilized coagulation factor as described herein.

In another embodiment, the pharmaceutical composition comprising a coagulation factor as described herein provides a liquid formulation permitting storage for a long period of time in a liquid state facilitating storage and shipping prior to administration.

In another embodiment, the pharmaceutical composition comprising a coagulation factor as described herein comprises solid lipids as matrix material. In another embodiment, the injectable pharmaceutical composition comprising a coagulation factor as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a coagulation factor as described herein comprises polymeric microparticles. In another embodiment, the pharmaceutical composition comprising a coagulation factor as described herein comprises nanoparticles. In another embodiment, the pharmaceutical composition comprising a coagulation factor as described herein comprises liposomes. In another embodiment, the pharmaceutical composition comprising a coagulation factor as described herein comprises lipid emulsion. In another embodiment, the pharmaceutical composition comprising a coagulation factor as described herein comprises microspheres. In another embodiment, the pharmaceutical composition comprising a coagulation factor as described herein comprises lipid nanoparticles. In another embodiment, the pharmaceutical composition comprising a coagulation factor as described herein comprises lipid nanoparticles comprising amphiphilic lipids. In another embodiment, the pharmaceutical composition comprising a coagulation factor as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the coagulation factors of the present invention can be provided to the individual with additional active agents to achieve an improved therapeutic effect as compared to treatment with each agent by itself. In another embodiment, measures (e.g., dosing and selection of the complementary agent) are taken to avoid adverse side effects which are associated with combination therapies.

In another embodiment, the present invention provides a CTP-modified Factor VIIa (FVIIa) polypeptide consisting of a FVIIa polypeptide and five gonadotropin carboxy terminal peptides (CTPs) attached to the carboxy terminus of said FVIIa.

In another embodiment, the present invention provides a pharmaceutical composition comprising a CTP-modified Factor VIIa (FVIIa) polypeptide consisting of a FVIIa polypeptide and five gonadotropin carboxy terminal peptides (CTPs) attached to the carboxy terminus of said FVIIa.

In another embodiment, the present invention provides a polynucleotide encoding a CTP-modified polypeptide consisting of a Factor VIIa (FVIIa) polypeptide and three gonadotropin carboxy terminal peptides (CTPs) attached to the carboxy terminus of said FVIIa polypeptide.

In another embodiment, the present invention provides an expression vector comprising a polynucleotide encoding a CTP-modified polypeptide consisting of a Factor VIIa (FVIIa) polypeptide and three gonadotropin carboxy terminal peptides (CTPs) attached to the carboxy terminus of said FVIIa polypeptide.

In another embodiment, the present invention provides a cell comprising an expression vector comprising a polynucleotide encoding a CTP-modified polypeptide consisting of a Factor VIIa (FVIIa) polypeptide and three gonadotropin carboxy terminal peptides (CTPs) attached to the carboxy terminus of said FVIIa polypeptide.

In another embodiment, the present invention provides a composition comprising an expression vector comprising a polynucleotide encoding a CTP-modified polypeptide consisting of a Factor VIIa (FVIIa) polypeptide and three gonadotropin carboxy terminal peptides (CTPs) attached to the carboxy terminus of said FVIIa polypeptide.

In another embodiment, the present invention provides a method of extending the biological half-life of a Factor VIIa (FVIIa) polypeptide, comprising the step of attaching three chorionic gonadotrophin carboxy terminal peptides (CTPs) to the carboxy terminus of said FVIIa polypeptide, thereby extending the biological half-life of said FVIIa polypeptide.

In another embodiment, the present invention provides a method of improving the area under the curve (AUC) of a Factor VIIa (FVIIa) polypeptide, comprising the step of attaching three chorionic gonadotrophin carboxy terminal peptides (CTPs) to the carboxy terminus of said FVIIa polypeptide, thereby improving the AUC of said FVIIa polypeptide.

In another embodiment, the present invention provides a method of reducing the dosing frequency of a Factor VIIa (FVIIa) polypeptide, comprising the step of attaching three chorionic gonadotrophin carboxy terminal peptides (CTPs) to the carboxy terminus of said FVIIa polypeptide, thereby reducing the dosing frequency of said FVIIa polypeptide.

In another embodiment, the present invention provides a method of reducing the clearance rate of a Factor VIIa (FVIIa) polypeptide, comprising the step of attaching three chorionic gonadotrophin carboxy terminal peptides (CTPs) to the carboxy terminus of said FVIIa polypeptide, thereby reducing the clearance rate of said FVIIa polypeptide.

In another embodiment, the present invention provides a method of producing a CTP-modified Factor VIIa (FVIIa) polypeptide, comprising the step of attaching three chorionic gonadotrophin carboxy terminal peptides (CTPs) to the carboxy terminus of said FVIIa polypeptide, thereby producing a CTP-modified FVIIa polypeptide.

In another embodiment, the present invention provides a method of treating hemophilia in a subject comprising administering a CTP-modified Factor VIIa (FVIIa) polypeptide comprising a FVIIa polypeptide and three chorionic gonadotrophin carboxy terminal peptides (CTPs) attached to the carboxy terminus of said FVIIa polypeptide to said subject, thereby treating hemophilia in said subject.

In one embodiment, the present invention provides a CTP-modified Factor IX (FIX) polypeptide consisting of a FIX polypeptide and three gonadotropin carboxy terminal peptides (CTPs) attached to the carboxy terminus of said CTP-modified FIX polypeptide. In another embodiment, the present invention provides a CTP-modified FIX polypeptide, wherein the sequence of said CTP-modified FIX polypeptide is the sequence set forth in SEQ ID NO: 31. In another embodiment, the present invention provides a CTP-modified FIX polypeptide, wherein at least one CTP is encoded by an amino acid sequence selected from the group consisting of; SEQ ID NO: 1 and SEQ ID NO: 2. In another embodiment, the present invention provides a CTP-modified FIX polypeptide, wherein at least one CTP is glycosylated. In another embodiment, the present invention provides a CTP-modified FIX polypeptide, wherein at least one CTP is truncated. In another embodiment, the present invention provides a CTP-modified FIX polypeptide, wherein at least one CTP is attached to said FIX polypeptide via a linker. In another embodiment, the present invention provides a CTP-modified FIX polypeptide, wherein said linker is a peptide bond.

In one embodiment, the present invention provides a pharmaceutical composition comprising the CTP-modified FIX polypeptide.

In one embodiment, the present invention provides a polynucleotide encoding a CTP-modified polypeptide consisting of a Factor IX (FIX) polypeptide and three gonadotropin carboxy terminal peptides (CTPs) attached to the carboxy terminus of said FIX polypeptide. In another embodiment, the present invention provides a polynucleotide, wherein the sequence of said polynucleotide is as set forth in SEQ ID NO: 30. In another embodiment, the present invention provides a polynucleotide, wherein at least one CTP is encoded by an amino acid sequence selected from the group consisting of: SEQ ID NO: 1 and SEQ ID NO: 2. In another embodiment, the present invention provides a polynucleotide, wherein at least one CTP is glycosylated. In another embodiment, the present invention provides a polynucleotide, wherein at least one CTP is truncated. In another embodiment, the present invention provides a polynucleotide, wherein at least one CTP is attached to said FIX polypeptide via a linker. In another embodiment, the present invention provides a polynucleotide, wherein said linker is a peptide bond. An expression vector comprising the polynucleotide.

In one embodiment, the present invention provides a cell comprising the expression vector.

In one embodiment, the present invention provides a composition comprising the expression vector.

In one embodiment, the present invention provides a method of extending the biological half-life of a Factor IX (FIX) polypeptide, comprising the step of attaching three chorionic gonadotrophin carboxy terminal peptides (CTPs) to the carboxy terminus of said FIX polypeptide, thereby extending the biological half-life of said FIX polypeptide. In another embodiment, the present invention provides a method, wherein at least one CTP is encoded by an amino acid sequence selected from the group consisting of: SEQ ID NO: 1 and SEQ ID NO: 2. In another embodiment, the present invention provides a method, wherein at least one CTP is glycosylated. In another embodiment, the present invention provides a method, wherein at least one CTP is truncated. In another embodiment, the present invention provides a method, wherein at least one CTP is attached to said FIX polypeptide via a linker. In another embodiment, the present invention provides a method, wherein said linker is a peptide bond.

In one embodiment, the present invention provides a method of improving the area under the curve (AUC) of a Factor IX (FIX) polypeptide, comprising the step of attaching three chorionic gonadotrophin carboxy terminal peptides (CTPs) to the carboxy terminus of said FIX polypeptide, thereby improving the AUC of said FIX polypeptide. In another embodiment, the present invention provides a method, wherein at least one CTP is encoded by an amino acid sequence selected from the group consisting of: SEQ ID NO: 1 and SEQ ID NO: 2. In another embodiment, the present invention provides a method, wherein at least one CTP is glycosylated. In another embodiment, the present invention provides a method, wherein at least one CTP is truncated. In another embodiment, the present invention provides a method, wherein at least one CTP is attached to said FIX polypeptide via a linker. In another embodiment, the present invention provides a method, wherein said linker is a peptide bond.

In one embodiment, the present invention provides a method of reducing the dosing frequency of a Factor IX (FIX) polypeptide, comprising the step of attaching three chorionic gonadotrophin carboxy terminal peptides (CTPs) to the carboxy terminus of said FIX polypeptide, thereby reducing the dosing frequency of said FIX polypeptide. In another embodiment, the present invention provides a method, wherein at least one CTP is encoded by an amino acid sequence selected from the group consisting of: SEQ ID NO: 1 and SEQ ID NO: 2. In another embodiment, the present invention provides a method, wherein at least one CTP is glycosylated. In another embodiment, the present invention provides a method, wherein at least one CTP is truncated. In another embodiment, the present invention provides a method, wherein at least one CTP is attached to said FIX polypeptide via a linker. In another embodiment, the present invention provides a method, wherein said linker is a peptide bond.

In one embodiment, the present invention provides a method of reducing the clearance rate of a Factor IX (FIX) polypeptide, comprising the step of attaching three chorionic gonadotrophin carboxy terminal peptides (CTPs) to the carboxy terminus of said FIX polypeptide, thereby reducing the clearance rate of said FIX polypeptide. In another embodiment, the present invention provides a method, wherein at least one CTP is encoded by an amino acid sequence selected from the group consisting of: SEQ ID NO: 1 and SEQ ID NO: 2. In another embodiment, the present invention provides a method, wherein at least one CTP is glycosylated. In another embodiment, the present invention provides a method, wherein at least one CTP is truncated. In another embodiment, the present invention provides a method, wherein at least one CTP is attached to said FIX polypeptide via a linker. In another embodiment, the present invention provides a method, wherein at least one CTP is attached to said FVII polypeptide via a linker. In another embodiment, the present invention provides a method, wherein said linker is a peptide bond.

In one embodiment, the present invention provides a method of producing a CTP-modified Factor IX (FIX) polypeptide, comprising the step of attaching three chorionic gonadotrophin carboxy terminal peptides (CTPs) to the carboxy terminus of said FIX polypeptide, thereby producing a CTP-modified FIX polypeptide. In another embodiment, the present invention provides a method, wherein the sequence of said CTP-modified FIX polypeptide is the sequence set forth in SEQ ID NO: 31. In another embodiment, the present invention provides a method, wherein at least one CTP is encoded by an amino acid sequence selected from the group consisting of: SEQ ID NO: 1 and SEQ ID NO: 2. In another embodiment, the present invention provides a method, wherein at least one CTP is glycosylated. In another embodiment, the present invention provides a method, wherein at least one CTP is truncated. In another embodiment, the present invention provides a method, wherein at least one CTP is attached to said FIX polypeptide via a linker. In another embodiment, the present invention provides a method, wherein said linker is a peptide bond.

In one embodiment, the present invention provides a method of treating hemophilia in a subject comprising administering a CTP-modified Factor IX (FIX) polypeptide comprising a FIX polypeptide and three chorionic gonadotrophin carboxy terminal peptides (CTPs) attached to the carboxy terminus of said FIX polypeptide to said subject, thereby treating hemophilia in said subject. In another embodiment, the present invention provides a method, wherein the sequence of said CTP-modified FIX polypeptide is the sequence set forth in SEQ ID NO: 31. In another embodiment, the present invention provides a method, wherein at least one CTP is encoded by an amino acid sequence selected from the group consisting of: SEQ ID NO: 1 and SEQ ID NO: 2. In another embodiment, the present invention provides a method, wherein at least one CTP is glycosylated. In another embodiment, the present invention provides a method, wherein at least one CTP is truncated. In another embodiment, the present invention provides a method, wherein at least one CTP is attached to said FIX polypeptide via a linker. In another embodiment, the present invention provides a method, wherein said linker is a peptide bond.

As is generally known in the art, the modified peptides and proteins of the invention may be coupled to labels, drugs, targeting agents, carriers, solid supports, and the like, depending on the desired application. The labeled forms of the modified biologicals may be used to track their metabolic fate; suitable labels for this purpose include, especially, radioisotope labels such as iodine 131, technetium 99, indium 111, and the like. The labels may also be used to mediate detection of the modified proteins or peptides in assay systems; in this instance, radioisotopes may also be used as well as enzyme labels, fluorescent labels, chromogenic labels, and the like. The use of such labels is particularly helpful if the peptide or protein is itself a targeting agent such as an antibody or a receptor ligand.

Similar linking techniques, along with others, may be employed to couple the modified peptides and proteins of the invention to solid supports. When coupled, these modified peptides and proteins can then be used as affinity reagents for the separation of desired components with which specific reaction is exhibited.

Finally, the modified peptides and proteins of the invention may be used to generate antibodies specifically immunoreactive with these new compounds. These antibodies are useful in a variety of diagnostic and therapeutic applications, depending on the nature of the biological activity of the unmodified peptide or protein. It is to be understood that the invention provides antibodies that are immunoreactive with CTP-modified FIX, FVII, or FVIIa as described herein. In one embodiment, such antibodies may be used to distinguish or identify CTP-modified coagulation factors that were administered from endogenous coagulation factors. In another embodiment, the antibodies may be used to localize administered CTP-modified coagulation factors.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology". John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds). "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281.521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal. B., (1984) and "Methods in Enzymology" Vol. 1-317, Academic Press; "PCR Protocols: A Guide To Methods And Applications". Academic Press, San Diego, CA (1990); Marshak et al., "Strategies for Protein Purification and Characterization—A Laboratory Course Manual" CSHL Press (1996); all of which are incorporated by reference. Other general references are provided throughout this document.

Example 1

Generation and Utilization of Coagulation Factor IX
Cloning and Expression of Recombinant FIX Molecule:

Factor IX clones were constructed in our eukaryotic expression vector pCI-neo (Promega, catalog no. E1841). ORF Clone of *Homo sapiens* coagulation factor IX was ordered from "OriGene" (RC219065). Primers were ordered from Sigma-Genosys.

Construction of 301-1-pCI-neo-p200-11 (Factor IX-ctp x2):

Primer 101:
    (SEQ ID NO: 36)
5' GTTTAGTGAACCGTCAGAAT 3'

Primer 103$^R$:
    (SEQ ID NO: 37)
5' TTGAGGAAGATGTTCGTGTA 3' (contains the SspI site of factor IX)

A PCR reaction was conducted with primer 101 and primer 103$^R$ and plasmid DNA, cDNA clone of Factor IX (OriGene" RC219065) as a template; as a result of the PCR amplification, a ~1085 bp (pcr 10) product was formed and purified from the gel (the fragment containing the amino terminus of Factor IX sequence).

Primer 98:
    (SEQ ID NO: 38)
5' ATTACAGTTGTCGCAGGTGA 3'

Primer 99$^R$:
    (SEQ ID NO: 39)
5' GCTGGAGCTAGTGAGCTTTGTTTTTCCTT 3'

Primer 100:
    (SEQ ID NO: 40)
5' GCTCACTAGCTCCAGCAGCAAGGCC 3'

Primer 27$^R$:
    (SEQ ID NO: 41)
5' TTTTCACTGCATTCTAGTTGTGG 3'

Three PCR reactions were performed. The first reaction was conducted with primer 98 and primer 99$^R$ and plasmid DNA, cDNA clone of Factor IX (OriGene", RC219065) as a template; as a result of the PCR amplification, a ~540 bp product was formed.

The second reaction was conducted with primer 100 and primer 27$^R$ and plasmid DNA of 402-2-p72-3 (hGH-CTP-CTP) as a template; as a result of the PCR amplification, a ~258 bp product was formed.

The last reaction (pcr 3) was conducted with primers 98 and 27$^R$ and a mixture of the products of the previous two reactions as a template; as a result of the PCR amplification, a ~790 bp product was formed and ligated into TA cloning vector (Invitrogen, catalog K2000-01). SspI-EcoRI fragment was isolated (TA 3-3).

Another PCR reaction was conducted (pcr 12) with primer 101 and primer 27$^R$ and a mixture of the products of pcr 10 and SspI-EcoRI fragment from pcr 3 as a template; as a result of the PCR amplification, a ~1700 bp product was formed (Factor IX-ctp-ctp) and ligated into TA cloning vector (Invitrogen, catalog K2000-01) (lig 180).

A mistake was found in the Factor IX sequence so fragments were replaced in order to form an insert of Factor IX-ctp-ctp with the correct DNA sequence.

TA-pcr 3-3 was digested with SspI and XbaI and the large fragment was isolated (vector). TA 180-4 was digested with SspI and XbaI and the small fragment (insert) was isolated and ligated to the isolated large fragment of TA-pcr-3-3digested with SspI and XbaI. The new plasmid TA-183-2 was digated with Sal I and NotI, and the Factor IX-CTP-CTP insert was isolated (~1575 bp). This fragment was inserted into eukaryotic expression vector pCI-neo (digested with Sal I and Not I) to yield the 301-2-p200-11 clone.

pCI-dhfr-Factor 9-ctpx2 (p223-4) construction: Vector pCI-dhfr (p6-1) was digested with SmaI and NotI. Factor IX-CTP-CTP (p200-11) was digested with ASisI F.I. and NotI. The two fragments were ligated.

pCI-dhfr Factor 9-ctp x3 (p225-7) construction: Vector pCI-dhfr OXM-CTPx3 (p216-4) was digested with XbaI and ApaI. Factor IX-CTP-CTP (223-4) was digested with XbaI and ApaI. The two fragments were ligated.

pCI-dhfr Factor 9-ctp x3 T148A (p243-2) construction: Plasmid p225-7 contained Threonine at position 148, since the more common version of FIX contains Alanine at this position, Thr was replaced to Ala using site directed mutagenesis method.

```
Primer 75:
                                  (SEQ ID NO: 42)
ctcccagttcaattacagct Primer 122r:
                                  (SEQ ID NO: 43)
ggaaaaactgcctcagcacgggtgagc Primer 123:
                                  (SEQ ID NO: 44)
gtgctgaggcagttttcctgatgtggactat Primer 124r:
                                  (SEQ ID NO: 45)
caacacagtgggcagcag
```

Three PCR reactions were performed. The first reaction was conducted with primer 75 and primer 122r and plasmid DNA p225-7 as a template; as a result of the PCR amplification, a ~692 bp product was formed and purified from the gel. A second PCR reaction was conducted with primer 123 and primer 124r and plasmid DNA p225-7 as a template; as a result of the PCR amplification, a ~237 bp product was formed and purified from the gel. The third-overlap PCR reaction was conducted with primers 75 and 124r, and a mixture of the products of the previous two reactions as a template; as a result of the PCR amplification, a ~910 bp product was formed. This overlap PCR product was digested with XbaI and NsiI and re ligated into p225-7 plasmid (digested with XbaI and NsiI) to yield Factor IX-ctpx3 T148A designated p243-2.

FIX-4CTP (p259-4) construction: 3.5CTP fragment was isolated from oxym-4CTP (p254-3) by restriction enzymes ApaI and XbaI. FIX+0.5CTP fragment was isolated from FIX-3CTP (p243-2) with restriction enzymes ApaI and XbaI. The two fragments were ligated.

FIX-5CTP (p260-18) construction: 4.5CTP fragment was isolated from oxym-5CTP (255-1) by restriction enzymes ApaI and XbaI. FIX+0.5CTP fragment was isolated from FIX-3CTP (p243-2) using enzymes ApaI and XbaI. The two fragments were ligated. Dg44 cells were plated in 100 mm tissue culture dishes and grown to 50-60% confluence. A total of 2 μg (microgram) of FIX cDNA was used for the transfection of one 100 mm plate using the FuGene reagent (Roche) in protein-free medium (Invitrogene CD Dg44). The media was removed 48 hours after transfection and replaced with a protein-free medium (Invitrogene CD Dg44) without nucleosides and in the presence of 800 μg/ml of G418 (Neomycin). After 14 days, the transfected cell population was transferred into T25 tissue culture flasks, and selection continued for an additional 10-14 days until the cells began to grow as stable clones. High expressing clones were selected. Approximately 2×10$^7$ cells were used to inoculate 300 ml of growth medium in a 1700 cm$^2$ roller bottle (Corning. Corning NY) supplemented with 5 ng/ml of Vitamin K3 (menadione sodium bisulfate; Sigma). The production medium (harvest) was collected after a rapid decrease in cell viability to about 70%. The production medium was first clarified and then concentrated approximately 20-fold and dialyzed with PBS using flow filtration cassette (10 KDa MWCO; Millipore Corp.).

Determination of FIX antigen level: FIX-CTP harvest antigen levels were determined using AssayMax Human FIX ELISA kit (AssayPro-EF1009-1). The calculated protein concentration is the average of three different dilutions in two independent runs (FIG. 1A, Table 1).

TABLE 1

| Calculated protein concentration | | |
| --- | --- | --- |
|  | FIX-CTP | FIX-CTP-CTP |
| FIX Ag level (μg/ml) | 41.9 | 19.2 |
| SD | 8.76 | 3.67 |
| % CV | 20.92 | 19.15 |

FIX SDS-PAGE-immune blot: FIX-CTP harvests or purified rhFIX (American Diagnostics), 100 ng of protein, were loaded on 12% Tris-Glycine gel using Precision Plus Dual Color Protein Marker (Bio-Rad). The SDS-PAGE analysis was performed by Western immunoblot using anti-human FIX polyclonal antibody and anti-human gamma carboxylation monoclonal antibody (American Diagnostics). As previously reported, rhFIX migrated at 55 KDa, while FIX fused to two CTPs migrated at 75 KDa. Both variants of FIX-CTP proteins were shown to be gamma carboxylated, an essential post-translation modification for FIX activity and function (FIG. 1B).

Determination of FIX chromogenic activity: A comparative assessment of the in vitro potency of FIX-CTP harvests versus rhFIX protein (American Diagnostics) was performed using the commercially available chromogenic activity test kit, BIOPHEN (Hyphen BioMed 221802). In the presence of thrombin, phospholipids, calcium, excess amounts of FXIa activates sampled FIX into FIXa. FIXa forms an enzymatic complex with thrombin, activated FVIII:C (supplied in an excess amounts), phospholipids, and calcium and activates Factor X, present in the assay system, into FXa. The activity directly correlates with the amount of FIX, which is the limiting factor. The generated FXa is then measured by its specific activity on FXa chromogenic substrate (pNA). The amount of pNA generated is directly proportional to FIXa activity. rhFIX and FIX-CTP harvests were serially diluted, and the potency was assessed by comparing a dose-response curve of the FIX harvests to a reference preparation consisting of rhFIX or human plasma. The average EC50 of FIX was 21 ng/ml, while the FIX-(CTP)$_2$ harvest calculated EC50 was 382 ng/ml, and the FIX-CTP harvest calculated EC50 was 1644 ng/ml. An approximately 15-fold decrease in the enzymatic activity of the FIX-(CTP)$_2$ harvest was observed (FIG. 2).

FIX Clotting activity (aPTT): The activated partial thromboplastin time (aPTT) is a measure of the integrity of the intrinsic and common pathways of the coagulation cascade. The aPTT is the time, in seconds, for plasma to clot following the addition of an intrinsic pathway activator, phospholipid and calcium. The aPTT reagent is called a partial thromboplastin because tissue factor is not included with the phospholipid as it is with the protime (PT) reagent. The activator initiates the system and then the remaining steps of the intrinsic pathway take place in the presence of phospholipid. Reference aPTT range varies from laboratory to laboratory, but is usually in the range of 27-34 seconds.

The principal of the assay was to quantitate the ability of FIX-CTP harvests to restore the clotting activity of FIX-depleted human plasma by the addition of rhFIX. 300 µl of FIX-deficient human plasma was mixed with 100 µl of rhFIX or FIX-CTP harvests and serially diluted. Following a 60 second incubation at 37° C., thromboplastin, CaCl$_2$, and phospholipids were added to the mixture, and clotting time in seconds was determined (performed by American Medical Laboratories). The potency was assessed by comparing a dose-response curve of the FIX harvests to a reference preparation consisting of rhFIX or human plasma. One unit of FIX activity corresponds to the FIX concentration that equals the activity of one ml normal human plasma. The presented aPTT results indicate that FIX-(CTP)$_2$ exhibit a 5.7-fold reduction in its specific coagulation activity compared to rhFIX (Table 2). Moreover, the aPTT results together with the chromogenic activity in vitro assay suggest that FIX-(CTP)$_2$ harvest has an improved enzymatic activity vs. FIX-CTP harvest (Table 2). An improved activity of FIX-CTP proteins can be obtained following optimization of the expression system (i.e. co-transfection with Furin and optimization of Vitamin K3 medium concentration), which was strengthened following super-transfection with Furin (data not shown).

TABLE 2

FIX clotting activity

| rhFIX (AD) (µg/ml) | PTT (Sec) | FIX-CTP (µg/ml) | PTT (Sec) | FIX-CTP-CTP (µg/ml) | PTT (Sec) |
|---|---|---|---|---|---|
| 5 | 31.3 | 9 | 45.2 | 4 | 47.5 |
| 1.25 | 35.7 | 7.25 | 53.3 | 1 | 55.9 |
| 0.3125 | 43 | 0.5625 | 64.1 | 0.75 | 67 |
| 0.078125 | 52.1 | 0.140625 | 76.3 | 0.0625 | 77.4 |

Pharmacokinetic study: rhFIX (American Diagnostic) and FIX-CTP harvests were administered in a single intravenous injection to Sprague-Dawley rats (six rats per substance) at a dose of 75 µg/kg body weight (Table 3).

TABLE 3

PK study plan of operation

| Treated Groups | Test Article | No. of animals/group | Dose Route | Gender | Dose Level (µg/kg) | Dose Level (µg per animal) | Injected Vol.(µl) | con. (µg/ml) | *Time-Points (hours post-dose) |
|---|---|---|---|---|---|---|---|---|---|
| 1 | rFIX | 6 | IV | M | 75 | 15 | 500 | 30 | 0(Pre-dose) 0.083,0.5,1.5 4,8,24,48,72 |
| 2 | rFIX-CTP | 6 | IV | M | 75 | 15 | 500 | 30 | 0(Pre-dose) 0.083,0.5,1.5 4,8,24,48,72 |
| 3 | rFIX-CTP-CTP | 6 | IV | M | 75 | 15 | 1000 | 15 | 0(Pre-dose) 0.083,0.5,1.5 4,8,24,48,72 |

Figure 3:
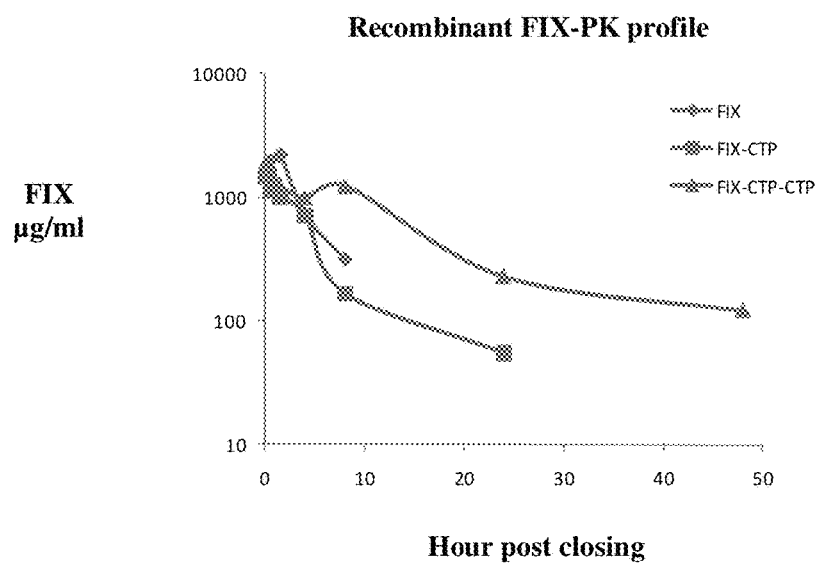
FIG. 3. Shows a graph showing PK profile of rhFIX, harvest of FIX-CTP-CTP, and harvest of FIX-CTP.

Blood samples were drawn retro-orbitally from 3 rats alternately at 0.083, 0.5 1.5, 4, 8, 24, 48, and 72 hours post-dosing. Plasma was prepared immediately after sampling and stored at −20° C. until analysis. FIX concentration was quantitated by FIX ELISA-specific assay (AssayPro). A pharmacokinetic profile was calculated for each protein and represents the mean of 3 animals at each time point (FIG. 3). The terminal half-lives were calculated using PK solutions 2.0 software. Table 4 summarizes the observed FIX concentrations at the different sampling time pints.

TABLE 4

Observed FIX concentrations

| Time (Hr) | FIX-AD (ng/ml) | FIX-CTP (ng/ml) | FIX-CTP-CTP (ng/ml) |
|---|---|---|---|
| 0.083 | 1506.7 | 1477.5 | 1914.8 |
| 0.5 | 1949.8 | 1150.1 | 1830.1 |
| 1.5 | 2189.4 | 1009.0 | 1264.3 |
| 4 | 733.90 | 709.33 | 1000.00 |
| 8 | 319.80 | 167.20 | 1234.67 |
| 24 | BLQ | 54.625 | 230 |
| 48 | BLQ | BLQ | 120.9 |

The PK profile and summary of the terminal half-lives are summarized in Table 5. FIX-CTP harvests exhibit an improved T$\frac{1}{2}$$_\beta$ values compared to rhFIX (2- and 5-fold increases, respectively). Since in FIX dosing collection, animal serum concentrations of FIX at 24 hr were below limit of quantitation (BLQ), additional PK parameters were not calculated.

TABLE 5

Summary of PK parameters

| Product | Terminal half-life-(hr) | Ratio (FIX-(CTP)x/rhFIX) |
|---|---|---|
| rhFIX (American Diagnostics | 2.62 | — |
| FIX-CTP | 5.55 | 2.11 |
| FIX-CTP (FIX-CTP-CTP) | 12.9 | 4.92 |

In this study, a novel approach was described for prolonging FIX half-life while retaining the therapeutic potency. Adding a CTP peptide to an active protein has a harmful potential in interfering with the protein's activity. Therefore, the generation of an active recombinant FIX-CTP by adding a CTP sequence at the C-terminus of the FIX is unexpected.

Characterization of an Immunoaffinity Purified FIX-CTP-CTP

FIX-CTP-CTP Purification

In order to evaluate a protein at high grade content with increased activity whose PK profile mimics and can be extrapolated to a clinical setting, FIX-CTP-CTP is a FIX modified with 2 CTP units in tandem in its carboxy-terminal. FIX-CTP-CTP was purified using matrix-bound monoclonal antibody against γ carboxyglutamyl (Gla) residues present in the N-terminal region of FIX (American Diagnostics Cat. #3570MX). The monoclonal antibody was bound to Sepharose CL-4B. The FIX-CTP-CTP harvest at a concentration of 88 µg/ml was dialyzed against 20 mM Tris, 150 Mm NaCl and 10 mM EDTA at PH=7.4. The loading rate was 0.5 ml/min, elution was performed using 20 Mm Tris-HCl, 350 mM NaCl and 50 mM CaCl, and the unbound fraction was recycled five times. Finally, the elution fraction was dialyzed with PBS, pulled and concentrated.

Determination of FIX antigen level: FIX-CTP harvests, FIX-(CTP)$_2$ harvests, and FIX-(CTP)$_2$ purified protein levels were determined using the Human FIX ELISA kit (Affinity Biologicals; Cat. #FIX-AG RUO). The calculated protein concentration (µg/ml) is the average of two independent runs (FIG. 4, Table 6).

TABLE 6

Calculated protein concentration

| | FIX-CTP | FIX-CTP-CTP | FIX-CTP-CTP (purified) |
|---|---|---|---|
| FIX Ag level (µg/ml) | 125.78 | 88.53 | 172.9 |
| SD | 17.28 | 21.31 | 2.63 |
| % CV | 13.74 | 24.08 | 1.52 |

Additionally, FIX-CTP-CTP was quantitated by Bradford assay. The calculated concentration was 202 µg/ml, which is similar to the concentration obtained by human FIX ELISA.

SDS-PAGE blots: FIX-CTP-CTP harvest, unbound fraction and purified protein, were loaded on a 12% Tris-Glycine gel using Precision Plus Dual Color Protein Marker (Bio-Rad). The SDS-PAGE Coomassie analysis was performed by staining the gel with Coomassie blue reagent (800 ng of protein). A Western immunoblot was performed with 100 ng of protein, anti-human FIX polyclonal antibody (Ab), and anti-human gamma carboxylation monoclonal Ab (American Diagnostics Cat #499 and #3570). The immunoaffinity purification procedure significantly enriched the FIX-CTP-CTP portion while reduced impurity (FIG. 5).

N-terminal sequencing: FIX-CTP-CTP purified protein was separated by 12% Tris-Glycine SDS-PAGE and subsequently electro-blotted to PVDF membrane. The band of interest was cut out and put on a purified Biobrene treated glass fiber filter. The N-terminal sequence analysis was carried out by Edmann degradation using a pulsed liquid protein sequencer equipped with a 140 C HPLC microgradient system. N-terminal sequencing revealed that FIX-CTP-CTP is a mixture of incomplete and complete pro-peptide cleaved proteins. Inadequate pro-peptide cleavage was shown to reduce FIX coagulation activity. By co-transfection with Furin, the pro-peptide cleavage process can be an improved.

Figure 6:
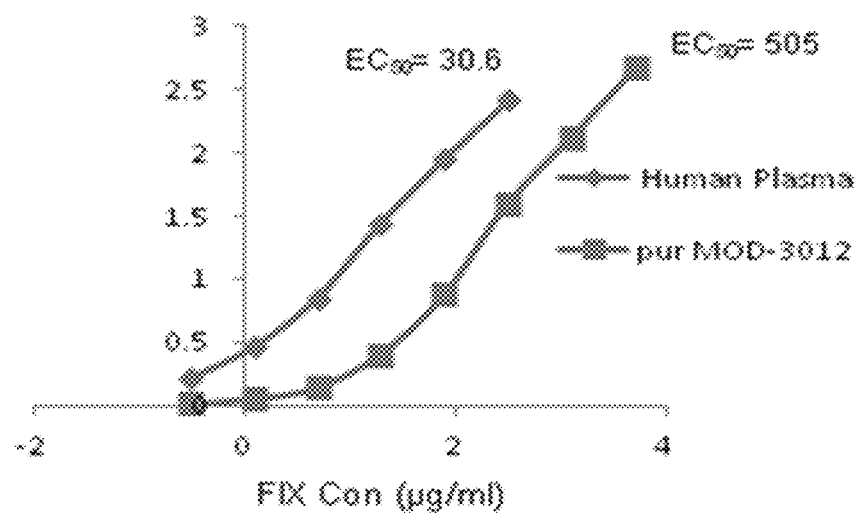
FIG. 6. Shows a graph showing FIX-(CTP)$_2$ chromogenic activity (sample concentration/O.D.) compared to human normal pool plasma and rhFIX (American Diagnostics).

Determination of FIX chromogenic activity: A comparative assessment of the in vitro potency of FIX-CTP-CTP purified protein versus rhFIX (American Diagnostics) and a pool of human normal plasma was performed using the commercially available chromogenic activity test kit, BIO-PHEN (Hyphen BioMed 221802). In the presence of thrombin, phospholipids and calcium, excess amounts of FXIa activates FIX into FIXa. FIXa forms an enzymatic complex with thrombin (supplied in excess amounts), phospholipids and calcium activates Factor X, present in the assay system, into FXa. The activity directly correlates with the amount of FIX, which is the limiting factor. The generated FXa was measured by its specific activity on FXa chromogenic substrate (pNA). The amount of pNA generated was directly proportional to FIXa activity. rhFIX, human plasma and FIX-CTP-CTP were serially diluted, and potency was assessed by comparing a dose-response curve (FIG. 6). The average EC$_{50}$ of rhFIX was 68.74 ng/ml while FIX-CTP-CTP calculated EC$_{50}$ was 505 ng/ml. An approximately 7-fold decrease in the enzymatic activity of FIX-CTP-CTP was observed vs. recombinant FIX and a 16.5-fold decrease versus normal human pulled plasma. This reduced activity could be explained by inadequate cleavage of N-terminal pro-peptide, which was identified by N-terminal analysis.

FIX Clotting activity (aPTT): The activated partial thromboplastin time (aPTT) is a measure of the integrity of the intrinsic and common pathways of the coagulation cascade. The aPTT is the time (measured in seconds) it takes plasma to clot following the addition of an intrinsic pathway activator, phospholipid and calcium.

The assay quantitated the ability of the FIX-CTP-CTP protein to restore the clotting activity of FIX depleted human plasma by the addition of rhFIX. 300 µl of FIX-deficient human plasma was mixed with 100 µl of rhFIX, FIX-CTP-CTP (FIX-CTP-CTP (the CTP are in tandem at the C-terminal)), or normal pool human plasma which was further diluted. Following a 60 second incubation at 37° C., Tissue Factor (TF), CaCl$_2$, and phospholipids were added to the mixture. Clotting time in seconds was determined. Potency was assessed by comparing a dose-response curve of FIX-CTP-CTP to a reference preparation of rhFIX or human plasma. One unit of FIX was defined as the amount of FIX which equals to the activity of 1 ml human normal plasma.

The aPTT results indicate that FIX-CTP-CTP coagulation activity is only 1.4 less than normal pool human plasma and similar to the rhFIX. The aPTT results together with the chromogenic activity in vitro assay suggest that FIX-CTP-CTP purification did not damage its activity.

Pharmacokinetic activity of FIX-CTP-CTP: Purified FIX-CTP-CTP, rhFIX (American Diagnostic) and harvests containing FIX-CTP-CTP and FIX-CTP were administered in a single intravenous injection to Sprague-Dawley rats (eight rats per substance) in a dose of 100 µg/kg body weight (Table 7).

TABLE 7

PK study outline

| Treated group Test Article | Test article | No.of animals/group/ time point | Dose Level (µg/kg) | Dose Level (µg per animal) | Injected Vol. (µl) | Con. (µg/ml) | Time-Points (hours post-dose) |
|---|---|---|---|---|---|---|---|
| A | rFIX | 8 | 100 | 20 | 500 | 40 | 0(Pre-dose) 0.083,0.5,1,2, 4,7,10,24,48,72 |
| B | rFIX-CTP (harvest) | 8 | 100 | 20 | 500 | 40 | 0(Pre-dose) 0.083,0.5,1,2, 4,7,10,24,48,72 |
| C | rFIX-CTP CTP(harvest) | 6 | 100 | 20 | 500 | 40 | 0(Pre-dose) 0.083,0.5,1,2, 4,7,10,24,48,72 |
| D | rFIX-CTP CTP(purified) | 4 | 100 | 20 | 500 | 40 | 0(Pre-dose) 0.083,0.5,1,2, 4,7,10,24,48,72 |

Figure 7:
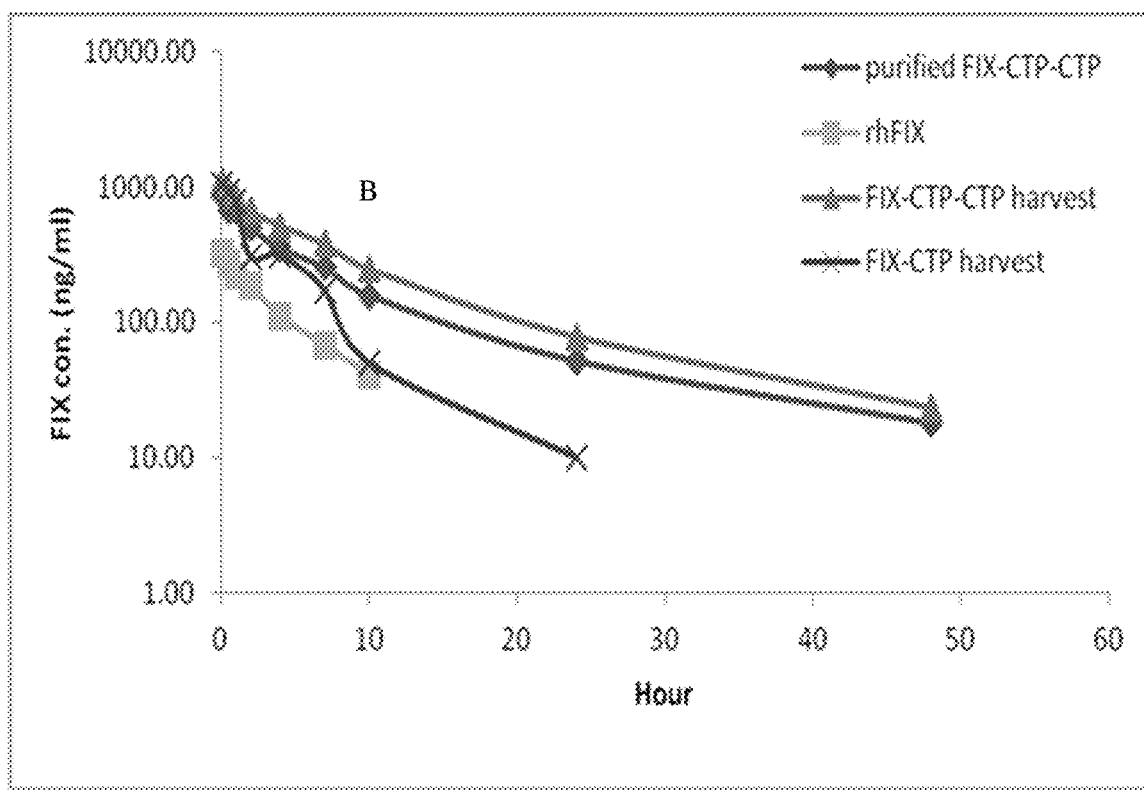
FIG. 7. Shows a graph showing the PK profile of purified FIX-CTP-CTP, rhFIX, harvest of FIX-CTP-CTP, and harvest of FIX-CTP.

Blood samples were drawn retro-orbitally from 4 rats alternately at 0.083, 0.5, 2, 4, 7 10, 24, 48, and 72 hours post-dosing. Citrated plasma (0.32%) was prepared immediately after sampling and stored at −20° C. until analysis. FIX concentration was quantitated using a human FIX ELISA kit (Affinity Biologicals). The pharmacokinetic profile was calculated for each protein as the mean of 4 animals at each time point (FIG. 7). The terminal half-life was calculated using PK Solutions 2.0 Software. Table 8 summarizes the observed FIX concentrations at different sampling time points.

TABLE 8

Observed FIX concentrations

| Time (hr) | FIX-CTP harvest ng/ml | FIX-(CTP)$_2$ harvest ng/ml | rhFIX ng/ml | Purified FIX-CTP-CTP ng/ml |
|---|---|---|---|---|
| 0.085 | 1038.97 | 1123.62 | 325.05 | 886.48 |
| 0.5 | 939.12 | 956.80 | 274.58 | 670.92 |
| 1 | 791.97 | 843.85 | 222.90 | 674.17 |
| 2 | 304.98 | 673.31 | 186.00 | 503.91 |
| 4 | 315.37 | 525.50 | 109.69 | 357.36 |
| 7 | 171.45 | 384.36 | 67.62 | 257.02 |
| 10 | 50.34 | 250.73 | 40.20 | 158.66 |
| 24 | 10.07 | 78.50 | BLQ | 52.13 |
| 48 | BLQ | 23.40 | BLQ | 18.07 |

A summary of the PK parameters are presented in Table 9.

TABLE 9

Summary of PK parameters

| | T1/2 (hr) | AUC ng-hr/ml | MRT (hr) | Vd ml/Kg | CL Ml/hr/Kg |
|---|---|---|---|---|---|
| FIX-CTP harvest | 4.17 | 3622 | 4.5 | 155.1 | 27.6 |
| FIX-(CTP)$_2$ harvest | 10.44 | 9105.7 | 12 | 165.4 | 10.9 |
| rhFIX | 3.72 | 1416.8 | 5.1 | 373.8 | 70.183 |
| Purified FIX-CTP-CTP | 11.14 | 6314.2 | 12.3 | 254.5 | 15.83 |

The FIX-CTP-CTP harvest demonstrated an improved PK profile compared to FIX-CTP harvest. Furthermore, purified FIX-CTP-CTP exhibited a 3-fold increase in T½$_\beta$ value and a 4.5-fold increase in AUC compared to rhFIX.

The reduced amount of secreted FIX fused to tandem CTP molecules versus fusion of a single CTP appears to be due to the addition of an extra CTP and not to reduced detection by ELISA, because the Bradford-purified FIX-CTP-CTP calculated concentration was similar to the ELISA-calculated concentration.

FIX-CTP-CTP clotting activity was similar to pooled human plasma; however, its in vitro chromogenic activity was significantly lower when compared to rhFIX or pooled human plasma. The chromogenic activity assay was reported as a very sensitive assay compared to the coagulation assay. The reason for reduced activity of FIX-CTP-CTP may vary. Addition of CTP may decrease the affinity of FIX to FXIa or reduce post-transcriptional modifications (e.g. 12-10 GLA residues and pro-peptide cleavage). N-terminal analysis revealed that the proteolytic cleavage of the FIX-CTP-CTP pro-peptide was not fully completed prior to secretion. Since this post-transcriptional modification is crucial for the normal enzymatic activity of the protein, co-transfection with Furine-PACE plasmid is favorable and may improve FIX-CTP-CTP activity.

Finally, FIX-CTP-CTP comparative PK study in rats demonstrated that fusion of two tandem CTPs to the C-terminal of FIX generated a FIX with an extended half-life.

FIX depleted mouse model: In order to assess the in vivo activity, FIX knockout mice are obtained, and a breeding colony is established. 10 µg of either commercial recombinant hFIX (BeneFIX®) or rFIX-(CTP)$_2$ (FIX-CTP-CTP) are injected into the tail vein of an anaesthetized FIX knockout mouse (22-28 g). The amount of injected protein equals to the required concentration of FIX in normal plasma (5 µg/ml). Blood samples are taken from the clipped tail into heparinized capillary tubes at specific time points. Plasma samples are assessed for FIX levels by ELISA and efficacy is measured by aPTT coagulation assay.

Increasing FIX Propeptide cleavage efficacy: CTP peptide cDNA was fused to the 3' end of human FIX cDNA. The corresponding rFIX and Furin expressing constructs were co-transfected into Dg44 cells; a human rFIX cDNA was also co-transfected with the Furin plasmid as a control. Secretion of high level of FIX leads to secretion of a mixture of pro-factor and a mature factor FIX, due to limited amount of the Furin protease in the cell. Co-transfection of a Furin expressing vector with a pro-factor expressing vector increases the recovery and result in the secretion of fully processed FIX in to the medium.

Following FIX-(CTP)$_2$ and Furin co-transfection, stable clones are generated and harvest is collected for pro-peptide cleavage evaluation. 100 ng of protein, are loaded on 12% Tris-Glycine gel using Precision Plus Dual Color Protein Marker (Bio-Rad). The SDS-PAGE analysis is performed by Western immunoblot using anti-human FIX polyclonal Ab (American Diagnostics) and anti-pro-peptide polyclonal antibody. As previously reported, rhFIX migrated at 55 KDa, while FIX fused to two CTPs migrated at 75 kDa. Both variants of FIX proteins are shown to undergo a proper, full pro-peptide cleavage.

To determine whether proper pro-peptide cleavage improves FIX-(CTP)$_2$ enzymatic activity, a comparative assessment of chromogenic and coagulation activity of FIX-(CTP)$_2$ harvest cotransfecated with Furin is performed. A significant improvement in FIX-(CTP)$_2$ specific activity is observed, which is similar to rhFIX.

In conclusion, the results described herein suggest that FIX-CTP-CTP can be used efficiently for treating Hemophilia B patients. FIX fused to CTP constructs benefit from improved in vivo pharmacologic performance that overcomes the drawback in certain in vitro measures. This proposed treatment is advantageous over previous treatments as the rate of infusions and the amount of required doses are reduced.

It is important to notice that when an albumin-fused molecule strategy was used to improve the FIX half-life, the recombinant FIX became inactive. The present novel approach lead to the design and purification of a novel recombinant FIX-fused protein that presents an improved long-lasting activity. Since mere size modifications did not improve the pharmacokinetics of injected FIX, the finding that CTP fused to FIX facilitates pharmacokinetic parameters was unexpected. The presence of highly glycosylated peptide-sialic acid residues stabilized the protein and protected it from interactions with vascular receptors without abrogating key determinants of FIX function.

FIX-CTP has a similar therapeutic efficacy to rFIX in hemophilia B patients and required less frequent dosing. A single injection of FIX-CTP is sufficient to control bleeding episodes and reduce the number of injections that are needed during surgical intervention in hemophilia B patients.

The CTP technology was utilized for the development of a long-acting FIX. Specifically, extending the half-life of recombinant rFIX molecule was performed by fusion of at least one human CTP to FIX. The recombinant FIX-CTP was expressed in mammalian cells and characterized in vitro and in vivo. It was demonstrated that the in vitro activity of rFIX-CTP was comparable to rFIX. Pharmacokinetics and efficacy studies in rats demonstrated improved properties of the rFIX-CTP. The results of this study demonstrate that it is feasible to develop a half-life extended rFIX molecule having similar haemostatic properties to the wild type enzyme.

Example 2

Comparative Assessment of Purified FIX-CTP$_3$ vs. FIX-CTP$_4$ and FIX-CTP$_5$ 2.1 Study Objective A comparative assessment of the pharmacokinetic parameters of FIX-CTP$_4$ and FIX-CTP$_5$ versus FIX-CTP$_3$ following a partial purification process.

2.2 Production of FIX-CTP$_4$ and FIX-CTPs Harvests

FIX cDNA (OriGene RC219065) fused at the C-terminal to four or five tandem CTP sequences was expressed in Dg44 cells using Excellgene expression system in the presence of 10 ng/L of vitamin K3 (Sigma, Mennadion). The harvests were collected (300 ml), filtered and frozen.

2.3 Production of FIX-CTPs Harvest

FIX-CTP$_3$ was expressed in-house in CHO cells using pCI-DHFR vector, clone 196. BR-9 in the presence of 25 ng/L of vitamin K3 (Sigma). The harvests were collected and filtered.

All FIX-CTP samples (3, 4 and 5 CTP) were purified only by Jacalin column because of a lack of material.

2.4 Determination of FIX Antigen Level

FIX antigen level was determined using Human FIX ELISA kit (Affinity Biologicals; Cat. #FIX-AG RUO). The calculated protein concentration is the average of four independent runs. FIX-CTP$_3$ concentration was slightly higher as compared to the two additional versions (Table 10).

TABLE 10

| | FIX antigen level | | |
|---|---|---|---|
| | 3 CTP Final Jacalin40 | 4 CTP Final Jacalin40 | 5 CTP Final Jacalin40 |
| Av. (ng/ml) | 1016.69 | 4644.11 | 1686.82 |
| SD | 225.41 | 925.63 | 160.07 |
| % CV | 22.17 | 19.93 | 9.49 |

2.5 FIX-CTP Coomassie Stain and Immune-Blot

FIX-CTP$_3$, FIX-CTP$_4$, and FIX-CTP$_5$ harvests were loaded on 12% Tris-Glycine gel using Precision Plus Dual Color Protein Marker (Bio-Rad). The SDS-PAGE analysis was performed by Western immuno-blot using anti-CTP polyclonal Ab (Adar Biotech Production) or anti-Gla Ab (American Diagnostica).

Figure 8A:
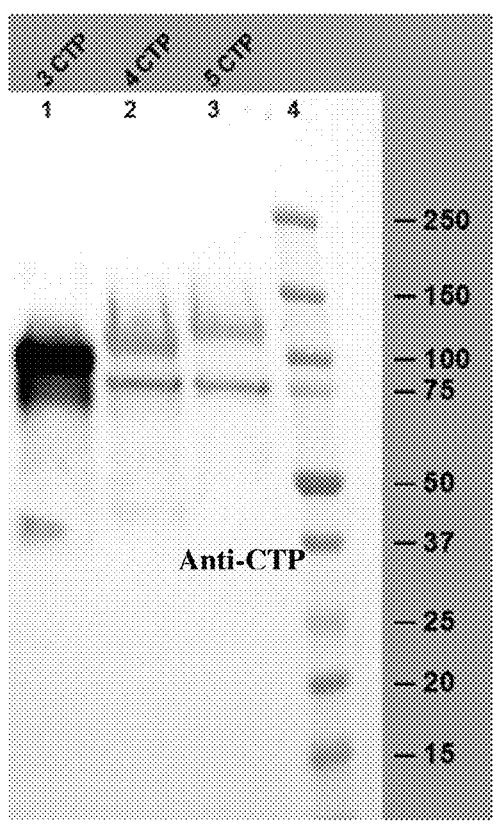
FIG. 8A. Shows an anti-CTP and anti-gamma carboxylation antibodies Western blots of FIX fused to three, four or five CTPs. FIX-CTP$_3$, FIX-CTP$_4$, and FIX-CTP$_5$ harvests were loaded on 12% Tris-Glycine gel using Precision plus dual color protein marker (Bio-Rad). The SDS-PAGE analysis was performed by Western immuno-blot using anti-CTP polyclonal Ab (Adar Biotech Production).
Figure 8B:
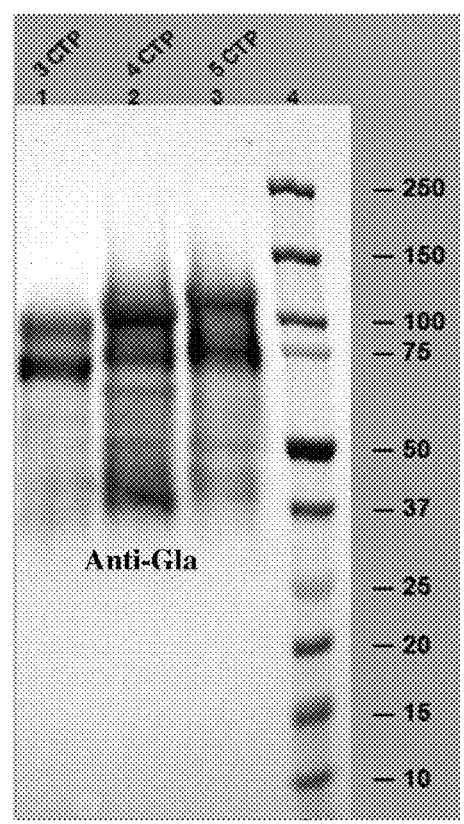
FIG. 8B. Shows an anti-CTP and anti-gamma carboxylation antibodies Western blots of FIX fused to three, four or five CTPs. FIX-CTP$_3$, FIX-CTP$_4$, and FIX-CTP$_5$ harvests were loaded on 12% Tris-Glycine gel using Precision plus dual color protein marker (Bio-Rad). The SDS-PAGE analysis was performed by Western immuno-blot using anti-Gla Ab (American Diagnostica).

As previously reported, FIX fused to three CTPs migrated at 80 kDa while FIX fused to four or five CTPs migrated at 85 KDa or 90 KDa, respectively. As expected, FIX-CTP$_4$ and FIX-CTPs harvests from Excellgene showed very low levels of gamma carboxylation compared to FIX-CTP$_3$ harvest, which was produced at Prolor (FIG. 8).

Figure 9:
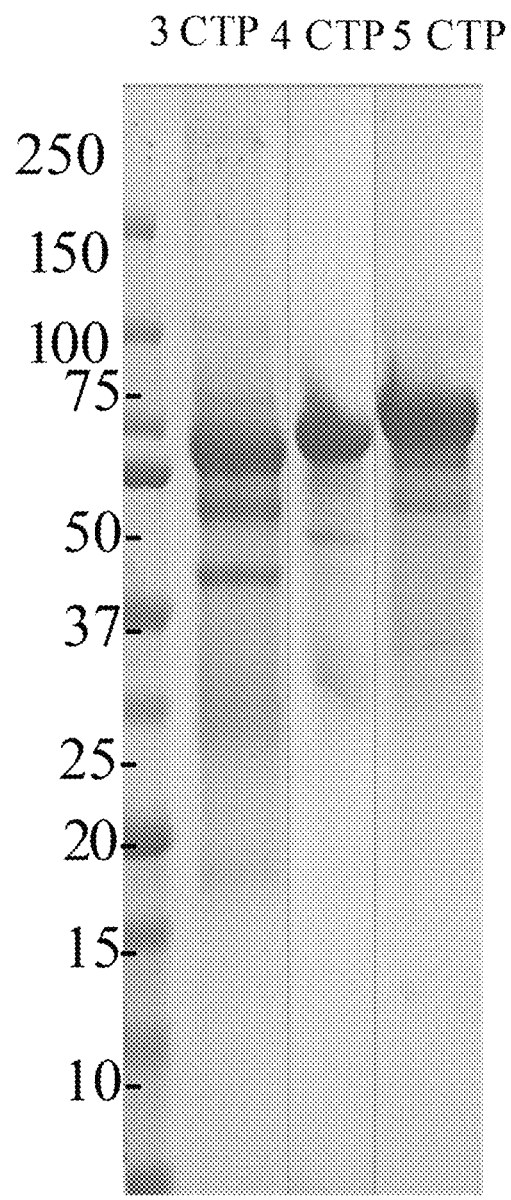
FIG. 9. Shows a coomassie blue detection of FIX-CTP$_3$, FIX-CTP$_4$, and FIX-CTP$_5$. After a purification process utilizing Jacalin column (immunoaffinity purification of glycosylated proteins), FIX-CTP$_3$, FIX-CTP$_4$, and FIX-CTP$_5$ were loaded on 12% Tris-Glycine gel using Precision Plus Dual Color Protein Marker (Bio-Rad). The SDS-PAGE was stained by Coomassie blue dye for sample detection.

After a purification process utilizing Jacalin column (immunoaffinity purification of glycosylated proteins), FIX-CTP$_3$, FIX-CTP$_4$, and FIX-CTPs were loaded on 12% Tris-Glycine gel using Precision Plus Dual Color Protein Marker (Bio-Rad). The SDS-PAGE was stained by Coomassie blue Dye for samples detection. All variants showed much cleaner band profiles (FIG. 9), suggesting an improved purity.

2.6 Determination of FIX Chromogenic Activity

Figure 10:
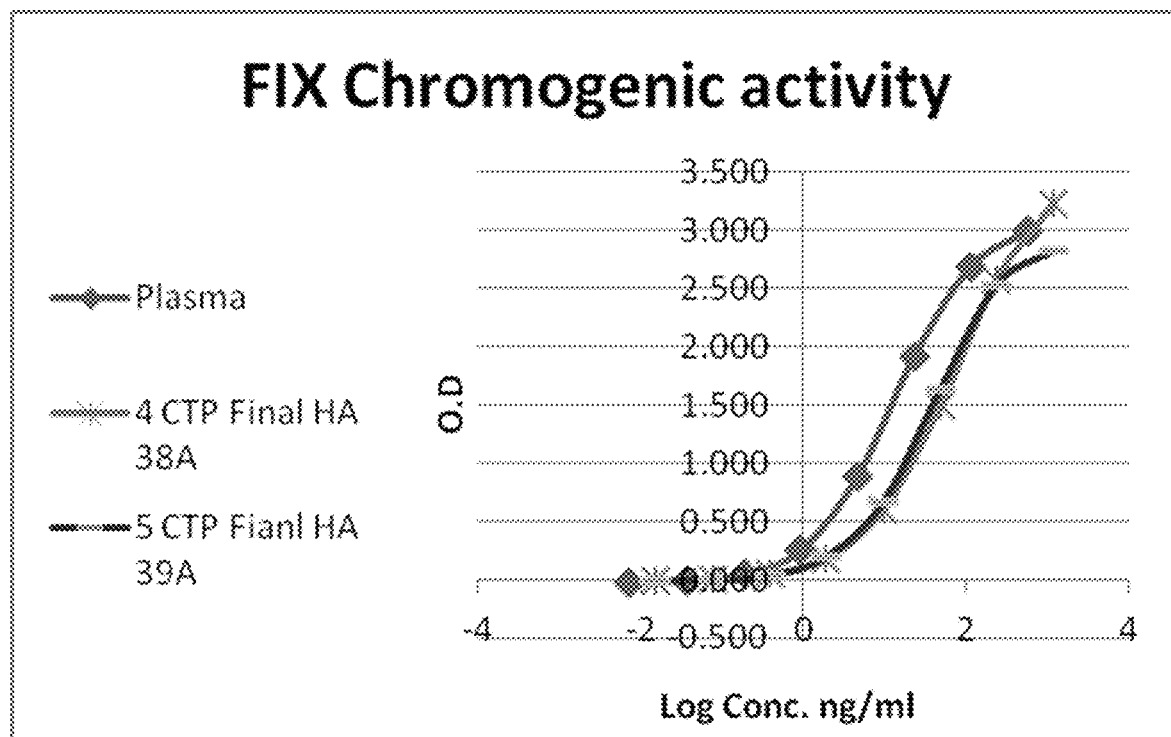
FIG. 10. Shows FIX Chromogenic activity. A comparative assessment of the in vitro potency of fully purified (HA column) FIX-CTP$_3$ FIX-CTP$_4$ and FIX-CTP$_5$ versus human pool normal plasma was performed using a commercially available chromogenic activity test kit, BIOPHEN (Hyphen BioMed 221802). All samples were serially diluted and the potency was assessed by comparing a dose response curve to a reference preparation consisting of normal human plasma.

A comparative assessment of the in vitro potency of fully purified (HA column) FIX-CTP$_3$, FIX-CTP$_4$, and FIX-CTP$_5$ versus human pool normal plasma was performed using a commercially available chromogenic activity test kit, BIOPHEN (Hyphen BioMed 221802). All samples were serially diluted, and the potency was assessed by comparing a dose-response curve to a reference preparation of normal human plasma. The reduced chromogenic activity of FIX-CTP$_4$ and FIX-CTP$_5$ (FIG. 10) as compared to plasma can be a consequence of improper post-transcriptional modifications of FIX proteins, e.g. inappropriate gamma carboxylation and pro-peptide cleavage or, alternatively, due to the addition of CTP cassettes. The fluctuation in the FIX-CTP$_4$ and FIX-CTPs activity (Table 11) might be caused by inappropriate quantitation capabilities of the FIX ELISA due to CTP masking of the antigen site.

TABLE 11

Sample/plasma EC50 ratio

| Sample | Sample/plasma EC50 ratio |
|---|---|
| Plasma | 1 |
| 3 CTP Final HA | 2 |
| 4 CTP Final HA | 5.35 |
| 5 CTP Final HA | 2.73 |

2.7 Pharmacokinetic Study

Jacalin-purified FIX-CTP$_3$, FIX-CTP$_4$, and FIX-CTP$_5$ (Group A, B and C, respectively) were administered in a single intravenous injection to Sprague-Dawley rats (six rats per treatment group) at a dose of 250 µg/kg body weight. Blood samples were drawn retro-orbitally from 3 rats alternately at 0.083, 0.5 2, 5, 8, 24, 48, 72 and 96 hours post-dosing (Table 12). Citrated plasma (0.38%) was prepared immediately after sampling and stored at −20° C. until analysis.

TABLE 12

PK study plan of operation

| Treatment Group group | Treatment | No. of animals/ group | Dose Route | Dose Level (µg per animal) | Injected Vol.(µl) | Conc. (µg/ml) | Time-Points (hr post-dose) |
|---|---|---|---|---|---|---|---|
| A | FIX-CTP*3 Jacalin 40 | 6 | IV | 50 | 200 | 250 | 0.083, 0.5, 2,5, 8, 24, 48, 72, 96 |
| B | FIX-CFP*4 Jacalin 40 | 6 | IV | 50 | 200 | 250 | 0.083,05,2, 5, 8, 24, 48, 72, 96 |
| C | FIX-CTP*5 Jacalin 40 | 6 | IV | 50 | 200 | 250 | 0.083,0,5,2 8, 24, 48, 72, 96 |

FIX concentration in plasma samples were quantified using human FIX ELISA kits (Affinity Biologicals). The pharmacokinetic profile was calculated and is the mean of 3 animals at each time point. Terminal half-lives were calculated using PK Solutions 2.0 Software. Table 13 below summarizes the calculated FIX concentrations at the different sampling time points.

TABLE 13

Calculated FIX concentrations

| Time (hr) | AV, 3 CTP ng/ml | SD 3 CTP | Av. 4 CTP rtig/ml | SD 4 CTP | Av. 5 CTP ng/ml | SD 5 CTP |
|---|---|---|---|---|---|---|
| 0.083 | 1087.82 | 72.39 | 904.54 | 21.06 | 1097.23 | 82.24 |
| 0.5 | 774.18 | 86.31 | 736.82 | 66.93 | 998.79 | 70.43 |
| 2 | 562.23 | 3.70 | 627.09 | 32.47 | 747.85 | 14.02 |
| 5 | 357.44 | 8.63 | 431.23 | 29.41 | 576.49 | 27.36 |
| 8 | 239.20 | 7.82 | 327.46 | 30.26 | 394.96 | 36.48 |
| 24 | 77.08 | 4.26 | 107.38 | 5.18 | 142.42 | 16.13 |
| 48 | 27.73 | 2.02 | 39.83 | 1.85 | 53.66 | 3.33 |
| 72 | 12.55 | 1.48 | 21.53 | 1.55 | 23.54 | 3.32 |
| 96 | 6.66 | 1.23 | 10.63 | 0.13 | 18.54 | 3.39 |

Figure 11:
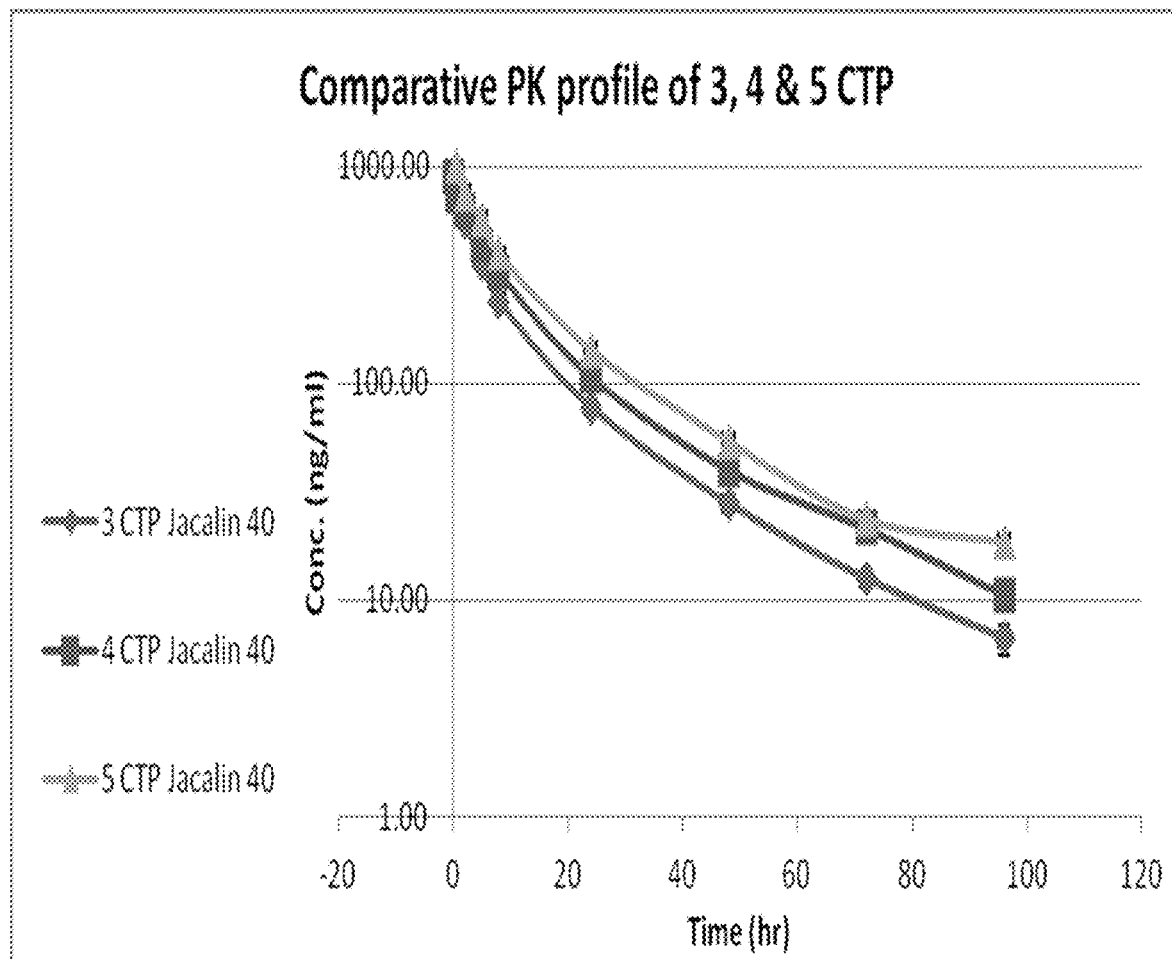
FIG. 11. Shows the comparative pharmacokinetic (PK) profile of FIX-CTP$_3$ FIX-CTP$_4$ and FIX-CTP$_5$. FIX concentration in plasma samples were quantified using human FIX Elisa kits (Affinity Biologicals). Pharmacokinetic profile was calculated and is the mean of 3 animals at each time point. Terminal half-lives were calculated using PK Solutions 2.0 software.

The PK profile and a summary of the PK parameters are presented in Table 14 below and in FIG. 11. A full PK analysis profile at all time points suggested that addition of 4 or 5 CTP cassettes to FIX did not increase its half-life as compared to FIX-CTP$_3$. The AUC following FIX-CTP$_5$ administration increased by 1.4- to 1.6-fold versus FIX-CTP$_3$, which was not statistically significant.

TABLE 14

PK profile and a summary of the PK parameters

| 24-96 hr | 3 CTP | 4 CTP | 5 CTP |
|---|---|---|---|
| Half-life (hr) | 20.43 | 22.02 | 23.96 |
| AUC (ng-hr/ml) | 8218.38 | 10504.49 | 13329.41 |
| Vd (ml/kg) | 700.76 | 586.02 | 494.89 |
| CL (ml/hr/kg) | 23.77 | 18.45 | 14.32 |

Since 96 hr post-dosing samples were shown to have very low FIX concentrations, which were at the lower limit of quantification of the assay, the terminal half-life was recalculated providing a more precise and scientifically appropriate calculation (Table 15). According to this calculation, even smaller differences were obtained between the half-life of FIX-CTP$_3$, FIX-CTP$_4$, and FIX-CTP$_5$.

TABLE 15

Recalculated terminal half-life

| 8-72 hr | 3 CTP | 4 CTP | 5 CTP |
|---|---|---|---|
| Half-life (hr) | 15.38 | 16.63 | 16.04 |

2.8 Conclusions:

In this study, the pharmacokinetic parameters and potential clotting activity of FIX-CTP$_3$, FIX-CTP$_4$, and FIX-CTP$_5$ were assessed. Fusion of 4 and 5 CTPs to FIX did not provide a superior or improved half-life extension, as compared to FIX-CTP$_3$, and reduced chromogenic activity was observed. Table 16 below summarizes the percent improvement of half-life for the different FIX-CTP fused variants (1 to 5 CTPs). Fusion of CTP to FIX improved its pharmacokinetic behavior, but, unpredictably, this improvement was limited. Surprisingly, following fusion of 3, 4 or 5 CTPs in tandem to FIX, a similar half-life value was calculated.

TABLE 16

Summary of the percent improvement of half-life

| FIX Version | T½ (8-72 hr) % increase |
|---|---|
| rhFIX vs. 1 CTP | 112 |
| 1 CTP vs. 2 CTP | 141 |

TABLE 16-continued

Summary of the percent improvement of half-life

| FIX Version | T½ (8-72 hr) % increase |
|---|---|
| 2 CTP vs. 3 CTP | 37 |
| 3 CTP vs. 4 CTP | 6 |
| 4 CTP vs. 5 CTP | 0 |

These data suggest that fusion of 3 CTPs to FIX produces a maximal improvement in protein half-life, confirming that FIX-CTP$_3$ is the optimal variant in terms of half-life, structure and potential clotting activity for further clinical development.

Example 3

FIX-CTP$_3$ Treatment of FIX−/− Hemophilic Mouse Model

As described above, a study testing FIX-CTP, FIX-CTP$_2$ and FIX-CTP$_3$ harvest PK profile and coagulation activity vs. rhFIX was conducted. FIX-CTP$_3$ exhibited an improved PK profile while maintaining its coagulation activity vs. FIX-CTP$_1$ and FIX-CTP$_2$ harvests or rhFIX. To further evaluate this result, FIX-CTP$_3$ γ-Carboxyglutamate protein was purified. FIX-CTP$_3$ exhibits a 3-fold increase in half-life and 4.5-fold higher AUC compared to rhFIX in normal rats following a single IV administration. FIX-CTP$_3$ demonstrated a reduced in vitro chromogenic and clotting activity, most likely due to insufficient cleavage of N-terminal propeptide and in appropriate post-transcriptional modifications (PTMs), such as appropriate gamma carboxylation.

In the current study, the pharmacokinetic and pharmacodynamic properties of human recombinant FIX fused to three tandem CTPs were tested in FIX-deficient mice.

Study Purpose:

To determine the pharmacokinetic and pharmacodynamic parameters of rFIX-(CTP)$_3$ vs. commercial rhFIX (BeneFIX®) in FIX-deficient mice following a single IV administration of FIX-(CTP)$_3$ at a similar specific activity and dose (similar specific activity to PD and similar FIX constant for PK).

Production of FIX-CTP$_3$ Harvest:

FIX cDNA (OriGene RC219065-Thr 148) fused at the C-terminal to three tandem CTP sequences was expressed in Dg44 cells using Excellgene expressing system in the presence of 25 ng/ml of Vitamin K3 (Sigma, Mennadion). Five separate batches containing 5 liters of cell suspension was cultured (total of twenty-five liters) and harvested following viability decline to 60-70%. The harvest was filtered and frozen at −70° C.

Determination of Harvest FIX Antigen Level:

Harvest FIX antigen level was determined using a human FIX ELISA kit (Affinity Biologicals; Cat. #FIX-AG RUO). The antigen level was calculated per each batch. The FIX concentration was maintained through the different batches (Table 17).

TABLE 17

| | FIX antigen level | | |
|---|---|---|---|
| | FIX antigen level | | |
| Batch | #1 | Bat #2 | Bat #3 |
| Av (μ/ml) | 28.81 | 32.74 | 42.9 |
| STD | 2.5 | 2.69 | 4.0 |
| % CV | 8.84 | 8.38.2 | 9.4 |

FIX-CTP$_3$ Purification Process:

Following a short purification study, a purification process using the following 3 columns was performed: DEAE Sepharose, Heparin Sepharose and HA Bio Rad Ceramic Hydroxyapatite type 1 (40 μm), FIX-CTP$_3$. γ-carboxylated enriched protein was purified. In brief: Five liters of clarified harvest was thawed at 4° C. over a 4 day period. For each purification batch, the clarified harvest (2 liters) was concentrated 4-fold and dialyzed against 20 mM Tris-HCl pH 8.2 using a disposable hollow fiber cartridge with a nominal molecular weight cutoff size of 10 KDa. This process (UFDF1) was performed twice, and one liter of UFDF1 was loaded on DEAE Sepharose column, and Factor IX was eluted with 20 mM Tris-HCl, 200 mM NaCl, 10 mM CaCl$_2$) pH 8.2. The product was diluted 1:1 with 20 mM Tris-HCl, 10 mM CaCl2 pH 7.5, and the pH was adjusted to 7.5 before loading on Heparin Sepharose column. The elution was performed with 20 mM Tris-HCl, 300 mM NaCl, and 10 mM CaCl$_2$) pH 7.5. The eluted product was concentrated and dialyzed against 10 mM phosphate pH 6.8 using a Pellicon XL cassette 10 KDa cutoff membrane (UFDF2). The product was loaded on an HA column, and the activated fraction of Factor IX was eluted with 150 mM phosphate pH 6.8. The purification product was concentrated to a target concentration of 2 mg/ml and dialyzed against TBS pH 7.45, divided in aliquots and stored at −70° C.

The purification process was repeated five times, on a weekly basis in order to purify the total volume (25 liters). The purification processes were named HA #6-10. Each purification product was separately evaluated (App #1-5). At the end of the purification process, the different batches were pooled and further concentrated to a target concentration of 4 mg/ml.

FIX-CTP$_3$ Analytical Properties:

Determination of FIX Antigen Level

FIX-CTP$_3$ γ-carboxylated enriched protein antigen level was determined using a human FIX ELISA kit (Affinity Biologicals; Cat. #FIX-AG RUO). The calculated protein concentration is the average of two independent runs (Table 18).

TABLE 18

| FIX-CTP3 antigen level | | | | | | | | |
|---|---|---|---|---|---|---|---|---|
| FIX-CTP3 HA purified pool ELISA #1 | | | | FIX-CTP3 HA purified pool ELISA #2 | | | | Final |
| Dil | 1 | 2 1 | Av. | Dil | 1 | 2 | Av. | Av. |
| 130000 | 3412240 | 3781830 | 3597035 | 130000 | 3692260 | 3568240 | 3630250 | 3613643 |
| 260000 | 3915600 | 4158440 | 4037020 | 260000 | 3706820 | 3595540 | 3651180 | 3844100 |

TABLE 18-continued

| FIX-CTP3 antigen level | | | | | | | | |
|---|---|---|---|---|---|---|---|---|
| FIX-CTP3 HA purified pool ELISA #1 | | | | FIX-CTP3 HA purified pool ELISA #2 | | | | Final |
| Dil | 1 | 2 1 | Av. | Dil | 1 | 2 | Av. | Av. |
| 520000 | 4158544 | 4334096 | 4246320 | 520000 | 3831464 | 3530748 | 3681106 | 3963713 |
| 1040000 | 4096352 | 4004104 | 4050228 | 1040000 | 3863392 | 3684304 | 3773848 | 3912038 |
| Av.(ng/ml) | 3895684 | 4069618 | 3982651 | Av.(ng/ml) | 3773484 | 3594708 | 3684096 | 3833373 |
| STD | 338367.5 | 234486,7 | 274313.5 | STD | 86576.66 | 65369.65 | 63369,86 | 154459.6 |
| % CV | 8.685703 | 5.761884 | 6.887712 | % CV | 2.294343 | 1.818497 | 1.720092 | 4.029338 |
| Av.(ng/ml) | 3.895684 | 4.069618 | 3.982651 | Av.(ng/ml) | 3.773484 | 3.594708 | 3.684096 | 3.833373 |

Figure 12A:
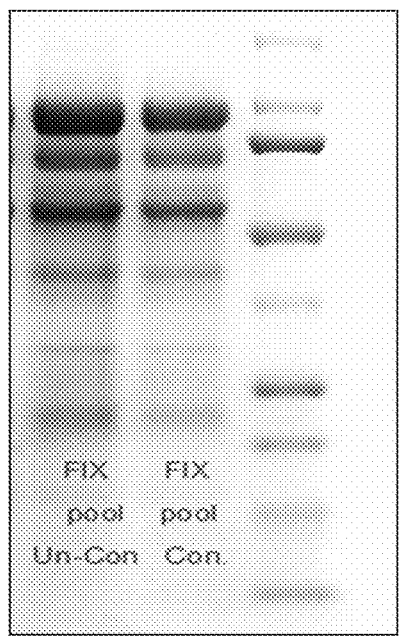
FIG. 12A. Shows the FIX-CTP$_3$ SDS-PAGE analysis—Coomassie SDS-PAGE. FIX-CTP$_3$ γ-carboxylated enriched protein, rhFIX and rFIXa (activated FIX) were loaded on 12% Tris-Glycine gel using Precision Plus Dual Color Protein Marker (Bio-Rad). The SDS-PAGE Coomassie analysis was performed by staining the gel with Coomasie blue reagent (800 ng of protein).
Figure 12B:
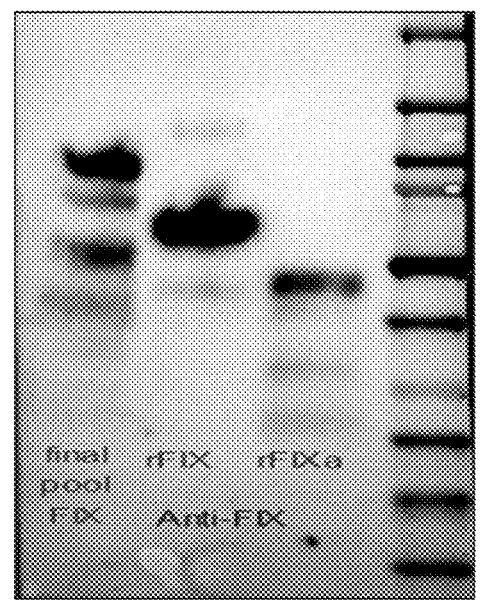
FIG. 12B. Shows the FIX-CTP$_3$ SDS-PAGE analysis—Coomassie SDS-PAGE. FIX-CTP$_3$ γ-carboxylated enriched protein, rhFIX and rFIXa (activated FIX) were loaded on 12% Tris-Glycine gel using Precision Plus Dual Color Protein Marker (Bio-Rad). A Western immunoblot was performed using 100 ng of protein with anti-human FIX polyclonal Ab.
Figure 12C:
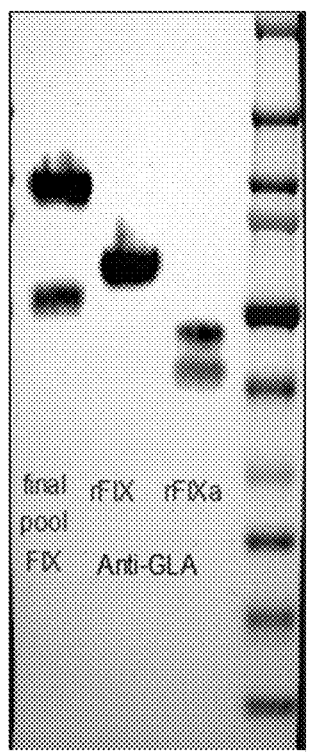
FIG. 12C. Shows the FIX-CTP$_3$ SDS-PAGE analysis—Coomassie SDS-PAGE. FIX-CTP$_3$ γ-carboxylated enriched protein, rhFIX and rFIXa (activated FIX) were loaded on 12% Tris-Glycine gel using Precision Plus Dual Color Protein Marker (Bio-Rad). A Western immunoblot was performed using 100 ng of protein with anti-human gamma carboxylation monoclonal antibody (American Diagnostics Cat #499, 3570).
Figure 12D:
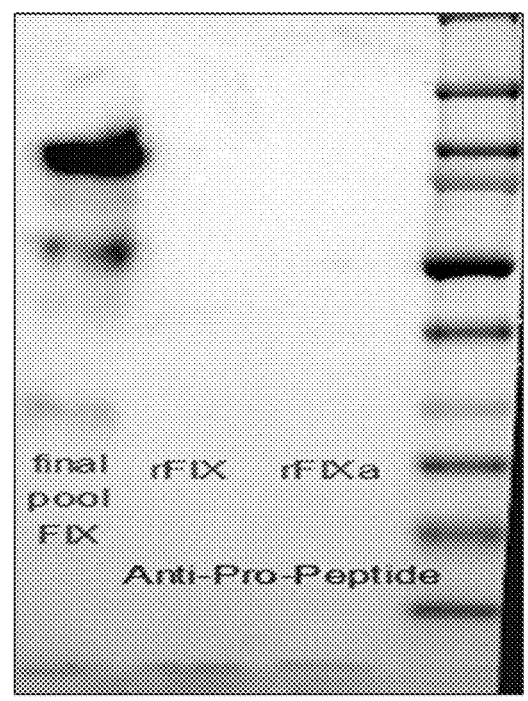
FIG. 12D. Shows the FIX-CTP$_3$ SDS-PAGE analysis—Coomassie SDS-PAGE. FIX-CTP$_3$ γ-carboxylated enriched protein, rhFIX and rFIXa (activated FIX) were loaded on 12% Tris-Glycine gel using Precision Plus Dual Color Protein Marker (Bio-Rad). A Western immunoblot was performed using 100 ng of protein with anti-FIX pro-peptide polyclonal Ab (FIG. 12D).
Figure 12E:
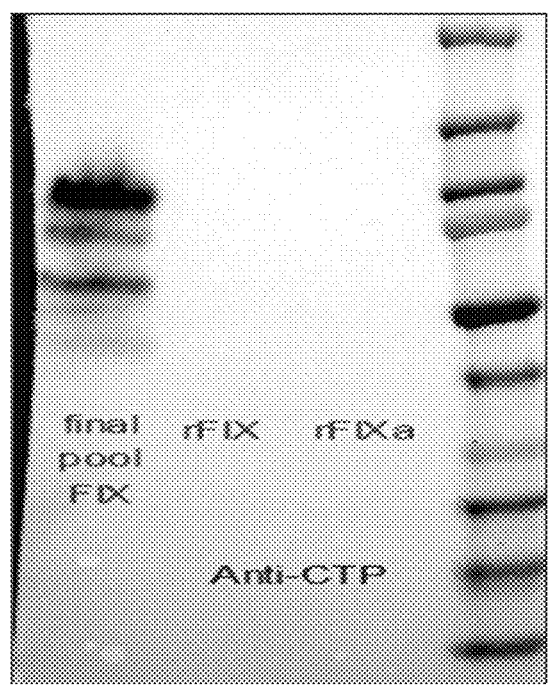
FIG. 12E. Shows the FIX-CTP$_3$ SDS-PAGE analysis—Coomassie SDS-PAGE. FIX-CTP$_3$ γ-carboxylated enriched protein, rhFIX and rFIXa (activated FIX) were loaded on 12% Tris-Glycine gel using Precision Plus Dual Color Protein Marker (Bio-Rad). A Western immunoblot was performed using 100 ng of protein with anti-CTP polyclonal Ab.

SDS-PAGE Blots:

FIX-CTP$_3$ γ-carboxylated enriched protein, rhFIX and rFIXa (activated FIX) were loaded on 12% Tris-Glycine gel using Precision Plus Dual Color Protein Marker (Bio-Rad). The SDS-PAGE Coomassie analysis was performed by staining the gel with Coomassie blue reagent (800 ng of protein) (FIG. 12). A Western immunoblot was performed using 100 ng of protein with anti-human FIX polyclonal Ab (FIG. 12B), anti-human gamma carboxylation monoclonal antibody (American Diagnostics Cat #499, 3570) (FIG. 12C), anti-FIX pro-peptide polyclonal Ab (FIG. 12D), and anti-CTP polyclonal Ab (FIG. 12E). As previously reported, FIX-CTP$_3$ migrated at 75 KDa.

The purification procedure significantly enriched FIX-CTP$_3$ portion while reducing impurities. The purification process yield was very low ranging around 2-3% (data not shown) due to the requirement to collect only the γ-carboxylated FIX-CTP$_3$ fractions, as demonstrated in the anti-Gla immunoblot (FIG. 12B). Based on the Coomassie and FIX immunoblot, the FIX-CTP$_3$ portion is only around 60-70%, and additional lower molecular weight bands, presumably with lower glycosylation forms, were also detected.

Figure 13:
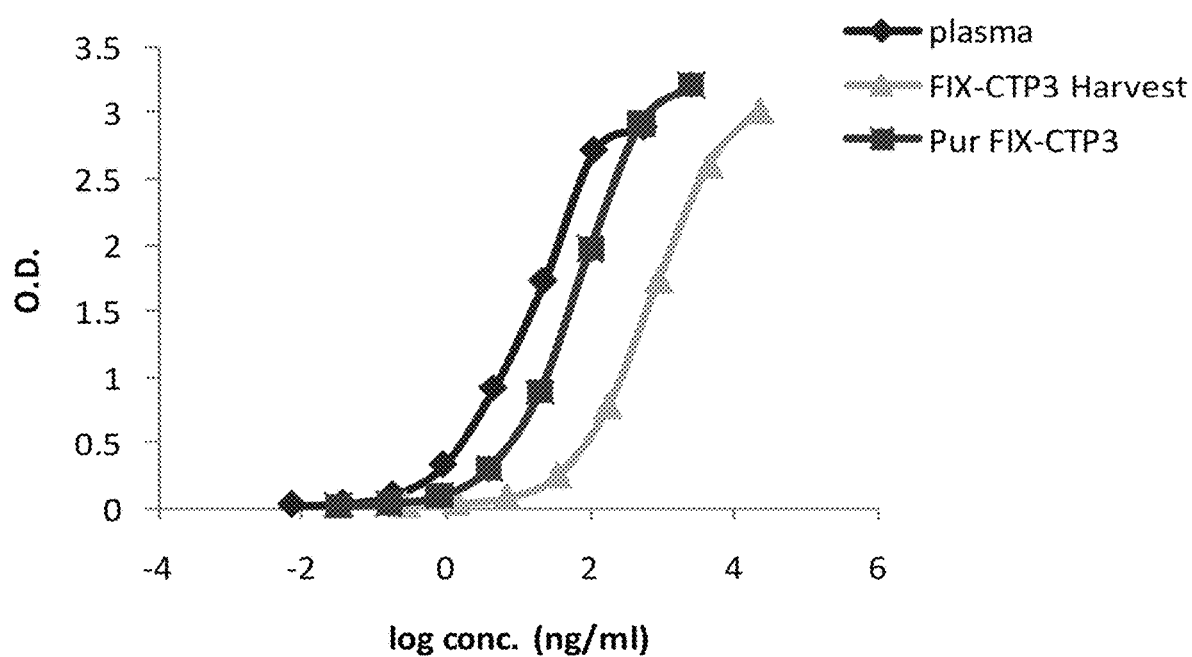
FIG. 13. Shows the FIX-CTP$_3$ chromogenic activity. A comparative assessment of the in vitro potency of FIX-CTP$_3$ harvest and FIX-CTP$_3$ γ-carboxylated enriched protein, versus human pool normal plasma was performed using a commercially available chromogenic activity test kit, BIO- PHEN (Hyphen BioMed 221802). FIX-CTP$_3$ harvest and protein were serially diluted, and the potency was assessed by comparing a dose-response curve to a reference preparation consisting of normal human plasma.

FIX-CTP$_3$ Clotting Activity:

FIX-CTP$_3$ Chromogenic Activity:

A comparative assessment of the in vitro potency of FIX-CTP$_3$ harvest and FIX-CTP$_3$ γ-carboxylated enriched protein, versus human pool normal plasma was performed using a commercially available chromogenic activity test kit, BIOPHEN (Hyphen BioMed 221802). FIX-CTP$_3$ harvest and protein were serially diluted, and the potency was assessed by comparing a dose-response curve to a reference preparation consisting of normal human plasma. As previously demonstrated, FIX-CTP$_3$ harvest was 50 times less active then human pool plasma (Table 19, FIG. 13). Following FIX-CTP$_3$ purification, the chromogenic activity was significantly improved and was only 4.72 times less active then human pool plasma (Table 19, FIG. 13). Harvest reduced chromogenic activity can be a consequence of improper post-transcriptional modifications of FIX protein variants, e.g. inappropriate gamma carboxylation and pro-peptide cleavage. Following purification and enrichment of the FIX-CTP$_3$ γ-carboxylated fraction, the activity was improved, demonstrating the important contribution of γ-carboxylation to FIX activity.

TABLE 19

| FIX-CTP$_3$ chromogenic activity | | |
|---|---|---|
| Sample | EC$_{50}$ (ng/ml) | Sample/plasma EC$_{50}$ ratio |
| FIX-CTP$_3$ Harvest | 741.3 | 54.4 |
| Pur. FIX-CTP$_3$ | 64.6 | 4.72 |
| Plasma | 13.63 | 1 |

One Stage Clotting Assay (aPTT):

The activated partial thromboplastin time (aPTT) is a measure of the integrity of the intrinsic and common pathways of the coagulation cascade. The aPTT is the time, in seconds, for plasma to clot following the addition of an intrinsic pathway activator, phospholipid and calcium. The principal of the assay was to quantitate the ability of FIX-CTP$_3$ to restore the clotting activity of FIX-depleted human plasma by the addition of rhFIX. 200 μl of FIX-deficient human plasma was mixed with 25 μg/ml of FIX-CTP$_3$ and further diluted in TBS. Following a 60 second incubation at 37° C., 50 μl of PTT activator (Actin FS) and 50 μl of calcium 25 mM were added to the mixture, and the clotting time in seconds was determined using a Sysmex® CA 1500 Coagulator (performed by Sheba hospital, National Coagulation Center using validated aPTT assay). The potency was assessed by comparison of FIX-CTP$_3$ to the dose-response curve of a reference preparation of normal human pool plasma. The results are expressed in percent of activity interpolated from the standard curve covering FIX levels of <1-110%. FIX-CTP$_3$ exhibited a 15-20-fold reduction in its coagulation activity versus normal human pool plasma since the activity at 5 μg/ml, which is the normal value of FIX in the body, was shown to be 6.5% (Table 20).

TABLE 20

| FIX-CTP$_3$ clottting activity | | |
|---|---|---|
| FIX-CTP$_3$ | | |
| FIX Concentration by provider (mg/ml) | Concentration in tested sample (μg/ml) | FIX % of activity (nommlized to human normal pool plasma) |
| 3.83 | 25 | 34.7 |
| | 5 | 6.5 |

Figure 14:
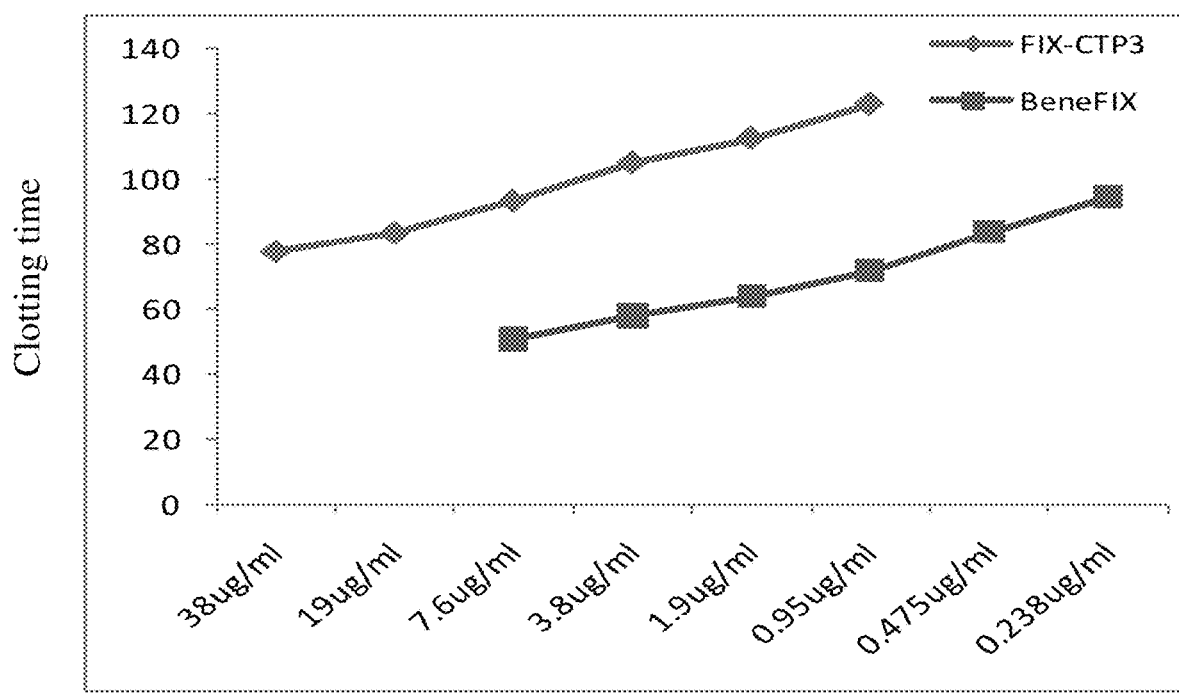
FIG. 14. Shows the comparative clotting time. An in vitro aPTT (activated Partial Thrombin Time Assay) was performed comparing the clotting activity of FIX-CTP$_3$ to BeneFIX. The proteins were serially diluted and spiked into human FIX-depleted plasma, and the clotting time was evaluated.

FIX-CTP$_3$ also exhibited increased clotting time compared to BeneFIX® (Table 21 and FIG. 14).

TABLE 21

Comparative clotting time (aPTT)

Clotting time

| | FIX-CTP$_3$ | BeneFIX ® |
|---|---|---|
| 38 ug/ml | 77.6 | |
| 19 ug/ml | 83.4 | |
| 7.6 ug/ml | 93.2 | 50.6 |
| 3.8 ug/ml | 104.8 | 57.6 |
| 1.9 ug/ml | 112.2 | 63.7 |
| 0.95 ug/ml | 122.6 | 71.5 |
| 0.475 ug/ml | | 83.7 |
| 0.238 ug/ml | | 94.3 |

An additional clotting assay was performed independently in FIX-deficient mice by Dr. Paul Monahan at University of North Carolina prior to the initiation of the PK-PD study. The aPTT results suggested that FIX-CTP$_3$ coagulation activity is 40 times less than normal pooled human plasma as demonstrated by the longer period (as measured in seconds) and higher concentration that are required for proper clotting activity (Table 22).

TABLE 22

Comparative clotting activity

FIXactivity (Units)

| | FIX-CTP$_3$ | BeneFIX ® |
|---|---|---|
| 38 ug/ml | 13.9 | |
| 19 ug/ml | 8.8 | |
| 7.6 ug/ml | 4 | 116.8 |
| 3.8 ug/ml | 1.6 | 67.4 |
| 1.9 ug/ml | 0.9 | 41.7 |
| 0.95 ug/ml | 0.4 | 22.4 |
| 0.475 ug/ml | | 8.5 |
| 0.238 ug/ml | | 3.7 |

The specific activity (u/ml), which was based on FIX antigen level as calculated by ELISA for FIX-CTP$_3$ and BeneFIX®, was 4.46 and 198.9 respectively.

The inconsistency in the calculated FIX-CTP$_3$ activity as demonstrated in the chromogenic vs. aPTT assays can be explained by the superior sensitivity of the aPTT assay and in vivo relevance. In the chromogenic activity assay, an excess amount of reagents and enzymes are present which can activate less potent FIX versions. The difference in the FIX-CTP specific activity values can be explained by the use of different reagents and automated machines. The activity value as calculated at University of North Carolina was used for the PK-PD study design.

FIXa Protein Detection:

In order to confirm that following the purification process, FIX activation (FIXa) did not occur, a FIXa detection assay was performed using FIXa Biophen Chromogenic Assay (Cat. #Ref. 221812). The assay measures the amount of FIXa present in a specific sample using the chromogenic activity cascade, as previously described. FIX-CTP$_3$ and rhFIX were diluted and FIXa levels were evaluated. FIX-CTP$_3$ wasn't activated through purification or storage (Table 23).

TABLE 23

FIXa detection

| Sample | FIX-CTP$_3$ | rhFIX |
|---|---|---|
| Initial Con. (mg/ml) | 1000 | 5.7 |
| rFIXa (mg/ml) | BLQ | 0.00487 |
| % FIXa in sample | BLQ | 0.085 |

FIX-CTP$_3$ PK-PD study: FIX-CTP$_3$ and rhFIX (BeneFIX®) were administered in a single intravenous injection to C57Bl FIX-deficient mice in a dose of 625 μg/kg body weight containing 100 IU FIX/kg body weight. Blood samples were drawn retro-orbitally from 3 mice alternately at 0.25, 4, 24, 48, 72, and 96 hours post-dosing. Citrated plasma (0.32%) was prepared immediately after sampling and stored at −20° C. until analysis. hFIX antigen level was evaluated, and a detailed PK analysis was performed. In order to evaluate the ability of FIX-CTP$_3$ to elongate the clotting activity of FIX-deficient animals compared to BeneFIX®, FIX activity in citrated plasma samples, collected from the FIX−/− treated mice, was calculated using an automated FIX activity assay (Table 24).

TABLE 24

Study outline

| | Product | Administration | Dose | # mice | Collection Points (hr post-dosing) | Required amount |
|---|---|---|---|---|---|---|
| **Cohort 1 | FIX-CTF3 | Single dose:IV | 100IU/Kg 2.5IU/mouse 553μg/mouse | 12 mice, | 0.25, 1, 4,8, 1 24, 48 | 6636μg |
| Cohort 2 | FIX-CTF3 | Single dose:IV | **472μg/Kg 12.57μg/mouse | 18 mice | *0.25,1*,4*,8*, 16*,24*48,72*,96* | 200μg/mouse |
| **Cohort 3 | BeneFIX® | Single dose:IV | 100IU/Kg 2.5IU/mouse | 18 mice | 0.25,1,4,8,16,24,48 *72,*96 | 266.3μg/mouse |

*PK collection points only

** Tail vein bleeding at T=48 post-dosing; cohorts 1 & 3

FIX-CTP₃ Pharmacokinetic Profile in FIX⁻/⁻ Mice

Figure 15:
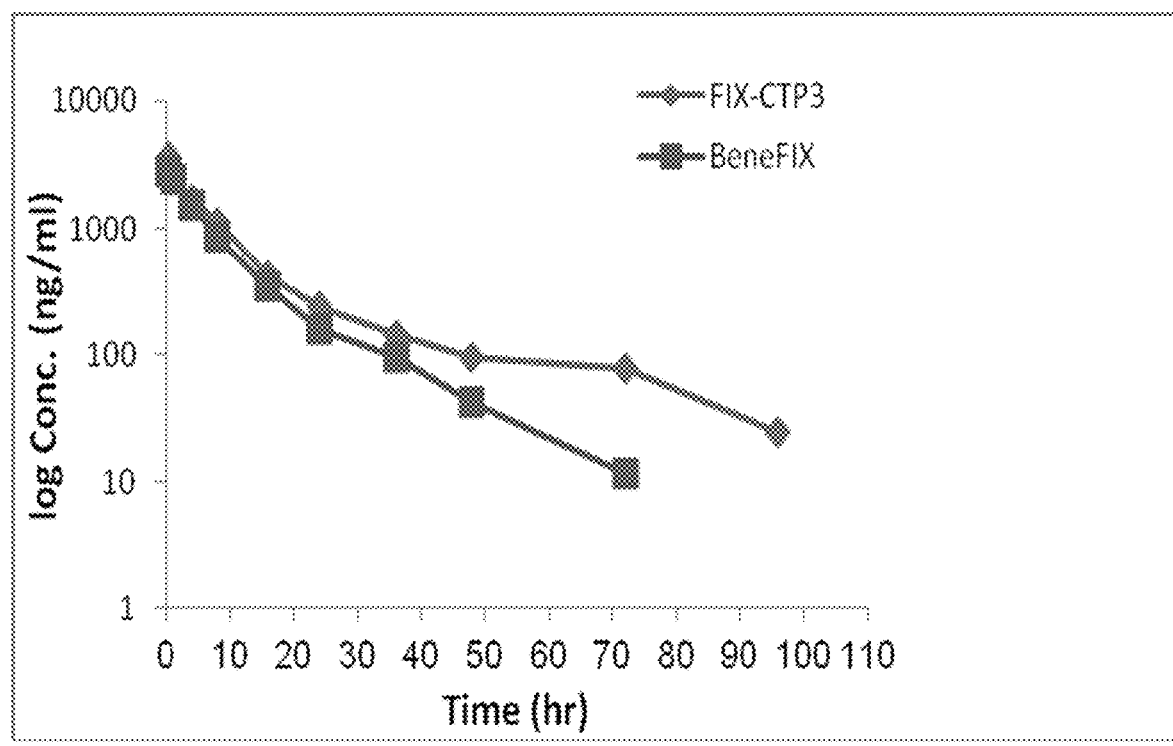
FIG. 15. Shows FIX-CTP$_3$ comparative PK profile. FIX concentration was quantitated using human FIX ELISA kits (Affinity Biologicals; Cat. #FIX-AG RUO). The pharmacokinetic profile was calculated for each protein and is the mean of 3 animals at each time point.

FIX concentration was quantitated using human FIX ELISA kits (Affinity Biologicals; Cat. #FIX-AG RUO). The pharmacokinetic profile was calculated for each protein and is the mean of three animals at each time point. Table 25 below and FIG. 15 summarize the calculated FIX concentrations at the different sampling time points for Cohorts 1 & 3. The PK profile and a summary of the PK parameters are presented below (Tables 26 & 27). A PK analysis was also performed for Cohort #2 in order to verify exposure (data not shown).

TABLE 25

FIX concentrations

| Time point (hr) | FIX-CTP₃ ng/ml | BeneFIX ® ng/ml |
|---|---|---|
| 0.25 | 3645.397 | 2823.073 |
| 1 | 2411.09 | 2416.248 |
| 4 | 1703.205 | 1506.228 |
| 8 | 1139.736 | 864.764 |
| 16 | 415.32 | 347.465 |
| 24 | 238.37 | 158.7973 |
| 36 | 141.0105 | 94.40067 |
| 48 | 95.461 | 42.28833 |
| 72 | 76.90953 | 11.87567 |
| 96 | 24.955 | BLQ |

A two-compartmental module was used (WinLin software) to determine AUC0-inf, $T_{terminal}$ and clearance (CL). The PK parameters are described below in Table 26.

TABLE 26

PK properties

| FIX Version | T½αβ (1/hr) | T½β (1/hr) | AUC ng/ml*hr | CL ml/Kg/hr | MRT(hr) | Vss ml/Kg |
|---|---|---|---|---|---|---|
| BeneFIX® | 3.4 | 12.7 | 22428 | 29 | 11.5 | 320.8 |
| FIX-CT/13 | 4 | 28.7 | 31770 | 19 | 22 | 425.2 |

The addition of the three CTP "cassettes" to rhFIX elongated FIX half-life in vivo by at least 2.5-fold. AUC following in vivo FIX-CTP₃ administration increased 2-fold versus rhFIX. FIX-CTP₃-injected mice demonstrated an improved PK profile compared to BeneFIX®-injected mice.

FIX-CTP₃ Pharmacodynamic Profile in FIX-Deficient Mice:

In parallel to PK sampling, FIX-deficient animals administered with either BeneFIX® or FIX-CTP₃, citrated plasma samples, were evaluated for their clotting activity by aPTT assay, which was translated to % activity. The % activity at each collection point was calculated as the current clotting time/clotting time of normal pool mice plasma*100. Table 27 summarizes the activity values following administration of either BeneFIX® or FIX-CTP₃.

Figure 16A:
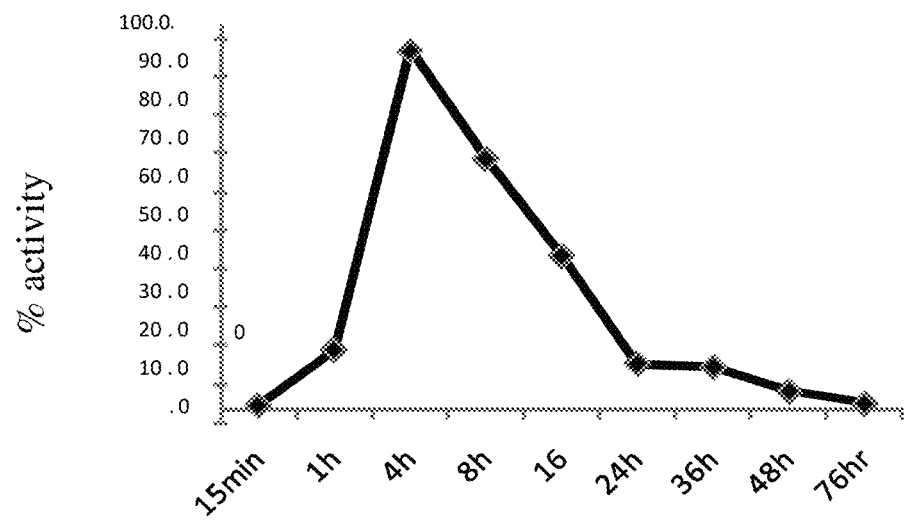
FIG. 16A. In parallel to PK sampling, FIX-deficient animals administered with FIX-CTP$_3$, citrated plasma samples, were evaluated for their clotting activity by aPTT assay, which was translated to % activity. The % activity at each collection point was calculated as the current clotting time/clotting time of normal pool mice plasma*100.
Figure 16B:
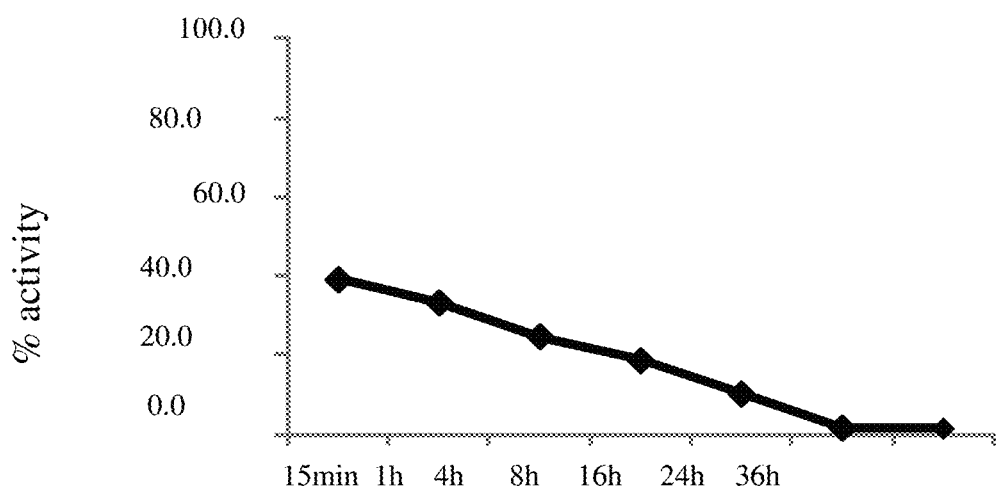
FIG. 16B. In parallel to PK sampling, FIX-deficient animals administered with either BeneFIX®, citrated plasma samples, were evaluated for their clotting activity by aPTT assay, which was translated to % activity. The % activity at each collection point was calculated as the current clotting time/clotting time of normal pool mice plasma*100.

Following FIX-CTP₃ administration, significant clotting activity was detected one hour after administration reaching 96% activity at four hours post-dosing, while BeneFIX® highest activity value was 40% (Table 27, FIG. 16). FIX-CTP₃ clotting activity was maintained for a longer period of time, demonstrating elongated activity. Clotting activity for the BeneFIX®-treated mice was undetectable at time points later than 36 hours, while FIX-CTP₃-treated mice continued to retain measurable activity at 72 hours post-dosing (Table 27, FIG. 16). Analysis of the % clotting pharmacokinetic profile suggest that FIX-CTP₃ clotting activity is maintained for a significantly longer period and its half-life is almost 2-fold higher than Benefix® (Table 28).

TABLE 27

FIX % of activity

| Hr post-dosing | BeneFIX ® % of activity | FIX-CTP₃ % of activity |
|---|---|---|
| 0.25 | 39.9 | 1.0 |
| 1 | 33.4 | 15.5 |
| 4 | 24.9 | 93.6 |
| 8 | 18.8 | 65.2 |
| 16 | 10.3 | 39.9 |
| 24 | 1.7 | 11.9 |
| 36 | 1.4 | 11.0 |
| 48 | <1 | 4.6 |
| 72 | <1 | 1.4 |

TABLE 28

Clotting Activity

| FIX Version | T½α (1/hr) | T½ β (1/hr) |
|---|---|---|
| BeneFIX ® | 5.7 | — |
| FIX-CTP₃ | 7.3 | 16 |

9.3 FIX-Deficient Mice Bleeding Challenge

Figures 17A, 17B:
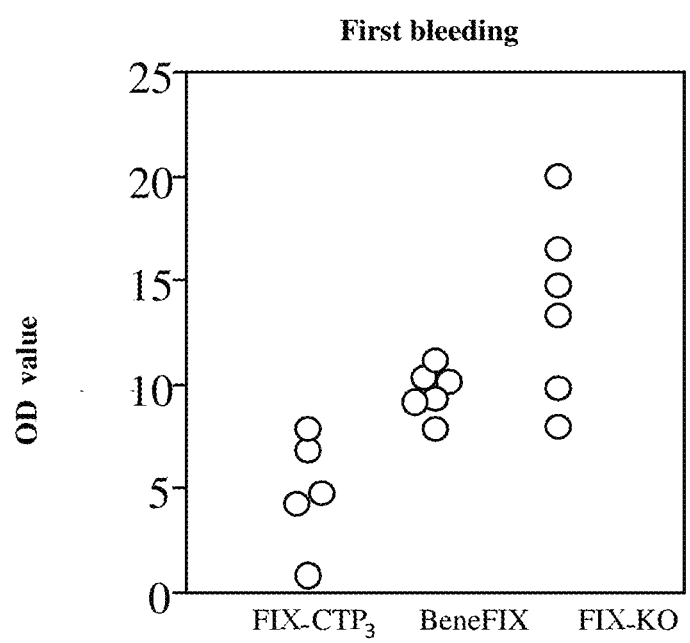
FIG. 17A. Shows a first challenge bleeding parameters. FIX-deficient mice were administered a single intravenous injection of 100 IU/Kg of BeneFIX®, or rFIX-CTP$_3$. The tail vein was slightly clipped 48 hours post-dosing and tail vein bleeding time (TVBT) was evaluated. A second bleeding challenge was performed 15 minutes after reaching homeostasis, and the same parameters were measured.
FIG. 17B. Shows a first challenge bleeding parameters. FIX-deficient mice were administered a single intravenous injection of 100 IU/Kg of BeneFIX® or rFIX-CTP$_3$. The tail vein was slightly clipped 48 hours post-dosing and tail vein bleeding time (TVBT) was evaluated. A second bleeding challenge was performed 15 minutes after reaching homeostasis, and the same parameters were measured.
Figures 17C, 17D:
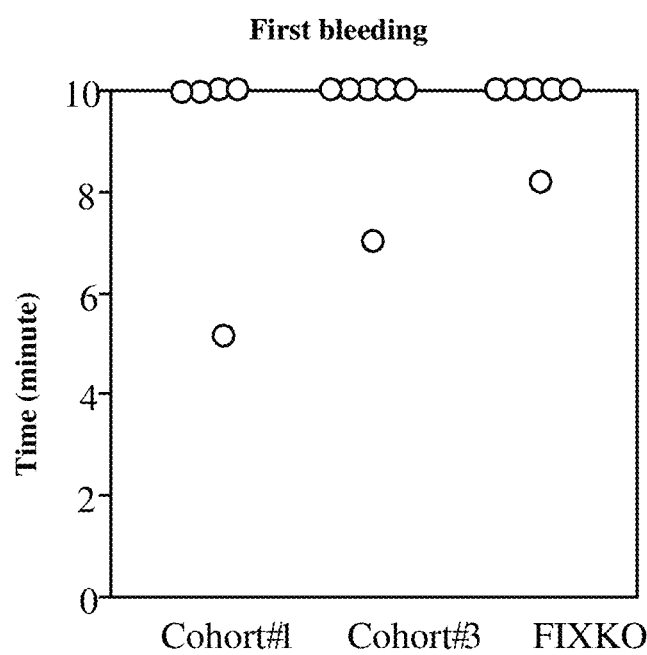
FIG. 17C. Shows a first challenge bleeding parameters. FIX-deficient mice were administered a single intravenous injection of 100 IU/Kg of BeneFIX® or rFIX-CTP$_3$. The tail vein was slightly clipped 48 hours post-dosing and bleeding intensity (hemoglobin OD) was evaluated. A second bleeding challenge was performed 15 minutes after reaching homeostasis, and the same parameters were measured.
FIG. 17D. Shows a first challenge bleeding parameters. FIX-deficient mice were administered a single intravenous injection of 100 IU/Kg of BeneFIX® or rFIX-CTP$_3$. The tail vein was slightly clipped 48 hours post-dosing and bleeding intensity (hemoglobin OD) was evaluated. A second bleeding challenge was performed 15 minutes after reaching homeostasis, and the same parameters were measured.

FIX-deficient mice were administered a single intravenous injection of 100 IU/kg of BeneFIX® or rFIX-CTP₃. The tail vein was slightly clipped 48 hours post-dosing, and tail vein bleeding time (TVBT) and bleeding intensity (hemoglobin OD) were evaluated. A second bleeding challenge was performed 15 minutes after reaching homeostasis, and the same parameters were measured. Following the first bleeding challenge, FIX-CTP₃-administered animals' bleeding was significantly less intense then BeneFIX® bleeding as demonstrated by the Hemoglobin OD values (FIG. 17).

Figures 18A, 18B:
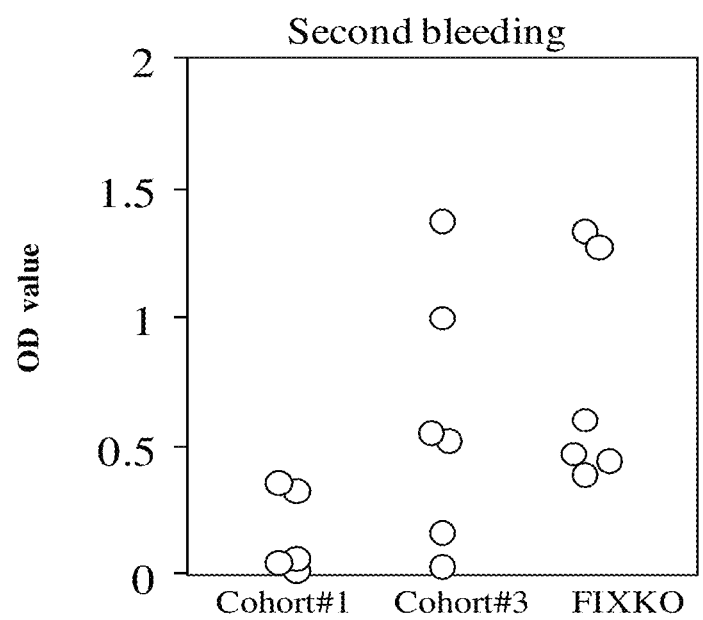
FIG. 18A. Shows a second challenge bleeding parameters. Once the first bleeding described in the legend to FIG. 19 was spontaneously or manually stopped, a second bleeding challenge was performed 15 minutes following the first one, and the time was re-measured.
FIG. 18B. Shows a second challenge bleeding parameters. Once the first bleeding described in the legend to FIG. 19 was spontaneously or manually stopped, a second bleeding challenge was performed 15 minutes following the first one, and the time was re-measured.
Figures 18C, 18D:
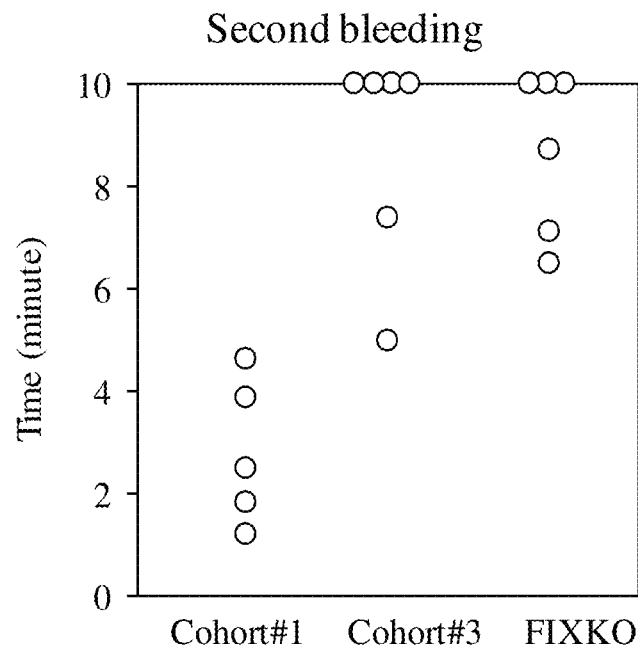
FIG. 18C. Shows a second challenge bleeding parameters. Once the first bleeding described in the legend to FIG. 19 was spontaneously or manually stopped, a second bleeding challenge was performed 15 minutes following the first one, and the bleeding intensity was re-measured.
FIG. 18D. Shows a second challenge bleeding parameters. Once the first bleeding described in the legend to FIG. 19 was spontaneously or manually stopped, a second bleeding challenge was performed 15 minutes following the first one, and the bleeding intensity was re-measured.
Figure 19A:
FIG. 19A. Shows a diagram illustrating the rFVII-CTP construct.
Figure 19B:
FIG. 19B. Shows a diagram illustrating the rFVII-CTP-CTP construct.
Figure 19C:
FIG. 19C. Shows a diagram illustrating the rFIX-CTP construct.
Figure 19D:
FIG. 19D. Shows a diagram illustrating the rFIX-CTP-CTP construct.

Since it was previously reported that during the first bleeding challenge in hemophilic mice, the bleeding time does not necessarily correlate with treatment efficacy, it is recommended to evaluate the homeostasis following additional bleeding. Once the first bleeding was spontaneously or manually stopped, a second bleeding challenge was performed minutes following the first one, and the time and bleeding intensity were re-measured. During the second bleeding episode FIX-CTP₃-administered animals had reduced bleeding time and intensity, demonstrating that FIX-CTP₃ was potent at a later time points (FIG. 18).

Finally, the animals were further observed for the 12 hours following the second bleeding challenge, and all recurring bleeding events were documented. FIX-CTP₃-administered animals were able to maintain blood homeostasis for the next 12 hours with no re-occurring bleeding events. In contrast, 50% of BeneFIX®-treated mice had spontaneous bleeding episodes from the tail (Table 29).

TABLE 29

Outcome 12 hours after tail transection

| Mouse group | Delayed rebleeding | Death or Distress Requiring Euthanasia |
|---|---|---|
| FIX-CTP₃ (100 IU/kg) | 0/5 (0%) | 0/5 |
| BeneFIX ® (100 IU/kg) | 3/6 (50%) | 0/6 |
| F1X-/- (untreated) | 5/6 (100%) | 1/6 |

Recombinant FIX-CTP$_3$, a fusion protein comprised of a single molecule of FIX fused to three CTP "cassettes" in tandem was developed to address the short half-life of currently available FIX products used to treat patients with hemophilia B. We have demonstrated that the elimination half-life of rFIX-CTP$_3$ was consistently 2.5- to 4-fold longer than rFIX in rats (as previously reported) and in FIX-deficient mice.

Without being bound by theory, the fusion protein reduces clearance of FIX and protects FIX from protease activity, degradation by masking and reduces the affinity of FIX for hepatic receptors. Taken together these characteristics of the CTP domain extend the half-life of FIX.

In addition to pharmacokinetic analysis of rFIX-CTP$_3$, we examined the pharmacodynamic properties of FIX-CTP$_3$ in FIX-deficient mice. rFIX-CTP$_3$ and rFIX, were administered at comparable doses (in units) to compensate for the clotting deficiency levels in FIX-deficient mice. However, the effect of rFIX-CTP$_3$ in FIX-deficient mice was significantly prolonged to at least 76 hr after dosing, reaching a higher activity peak. FIX-CTP$_3$ clotting activity began after a 1-hour delay compared to BeneFIX®. FIX activation may be required since the addition of three tandem CTPs might theoretically mask the activation site and delay cascade onset. Following FIX-CTP$_3$ administration, a 100% peak activity was observed, while BeneFIX® activity was only 40%. The superior initial activity is a very important parameter and demonstrates that addition of 3 CTPs has the potential to improve recovery.

Prophylactic FIX replacement therapy for patients with hemophilia B aims to maintain plasma levels of 1-2% normal clotting activity. The tail vein bleeding assay is a sensitive in vivo test that measures the ability to maintain bleeding homeostasis at low activity values mimicking human bleeding homeostasis model. In response to tail vein bleeding challenge 48 hours post-dosing, rFIX-CTP$_3$-administered animals maintained blood homeostasis with shorter and less severe bleeding episodes, demonstrating sustained clotting activity.

FIX is a complex protein that contains a number of functional domains which undergo extensive post-translational modifications. One of the essential post-translational modifications for FIX activity is gamma-carboxylation of the first 12 glutamic acids in the Gla domain by vitamin K-dependent γ-glutamyl carboxylase. This modification facilitates the binding of FIX to phospholipid membranes and, thus, is critical to its function. FIX that is not gamma-carboxylated is not functional, and hence gamma-carboxylation is a rate-limiting step.

This PK-PD study was conducted using transiently transfected cells. An extensive analytical evaluation of post-translational modifications is performed on the stable FIX-CTP$_3$ protein produced and secreted from stable optimized clone.

Based on the presented data. FIX-CTP$_3$ coagulation factor has the potential to reduce the frequency of injections in patients receiving routine prophylactic doses of FIX replacement therapy. It is anticipated that rFIX-CTP$_3$ can confer prolonged protection from bleeding following each dose of factor, decrease the overall units of factor needed to treat bleeding episodes, and/or maintain adequate hemostasis during surgical procedures with fewer injections.

Example 4

Generation and Utilization of Coagulation Factor FVII

A long-acting version of activated Factor VII (FVIIa) coagulation factor will be useful for the treatment of patients with hemophilia A and B. FVIIa-CTP$_3$ recombinant protein has the clinical potential to improve the treatment of hemophilia patients by reducing the frequency of infusions and even by reducing the drug load, enabling a prophylactic treatment approach which can significantly improves a patient's quality of life, avoid spontaneous bleeding episodes and accumulated damage to the joint and other organs.

The generation of a recombinant FVIIa-CTP molecule with an extended half-life based on fusion of FVII to a human CTP is described herein. The recombinant FVIIa-CTP was expressed in mammalian cells and characterized in vitro and in vivo. It was demonstrated that rFVII-CTP activity was comparable to rFVII. Pharmacokinetic and efficacy studies in rats demonstrated improved properties of rFVII-CTP. The results of this study demonstrated that it is feasible to develop a half-life extended rFVIIa molecule with very similar haemostatic properties to the wild-type enzyme.

Cloning and expression of recombinant FVII molecule: Several Factor VII clones were constructed in our eukaryotic expression vector (pCI-dhfrr) (FIG. 19). Human MGC verified FL cDNA clone (IRCM) containing the sequence of Homo sapiens coagulation Factor VII was ordered from "Open Biosystems" (OB-MHS4426). The following primers were synthesized by Sigma-Genosys in the following sequence: Primer 67: 5'CTCGAGGA-CATGGTCTCCCAGGCCC3' (contains the 5' end of Factor VII DNA and the restriction site of XhoI) (SEQ ID NO: 5); Primer 68$^R$: 5' TCTAGAATAGGTATITiCCACATG3' (contains the restriction site of XbaI) (SEQ ID NO: 6); Primer 69: 5' TCTAGAAAAAAGAAATGCCAGC3' (contains the restriction site of XbaI) (SEQ ID NO: 7); and Primer 70$^R$: 5'GCGGCCGCATCCTCAGGGAAATGGGGCTCGCA3' (contains the 3' end of Factor VII DNA and the restriction site of NotI) (SEQ ID NO: 8).

Cloning was performed in two sets of PCR reactions. The first reaction was conducted with primer 67 and primer 68$^R$ using a cDNA plasmid with the Factor VII sequence (OB-MHS4426) as a template; as a result of the PCR amplification, a ~534 bp product was formed, isolated and ligated into a TA cloning vector (Invitrogen, Catalog No: K2000-01). A XhoI-XbaI fragment containing the amino terminus of the Factor VII sequence was isolated. The second reaction was conducted with primer 69 and primer 70$^R$ and again, a cDNA plasmid with the Factor VII sequence (OB-MHS4426) was used as a template. As a result of the PCR amplification, a ~813 bp product was formed and ligated into TA cloning vector (Invitrogen, Catalog No: K2000-01). A XbaI-NotI fragment containing the carboxy terminus of Factor VII sequence was isolated. The two fragments were inserted into our eukaryotic expression vector pCI-dhfr (triple ligation) to yield the 501-0-p136-1 clone.

Plasmid 501-p136-1 (Factor VII in pCI-dhfr vector) was digested with restriction enzymes XhoI and KpnI. A fragment of ~1186 bp was isolated. A partial Factor VII clone (1180 bp-1322 bp) followed by a CTP sequence, termination sequence and NotI sequence that was synthesized by GeneArt (0721543) was digested with restriction enzymes KpnI and NotI. A fragment of ~253 bp was isolated. The two fragments were inserted into our eukaryotic expression vector pCI-dhfr (triple ligation) to yield the 501-1-p137-2 clone. pCI-dhfr-701-2-p24-2 was digested with restriction enzymes XhoI and ApaI, and the large fragment (vector) was isolated.

pCI-dhfr-501-2-p137-2 (Factor VII-ctp x1) was digested with restriction enzymes XhoI and ApaI, and a ~1200 bp insert was isolated. The vector and insert were ligated to yield 501-2-p139-2. Dg44 cells were plated in 100 mm tissue culture dishes and grown to confluence of 50-60%. A total of 2 µg of DNA was used for transfection of one 100 mm plate using the FuGene reagent (Roche) in protein-free medium (Invitrogen CD Dg44). The medium was removed 48 hours post-transfection and replaced with a protein-free medium (Invitrogen CD Dg44) without nucleosides. After 14 days, the transfected cell population was transferred into T25 tissue culture flasks, and the selection was continued for 10-14 days until the cells began to grow well as a stable clone. High-expressing clones were selected and approximately $2 \times 10^7$ cells were used to inoculate 300 ml of growth medium in a 1700 $cm^2$ roller bottle (Corning, Corning NY) supplemented with 5 ng/ml of Vitamin K3 (menadione sodium bisulfate; Sigma). The production medium (harvest) was collected after a rapid decrease in the cell viability to around 70%. The production medium was first clarified and then concentrated approximately 20-fold and dialyzed to PBS using flow filtration cassette (10 KDaMWCO; Millipore Corp, Billerica, MA).

Determination of FVII Antigen Level

Figure 20A:
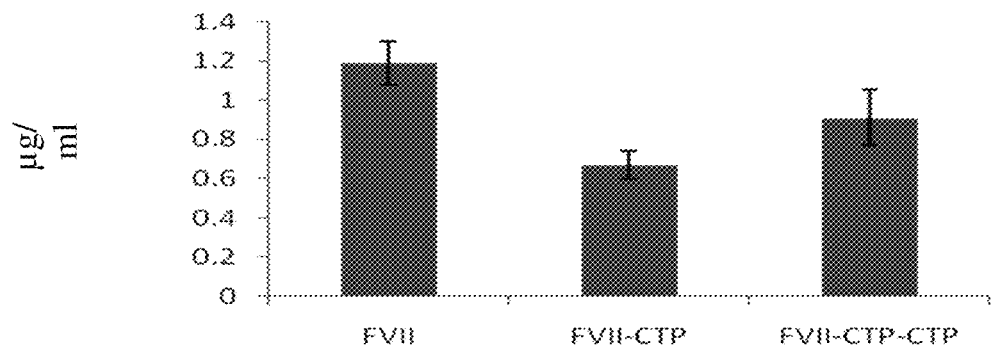
FIG. 20A. Shows a bar graph showing harvests limited diluted clone transfected and selected cells with FVII-CTP variants in the presence of 5 µg/ml of Vitamin K3. The level of FVII was quantified using FVII ELISA (AssayPro).

The cDNA coding the CTP peptide was fused to the 3' end of the cDNA coding human FVII. The corresponding rFVII construct was transfected into Dg44 cells. As a control, a human rFVII cDNA was utilized. The production medium (harvest) was collected, concentrated and the secreted recombinant FVII was further evaluated. rFVII, rFVII-CTP and rFVII-CTP-CTP antigen levels were determined by AssayMax Human FVII ELISA kit (AssayPro) (FIG. 20A). There was no significant difference in the secretion level of rFVII-CTP and rFVII-(CTP)$_2$ compared to native rFVII.

SDS-PAGE Blots

SDS-PAGE analysis was done by loading 50 ng of either harvest, purified or activated rFVII protein. Samples were loaded on 12% Tris-Glycine gel using Precision Plus Dual Color Protein Marker (Bio-Rad). The SDS-PAGE analysis was done by performing a Western immunoblot using an anti-human FVI monoclonal antibody (Ab) (R&D systems) or anti-CTP polyclonal antibody generated in Rabbit.

The level of rFVII antigen correlated with the detected protein level in a SDS-PAGE immunoblotted with anti-FVII Ab. rFVII-CTP migrated as a single band, while the corresponding molecular weight of the FVII control was approximately 52 KDa (data not shown). Both proteins reacted with antibodies specific for FVII on immunoblots. The rFVII-CTP also reacted with antibodies specific for CTP. rFVII was secreted in its zymogene form with no trace of activated protein.

Figure 20B:
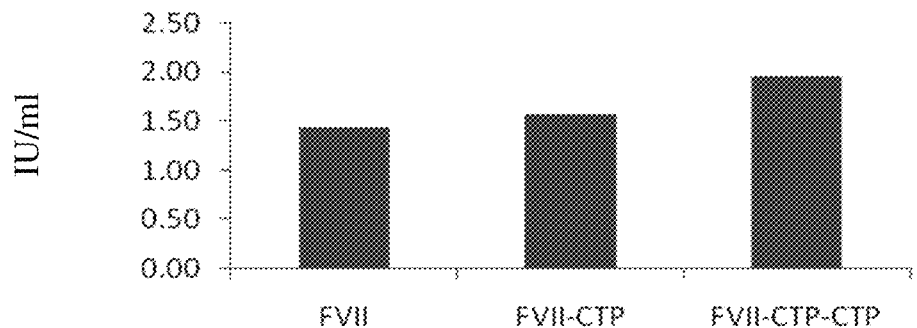
FIG. 20B. Shows a bar graph showing harvests of limited diluted transfected and selected cells with FVII-CTP variants in the presence of 5 µg of Vitamin K3.activity. FVII activity was quantified using FVII chromogenic activity assay (AssayPro).
Figure 20C:
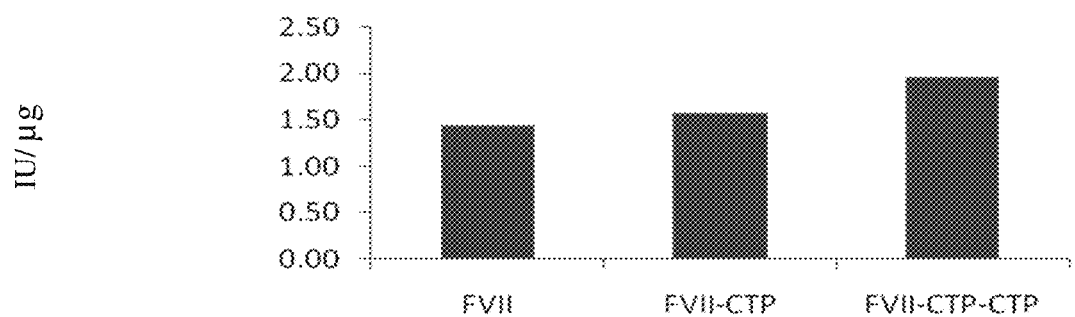
FIG. 20C. Shows a bar graph showing harvests of limited diluted transfected and selected cells with FVII-CTP variants in the presence of 5 µg of Vitamin K3. The specific activity of FVII was calculated for each version by dividing the activity value by the harvest FVII concentration.
Figure 20D:
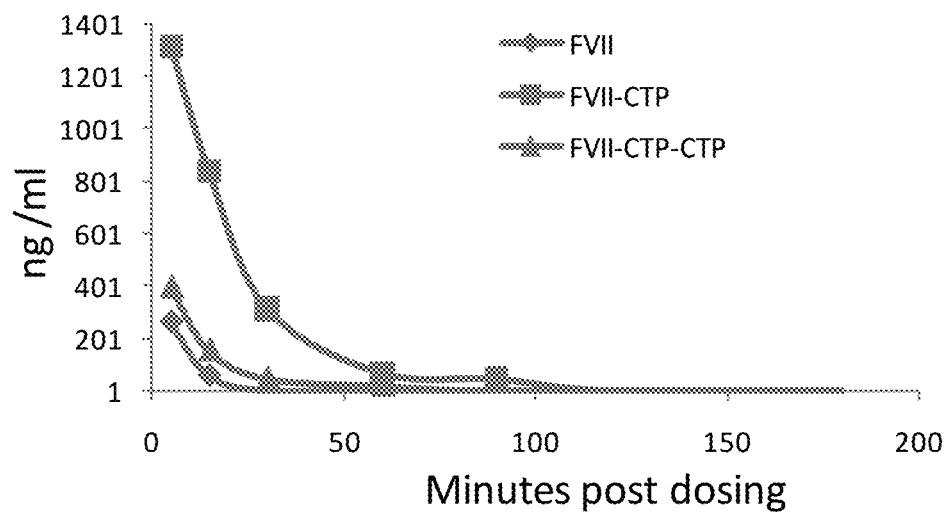
FIG. 20D. Shows a graph showing PK profile of FVII, FVII-CTP-CTP, and FVII-CTP harvests.

FVII Chromogenic Activity:

rFVII, rFVII-CTP and rFVII-(CTP)$_2$ harvest activities were determined using a commercially available chromogenic test kit (AssaySense Human FVII Chromogenic Activity Assay Kit (AssayPro). For functional characterization of the rFVII-CTP and its ability to be further activated (FVIIa), concentrated rFVII-CTP (harvests) were placed in a commercially available chromogenic test kit that measure the ability of TF/FVIIa to activate Factor X to Factor Xa that in the presence of FXa specific substrate releases a quantitated signal (AssayPro). The addition of the CTP peptide at the C-terminal of the rFVII protein did not impair the FVII serine protease activity (FIG. 20B, 20C).

FVII Clotting Activity:

Prothrombin time (PT) measures the extrinsic pathway of coagulation. The PT is the time (measured in seconds) it takes plasma to clot following the addition of an extrinsic pathway activator, phospholipid and calcium. It is used to determine the clotting tendency of blood, specifically in the measure of warfarin dosage, liver damage, and vitamin K status. The reference range for prothrombin time is usually around 12-15 seconds. Specifically, the assay quantitated the ability of FVII-CTP and FVII-(CTP)$_2$ harvest to restore the clotting activity of FVII-depleted human plasma by the addition of rhFVII. 300 µl of FVII-deficient human plasma was mixed with 100 µl of FVII, FVII-CTP and FVII-(CTP)$_2$ harvests at specific concentrations, or normal pool human plasma and were further diluted. Following a 60 second incubation at 37° C. Tissue Factor (TF), CaCl$_2$, and phospholipids were added to the mixture. The clotting time in seconds was determined. Potency was assessed by comparing a dose-response curve of FVII-CTP and FVII-(CTP)$_2$ harvests to a reference preparation consisting of rhFVII or human pool plasma. One unit of active FVII was defined as the amount of FVII which equals to the activity of one ml human normal plasma. The PT Clotting activity of rFVII and rFVII-CTP was measured on a coagulometer (Instrumentation Laboratory).

As previously shown, the addition of a CTP peptide at the C-terminal of the rFVII protein did not damage its serine protease activity and lead to the initiation and activation of a native Factor X and Factor IX in human plasma. Following the insertion of an additional CTP at the C terminal, there was a three-fold reduction in the serine protease activity (data not shown).

Pharmacokinetics Study:

rFVII, rFVII-CTP, and rFVII-(CTP)$_2$ harvests were administered intravenously to Sprague-Dawley rats (six rats per substance) with a dose of 100 µg/kg body weight. For all of the in vivo experiments, the amount of the respective protein was determined on the basis of FVII ELISA kit. For each FVII test substance, the injected amount was calculated by taking into account the differences in the molecular weight of rFVII versus rFVII-CTP, which leads to a different molar concentration.

Blood samples were drawn retro-orbitally using an altering sampling scheme to minimize interference of the sampling procedure levels to be quantified: from 3 rats at 30 and 90 min and at 2, 6, and 48 hrs, and from the remaining three rats at 15 and 60 min and at 1.5, 4, and 24 hrs alternately. Plasma was prepared immediately after sampling and stored at −20° C. until analysis. FVII concentration was quantified by FVII ELISA specific assay. Half-life and area under the curve (AUC) were calculated using a linear trapezoidal rule. Comparison of these clearance parameters revealed that the in vivo half-life and rFVII-(CTP)$_2$ AUC are significantly higher than those of rFVII (Table 30).

TABLE 30

PK study parameters

| Group | Route | Dose µg/kg | T½ min | AUC$_{0-4}$ ng/min/mL | CL/F mL/min/kg | MRT min |
|---|---|---|---|---|---|---|
| FVII | IV | 60 | 4.07 | 3314.7 | 6.195 | 6.2 |
| FVII-CTP | IV | 60 | β=51.06 | 31353.9 | 0.287 | 73.7 |
| FVII-CTP-CTP | IV | 60 | β=13.66 | 7626.8 | 1.18 | 15.4 |

Characterization of Recombinant FVIIa-CTP:

During activation, FVII is cleaved at R152 resulting in heavy and light chain domains that are held together by a single disulfide bridge. rFVIIa-(CTP)$_2$ is purified and activated by an ion exchange column purification process. In order to fully evaluate rFVIIa-(CTP)$_2$, the protein is loaded on SDS-PAGE under reducing conditions to commercial FVIIa (NovoSeven®). The heavy and the light chain domains are separated and migrate as separated bands of molecular weights 55 and 25 KDa. Both proteins react with antibodies specific for FVII, but the heavy chain of the rFVIIa-CTP specifically reacts with anti-CTP-specific antibodies, indicating that this band represents the FVII heavy chain fused to CTP. The light chain reacts specifically with anti-gamma carboxylase Ab. The FVIIa protein concentration is determined by FVIIa-specific ELISA kit.

FVIIa N-Terminal Sequencing:

rFVII-CTP-CTP in activated or zymogene purified proteins is separated by SDS-PAGE (on 12% Tris-Glycine) and subsequently electroblotted to a PVDF membrane. The bands of interest are cut out and put on a purified Biobrene-treated glass fiber filter. The N-terminal sequence analysis is carried out by Edmann degradation using a pulsed liquid protein sequencer equipped with a 140C HPLC microgradient system. The identity of the recombinant protein and proper pro-peptide cleavage is further verified by N-terminal sequencing.

FVIIa Clotting Activity:

In order to evaluate FVII-(CTP)$_2$ coagulation activity, activated partial thromboplastin time assay (aPTT) is performed. FVII-deficient plasma sample is substituted with rFVIIa (NovoSeven®) or rFVIIa-(CTP)$_2$. 300 μl of FVII deficient human plasma is mixed with 100 μl of FVIIa or rFVIIa-(CTP)$_2$ at specific concentrations, or normal pooled human plasma which is further diluted. Following 60 seconds incubation at 37° C. Tissue Factor (TF), CaCl$_2$), and phospholipids are added to the mixture. Clotting time in seconds is determined. Potency is assessed by comparing a dose-response curve of rFVIIa-(CTP)$_2$ to a reference preparation consisting of rhFVIIa or human pool normal plasma. One unit of FVIIa is defined as the amount of FVIIa which equals to the activity of 1 ml human normal plasma. The aPTT clotting activity of rFVII and rFVIIa-(CTP)$_2$ is measured on a coagulometer (Instrumentation Laboratory). The aPTT clotting activity of rFVIIa and rFVIIa-(CTP)$_2$ is similar.

Pharmacokinetics Studies in Rats:

In order to characterize the influence of the CTP addition to the rFVIIa on its longevity potential, a comparative pharmacokinetic study in rats is performed. NovoSeven® (rFVIIa) and rFVIIa-(CTP)$_2$ in TBS are injected IV to 6 SD rats. The levels of FVIIa over time are detected using a FVIIa ELISA kit. The half-life and AUC are calculated for each protein. Comparison of these clearance parameters reveals that the in vivo measures of half-life, recovery, and AUC of the rFVIIa-(CTP)$_2$ are superior to those of Novo-Seven®.

FVIIa-CTP In Vivo Efficacy Model (FVIII-Deficient Mouse Model of Hemophilia):

In order to assess the in vivo activity model, FVIII knockout mice are obtained, and a breeding colony is established. 10 μg of either commercial recombinant hFVIIa (NovoSeven®) or rFVIIa-(CTP)$_2$ are injected into the tail vein of an anaesthetized FVIII knockout mouse (22-28 g). The amount of injected protein equals to the required concentration of FVIII in normal plasma (5 μg/ml). Blood samples are taken from the clipped tail into heparinized capillary tubes at specific time points. Plasma samples are assessed for FVIIa levels by ELISA, and efficacy is measured by a PTT coagulation assay.

In this study, a fusion construct of FVII with CTP is generated. This recombinant protein is the basis for a treatment that provides a prolonged half-life and retention of therapeutic potency.

These results suggest that rFVIIa-(CTP)$_2$ has a similar therapeutic efficacy to rFVIIa in hemophilia patients. Moreover, this technology requires less frequent dosing. It appears that a single injection of rFVIIa-(CTP)$_2$ is sufficient to control bleeding episodes and reduce the number of injections that are needed during surgical intervention. This recombinant protein may be used as a long term prophylactic treatment.

Example 5

Comparative Assessment of Purified FVII-CTP$_3$, FVII-CTP$_4$, and FVII-CTP$_5$ 5.1 Study Objective Comparative assessment of pharmacokinetic parameters and clotting activity of FVII-CTP$_4$ and FVII-CTP$_5$ versus FVII-CTP$_3$.

5.2 Production of FVII-CTP$_4$ and FVII-CTP$_5$ Harvests

FVII cDNA fused at the C-terminal to four or five tandem CTP sequences was expressed in Dg44 cells using the Excellgene expressing system in the presence of 20 μg/L of vitamin K3 (Sigma, Mennadion). The harvest was collected (300 ml), filtered and frozen.

5.3 Production of FVII-CTP$_3$ Harvest

FVII-CTP$_3$ was expressed in-house in mammalian expressing system. CHO cells, using pCI-DHFR vector. Stable transfected pool #71 was grown in shake flasks, in the presence of 25 ng/L of vitamin K3 (Sigma). The harvests were collected and filtered.

All FVII-CTP harvests (3, 4 and 5 CTPs) were concentrated and dialyzed against TBS (50 mM Tris, 150 mM NaCl, pH 7.4) using Pellicon XL MWCO 10 kDa.

5.4 Determination of FVI Antigen Level

FVII antigen level was determined using Human FVII ELISA kit (Zymotest HyPhen) (Table 31). The calculated protein concentration is the average of two independent runs.

TABLE 31

| | FVII antigen level | | |
|---|---|---|---|
| | FVII-CIP$_3$ | FVII-CTP$_4$ | FVII-CTP$_5$ |
| Av. (ng/ml) | 224357.3 | 87884.1 | 589423 |
| SD | 44789.5 | 3248.7 | 5309 |
| % CV | 20.0 | 3.7 | 9 |

5.5 FVII-CTP Immune-Blot

FVII-CTP$_3$, FVII-CTP$_4$, and FVII-CTPs harvests were loaded on 12% Tris-Glycine gel (expedeon) using Precision plus dual color protein marker (Bio-Rad). The SDS-PAGE analysis was performed by Western immune-blot using anti-CTP polyclonal Ab (Adar Biotech Production) or anti-Gla Ab (American Diagnostica).

Figures 21A, 21B, 21C:
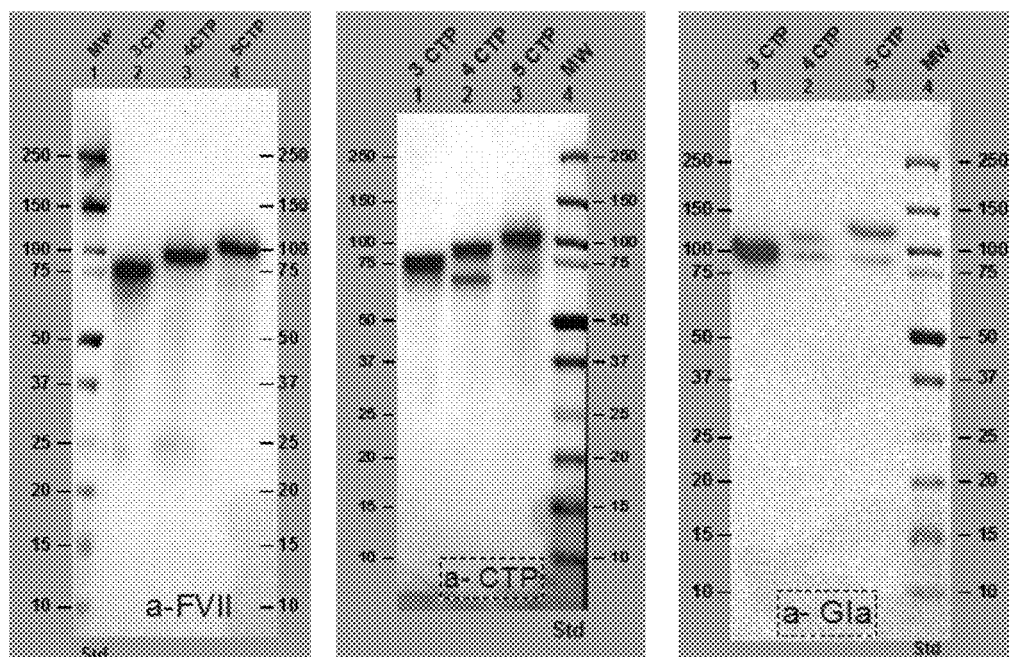
FIG. 21A. Shows western blots of FVII fused to three, four and five CTPs, detected using anti-FVII, anti-CTP, and anti-gamma carboxylation antibodies. FVII-CTP$_3$, FVII-CTP$_4$, and FVII-CTP$_5$ harvests were loaded on 12% Tris-Glycine gel (expedeon) using Precision plus dual color protein marker (Bio-Rad). The SDS-PAGE analysis was performed by Western immunoblot using anti-FVII.
FIG. 21B. Shows western blots of FVII fused to three, four and five CTPs, detected using anti-FVII, anti-CTP, and anti-gamma carboxylation antibodies. FVII-CTP$_3$, FVII-CTP$_4$, and FVII-CTP$_5$ harvests were loaded on 12% Tris-Glycine gel (expedeon) using Precision plus dual color protein marker (Bio-Rad). The SDS-PAGE analysis was performed by Western immunoblot using anti-CTP polyclonal Ab (Adar Biotech Production).
FIG. 21C. Shows western blots of FVII fused to three, four and five CTPs, detected using anti-FVII, anti-CTP, and anti-gamma carboxylation antibodies. FVII-CTP$_3$, FVII-CTP$_4$, and FVII-CTP$_5$ harvests were loaded on 12% Tris-Glycine gel (expedeon) using Precision plus dual color protein marker (Bio-Rad). The SDS-PAGE analysis was performed by Western immunoblot using anti-Gla Ab (American Diagnostica).

FVII fused to three, four and five CTP migrated at 80, 90 and 100 kDa, respectively. As expected, FVII-CTP$_4$ and FVII-CTP$_5$ harvests from Excellgene contain low gamma carboxylation content as compared to FVII-CTP$_3$ harvest which was produced at Prolor since the production process wasn't optimized (FIG. 21).

5.6 Comparative Assessment of FVII In Vitro Potency

Figure 22:
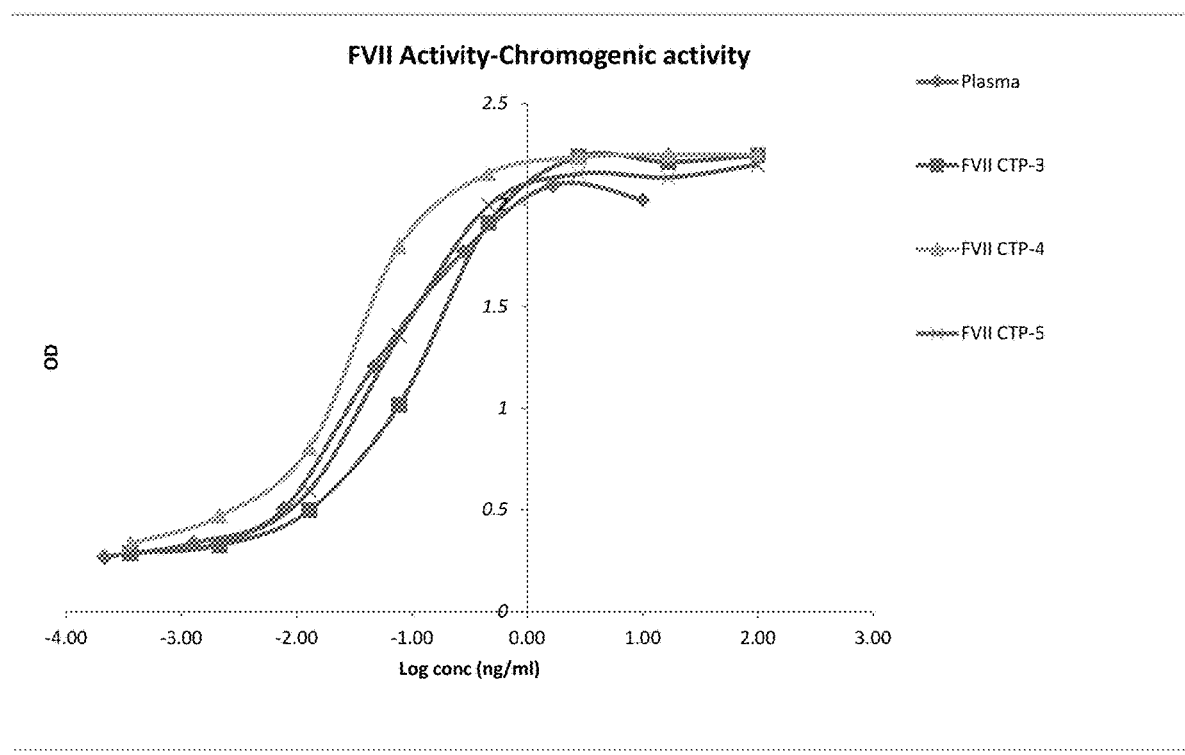
FIG. 22. Shows the FVII Activity—Chromogenic activity. A comparative assessment of the in vitro potency of HA purified (highly gamma carboxylated fraction) FVII-CTP$_3$, FVII-CTP$_4$, and FVII-CTP$_5$ versus normal human pool plasma was performed using a commercially available chromogenic activity test kit, BIOPHEN (Hyphen BioMed 221304). All samples were serially diluted and the potency was assessed by comparing a dose response curve to a reference preparation consisting of normal human plasma.

A comparative assessment of the in vitro potency of HA purified (highly gamma carboxylated fraction) FVII-CTP$_3$, FVII-CTP$_4$, and FVII-CTP$_5$ versus normal human pool plasma was performed using a commercially available chromogenic activity test kit, BIOPHEN (Hyphen BioMed 221304). All samples were serially diluted, and the potency was assessed by comparing a dose-response curve to a reference preparation consisting of normal human plasma. FVII-CTP$_3$ and FVII-CTP$_5$ demonstrated chromogenic activity lower than pooled normal plasma (FIG. 22). FVII-CTP$_4$ demonstrated higher activity as reflected by EC50 ratios, compared to FVII-CTP$_3$ and FVII-CTP$_5$ (Table 32).

TABLE 32

FVII In Vitro Clotting Activity

| Sample | EC50 ng/ml | Sample/plasma EC50 ratio |
|---|---|---|
| Plasma | 0.05 | |
| FVII 3CTP | 0.12 | 2.72 |
| FVII 4CTP | 0.03 | 0.71 |
| FVII 5CTP | 0.06 | 1.35 |

5.7 FVII In Vitro Clotting Activity:

Factor VII (FVII) activity assay, which was performed in Sheba Medical Center, the Israel National Coagulation Center, is a prothrombin (PT)-based assay using immuno-adsorbed plasma deficient in Factor VII (Siemens). The PT reagent is innovin, and the assay is performed in the Sysmex® CA 1500 instrument. FVII normal range is within 55-145%.

TABLE 33

FVII In Vitro Chromogenic Activity

| Sample | FVII % of activity | Concentration in tested sample (µg/ml) | Concentration (µg/ml) |
|---|---|---|---|
| FVII 3 CTP | 36 | 0.5 | 224.2 |
| | 18 | 0.25 | |
| | 6 | 0.125 | |
| FVII 4 CTP | 334 | 0.5 | 87.9 |
| | 176 | 0.25 | |
| | 93 | 6.25 | |
| FVII 5 CTP | 38 | 0.5 | 58.9 |
| | 19 | 0.25 | |
| | 10 | 0.125 | |

Since the normal level of circulating FVII in the body is around 0.5 µg/ml, FVII-CTP$_3$ and FVII-CTP$_5$ harvests exhibit 3-fold reductions in their coagulation activity versus normal human pool plasma; this result correlates with the obtained chromogenic activity (Table 33).

The FVII-CTP$_4$ harvest exhibits a 3-fold increase in its potential coagulation activity versus normal human pool plasma as observed in the chromogenic activity assay (Table 33). The activity percentage of FVII-CTP; is much higher compared to activity percentage of FVII-CTP$_3$ and FVII-CTP$_5$. Methodological limitations of the ELISA method may limit the accuracy of Ag level calculations of FVII-CTP$_4$.

5.8 Pharmacokinetic Study

Two pharmacokinetic studies were performed in order to determine the FVII-CTP$_3$, FVII-CTP$_4$, and FVII-CTP$_5$ pharmacokinetics (PK) parameters. During the first study, FVII-CTP$_3$, FVII-CTP$_4$, and FVII-CTP$_5$ (Group A, B and C, respectively) were administered in a single intravenous injection to Sprague Dawley rats (six rats per treatment) in a dose of 250 µg/kg body weight. Blood samples were drawn retro-orbitally from 3 rats alternately at 0.083, 0.5 2, 5, 8, 24, 48, 72 and 96 hours post-dosing (Table 34). Citrated plasma (0.38%) was prepared immediately after sampling and stored at −20° C. until analysis.

TABLE 34

Pharmacokinetic Study Design-Concentrated Harvest

| Treatment Group | Test Article | No. of animals/ group/ time point | Dose Route | Dose Level (µg per animal) | Injected Vol (µl) | Conc. (µg/ml) | Time-Points (hours post-dose) |
|---|---|---|---|---|---|---|---|
| A | FVII-CTP*3 | 6 | IV | 50 | 200 | 250 | 0 (Pre-dose) 0.083, 0.5, 2, 5, 8, 24, 48, 72, 96 |
| B | FVII-CTP*4 | 6 | IV | 50 | 200 | 250 | 0 (Pre-dose) 0,083, 0.5, 2, 5, 8, 24, 48, 72, 96 |
| C | FVII-CTP*5 | 6 | IV | 50 | 200 | 250 | 0 (Pre-dose) 0.083, 0.5, 2, 5 8, 24, 48, 72, 96 |

Figure 23:
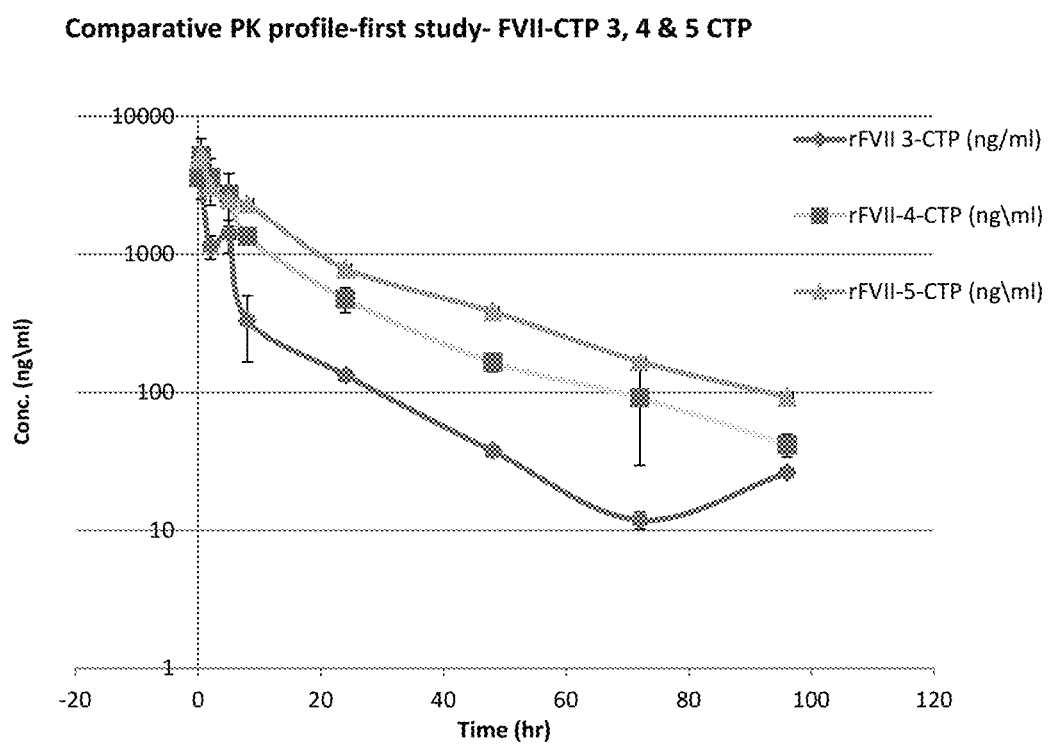
FIG. 23. Shows a first comparative pharmacokinetic (PK) profile-FVII 3, 4 and 5 CTPs. FVII-CTP$_3$, FVII-CTP$_4$, and FVII-CTP$_5$ (Group A, B and C, respectively) were administered in a single intravenous injection to Sprague Dawley rats (six rats per treatment) in a dose of 250 µg/kg body weight. Blood samples were drawn retro-orbitally from 3 rats alternately at 0.083, 0.5 2, 5, 8, 24, 48, 72 and 96 hours post dosing. Citrated plasma (0.38%) was prepared immediately after sampling and stored at −20° C. until analysis. FVII-CTP$_5$ demonstrated a superior profile as compared to the two other versions.
Figure 24:
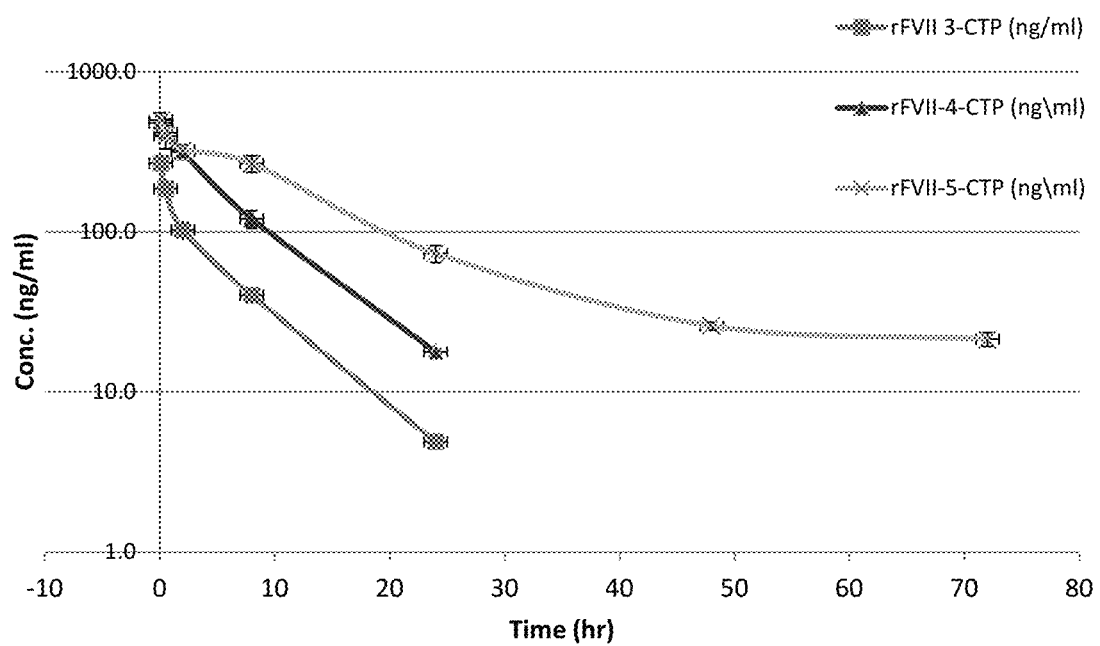
FIG. 24. Shows a second comparative PK profile-FVII 3, 4 and 5 CTPs. FVII-CTP$_3$, FVII-CTP$_4$, and FVII-CTP$_5$ following FVII selection and the HA purification process (Group A, B and C, respectively) were administered in a single intravenous injection to Sprague Dawley rats (three rats per substance) in a dose of 29.45 µg/kg body weight. Blood samples were drawn retro-orbital at 0.083, 0.5 2, 8, 24, 48, and 72 hours post-dosing. Citrated plasma (0.38%) was prepared immediately after sampling and stored at −20° C. until analysis.

FVII concentration in plasma samples were quantified using human FVII Elisa kits (Zymutest FVII-Biophen). The pharmacokinetic profile was calculated and is the mean of 3 animals at each time point. Terminal half-life values were calculated using PK Solutions 2.0 Software. Table 35 below summarizes the calculated FVII concentrations at the different sampling time points. The PK profile (FIGS. 23-24) and a summary of the PK parameters (Table 36) are also presented below. FVII-CTP$_3$ demonstrated a superior profile as compared to FVII-CTP$_3$ and FVII-CTP$_4$ (Table 36).

TABLE 35

First Pharmacokinetic Study-FVII Concentrations

| Time (hr) | AVE-FVII-3-CTP (ng/ml) | SD | AVE-FVII-4-CTP (ng/ml) | SD | AVE-FVII-5-CTP (ng/ml) | SD |
|---|---|---|---|---|---|---|
| 0.083 | 4214 | 583 | 3600 | 427 | 4888 | 504 |
| 0.5 | 3386 | 892 | 5213 | 1682 | 5384 | 2549 |
| 2 | 1138 | 219 | 3603 | 1338 | 3082 | 289 |
| 5 | 1390 | 374 | 2726 | 1127 | 2480 | 561 |
| 8 | 333 | 167 | 1349 | 44 | 2316 | 633 |
| 24 | 133 | 12 | 476 | 98 | 788 | 34 |

TABLE 35-continued

First Pharmacokinetic Study-FVII Concentrations

| Time (hr) | AVE-FVII-3-CTP (ng/ml) | SD | AVE-FVII-4-CTP (ng/ml) | SD | AVE-FVII-5-CTP (ng/ml) | SD |
|---|---|---|---|---|---|---|
| 48 | 38 | 3 | 165 | 24 | 384 | 61 |
| 72 | 12 | 2 | 91 | 62 | 167 | 31 |
| 96 | 26 | 1 | 42 | 8 | 93 | 49 |

TABLE 36

Pharmacokinetic Analysis

|  | FVII 3-CTP | FVII-4-CTP | FVII-5CTP |
|---|---|---|---|
| half-life (0.083-8 hr) (hr) | 2.5 | 4.9 | 6.6 |
| half-life (8-72 hr) (hr) | 13.3 | 16.6 | 17.7 |
| AUC (ng-hr/ml) (8-72 hr) | 18374.6 | 51224.4 | 72954.2 |
| Vd (ml/kg) (8-72 hr) | 203.7 | 91.9 | 67.7 |
| CL (ml/hr/kg) (8-72 hr) | 10.6 | 3.8 | 2.7 |

The addition of four or five CTPs significantly elongated FVII half-life as compared to 3 CTPs by 2- and 3-fold, respectively (Table 36). This superiority was more significant in the initial part of the study (0.083-8 hr), suggesting a potential improved protein recovery and reduced extra vascular clearance. AUC following FVII-CTP$_4$ and FVII-CTP$_5$ administration increased by 3- and 4-fold, respectively, versus FVII-CTP$_3$. Clearance was also reduced while adding 4 and 5 CTPs to FVII (Table 36).

As observed in the study, the addition of four and five CTPs significantly elongated FVII half-life as compared to 3 CTPs, both in the initial and terminal half-life. The half-life values in the first and second study are different due to a different analysis approach which was effected by the dose and study duration, nevertheless the overall trend was maintained. The AUC following FVII-CTP$_4$ and FVII-CTPs administration increased by 2.5- and 7-fold, respectively, versus FVII-CTP$_3$.

5.9 Conclusions:

In this study, the PK parameters and potential clotting activity of FVII-CTP$_3$, FVII-CTP$_4$, and FVII-CTPs were assessed. Fusion of 4 and 5 CTPs to FVII provided a superior and improved half-life, exposure and reduced clearance as compared to FVII-CTP$_3$ while maintaining a similar chromogenic and in vitro clotting activity. These results were observed at different concentrations of protein and were consistent for both harvest and purified protein. While evaluating the overall effect of fusion of CTP at the C terminus to FVII, fusion of 1-5 CTPs considerably increased the half-life and AUC of FVII in a CTP proportional manner, suggesting that as the CTP portion of the molecule increases, FVII longevity and stability is significantly improved while maintaining its initial in vitro clotting activity, as summarized in Table 37 hereinbelow.

TABLE 37

| Comparative assessment | T$_{1/2}$ percent increase | AUC percent increase |
|---|---|---|
| FVII vs. FVII-CTP$_2$ | 268 | 200 |
| FVII-CTP$_2$ vs. FVII-CTP$_3$ | 67 | 57.8 |
| FVII-CTP$_3$ vs. FVII-CTP$_4$ | 24 | 178 |
| FVII-CTP$_4$ vs. FVII-CTP$_5$ | 6 | 42 |

As previously reported, FVII half-life correlates with the half-life of the activated form of FVII (FVIIa) both in humans and animals. Therefore, it is anticipated that a similar improvement in half-life will be obtained for the activated versions following CTP fusion.

Example 6

FVII-CTP$_3$Feasibility Studies in FVIII-Deficient Hemophilic Mice

Studies described hereinabove testing FVII-CTP, FVII-CTP$_2$ and FVII-CTP$_3$ harvest PK profile and coagulation activity vs. a commercial FVII were conducted. FVII-CTP$_3$ exhibited an improved PK profile while maintaining its coagulation activity vs. FVII-CTP and FVII-CTP$_2$ harvests or rhFVII. In order to further characterize FVII-CTP$_3$ in vitro and in vivo properties, a mini stable pool expressing and secreting the protein was generated, and purification and activation processes were developed.

In the current study, the pharmacokinetic and pharmacodynamic properties of FVIIa-CTP$_3$ were tested in FVIII-deficient mice. The PK profile of the protein was evaluated. A FVIIa specific activity-based PK profile was established and compared to commercial product NovoSeven®. In addition, the long-lasting in vivo hemostatic capabilities of FVIIa-CTP$_3$ to induce coagulation in FVIII-deficient mice after a tail vain transection (survival study) were tested.

Study Objectives:

To evaluate the pharmacokinetic and pharmacodynamic parameters of FVIIa-CTP$_3$ vs. commercial rhFVIIa (NovoSeven®) in FVIII-deficient mice following a single IV administration at a similar activity dose.

To determine the in vivo ability of FVIIa-CTP$_3$ to maintain homoeostasis in FVIII-deficient mice by a single IV administration of FVIIa-CTP$_3$ and NovoSeven® at a similar activity dose followed by a challenge of tail vein transection (survival study).

Production of FVII-CTP$_3$ Harvest:

FVII-CTP$_3$ was expressed in-house in Dg44 cells using a pCI-DHFR vector. Stable transfected pool #71 was grown in shake flasks, in the presence of 25 ng/L of Vitamin K3 (Sigma). Cell suspension was cultured and harvested following viability decline to 60-80%. The harvest was filtered and frozen at −70° C.

Determination of Harvest FVII Antigen Level:

FVII antigen level was determined using human FVII ELISA kit (Zymotest HyPhen) (Table 38). The antigen level was calculated per each pooled harvest batch.

TABLE 38

FVII-CTP$_3$ antigen level
FVII antigen level

|  | PK-PD study | | Survival study |
|---|---|---|---|
|  | harvest 31A | harvest 31B | harvest 38 |
| Av (μg/ml) | 16.0 | 15.9 | 16.6 |
| STD | 1.5 | 0.0 | 0.8 |
| % CV | 9.1 | 0.1 | 4.9 |

Figure 25A:
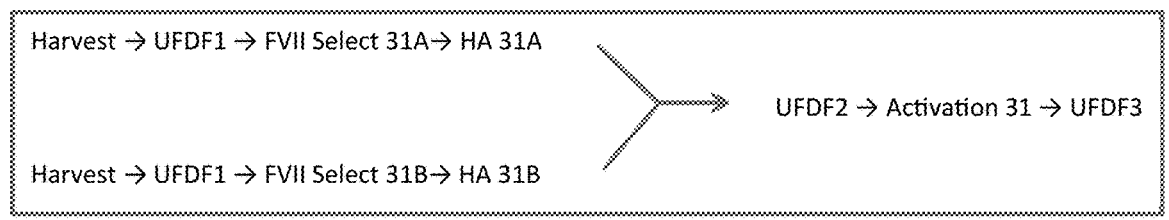
FIG. 25A. Shows a schematic diagram of FVII-CTP$_3$ purification process. Batch 31 was produced for the PK/PD study.
Figure 25B:
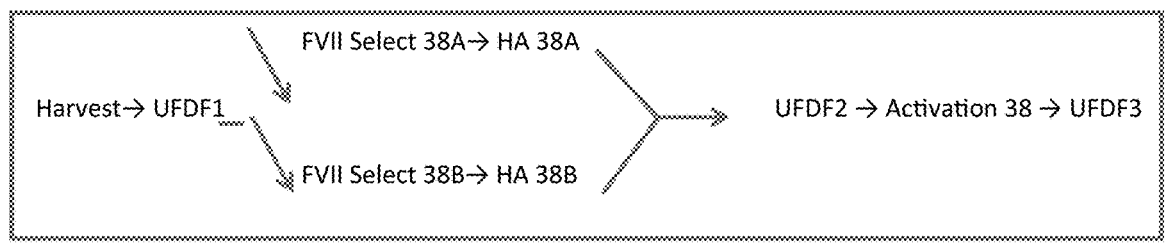
FIG. 25B. Shows a schematic diagram of FVII-CTP$_3$ purification process. Batch 38 was produced for the survival study.

FVII-CTP$_3$ Purification Process (FIG. 25)
Process Outline

Following a short purification study, the following purification process using 2 columns was performed. VII-Select affinity column (GE) and Ceramic Hydroxyapatite type 1 (HA), 40 μm (Bio Rad). FVII-CTP$_3$ γ-carboxylated enriched protein was purified. Auto-activation was induced by incubation of purified FVII-CTP$_3$ in the presence of CaCl$_2$) overnight at 2-8° C. The purification process is in its final developmental stage and is being optimized, thus part of the purification steps are not identical in the two batches.

Ultra-Filtration/Diafiltration (UFDF) Using 10 kDa Hollow Fiber or Pellicon Cassette Clarified harvest was thawed at 4° C. over the weekend (2-3 days).

In Batch 31, clarified harvest (12 liters) was concentrated 4-fold (in two successive runs) using a hollow fiber cartridge (GE Healthcare Catalog #UFP-10-C-4X2MA) with a 10 KDa molecular weight cut-off. Concentrated harvest was dia-filtrated against 1-2 volumes of TBS (50 mM Tris 150 mM NaCl pH 7.4).

In Batch 38, clarified harvest (8.5 liters) was concentrated 4-fold using a Pellicon 2 (Millipore) cassette with a 10 KDa molecular weight cut-off. Concentrated harvest was directly loaded on VII-Select column.

Both ultra-filtrations were performed on ice with ice cold buffers. UFDF samples were filtered 0.22 μm before loading.

Capture on FVII-Select Column

The UFDF or concentrated harvest was loaded on VII-Select column (XK16/20, CV 18 ml), pre-equilibrated with TBS pH 7.4. The column was washed with 50 mM Tris-HCl, 0.5M NaCl pH 7.5, and FVII-CTP$_3$ was eluted with 50 mM Tris-HCl, 1M NaCl 50% (v/v), Propylene Glycol pH 7.5. The process was performed in two successive cycles utilizing the same column.

Gamma Carboxylation-Based Separation on a Ceramic Hydroxyapatite Column

The eluted product was diluted 1:10 with 10 mM sodium phosphate pH 6.8 and loaded on ceramic hydroxyapatite columns (XK16/20, CV 24 ml). The column was washed with 59 mM sodium phosphate pH 6.8 and the γ-carboxylated rich fraction of Factor VII was eluted with 500 mM sodium phosphate pH 6.8. This process was performed in two successive cycles on the same column. At each batch, the eluates of the two cycles were pooled and concentrated to 1.7-2 mg/ml and dia-filtered with 20 mM Tris-HCl, 100 mM NaCl pH 8.2 to reduce volume and prepare the material for the activation step.

FVII Activation

Purified FVII-CTP$_3$ was diluted to 1 mg/ml and incubated in 20 mM Tris-HCl, 100 mM NaCl and 1 mM CaCl$_2$ pH 8.2 at 2-8° C. for 24 hours. Activation was terminated by buffer exchange (UFDF) to preliminary formulation buffer (20 mM Citrate, 240 mM NaCl, 13.3 mM Glycine, pH 6.9).

FVII-CTP$_3$ and FVIIa-CTP$_3$ Analytical Properties:

SDS-PAGE and Western Blots

Purified FVII-CTP$_3$, and FVIIa-CTP$_3$ were loaded on 12% Tris-Glycine gel using Precision Plus Dual Color Protein Marker (Bio-Rad). The SDS-PAGE Coomassie analysis was performed by staining the gel with Coomassie brilliant blue reagent (5 or 10 μg of protein/lane). Western blot analysis was performed (1 μg of protein/lane) using anti-human FVII polyclonal Ab (R&D systems; AF2338), anti-human gamma carboxylation monoclonal antibody (American Diagnostics Catalog #499, 3570), and anti-CTP polyclonal Ab. Under reduced conditions, FVII-CTP$_3$ migrated at 75 KDa, and FVIIa-CTP$_3$ migrated as two main bands: a heavy chain at 50 kDa, and a light chain at 25 kDa, represented in FIG. 26 as Bands 2 and 3, respectively.

Figures 26A, 26B, 26C, 26D:
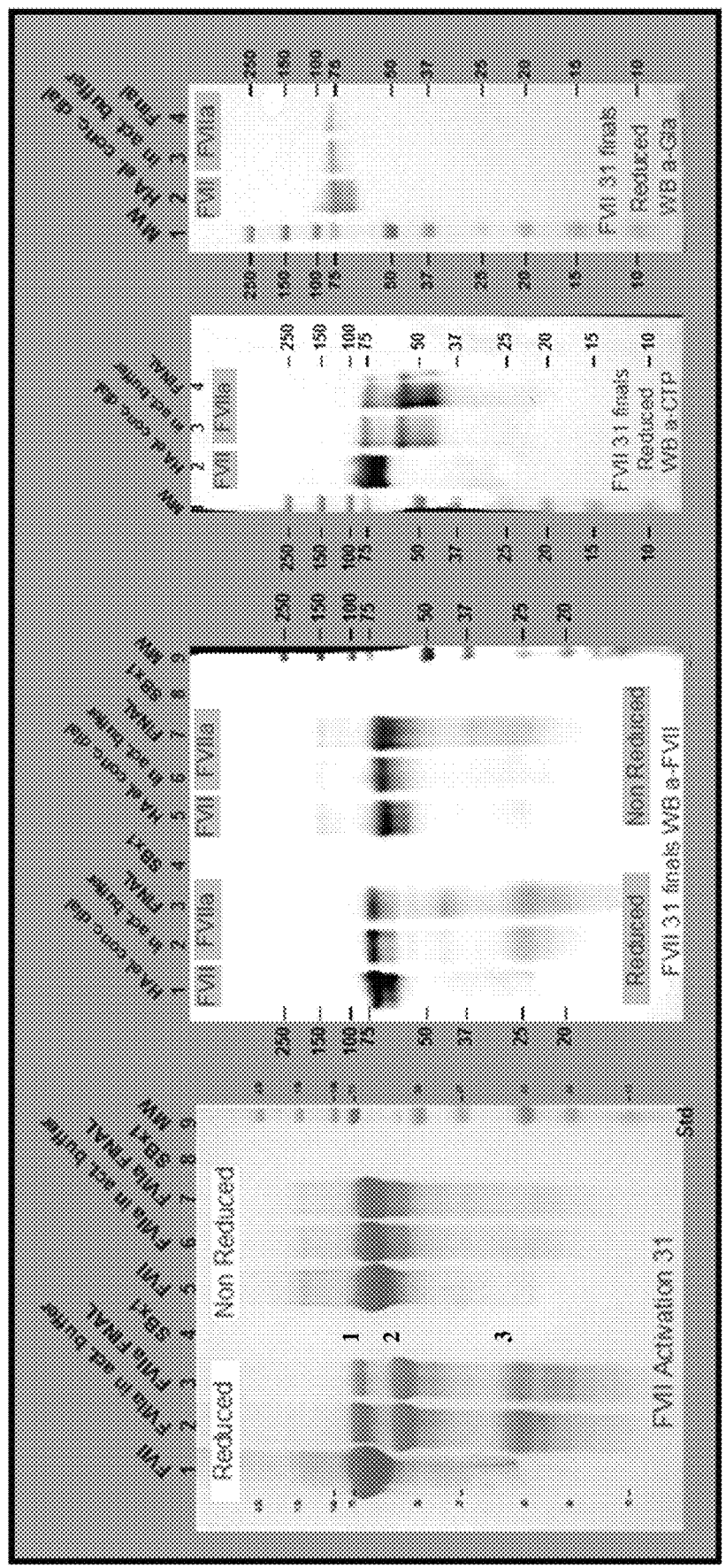
FIG. 26A. Shows an SDS-PAGE and Western blot of Final FVII and FVIIa. 10 µg (Batch 31) or 5 µg (Batch 38) were loaded in each lane of Coomassie stained SDS-PAGE. 1. FVII-CTP$_3$ polypeptide; 2. Heavy chain, including 3×CTP; 3. Light Chain. All three antibodies detect FVII.
FIG. 26B. Shows an SDS-PAGE and Western blot of Final FVII and FVIIa. 10 µg (Batch 31) or 5 µg (Batch 38) were loaded in each lane of Coomassie stained SDS-PAGE 1. FVII-CTP$_3$ polypeptide; 2. Heavy chain, including 3×CTP; 3. Light Chain.
FIG. 26C. Shows an SDS-PAGE and Western blot of Final FVII and FVIIa. 10 µg (Batch 31) or 5 µg (Batch 38) were loaded in each lane of Coomassie stained SDS-PAGE 1. FVII-CTP$_3$ polypeptide; 2. Heavy chain, including 3×CTP; 3. Light Chain.
FIG. 26D. Shows an SDS-PAGE and Western blot of Final FVII and FVIIa. 10 µg (Batch 31) or 5 µg (Batch 38) were loaded in each lane of Coomassie stained SDS-PAGE 1. FVII-CTP$_3$ polypeptide; 2. Heavy chain, including 3×CTP; 3. Light Chain.
Figures 26E, 26F, 26G, 26H:
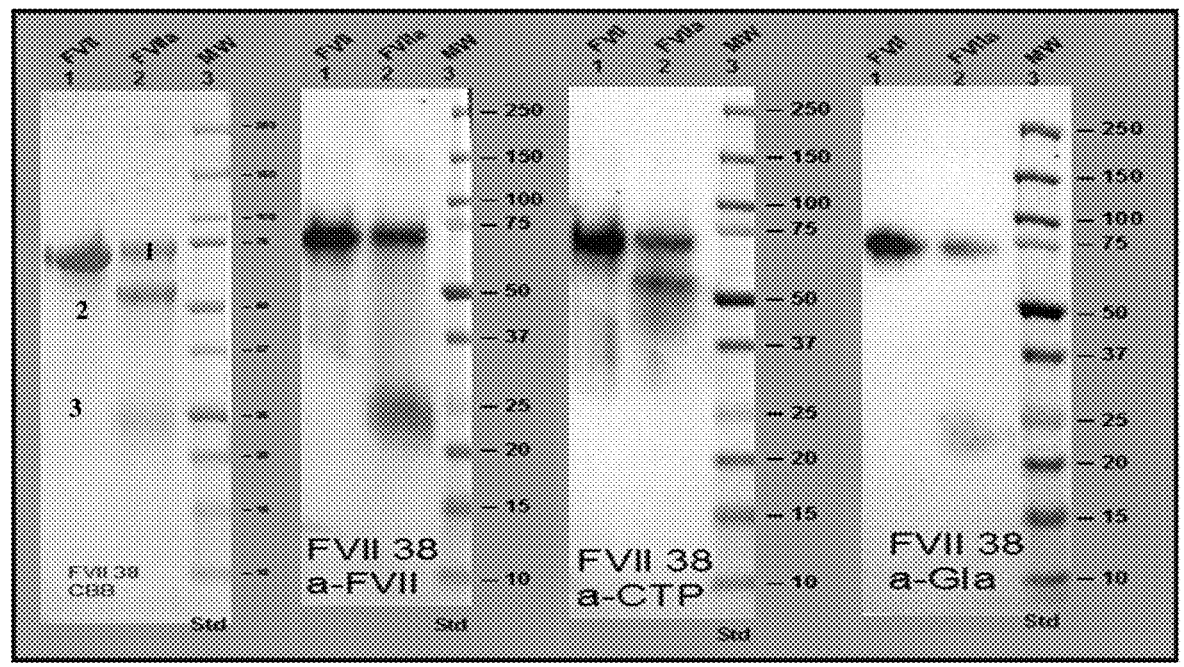
FIG. 26E. Shows an SDS-PAGE and Western blot of Final FVII and FVIIa. 10 µg (Batch 31) or 5 µg (Batch 38) were loaded in each lane of Coomassie stained SDS-PAGE 1. FVII-CTP$_3$ polypeptide; 2. Heavy chain, including 3×CTP; 3. Light Chain.
FIG. 26F. Shows an SDS-PAGE and Western blot of Final FVII and FVIIa. 1 µg protein was loaded in each lane of Western blot. 1. FVII-CTP$_3$ polypeptide; 2. Heavy chain, including 3×CTP; 3. Light Chain. All three antibodies detect FVII. FVIIa light chain is detected with both α-FVII.
FIG. 26G. Shows an SDS-PAGE and Western blot of Final FVII and FVIIa. 1 µg protein was loaded in each lane of Western blot. 1. FVII-CTP$_3$ polypeptide; 2. Heavy chain, including 3×CTP; 3. Light Chain. All three antibodies detect FVII. FVIIa heavy chain was detected by α-CTP.
FIG. 26H. Shows an SDS-PAGE and Western blot of Final FVII and FVIIa. 1 µg protein was loaded in each lane of Western blot. 1. FVII-CTP$_3$ polypeptide; 2. Heavy chain, including 3×CTP; 3. Light Chain. All three antibodies detect FVII. FVIIa heavy chain was detected by α-Gla.

The purification procedure significantly enriched the FVII-CTP$_3$ portion while reducing impurities. The purification process yield was 25-30% FVII (according to ELISA). Most of the protein lost during purification had low FVII chromogenic activity or no activity. Based on Coomassie-stained SDS-PAGE, the reduced FVIIa-CTP$_3$ contains more than the predicted bands. A band migrating to around ~75 kDa represents non-activated FVII (FIG. 26, Band 1). This band consists of two bands with minor MW differences, which might reflect different γ-carboxylation content. Additional bands with MW lower than 20 kDa were observed. This was previously reported to be degradation products of the heavy chain.

Figure 27:
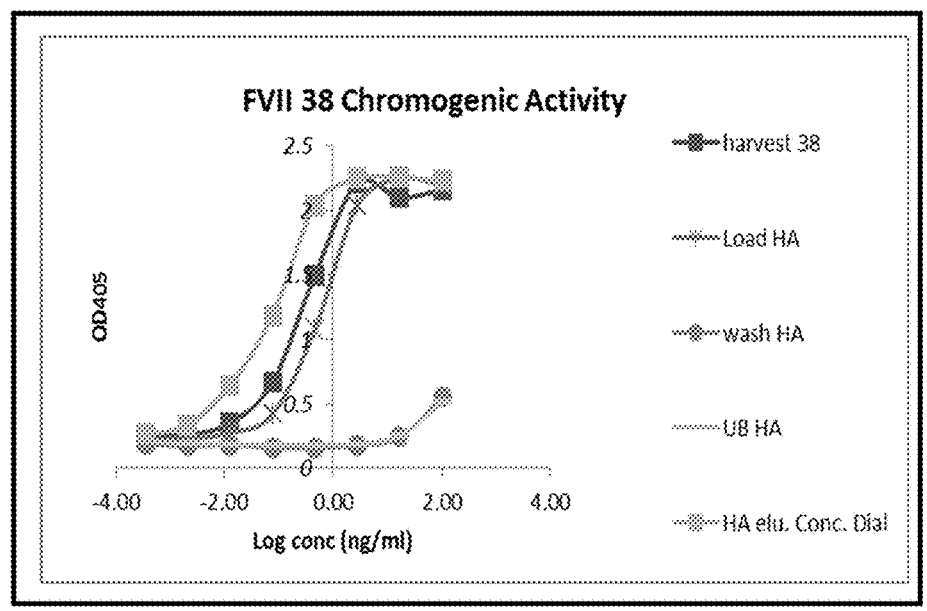
FIG. 27. Shows that FVII-CTP$_3$ chromogenic activity is enhanced as a result of purification on ceramic hydroxyapatite (HA) column. A comparative assessment of the in vitro potency of FVII-CTP$_3$ harvest, in-process fractions, and purified FVII-CTP$_3$ versus human pool normal plasma was performed using a commercially available chromogenic activity test kit, BIOPHEN (Hyphen BioMed 221304). FVII-CTP$_3$ harvest and protein were serially diluted and the potency was assessed by comparing a dose-response curve to a reference preparation of normal human plasma.

FVII-CTP$_3$ Chromogenic Activity:

A comparative assessment of the in vitro potency of FVII-CTP$_3$ harvest, in-process fractions, and purified FVII-CTP$_3$ versus human pool normal plasma was performed using a commercially available chromogenic activity test kit. BIOPHEN (Hyphen BioMed 221304). FVII-CTP$_3$ harvest and protein were serially diluted and the potency was assessed by comparing a dose-response curve to a reference preparation of normal human plasma. Following FVII-CTP$_3$ purification, the chromogenic activity was significantly improved, and non-active fractions were separated mainly by HA column (FIG. 27). A strong correlation between FVII chromogenic activity and detection of FVII with monoclonal anti-Gla antibodies in Western blot was observed. The potency of FVII chromogenic activity as reflected by EC50 value in harvest is affected from both carboxylated and non-carboxylated FVII fractions. Following purification and enrichment of FVII-CTP$_3$ γ-carboxylated fraction, the activity was improved, demonstrating the important contribution of γ-carboxylation to FVII activity (FIG. 27). This parameter is crucial for proper FVII in vivo activity and will be further addressed in a clone development program.

Protein Determination by A280

The theoretical extinction coefficient of FVIIa-CTP3 and NovoSeven® was calculated using the ProtParam algorithm (http://web.expasy.org/protparam). The calculation is based on amino acid sequence. The calculated extinction coefficients for FVII-CTP3 and NovoSeven® is 1.186 and 1.406, respectively. These values represent the absorbance of 1 g/L at 280 nm.

The extinction coefficient difference between the two proteins derives solely from the increase in molecular weight of FVIIa-CTP$_3$ compared to NovoSeven®, since CTP lacks aromatic and cysteine residues, thus does not contribute to the absorbance.

Protein determination by A280 is used for final FVII, and for purified in-process samples, starting from the elution of VII-Select column.

Determination of FVIIa Antigen Level

FVIIa antigen level was determined using Human FVIIa ELISA kit (IMUBIND, American Diagnostica). The antigen level was calculated per each batch. However, this tool was not useful for the determination of the dose for injection, since it did not represent the amount of active product.

Clotting Assay of FVIIa-Staclot® VIIa-rTF

FVIIa is derived from an intra-chain cleavage of the single-chain FVII. Native tissue factor (TF) is a cofactor of FVIIa. Upon binding to TF, FVII mediates the activation of Factor X to Xa, while itself is transformed to FVIIa. The soluble tissue factor is the extracellular part of native tissue factor. It can no longer activate FVII by auto-activation, but the FVIIa bound to tissue factor can activate FX to FXa.

The recombinant soluble tissue factor (rsTF) used in this assay utilizes the FVIIa specificity to construct a FVIIa clotting test. rsTF, in the presence of FVIIa, calcium and phospholipids leads to coagulation of plasma, without activating FVII to FVIIa.

The observed clotting time in this system has an inverse relationship with the FVIIa content in the tested sample, with no interference of FVII presence in the sample.

The assay was performed by Omri Laboratories (Nes-Ziona, Israel). FVIIa activity was evaluated for both NovoSeven® following reconstitution and FVIIa-CTP$_3$ prior to each study. NovoSeven® activity did not correlate with the anticipated activity as reported on the vial, but the discrepancy might be due to a different approach for activity evaluation. Table 39 summarizes the FVIIa clotting activity per volume without considering the protein concentration.

TABLE 39

FVIIa clotting activity of batch products

| | PK study | | Survival Study | |
|---|---|---|---|---|
| | FVIIa-3*CTP (FVIIa 31) | NovoSeven ® | FVIIa-3*CTP (FVIIa 38) | NovoSeven ® |
| Activity (U/ml) | 1.3E+06 | 2.5E+05 | 1.3E+06 | 7.4E+05 |

Specific Activity of FVIIa-CTP$_3$

FVIIa specific activity (which is calculated as the activity/ml divided by protein concentration) was calculated based on A280 and is presented in Table 40. When comparing the specific activity of the two molecules, which differ in MW, compensation must be made in order to normalize the activity (i.e. because of the molecular weight difference, the number of active sites in 1 mg of NovoSeven® is 1.185-fold higher than in FVIIa-CTP$_3$). Calculation of the conversion factor is presented in the following equation:

$$\text{Normalized\_SA} = \frac{SA(FVIIa\text{-}CTP_3)}{MW.(FVII\,CTP_3)} \times MW(\text{Native\_FVII}) = \frac{SA(FVIIa\,CTP_3)}{53419.5\,Da} \times 45079.1\,Da = SA(FVIIa\text{-}CTP_3)*1.185$$

TABLE 41

Study outline

| Treated Groups | Test Article | No. of animals/ group/ timepoint | Dose Route | Amount of Units/ animal | Injected Vol. (µl) | Time-Points (hours post-dose) |
|---|---|---|---|---|---|---|
| A | rhFVIIa | 4 | IV | 1.6e5 | 200 | 0 (Pre-dose) 0.166, 0.5, 2, 4, 8, 12, 24, 34, 48, 58, 72 |
| B | FVIIa-CTP$_3$ | 4 | IV | 1.6e5 | 200 | 0 (Pre-dose) 0.166, 0.5, 2, 4, 8, 12, 24, 34, 48, 58, 72 |

FVIIa-CTP$_3$ PK Profile in FVIII-Deficient Mice

Figure 28:
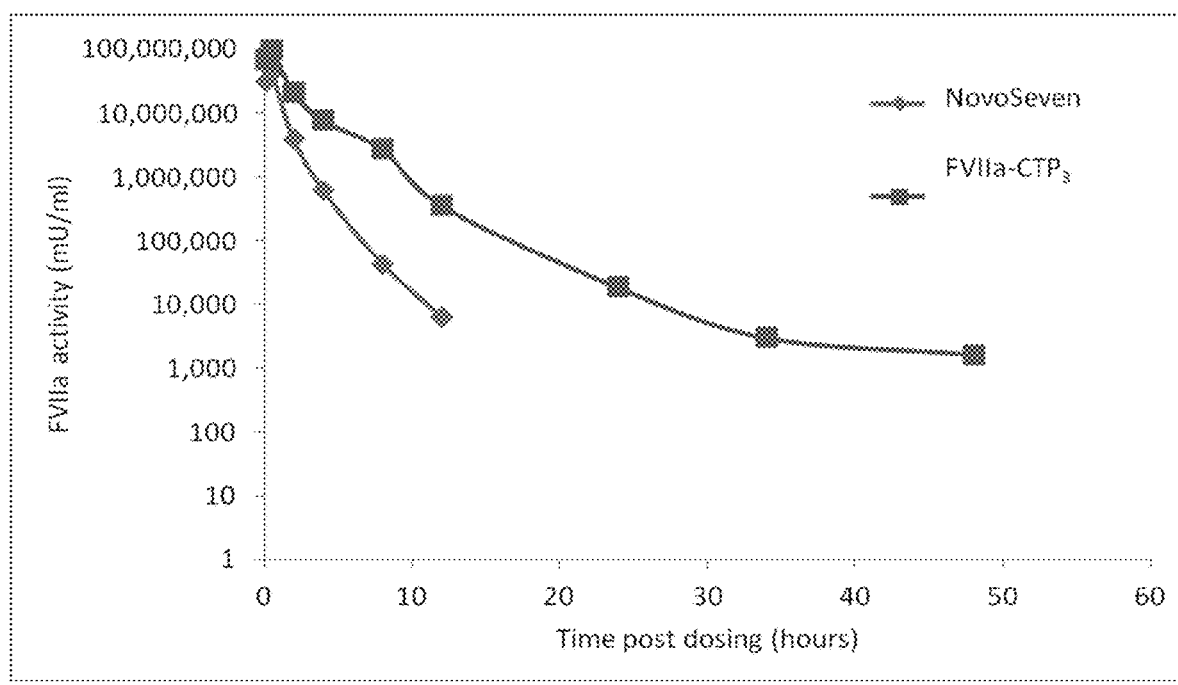
FIG. 28. Shows the PK profile of FVIIa-CTP$_3$ vs. NovoSeven® in FVIII-deficient mice. FVIIa-CTP$_3$ was produced following FVII selection, HA purification process and activation. FVIIa-CTP$_3$ or NovoSeven® was administered in a single intravenous injection to FVIII−/− hemophilic mice. Blood samples were drawn retro-orbitally at 0.083, 0.5 2, 8, 24, 48, and 72 hours post-dosing. Citrated plasma (0.38%) was prepared immediately after sampling and stored at −20° C. until analysis, and a PK profile was established based on FVIIa clotting activity using a STACLOT commercial kit.

FVIIa activity in blood samples was quantitated using a Staclot® VIIa-rTF kit (Stago, Parsippany, NJ). The pharmacokinetic profile was calculated for each protein and represents the mean of 4 animals at each time point. FIG. 28 presents the PK profile of FVIIa throughout the experiment. FVIIa recovery is presented in Table 43. A summary of the PK parameters is presented in Table 44.

Table 42 summarizes the clotting activity values following administration of either NovoSeven® or FVIIa-CTP$_3$. FVIIa-CTP$_3$ and NovoSeven® reached maximal activity half an hour post-dosing. NovoSeven®'s highest activity value reached only 43% of FVIIa-CTP$_3$'s maximal activity value. FVIIa-CTP$_3$ clotting activity was maintained for a longer period of time, demonstrating elongated activity. Clotting activity for the NovoSeven®-treated mice was undetectable at time points later than 12 hours, while FVII-CTP$_3$ treated mice continued h to retain measurable activity at 48 hours post dosing (Table 42 and FIG. 28).

The addition of three tandem CTP copies to FVIIa elevated recovery by 100% (Table 43), as measured by the highest activity post-dosing and compared to the anticipated activity based on in vitro analysis, and increased the half-life

TABLE 40

FVIIa-CTP$_3$ specific activity compared to NovoSeven ®

| Sample | Average A280 | STDV (n = 9) | % CV | Extinction coefficient | Prot conc. (mg/ml) | U/ml | Specific Activity U/mg protein | U/mg FVIIa | Fold decrease from NovoSeven ® |
|---|---|---|---|---|---|---|---|---|---|
| NovoSeven ® | 1.274 | 0.031 | 2.398 | 1.406 | 0.906 | 8.36E+05 | 9.23E+05 | 9.23E+05 | 1.0 |
| FVIIa-CTP$_3$ | 4.396 | 0.092 | 2.094 | 1.186 | 3.706 | 7.23E+05 | 1.95+05E | 2.31E+05 | 4.0 |

FVIIa-CTP$_3$ PK-PD Study:

Study Outline

FVIIa-CTP$_3$ and rhFVIIa (NovoSeven®, NS) were administered in a single intravenous injection to C57B FVIII-deficient mice at a dose of 6.4E6 U/kg body weight (160,000 U/animal). Blood samples were drawn retro-orbitally from 4 mice alternately at 0.166, 0.5, 2, 4, 8, 12, 24, 34, 48, 58, and 72 hours post-dosing (Table 41). Citrated plasma (0.32%) was prepared immediately after sampling and stored at −20° C. until analysis. FVIIa clotting activity level was evaluated, and a detailed PK analysis was performed. The study was performed by Omri Laboratories (Nes-Ziona, Israel).

and mean resident time (MRT) 5-fold. The exposure time (AUC) was increased 3-fold (Table 44).

TABLE 42

FVIIa clotting activity following single IV injection

| Time after administration (hours) | Average FVIIa Clotting Activity (U/ml) | |
|---|---|---|
| | FVIIa-CTP$_3$ | NovoSeven ® |
| 0.16 | 6.8E+07 | 3.2E+07 |
| 0.5 | 9.7E+07 | 4.3E+07 |
| 2 | 2.1E+07 | 3.9E+06 |
| 4 | 7.7E+06 | 7.3E+05 |
| 8 | 2.7E+06 | 4.2E+04 |
| 12 | 3.7E+05 | 6.2E+03 |

TABLE 42-continued

FVIIa clotting activity following single IV injection

| Time after administration (hours) | Average FVIIa Clotting Activity (U/ml) | |
|---|---|---|
| | FVIIa-CTP$_3$ | NovoSeven ® |
| 24 | 2.4E+04 | BLQ |
| 34 | 4.6E+03 | BLQ |
| 48 | 1.5E+03 | BLQ |

TABLE 43

FVIIa-CTP$_3$ recovery

| Treated. Groups | Test Article | Amount. of Units/ animal | Practical administered dose (U/ml) | *Anticipated Cmax (U/ml blood) | Cmax (U/ml) | % Recovery |
|---|---|---|---|---|---|---|
| A | rFVIIa | 1.60E+05 | 1.20E+06 | 1.40E+05 | 4.25E+04 | 30 |
| B | FVIIa-CTP$_3$ | 1.60E+05 | 1.29E+06 | 1.50E+05 | 9.74E+04 | 64.6 |

*anticipated Cmax is derived from administered dose divided in blood volume

TABLE 44

PK parameters of FVIIa-CTP$_3$ vs. NovoSeven ®

| PK Parameters | NovoSeven ® | FVIIa-CTP$_3$ |
|---|---|---|
| Half-life-$\alpha$ (0.5-12 hr) | 0.94 | 1.57 |
| Half-life-$\beta$ (12-48 hr) | NA | 4.62 |
| AUC (mU * hr/ml) | 5.80E+07 | 1.80E+08 |
| Vd/Kg (ml/Kg) | 1408 | 2375 |
| CL/Kg (ml/hr/Kg) | 1034 | 356 |
| MRT (hr) | 1.3 | 6.7 |

Thrombin Generation Assay (TGA)

Figure 29A:
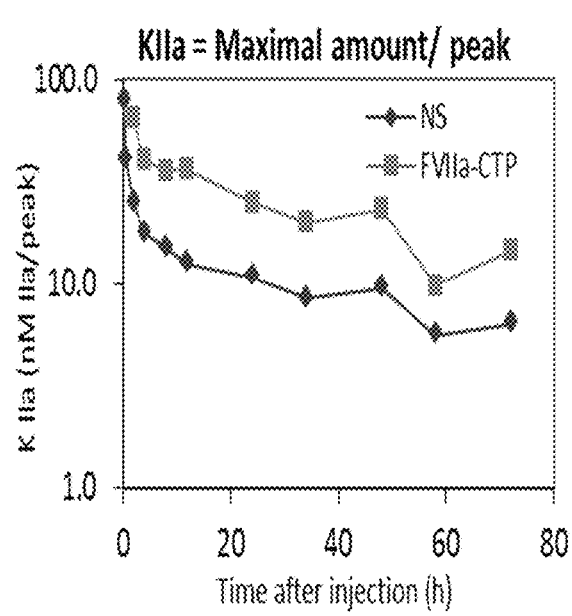
FIG. 29A. Shows that FVIIa-CTP$_3$ was produced following FVII selection, HA purification process and activation. FVIIa-CTP$_3$ or NovoSeven® was administered in a single intravenous injection to FVIII−/− hemophilic mice. Blood samples were drawn retro-orbitally at 0.083, 0.5 2, 8, 24, 48, and 72 hours post-dosing. Citrated plasma (0.38%) was prepared immediately after sampling and stored at −20° C. until analysis. Thrombin generation parameters were evaluated during the PK experiment, and parameters including maximal amount to peak was evaluated.
Figure 29B:
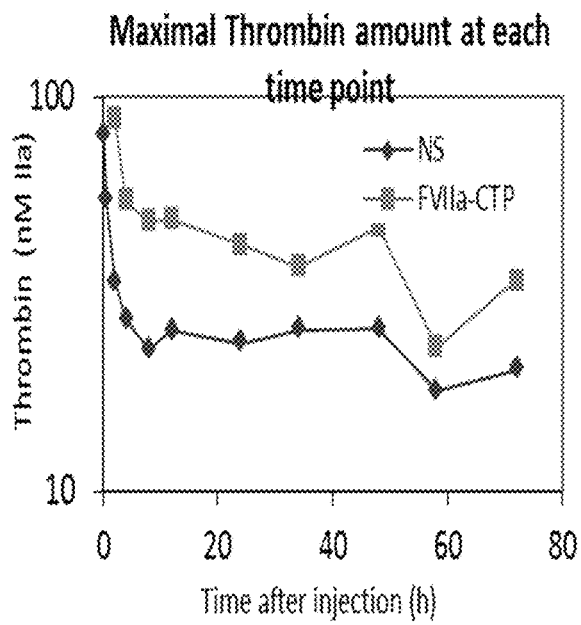
FIG. 29B. Shows that FVIIa-CTP$_3$ was produced following FVII selection, HA purification process and activation. FVIIa-CTP$_3$ or NovoSeven® was administered in a single intravenous injection to FVIII−/− hemophilic mice. Blood samples were drawn retro-orbitally at 0.083, 0.5 2, 8, 24, 48, and 72 hours post-dosing. Citrated plasma (0.38%) was prepared immediately after sampling and stored at −20° C. until analysis. Thrombin generation parameters were evaluated during the PK experiment, and parameters including amount of thrombin to time point was evaluated.
Figure 29C:
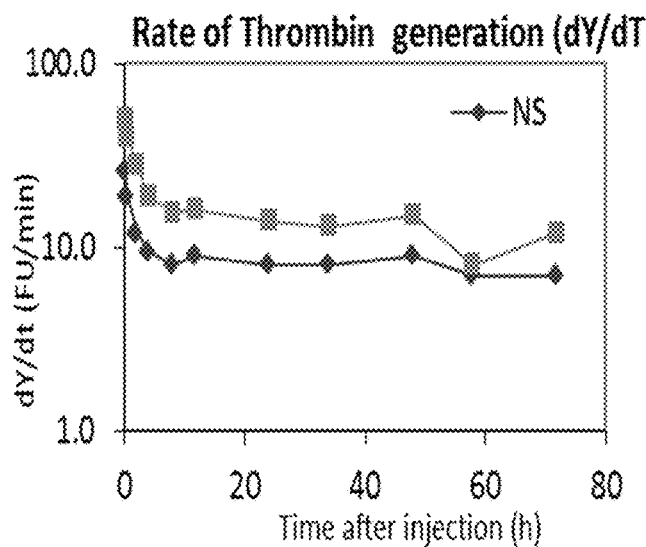
FIG. 29C. Shows that FVIIa-CTP$_3$ was produced following FVII selection, HA purification process and activation. FVIIa-CTP$_3$ or NovoSeven® was administered in a single intravenous injection to FVIII−/− hemophilic mice. Blood samples were drawn retro-orbitally at 0.083, 0.5 2, 8, 24, 48, and 72 hours post-dosing. Citrated plasma (0.38%) was prepared immediately after sampling and stored at −20° C. until analysis. Thrombin generation parameters were evaluated during the PK experiment, and parameters including rate of thrombin generation was evaluated.

The generation of thrombin is a fundamental part of the clotting cascade and as such an estimate of how well a particular individual can generate thrombin may correlate with either a risk of bleeding or thrombosis. Commonly measured variables when analyzing thrombin generation include: the lag time, the time to peak thrombin generation, the peak, the endogenous thrombin potential [ETP] (i.e., the area under the curve and the tail), the time course of the thrombogram ("TG"). After a lag time, a burst of thrombin is observed. However, clotting occurs at the end of the lag time, when more than 95% of all thrombin has not yet formed. The thrombin generation assay was performed at Omri Laboratories, using Thrombinoscope reagents supplemented with human hemophilic plasma. TGA reflects of the clotting ability in mice plasma, derived from injection of NovoSeven® and FVIIa-CTP$_3$. FIG. 29 presents TGA parameter values for mice plasma following administration of either FVIIa-CTP$_3$ or NovoSeven®. Following FVIIa-CTP$_3$ administration, all three parameters (rate of thrombin generation, maximal amount of generated thrombin and KIIa) demonstrate an advantage of FVII-CTP$_3$ over Novo-Seven® treatment. This further strengthens the notion of potential long-acting superiority of FVII-CTP$_3$ as compared to NovoSeven®.

FVIIa-CTP$_3$ Tail Vain Transection (TVT) Study:
Study Outline

The data obtained from the PK/PD test for FVIIa-CTP$_3$ provided insight into the functionality of FVIIa-CTP$_3$, and demonstrated that FVIIa-CTP$_3$ had a pharmacokinetic advantage when compared with NovoSeven®. However, the ability of the protein to induce a clot in vivo, after a traumatic event has not yet been demonstrated. In order to evaluate the ability of FVIIa-CTP$_3$ to stop bleeding, the same FVIII-deficient mice model was employed for a bleeding challenge.

FVIII-deficient mice were administered a single intravenous injection of FVIIa-CTP$_3$ or NovoSeven®. The mice were dosed with drug in amounts that provided equivalent FVIIa activity (1.6E05 units, 200 µl), calculated according to the potency of each drug evaluated in the FVIIa clot activity assay (Table 45). The administered doses were 9 mg/kg of NovoSeven®, and 40 mg/kg of FVII-CTP$_3$ due to the reduced activity of FVIIa-CTP$_3$. A control group was injected with 200 µl vehicle.

The tail vein was transected 2.7 cm from the tail tip 15 min (injection 1), 24 hours (injection 2) or 48 hours (injection 3) post-administration, and mice survival was recorded for 24 hours.

TABLE 45

Evaluation of injected samples

| | NovoSeven ® | | | FVIIa-CTP$_3$ | | | |
|---|---|---|---|---|---|---|---|
| Injection No. | protein conc. (mg/ml) | Activity (U/ml) | Specific Activity (U/mg) | protein conc. (mg/ml) | Activity (U/ml) | Specific Activity (U/mg) | Specific Activity (normalized) |
| 1 | 0.91 | 8.0E+05 | 8.8E+05 | 3.63 | 6.6E+05 | 1.8E+05 | 2.2E+05 |
| 2 | 0.92 | 8.3E+05 | 9.0E+05 | 3.81 | 7.8E+05 | 2.0E+05 | 2.4E+05 |
| 3 | 0.89 | 8.8E+05 | 9.9E+05 | 3.68 | 7.3E+05 | 2.0E+05 | 2.3E+05 |

Protein concentration was determined by A280.
Results

Data from the vehicle-injected control groups for the three injections (5 animals×3 injections), were summarized and are presented in FIG. 30. 30% survival was observed 24 hours after tail vein transection.

NovoSeven® and FVIIa-CTP$_3$-treated mice demonstrated proper hemostatic activity after tail vein transection performed 15 min after FVIIa administration. A 100% survival rate was observed in FVIIa-CTP$_3$ and NovoSeven® treated animals (FIG. 30).

The reduced clearance rate of FVII-CTP$_3$ which was demonstrated in the PK/PD study most clearly appreciated after a tail vein transection performed 24 hours post-administration. A decline in the survival rate of NovoSeven® is observed. Similar to the control group, 50% death is observed within 10 hours. Meanwhile, 90% of FVIIa-CTP$_3$ treated mice survived (FIG. 30). This result emphasizes the long-lasting efficacy of the FVIIa-CTP$_3$ treatment.

Figure 30A:
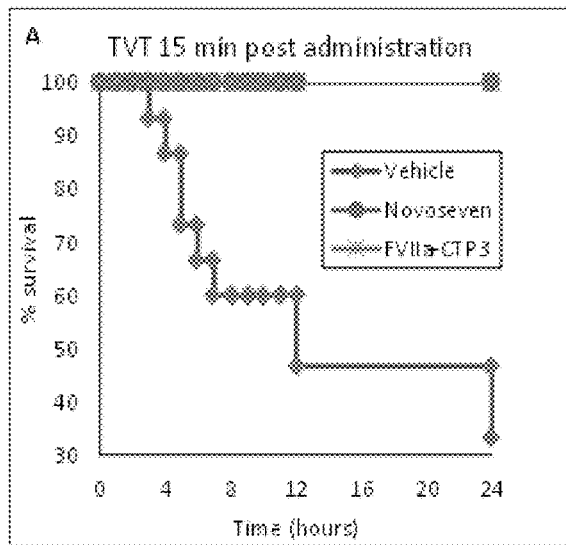
FIG. 30A. Shows hemophilic mice survival curves post tail vain transection (TVT). TVT was performed 15 min post administration. Mice Survival was observed for 24 hours after TVT and recorded every single hour for the first 12 hours, and after 24 hours. Control group data (vehicle) is the sum of the 3 experiments with 5 mice/experiment.
Figure 30B:
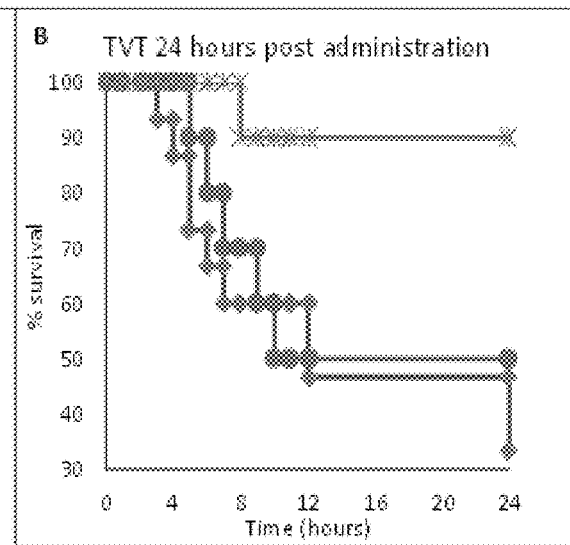
FIG. 30B. Shows hemophilic mice survival curves post tail vain transection (TVT). TVT was performed 24 hours post administration. Mice Survival was observed for 24 hours after TVT and recorded every single hour for the first 12 hours, and after 24 hours. Control group data (vehicle) is the sum of the 3 experiments with 5 mice/experiment.
Figure 30C:
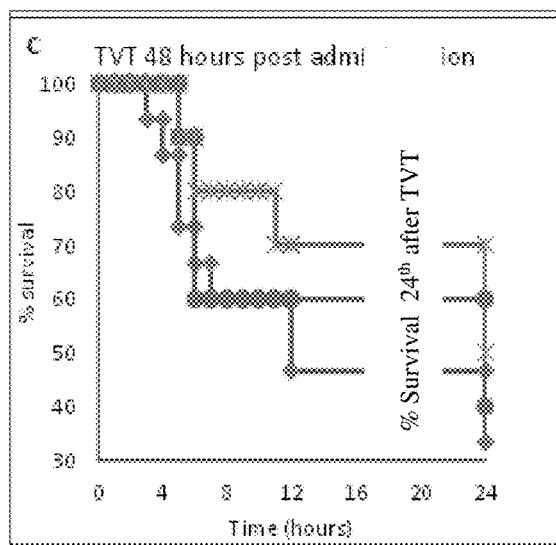
FIG. 30C. Shows hemophilic mice survival curves post tail vain transection (TVT). TVT was performed 48 hours post administration. Mice Survival was observed for 24 hours after TVT and recorded every single hour for the first 12 hours, and after 24 hours. Control group data (vehicle) is the sum of the 3 experiments with 5 mice/experiment.
Figure 30D:
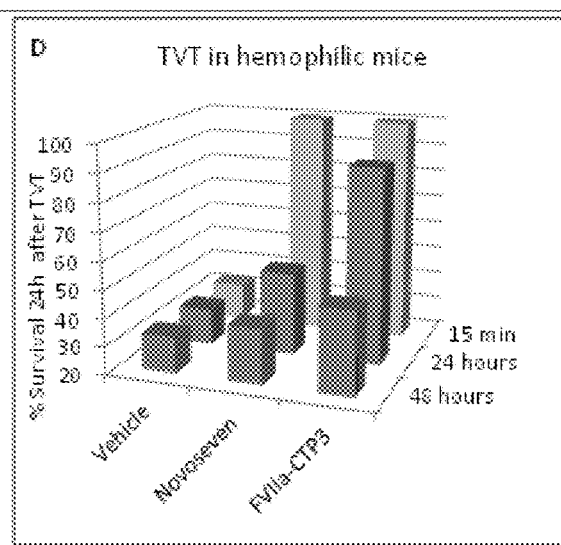
FIG. 30D. Summarizes mouse survival as recorded 24 hours post TVT.

48 hours after administration, a decline in survival rate is demonstrated in groups treated with either FVIIa-CTP$_3$ or NovoSeven® (FIG. 30C). A slight improvement in FVIIa-CTP mice was observed, but the difference did not reach statistical significance.

Discussion:

CTP fusion to recombinant proteins extends the circulatory half-life of proteins while maintaining comparable activity. While the mechanism behind the reduced clearance of protein above a threshold size of 70 KDa is well understood with respect to renal clearance, additional protection is achieved following CTP fusion. CTP fusion is believed to sweep around the protein shield and protect it from proteolytic cleavage, to increase its radial molecular weight due to the highly negative charge and to reduce its affinity to hepatic clearance receptors.

The present study was aimed to provide specific insight on the impact of CTP fusion to FVII on protein half-life and clearance and also address the paradigm of its specific activity following this modification. FVIII-deficient mice were administered with a single IV injection of FVIIa-CTP$_3$ or recombinant commercial FVIIa (NovoSeven®) at similar dose (unit based) and a PK activity-based analysis was performed. FVIIa-CTP$_3$ demonstrated a superior longevity as reflected by 5- and 3.5-fold increase in its half-life and AUC, respectively. The specific activity (U/mg) of FVIIa-CTP as calculated by the Staclot® activity kit divided by the protein concentration measured by A280 was shown to be 4-5 times lower than the specific activity of NovoSeven®.

To build on the understanding of how CTP affects the haemostatic effects of FVIIa in vivo, the ability of FVIIa-CTP$_3$ to reduce bleeding was investigated. In the tail vein transection bleeding model in hemophilic mice model, rFVIIa administration can improve the survival rate of challenged animals and avoid their bleeding to death. In the study described herein, animals were administered with FVIIa-CTP$_3$ or NovoSeven®. Both molecules were able to maintain homeostasis when the transection was performed 0.25 hours post-dosing. A significantly prolonged duration of activity was demonstrated for the FVIIa-CTP$_3$-treated group when the tail transection was performed 24 hr post dosing. The vehicle-treated group's survival rate was higher than anticipated and higher than that obtained in previous studies (50% vs. 20% in previous studies, data not shown). The percent survival of treated animals at is further evaluated at earlier time points, including at 36 hr post dosing.

In conclusion, it was demonstrated that FVIIa-CTP$_3$ has an increased duration of activity in hemophilic mice which translates into a longer duration of haemostatic effect when compared to NovoSeven®. The data gathered suggest that fusion of CTP to FVII is a technology with the potential to significantly improve prophylactic treatment in patients with hemophilia.

Example 7: Comparative Assessment of Purified FVII-CTP$_3$ Vs. FVII-CTP$_5$ Profile Following Single IV or Sc Injection to SD Rats Study Objective Two studies were carried out.

The first study objective was to determine the pharmacokinetic parameters of rFVII-CTP$_3$ versus rFVII-CTP$_5$ following FVII select- and HA-column purification in male Sprague Dawley rats, after a single intravenous administration of 50 µg/animal.

In the second study, rFVII-CTP$_3$-HA versus rFVII-CTP$_5$-HA pharmacokinetic parameters, were examined in male Sprague Dawley rats following a single intravenous or subcutaneous administration of 100 µg/animal.

Results

Determination of FVII-CTP 3 and FVII-CTP 5 Antigen Level

FVII antigen level was determined using Human FVII ELISA kit (Zymotest HyPhen) (Table 46). T

TABLE 46

Summarizes the calculated protein concentration which is the average of three independent runs.

| | FVII 3 CTP | | FVII 5 CTP | |
|---|---|---|---|---|
| | FVIIS 46 el. Conc. Dial | FVII HA 46 el. Conc. Dial | FVIIS el. Conc. Dial | FVII HA 5 100% B Conc. Dial |
| AVE (ng\ml) | 3.78E+06 | 1.59E+06 | 1.88E+06 | 7.92E+05 |
| SD | 1.30E+06 | 6.03E+05 | 7.15E+05 | 3.57E+05 |
| CV (%) | 3.43E+01 | 3.80E+01 | 3.80E+01 | 4.51E+01 |

Western Blot Analysis of the Examined Samples

Figure 31B:
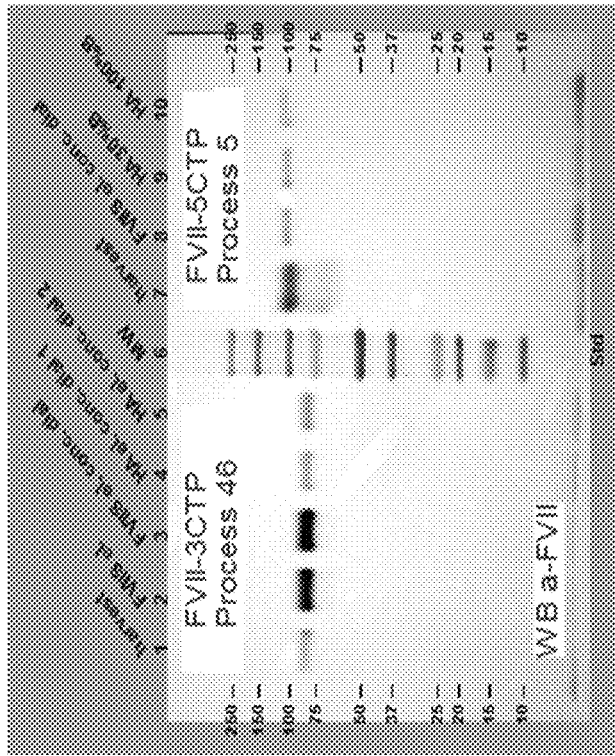
FIG. 31B. Shows FVII-3-CTP and FVII-5 CTP immuneblots, blotted for FVII.
Figure 31A:
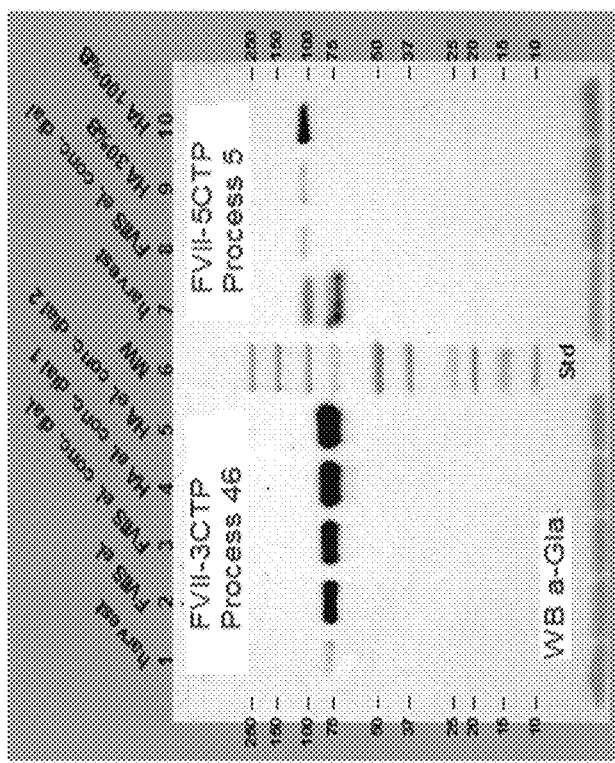
FIG. 31A. Shows FVII-3-CTP and FVII-5 CTP immuneblots, blotted for GLA.
Figure 31C:
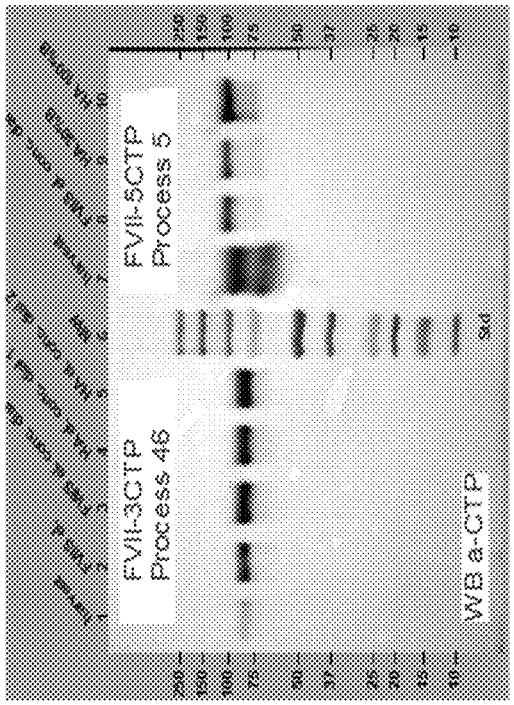
FIG. 31C. Shows FVII-3-CTP and FVII-5 CTP immuneblots, blotted for CTP.

FVII-CTP$_{3, 5}$ samples were loaded on 4-12% bisTrisgel (NuPage, invitrogene) using Precision plus dual color protein marker (Bio-Rad). The SDS-PAGE analysis was performed by western immune-blot using polyclonal anti FVII Ab (R&D systems), anti CTP polyclonal Ab (Adar biotech production) or anti Gla Ab (American diagnostica). In summary, FVII fused to three and five CTP migrated at 80 and 100 kDa, respectively (see FIG. 31).

Comparative Assessment of FVII In Vitro Potency

FVII activity assay, which was performed in Sheba medical center, the national coagulation center, is a PT based assay using immunoabsorbed plasma deficient in factor VII (Siemens). The PT reagent is innovin and the assay is performed in the Sysmex CA 1500 instrument. FVII normal range is within 55-145%. Sample activities are summarized in Table 47.

TABLE 47

Sample activity

| Sample | Concentration (mg/ml) according to (NANODROP) | Concentration in tested sample (µg/ml) | Results (%) | Average-% of plasma |
|---|---|---|---|---|
| FVII-5CTP | 2.19 | 2 | 87 | 16% |
| FVIIS el. | | 1 | 30 | |
| Conc. Dial | | 0.5 | 10 | |
| FVII-5CTP | 1 | 2 | 97 | 21% |
| HA 5 | | 1 | 36 | |
| 100% B | | 0.5 | 13 | |
| conc. Dial | | | | |
| FVIIS 46 el. | 3.17 | 2 | 100 | 18% |
| Conc. Dial | | 1 | 35 | |
| | | 0.5 | 12 | |
| FVII HA 46 el. | 1.5 | 2 | 92 | 20% |
| Conc. Dial (1) | | 1 | 33 | |
| | | 0.5 | 10 | |

The normal level of circulating FVII in the body is around 0.5 µg/ml. Both FVII-CTP$_3$ and FVII-CTP$_5$ exhibit about 5 fold reductions in their coagulation activity versus normal human pool plasma.

Pharmacokinetic Study

Two pharmacokinetic studies were performed in order to determine the FVII-CTP$_3$ and FVII-CTP$_5$ (after FVII select and FVII HA column) pharmacokinetics (PK) profile and parameters. In the first study. FVII-CTP$_3$, and FVII-CTP$_5$ following FVII select HA purification were administered in a single intravenous injection to Spargue Dawley rats (six rats per substance) in a dose of 50 µg/rat.

Blood samples were drawn retro-orbital from 3 rats alternately at 0.083, 0.5 2, 5, 8, 24, 48, 72, 96 and 120 hours post dosing. Citrated plasma (0.38%) was prepared immediately after sampling and stored at −20 until analysis.

In the second study, only samples after HA column were tested. These samples were administered in a single intravenous or subcutaneous injection to Spargue Dawley rats (six rats per substance) using a dose of 100 µg/rat. Blood samples were collected at the same time points and conditions as at the first study above.

TABLE 48

First study design (FVII select vs. FVII HA).

| Treated Groups | Test Article | No. of animals/group/ | Dose Route | Dose Level (µg per animal) | Injected Vol (µl) | Conc. (µg/ml) | Time-Points (hours post-dose) |
|---|---|---|---|---|---|---|---|
| A | FVII-CTP*3 batch 46 HA | 6 | IV | 50 | 200 | 750 | 0 (Pre-dose) 0.083 0.5, 2, 5, 8, 24, 48, 72, 96, 120 |
| B | FVII-CTP*3 batch 46 FVIIS | 6 | IV | 50 | 200 | 250 | 0 (Pre-dose) 0.083 0.5, 2, 5, 8, 24, 48, 72, 96, 120 |
| C | FVII-CTP*5 batch 5 HA | 6 | IV | 50 | 200 | 250 | 0 (Pre-dose) 0.083 0.5, 2, 5, 8, 24, 48, 72, 96, 120 |
| D | FVII-CTP*5 batch 5 FVIIS | 6 | IV | 50 | 200 | 250 | 0 (Pre-dose) 0.083 0.5, 2.5, 8, 24, 48, 72, 96, 120 |

TABLE 49

Second study design (IV vs. SC)

| Treated Groups | Test Article | No. of animals/group/ | Dose Route | Dose Level (µg per animal) | Injected Vol (µl) | Conc. (µg/ml) | Time-Points (hours post-dose) |
|---|---|---|---|---|---|---|---|
| A | FVII-CTP*3 batch 46 HA | 6 | IV | 100 | 200 | 500 | 0 (Pre-dose) 0.083 0.5, 2, 5, 8, 24, 48, 72, 96, 120 |
| B | FVII-CTP*3 batch 46 HA | 6 | SC | 100 | 200 | 500 | 0 (Pre-dose) 0.083 0.5, 2, 5, 8, 24, 48, 72, 96, 120 |
| C | FVII-CTP*5 batch 5 HA | 6 | IV | 100 | 200 | 500 | 0 (Pre-dose) 0.083 0.5, 2, 5, 8, 24, 48, 72, 96, 120 |
| D | FVII-CTP*5 batch 5 HA | 6 | SC | 100 | 200 | 500 | 0 (Pre-dose) 0.083 0.5, 2, 5, 8, 24, 48, 72, 96, 120 |

The main differences between these two studies are the dosages and the route of administration. In the first study, rats were injected IV with 50 µg/rat, while in the second study, the rats were injected IV or SC with 100 µg/rat (total 500 µg/kg; rats weigh 200 g). The increase in the dosage is due to the change in the type of administration, SC administration requires higher amounts to achieve effects similar to IV administration.

Analysis of PK Study

FVII concentration in plasma samples were quantified using human FVII Elisa kits (zymutest FVII-Biophen). Pharmacokinetic profiles were calculated and reflect the mean for 3 animals at each time point. Terminal half-live values were calculated using PK solutions 2.0 software. The table below summarizes the calculated FVII concentrations at the different sampling time points. PK profile and a summary of the PK parameters are presented in table below.

TABLE 50

First pharmacokinetic study (FVII select vs. FVII HA)-FVII concentrations (ng\ml).

| Time (hour) | FVII CTP*3 BATCH 46 HA | FVII CTP*3 BATCH 46 FVII S | FVII CTP*5 BATCH 5 HA | FVII CTP*5 BATCH 5 FVII S |
|---|---|---|---|---|
| 0.083 | 1816.3 | 1633.9 | 2064.3 | 1853.5 |
| 0.5 | 1523.7 | 1409.9 | 1351.4 | 1418.0 |
| 2 | 1284.9 | 1041.7 | 1389.7 | 834.4 |
| 5 | 607.9 | 531.6 | 722.7 | 737.2 |
| 8 | 524.2 | 430.0 | 712.2 | 614.6 |
| 24 | 115.5 | 132.9 | 272.5 | 201.8 |
| 48 | 21.1 | 31.6 | 623 | 90.4 |
| 72 | 9.5 | 15.8 | 29.1 | 31.8 |

TABLE 50-continued

First pharmacokinetic study
(FVII select vs. FVII HA)-FVII concentrations (ng\ml).

| Time (hour) | FVII CTP*3 BATCH 46 HA | FVII CTP*3 BATCH 46 FVII S | FVII CTP*5 BATCH 5 HA | FVII CTP*5 BATCH 5 FVII S |
|---|---|---|---|---|
| 96 | BLQ | 5.8 | 7.0 | 16.9 |
| 120 | BLQ | BLQ | 8.5 | 13.4 |

TABLE 51

Second pharmacokinetic study (IV vs. SC)-FVII concentrations (ng\ml).

| Time (hour) | FVII CTP*3 BATCH 46 HA-IV | FVII CTP*5 BATCH 5 HA-IV | FVII CTP*3 BATCH 46 HA-SC | FVII CTP*5 BATCH 5 HA-SC |
|---|---|---|---|---|
| 0.083 | 6452.6 | 6153.3 | 5.0 | BLQ |
| 0.5 | 3930.7 | 3660.6 | 14.5 | 14.6 |
| 2 | 1992.3 | 2176.2 | 113.6 | 96.2 |
| 5 | 1598.9 | 2087.3 | 106.6 | 70.5 |
| 8 | 781.6 | 1075.6 | 188.9 | 129.7 |
| 24 | 268.5 | 627.2 | 155.0 | 239.2 |
| 48 | 51.9 | 143.3 | 43.0 | 88.6 |
| 72 | 8.8 | 39.0 | 7.0 | 36.7 |
| 96 | BLQ | 10.8 | BLQ | 10.4 |
| 120 | BLQ | 8.2 | BLQ | 8.7 |

TABLE 52

PK Analysis-first pharmacokinetic study (FVII S vs. HA).

| | FVII CTP*3 BATCH 46 HA | FVII CTP*3 BATCH 46 FVII S | FVII CTP*5 BATCH 5 HA | FVII CTP*5 BATCH 5 FVII S |
|---|---|---|---|---|
| half-life (0.083-8 hr) (hr) | 4.3 | 4.0 | 5.51 | 5.59 |
| half-life (8-72\96\120 hr) (hr) | 11.1 | 12.1 | 16.46 | 20.29 |
| half-life (8-72) (hr) | 11.1 | 13.4 | 13.62 | 15.64 |
| AUC(O-t) (obs area) (8-72/96/120 hr) | 14566.9 | 13686.4 | 21812.7 | 19307.9 |
| AUC (∞) area (8-72/96/120 hr) | 14718.2 | 13788.1 | 22013.9 | 19701 |
| Vd (area)/kg (ml/kg) (8-2/96/120 hr) | 271.1 | 316.1 | 269.7 | 371.5 |
| CL (area)/kg (ml/hr/kg) (8-72/96/120 hr) | 17.0 | 18.1 | 11.356 | 12.69 |

Figure 32:
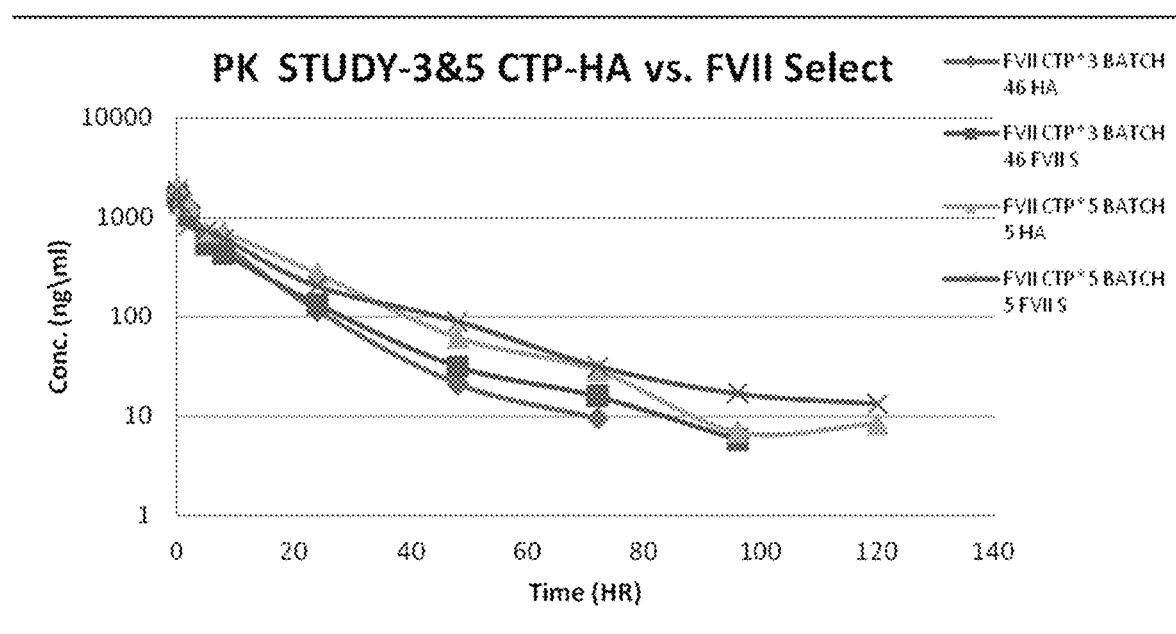
FIG. 32. Shows a comparative PK profile-FVII 3 & 5 CTP—from select and HA column purification (FVIIS vs. FVII HA).

The addition of five CTP elongated FVII half-life compared to 3 CTPs. Both forms of 5 CTP (i.e FVIIS and FVII HA) were detected at the long time points (96 and 120 hr), while FVII-3 CTP HA and FVIIS-3 CTP were detected until 72 hr and 96 hr, respectively. Based on this fact, the half-life of FVII-5 CTPs is longer than 3CTPs variants (see FIG. 32). Comparing half-life of all examined materials (3 and 5 CTPs) at the same time points (8-72 hr) showed that the half-life are similar, although 5 CTP are quite longer (FIG. 32).

TABLE 53

PK analysis-second pharmacokinetic study-(IV vs. SC).

| | FVII CTP*3 BATCH CTP*3 46 HA-IV | FVII CTP*5 BATCH CTP*5 5 HA-IV | FVII CTP*3 BATCH 46 HA-SC | FVII CTP*5 BATCH 5 HA-SC | Bioviability CTP*3 | Bioviability CTP*5 |
|---|---|---|---|---|---|---|
| half-life (0.083-8 hr) (hr) | 3.0 | 3.9 | −1.8 | −3.18 | | |
| half-life (8-72\96\120 hr) (hr) | 9.9 | 14.6 | 13.14 | 22.94 | | |
| half-life (8-72) (hr) | 9.9 | 13.0 | 13.14 | 29.47 | | |
| AUC(O-t) (obs area) (8-72/96/120 hr) | 28866.8 | 43761.0 | 6600 | 9822.7 | 22.9 | 22.4 |
| AUC (∞) area (8-72/96/120 hr) | 28993.0 | 43934.4 | 6733 | 10110.8 | 23.22 | 23.01 |
| Vd(area)/kg (ml/kg) (8-72/96/120 hr) | 246.4 | 240.5 | 1407.6 | 1636.8 | | |
| CL(area)/kg (ml/hr/kg) (8-72/96/120 hr) | 17.2 | 11.4 | 74.261 | 49.452 | | |

Figure 33:
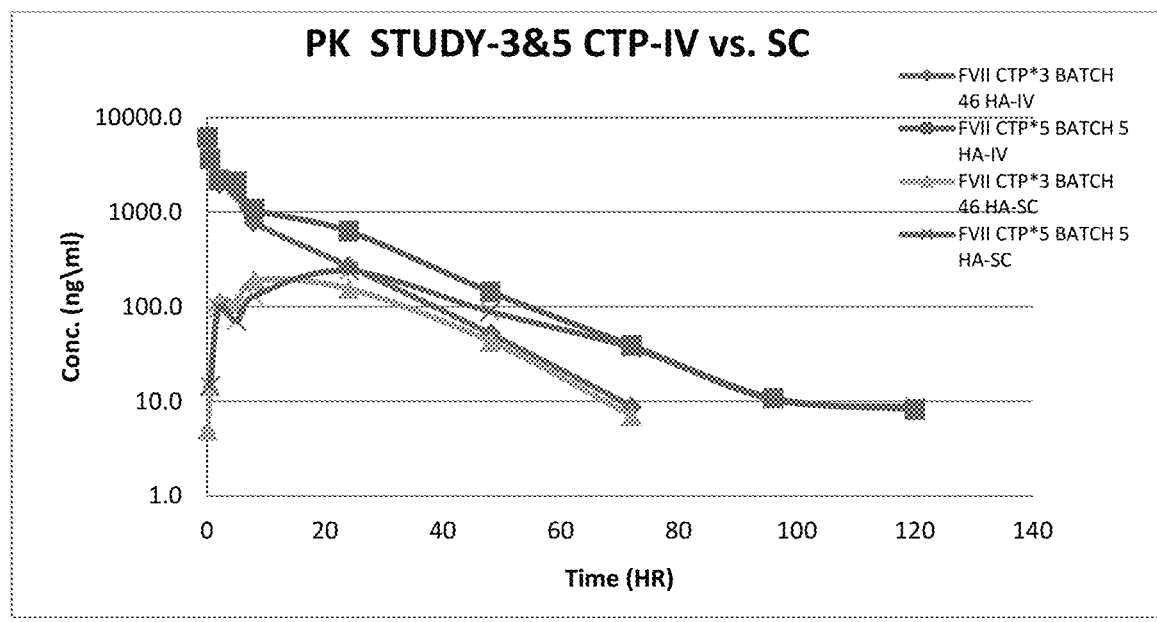
FIG. 33. Shows a comparative PK profile-FVII 3 & 5 CTP—The second study (IV vs. SC).

Again, as observed in the first study, the addition of 5 CTPs elongated FVII half-life as compared to adding 3 CTP, both in the initial and terminal half-life and in both administration ways (IV and SC, see FIG. 33). As expected, following SC administration, FVII was first detected in the blood at a later time point as compared to when it was administered IV.

In the above, two PK studies were summarized. The main purpose of the first study was to check the difference between FVII-3CTP and FVII-5 CTP after 2 different columns: FVII select and FVII HA. In our previous studies, harvest vs. purified proteins were checked and it was found that the difference between 3 and 5 CTP versions of FVII was greater when harvest was injected to the rats.

There was no significant difference between the results of FVII 3/5 CTP after both columns, hence it was decided to inject FVII HA 3/5 CTP in the second study (IV vs. SC).

Example 8: FVIIa-CTP$_3$ (MOD-5014) Survival Study in FVIII Deficient Mice Following Subcutaneous Injection Study Objective To evaluate the efficacy of NovoSeven®, MOD-5014 (FVIIA-CTP$_3$) and MOD-5019 (FVIIA-CTP$_5$) in a tail vein transection study, following subcutaneous administration.
FVIIa-CTP$_3$ (MOD-5014) and FVIIa-CTP$_5$ (MOD 5019)
Analytical Properties:
Protein Determination by A280

Theoretical extinction coefficient of NovoSeven® was calculated using ProtParam algorithm (http://web.expasy.org/protparam). The calculation is based on amino acid sequence. The calculated extinction coefficient for NovoSeven® is 1.406, and for MOD-5019 is 1.075 (values represent the absorbance of 1 g/L at 280 nm). Extinction coefficient of MOD-5014 was determined by amino acid analysis at Mscan. The extinction coefficients for MOD-5014 is 1.27.

Clotting Assay of FVIIa-STACLOT VIIa-rTF

FVIIa is derived from intra-chain cleavage of the single-chain FVII. Native tissue factor (TF) is a cofactor of FVIIa, upon binding to TF, FVII mediates the activation of Factor X to Xa, while itself is transformed to FVIIa. The soluble tissue factor is the extra cellular part of native tissue factor. It can no longer activate FVII by auto activation, but the FVIIa bound to tissue factor can activate FX to FXa.

The recombinant soluble tissue factor (rsTF) used in this assay is utilizing the FVIIa specificity to construct a FVIIa clotting test. Recombinant soluble tissue factor (rsTF), in the presence of FVIIa, calcium and phospholipids, produces coagulation of plasma without activating FVII to FVIIa.

The observed clotting time in this system has an inverse relationship with the FVIIa content in the tested sample, with no interference of FVII presence in the sample.

FVIIa activity was evaluated for reconstituted NovoSeven®, and for MOD-5014 and MOD-5019 prior to each study.

FVIIa specific activity (which is calculated as the activity/ml divided by protein concentration) was calculated based on A280 and is presented in Table 54. When comparing specific activity of the two molecules, which differ in molecular weight, compensation must be made in order to normalize the activity (i.e. because of the molecular weight difference, the number of active sites in 1 mg of NovoSeven® is 1.185 fold higher than in MOD-5014 and 1.307 fold higher than MOD-5019). Hence, calculation of the conversion factor is presented in the following formula:

$$\text{Normalized\_SA} = \frac{SA(FVIIa\text{-}CTP_3)}{MW.(\text{Native\_FVII})} \times MW(FVII\ CTP_3) =$$

$$\frac{SA(FVIIa\ CTP_3)}{45079.1 Da} \times 53419.50a = SA(FVIIa\text{-}CTP_3) * 1.185$$

TABLE 54

MOD-5014 Specific activity compared to NovoSeven ®

| Sample | Protein conc. By A280 (mg/ml) | Specific Activity (U/mg FVIIa) | Fold decrease from ® NovoSeven |
|---|---|---|---|
| ® NovoSeven | 0.93 | 52,487 | 1.0 |
| MOD-5014 batch 73 | 1.4 | 25,490 | 2.05 |
| MOD-5019 batch 9 | 3.0 | 11,698 | 4.48 |

Study Outline

The most significant measurement is the ability of the protein to induce a clot in vivo, after a traumatic event. In order to evaluate the ability of MOD-5014 to stop bleeding, the same FVIII deficient mice model was employed for a bleeding challenge.

FVIII deficient mice were administrated with a single subcutaneous injection of MOD-5014, MOD-5019 or NovoSeven® Group A and B were dosed with NovoSeven® and MOD-5014 respectively, in equivalent amounts as FVIIa activity. Group C was dosed with MOD-5019 in equivalent amount FVIIa protein as MOD-5014, in order to evaluate the critical factor (activity or amount of protein). The administrated doses were 4.2 mg/kg of NovoSeven®, and 8.6 mg/kg of MOD-5014 and MOD-5019. The tail vein was transected 2.7 cm from tail tip 12 hours post administration, and mice survival was recorded for 24 hours.

TABLE 55

Group designation

| Group | Injection date | Test Article | Administered Dose mg FVII/Kg | Administered Dose mU/Kg | Injected Volume (µl) | No. of mice per group | T Bleeding time, hours post dosing |
|---|---|---|---|---|---|---|---|
| A | 13 Jan. 2013 | ® NovoSeven | 4.23 | 221,876 | 100 | 10 | 12 |
| B | 15 Jan. 2013 | MOD-5014, batch 73 | 8.59 | 218,750 | 160 | 10 | 17 |
| C | 27 Jan. 2013 | MOD-5019, batch 9 | 8.59 | 100,496 | 160 | 10 | 12 |

Results

Figure 34:
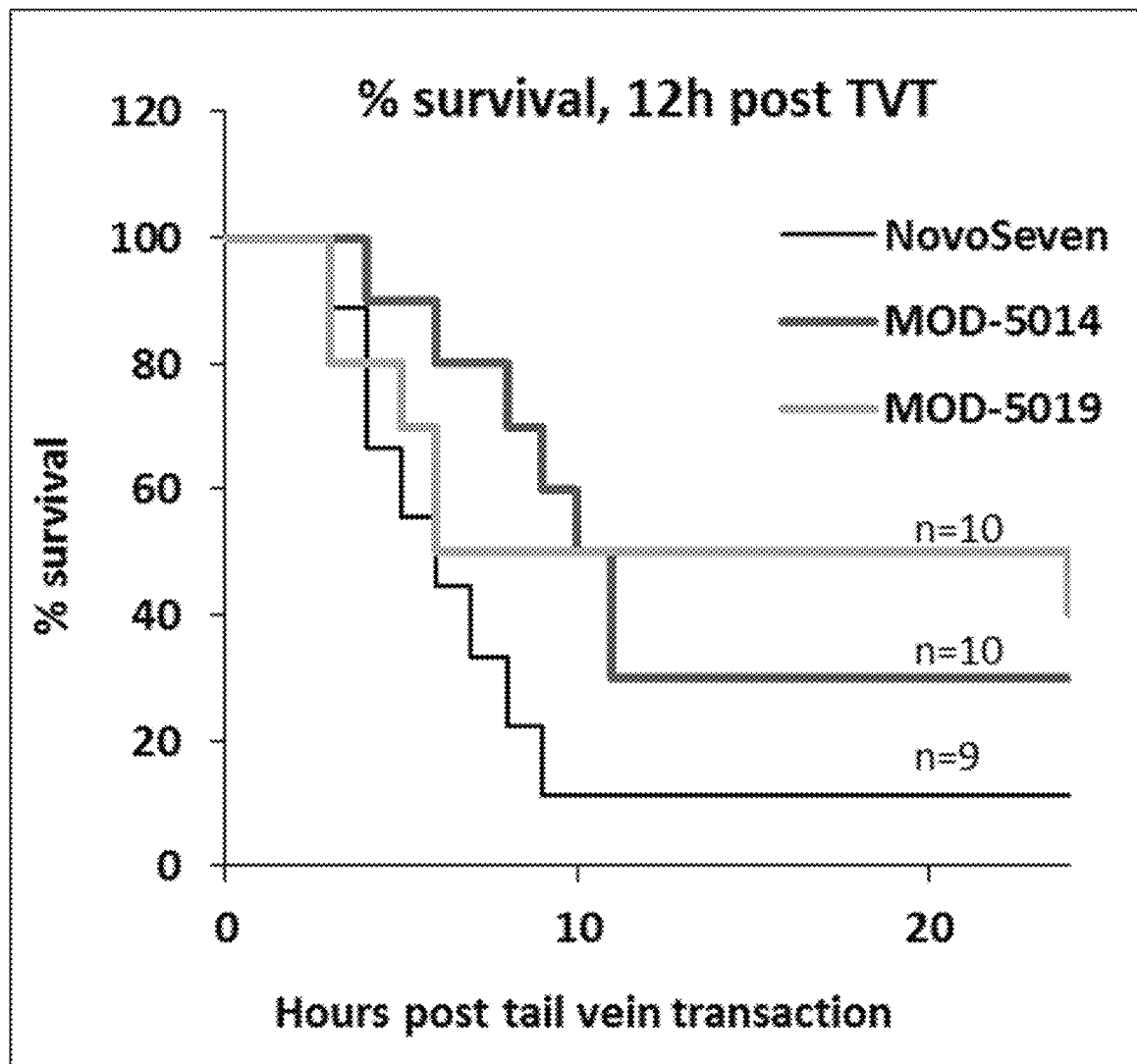
FIG. 34. Shows hemophilic mice survival curves post tail vain transection (TVT) following SC administration. TVT was performed 12 hours post administration. Mice Survival was observed for 24 hours after TVT and recorded every single hour for the first 12 hours, and after 24 hours.

The experiment data is summarized in Table 56 and in FIG. 34.

TABLE 56

TVT study results

| Time post TVT (h) | No. of surviving mice | | | % survival | | |
|---|---|---|---|---|---|---|
| | NovoSeven® | MOD-5014 | MOD-5019 | NovoSeven® | MOD-5014 | MOD-5019 |
| 0 | 9 | 10 | 10 | 100 | 100 | 100 |
| 1 | 9 | 10 | 10 | 100 | 100 | 100 |
| 2 | 9 | 10 | 10 | 100 | 100 | 100 |
| 3 | 8 | 10 | 8 | 89 | 100 | 80 |
| 4 | 6 | 9 | 8 | 67 | 90 | 80 |
| 5 | 5 | 9 | 7 | 56 | 90 | 70 |
| 6 | 4 | 8 | 5 | 44 | 80 | 50 |
| 7 | 3 | 8 | 5 | 33 | 80 | 50 |
| 8 | 2 | 7 | 5 | 22 | 70 | 50 |
| 9 | 1 | 6 | 5 | 11 | 60 | 50 |
| 10 | 1 | 5 | 5 | 11 | 50 | 50 |
| 11 | 1 | 3 | 5 | 11 | 30 | 50 |
| 12 | 1 | 3 | 5 | 11 | 30 | 50 |
| 24 | 1 | 3 | 4 | 11 | 30 | 40 |

24 hours post TVT, only 11% of NovoSeven® injected mice have survived. 30% of MOD-5014 and 40% of MOD-5019 have survived to this time point. Surprisingly, subcutaneously injected MOD-5014 and MOD-5019 shows improved mice survival in comparison to NovoSeven®.

Factor VIIa, like other coagulation factors, is normally injected intravenously, in order to be directly available in the blood stream. However, the present invention shows that the compositions provided herein are surprisingly more effectively absorbed into the bloodstream after SC administration. To be able to administer FVIIa subcutaneously serves as an advantage as it can be used for prophylactic applications. Subcutaneous injections are also much easier for patients to self-inject, and are advantage when the patients are very young and their veins are small and difficult to find.

Hence, the subcutaneous application can be used for prophylactic treatment.

Example 9: Comparative PK-PD Study of Recombinant MOD-5014 Vs. NovoSeven® Following Subcutaneous Administration in SD Rats Study Objectives To determine the pharmacokinetic and pharmacodynamic parameters of MOD-5014 versus commercial rFVIIa in SD rats following a single SC administration.

To compare two independent experiments (05010 & 05034) containing MOD-5014 products originated from two different clones (clone no. 28 vs. 61) by their pharmacokinetics parameters.

Experimental Methods

Animals 24 males SD rats arrived from Harlan Laboratories Israel, Ltd, at least 4 days before the injections begin. The animals were healthy young adults, at ~200 gr at study initiation. The body weight variation of animals at the time of treatment initiation should not exceed ±20% of the mean weight of each sex. The health status of the animals used in this study is examined on arrival. Only animals in good health are acclimatized to laboratory conditions and are used in the study.

Clotting Assay of FVIIa-STACLOT VIIa-Rtf

The recombinant soluble tissue factor (rsTF) used in this assay is utilizing the FVIIa specificity to construct a FVIIa clotting test. rsTF, In the presence of FVIIa, calcium and phospholipids produce coagulation of plasma, without activating FVII to FVIIa.

The observed clotting time in this system has an inverse relationship with the FVIIa content in the tested sample, with no interference of FVII presence in the sample.

FVIIa activity was evaluated for both NovoSeven® following reconstitution and MOD-5014 prior to each study. FVIIa specific activity was calculated based on A280. When comparing specific activity of the two molecules, which differ in MW, compensation must be made in order to normalize the activity (i.e. because of the molecular weight difference, the number of active sites in 1 mg of NovoSeven® is 1.185 fold higher than in MOD-5014).

PK Solver Software

The pharmacokinetic parameters were calculated using PK solver software. The IV administration curve analyzed as two compartmental CA bolus, and the SC administration as NCA Extravascular-Log linear trapezoidal analysis. Half-life, AUC, clearance and volume distribution specifications were calculated and the output parameters were studied in comparison between groups of experiments.

Experimental Materials

Experiment No. 05010:
  A. NovoSeven® RT: (Lot #AU61553 prepared on 31.7.12*) FVIIa concentration by A280: 0.86 mg/ml. FVIIa Staclot activity assay: 56,867 U/mg. Injected dose: 946 µg/kg. *Pool of NovoSeven® aliquots, all from the same Lot no.
  B. Clone 28: MOD-5014 RS12-001: 0.77 mg/ml** based on A280. FVIIa Staclot activity assay: 34,162 U/mg. Injected dose: 850 µg FVIIa/kg.

Experiment No. 05034:
  A. NovoSeven® RT. (Lot #AU61347 prepared on 1.1.13) FVIIa concentration by A280: 0.82 mg/ml, diluted to 0.4 mg/ml with sterile NS buffer. FVIIa Staclot activity assay: 55,688 U/mg. Injected dose: 360 µg/kg and 20,047.7 U/kg.
  B. Clone 61: MOD-5014 Batch 75: 1.9 mg/ml** based on A280, diluted to 0.89 mg/ml with formulation buffer.

Injected dose: 20,047.7 U/kg. FVIIa clotting activity: 25,002* U/mg based on FVIIa Staclot activity assay.

C. Clone 61: MOD-5014 Batch 81A: 2.36 mg/ml based on A280 (filtered on the morning of study day and re-measured at 280 nm), diluted to 0.4 mg/ml with formulation buffer. Injected dose: 360 μg FVIIa/kg. FVIIa clotting activity: 24943 U/mg on FVIIa Staclot activity assay.

D. Clone 61: MOD-5014 Batch 81A: 2.36 mg/ml based on A280, diluted to 0.89 mg/ml with formulation buffer. Injected dose: 20,047.7 U/kg. FVIIa clotting activity: 24,943 U/mg on FVIIa Staclot activity assay.

Study Outlines

Experiment No. 05010

MOD-5014 and NovoSeven® were administered in a single intravenous or subcutaneous injection to SD Rats in a dose of 0.9 mg/kg body weight. Blood samples were drawn from sinus orbital eye from 3 rats alternately at 0.5, 4, 8, 12, 24, 34, 48 and 58 hours post dosing. Citrated plasma (0.32%) was prepared immediately after sampling and stored at −20° C. until analysis. The study was performed at "Science in Action," Nes-Ziona. FVIIa clotting activity level was evaluated and detailed PK analysis was performed at Prolor-Biotech.

TABLE 57

Study design 05010

| Treated Groups | Test Article | No. of animals/ group | No. of animals/ group/ Time point | Dose Route | Gender | Dose Level (μg/kg) | Injected Vol. (μl) | Time-Points (hours post-dose) |
|---|---|---|---|---|---|---|---|---|
| A | rFVIIA (NovoSeven®) | 6 | 3 | IV | M | 946 | 220 | 0, 0.5, 4, 8, 12, 24, 34, 48, 58 |
| B | rFVIIa RS12-001 (clone 28) | 6 | 3 | IV | M | 850 | 220 | 0, 0.5, 4, 8, 12, 24, 34, 48, 58 |
| C | rFVIIA (NovoSeven®) | 6 | 3 | SC | M | 946 | 220 | 0, 0.5, 4, 8, 12, 24, 34, 48, 58 |
| D | rFVIIA RS12-001 (clone 28) | 6 | 3 | SC | M | 850 | 220 | 0, 0.5, 4, 8, 12, 24, 34, 48, 58 |

Experiment No. 05034

MOD-5014 and NovoSeven® were administered in a single subcutaneous injection to SD Rats in a dose of 0.9 mg/kg body weight. Blood samples were drawn from sinus orbital ee from 3 rats alternately at 0.5, 2, 4, 6, 8, 12, 24, 34, 48 and 72 hours post dosing. Citrated plasma (0.32%) was prepared immediately after sampling and stored at −20° C. until analysis. The study was performed at "Science in Action," Nes-Ziona.

FVIIa clotting activity level was evaluated and detailed PK analysis was performed at Prolor-Biotech.

TABLE 58

Study design 05034

| Treated. Groups | Test Article | No. of animals/ group/ Time-point *** | Dose Route | Gender | Dose Level Per Animal (μg/kg) | Dose Level Per Animal (U/kg) | Injected Vol. (μl) | Time-Points (hours post-dose) |
|---|---|---|---|---|---|---|---|---|
| A | FVIIa (NovoSeven®) | 3 | SC | M | 360 | 20047.7 | 207 | 0, 0.5, 2, 4, 6, 8, 12, 24, 34, 48, 72 |
| B | FVIIA 75 (clone 61) | 3 | SC | M | 801.84 | 20047.7 | 207 | 0, 0.5, 2, 4, 6, 8, 12, 24, 34, 48, 72 |
| C | FVIIa 81A (clone 61) | 3 | SC | M | 360 | 8979.48 | 207 | 0, 0.5, 2, 4, 6, 8, 12, 24, 34, 48, 72 |
| D | FVIIa 81A (clone 61) | 3 | SC | M | 803.74 | 20047.7 | 207 | 0, 0.5, 2, 4, 6, 8, 12, 24, 34, 48, 72 |

Results

FVIIa activity in blood samples was quantitated using STACLOT VIIa-rTF kit (Stago). Pharmacokinetic profile was calculated for each protein and is the mean of 3 animals at each time point.

Experiment No. 05010

Figure 35A:
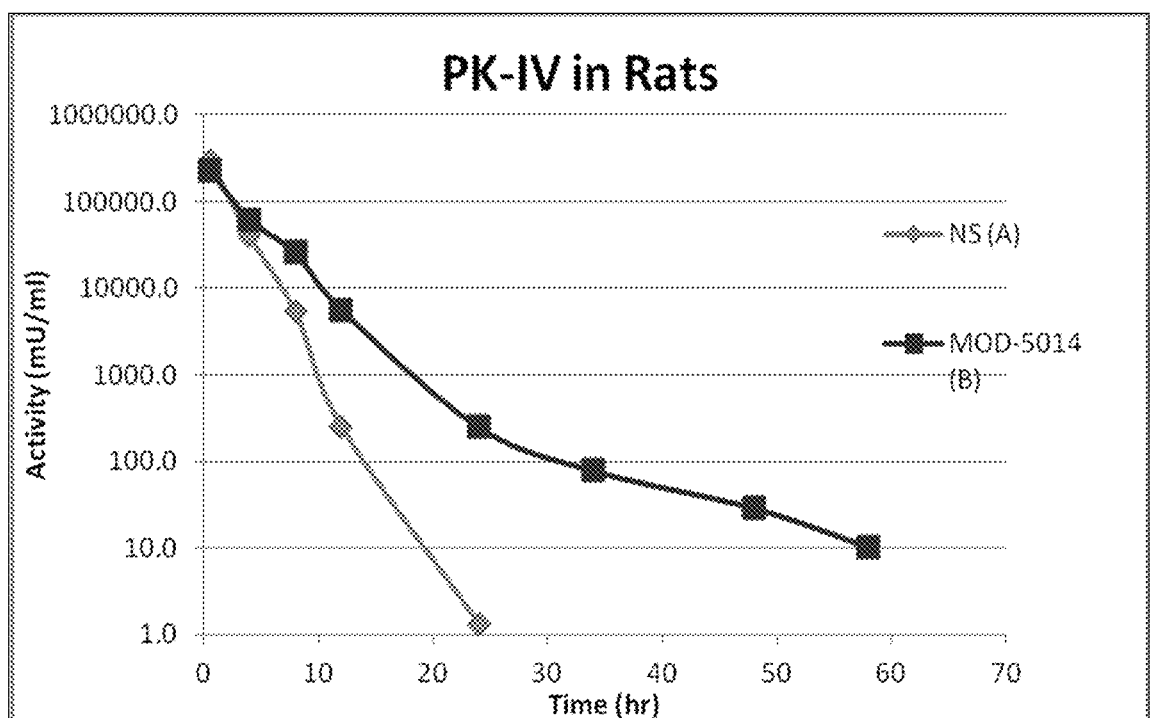
FIG. 35A. Shows the PK profile of MOD-5014 vs. NovoSeven® following IV administration.
Figure 35B:
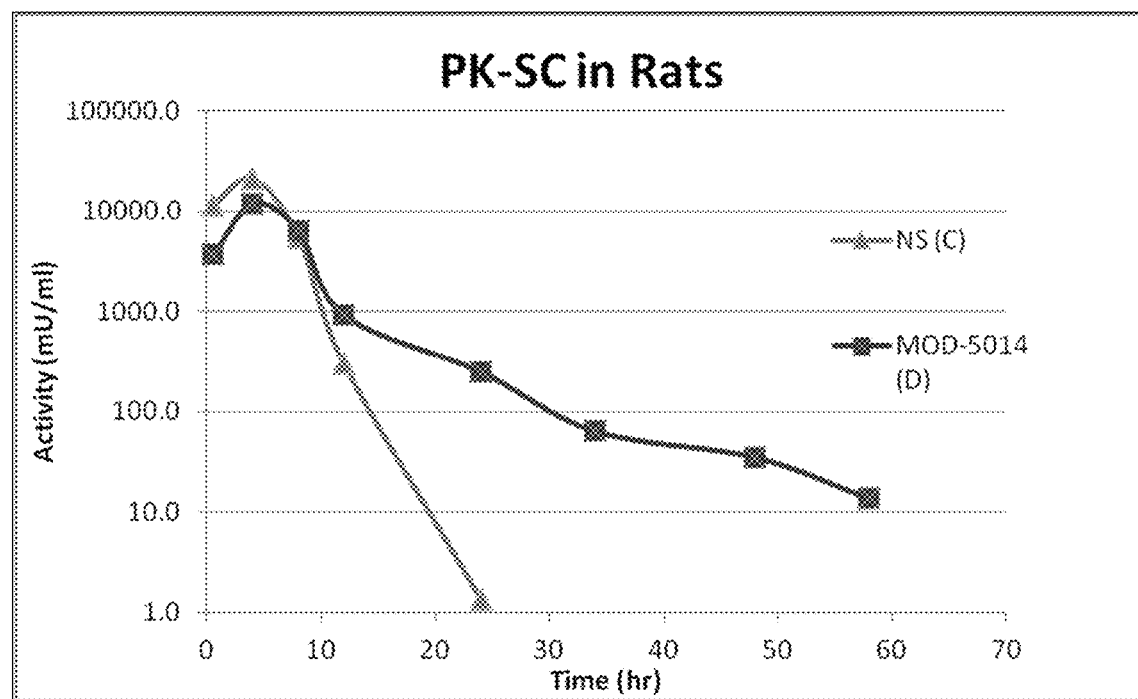
FIG. 35B. Shows the PK profile of MOD-5014 vs. NovoSeven® following SC administration.

FIG. 35 presents the PK profile of FVIIa following IV and SC administration of either NovoSeven® or MOD-5014. Summary of FVIIa activity values for each time point is presented in Table 59. V and SC administration have different PK pattern as presented in FIG. 35 similar to previous results. The Cmax following IV injection is higher than that obtained after SC injection, due to the presence of the drug immediately following administration in the blood (measured at 0.5 hr, Table 59 and Table 60). However, after SC administration drug molecules transfer to intracellular matrix and tissues, thus Cmax can be measured only after 2 hr from injection. The total recovery of the drug after SC administration is lower than Cmax value after IV injection. 8 hr after injection. Novoseven® manifested an equal PK pattern when injected by either IV or SC, (FIG. 35). Moreover, clotting activity for the NovoSeven®-treated mice was undetectable at time points later than 12 hours, while MOD-5014-treated mice continued to retain measurable activity at 58 hours post dosing (Table 59 and FIG. 35).

TABLE 59

FVIIa clotting activity of MOD-5014 vs. NovoSeven® following IV or SC administration

| Time | NovoSeven IV (A) | | MOD-5014 IV (B) | | NovoSeven SC (C) | | MOD-5014 SC (D) | |
|---|---|---|---|---|---|---|---|---|
| (hr) | mU/ml | % CV | mU/ml | % CV | mU/ml | % CV | mU/ml | % CV |
| 0.5 | 304651.7 | 18.7 | 232818.3 | 5.0 | 11491.7 | 2.4 | 3691.7 | 19.0 |
| 4 | 40068.3 | 7.8 | 62085.0 | 9.5 | 21385.0 | 22.6 | 12018.3 | 15.8 |
| 8 | 5276.7 | 2.5 | 25931.7 | 6.1 | 5525.0 | 32.5 | 6445.0 | 2.2 |
| 12 | 255.0 | 13.8 | 5633.3 | 9.3 | 297.7 | 41.4 | 924.7 | 24.1 |
| 24 | 1.3 | 7.1 | 251.3 | 11.8 | 1.3 | 89.2 | 249.3 | 60.3 |
| 34 | 0.0 | | 78.3 | 4.5 | 0.0 | | 63.7 | 85.5 |
| 48 | | | 29.0 | 9.9 | 0.0 | | 35.0 | 47.2 |
| 58 | | | 10.3 | 4.6 | 0.0 | | 13.7 | 33.5 |

After background reduction: 15 mU/ml.

TABLE 60

PK parameters of MOD-5014 vs. NovoSeven following IV or SC administration

A. IV

| PK Parameters | Novoseven RT (A) | MOD-5014 (RS 12-001) (B) |
|---|---|---|
| Half-life-α (0.5-4 hr) | 0.24 | 1.04 |
| Half-life-β (4-58 hr) | 1.31 | 3.17 |
| AUC o-inf mU/ml * h | 702467.95 | 820778.67 |
| Vss [U/Kg/(mU/ml)] | 0.13 | 0.13 |
| CL [(U/Kg)/(mU/ml)/h] | 0.08 | 0.04 |
| MRT (hr) | 1.74 | 3.62 |

TABLE 60-continued

PK parameters of MOD-5014 vs. NovoSeven following IV or SC administration

B. SC

| PK Parameters | Novoseven RT (B) | MOD-5014 (RS 12-001) (C) |
|---|---|---|
| Half-Life (hr) | 1.40 | 7.78 |
| Cmax (mU/ml) | 21385.00 | 12018.33 |
| AUC 0-inf (mU/ml * h) | 115099.72 | 84158.87 |
| MRT 0-inf (hr) | 4.32 | 7.04 |
| Vz/F (U/Kg)/(mU/ml) | 0.95 | 3.88 |
| Cl/F (U/Kg)/(mU/ml)/h | 0.47 | 0.35 |

Experiment No. 05034

FIG. 36 presents the PK profile of FVII a following SC administration of either NovoSeven® or MOD-5017. Two different batches of clone no. 61 (#75 and #81) were examined in the same concentration or the same activity units, compared to NovoSeven®. Summary of FVIIa activity values for each time point is presented in Table 61.

The results indicate a similar PK pattern after SC administration corresponding to previous experiments. Moreover, clotting activity for the NovoSeven® treated mice was undetectable at time points later than 12 hours, while MOD-5014 treated mice continued to retain measurable activity at 24 hours post dosing (Table 61 and FIG. 36, and after background reduction: 56 mU/ml (8, 12 hr) or 32 mU/ml (0.5, 2, 6, 14 hr)).

Clone no. 61 batch #81 (D) Cmax (1,301 mU/m) was lower than the Cmax values of clone no. 61 batch #75 (B) and NovoSeven® (A) (3,521 mU/ml and 5,908 mU/ml respectively, although they were all injected by the same unit activity (Table 61). However, batch #75 (B) and #81 (D) have the same activity units (559 mU/ml and 478 mU/ml respectively) measured 8 hr after injection (Table 61 and Table 62; and after background reduction: 56 mU/ml (8, 12 hr) or 32 mU/ml (0.5, 2, 6, 14 hr)).

TABLE 61

FVIIa clotting activity of MOD-5014 (Clone 61 #75, #81) vs. NovoSeven ® following single SC administration.

| Time (hr) | NovoSeven ® (A) mU/ml | % CV | MOD-5014 Clone 61 Batch 75 (B)-equal U/kg mU/ml | % CV | MOD-5014 Clone 61 Batch 81A (C)-equal conc. FVIIa µg/kg mU/ml | % CV | MOD-5014 Clone 61 Batch 81A (D)-equal U/kg mU/ml | % CV |
|---|---|---|---|---|---|---|---|---|
| 0.5 | 3271.3 | 46.5 | 350.3 | 26.6 | 101.3 | 24.1 | 208.7 | 51.2 |
| 2 | 5908.0 | 18.1 | 3521.3 | 70.9 | 1294.7 | 7.0 | 1301.3 | 31.6 |
| 6 | 1411.7 | 23.6 | 1349.7 | 45.6 | 425.3 | 27.6 | 663.0 | 13.4 |
| 8 | 1029.0 | 12.4 | 559.3 | 52.7 | 152.7 | 19.5 | 478.0 | 25.4 |
| 12 | 121.3 | 9.9 | 563.0 | 17.4 | 148.7 | 36.3 | 712.7 | 16.2 |
| 24 | 1.0 | 25.0 | 117.0 | 41.9 | 21.3 | 36.4 | 99.0 | 36.7 |

After background reduction: 56 mU/ml (8.12 hr) or 32 mU/ml (0.5, 2, 6, 14 hr).

TABLE 62

PK parameters of MOD-5014 (Clone 61 #75, #81) vs. NovoSeven ® following single SC administration.

| PK Parameters | NovaSeven ® RT (A) | MOD-5014 Clone 61 Batch 75 (B)- equal U/kg | MOD-5014 Clone 61 Batch 81A (C)- equal conc. FVIIa µg/kg | MOD-5014 Clone 61 Batch 81A (D)- equal U/kg |
|---|---|---|---|---|
| Half-Life (hr) | 1.67 | 5.70 | 4.62 | 6.41 |
| Cmax (mU/ml) | 5908.00 | 3521.33 | 1294.67 | 1301.33 |
| AUC 0-inf (mU/ml * h) | 24688.18 | 20456.96 | 6260.23 | 13098.16 |
| MRT 0-inf (hr) | 3.73 | 7.86 | 6.40 | 10.59 |
| Vz/F (U/Kg)/ (mU/ml) | 1.96 | 8.06 | 9.55 | 14.15 |
| Cl/F (U/Kg)/ (mU/ml)/h | 0.81 | 0.98 | 1.43 | 1.53 |

This report summarized two PK studies; 05010 & 05034. We aimed to provide specific insight on the impact of CTP fusion to FVII on protein half-life and clearance in subcutaneous administration and address the paradigm of its specific activity following this modification. In these studies, SD rats were administered with a single SC injection of MOD-5014 originated from two clones, and two different batches, compared to recombinant commercial FVIIa (NovoSeven®). The components were injected at similar FVIIa concentration (µg/Kg) or at the same activity level (U/Kg) and the PK activity based analysis was performed.

The purpose of the first study was to verify the different PK parameters after IV and SC administration. Based on this study we can conclude that there is a difference between the PK pattern measured after IV or SC administration. A $t^{1/2}$ of 7.78 hr measured after MOD-5014 SC injection, and only 4.2 hr after IV injection. AUC values were the same Table 60.

The second study however, focused on the differences between two batches of MOD-5014 clone no. 61, which were injected by the same FVIIa concentration or at an equal activity unit, compared to NovoSeven®. In this study we showed that clone 61 batch #75 manifested better PK parameters than batch #81. Batch #81, which was injected by the same unit activity level, had lower Cmax from an unknown reason. Moreover, the same Cmax was measured when injecting clone 61 batch #81 in two different doses (by FVIIa concentration or by unit activity), instead of 2.5 fold between the two activity values. Following analysis of both studies together, we can conclude that clone 28 manifested a prolonged $t^{1/2}$ parameter that clone 61 #75 (the better batch) after SC injection (7.78 hr and 5.7 hr respectively. Table 62). We can also conclude that dissimilar time point samples create different PK pattern, which lead to variation in the PK curves. The patterns of the curves can teach us more about the drug behavior in the blood. Therefore, we decided to determine the time points similar to those detected by Baxter (0, 0.5, 2, 6, 8, 12, 24, 34, 48, 72 hr). Moreover, the FVIIa concentration in 05010 experiment was too high, and was revised in the following SC experiment (05034). For future PK studies, we decided to inject the component at 360 µg FVIIa/kg for a dose.

Example 10: Warfarin Treated Rats as a Model for Evaluating Factor VIIa In Vivo

Materials & Methods

PT Assessment: SD rats were given orally 10 mg/Kg of Warfarin and at a designated time point plasma was collected and prothrombin time (PT) was measured using a standard procedure. In order to assess the long term hemostatic effect Placebo. NovoSeven or MOD-5014 were injected to the Warfarin treated animals and PT was measured.

Tail Clip Challenge: Warfarin treated animals were injected with Placebo, NovoSeven or MOD-5014 at designated time points the animals were challenged by complete cut of the tail tip (0.5 cm from the tip) and bleeding intensity was measured in gr for 30 min post transection.

Results

Warfarin Administration to SD-Rats Results in a Prolongation of PT and aPTT.

Figure 37:
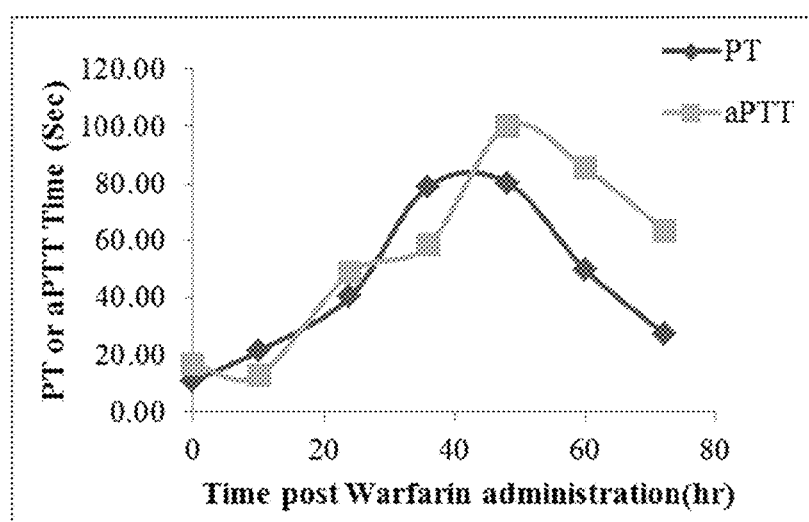
FIG. 37. Shows that warfarin increases PT and aPTT values. SD-rats received 10 mg/Kg warfarin per-os, and blood samples were taken at the designated time point. Plasma was prepared and PT and aPTT values were determined.

Warfarin prevent the reduction of vitamin K, and consequently decreases vitamin K dependent coagulation factors concentration in the blood. Male SD rats received oral treatment of warfarin. The reduction of Vitamin K dependent coagulation factors was accompanied by prolongation of PT and aPTT. Results are presented in FIG. 37.

Due to coagulation-factors wash out from the blood, PT and aPTT values increase gradually in the first 48 hours following warfarin administration. The effect decreases after that.

Warfarin Effect can be Restored by Acute IV Treatment with NovoSeven or MOD-5014.

Figure 38:
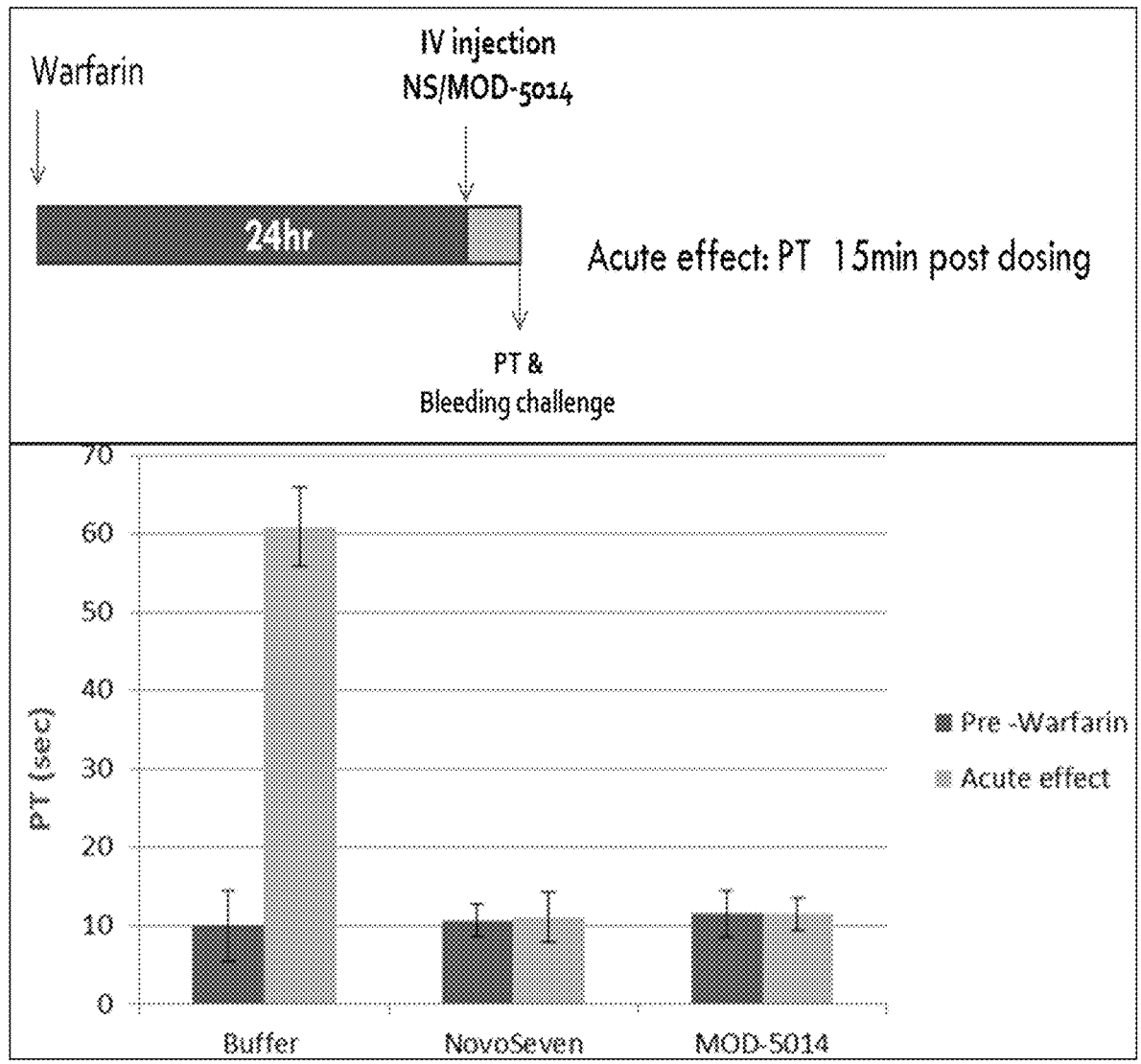
FIG. 38. Acute effect of IV injection of MOD-5014 and NovoSeven on Warfarin treated rats.

SD-rats received a pre-treatment of Warfarin. 24 hours later, MOD-5014, NovoSeven or buffer were injected intravenous blood samples were drawn 15 minutes post injection. 15 min post injection, MOD-5014 as well as NovoSeven successfully restored PT values to normal (FIG. 38).

The Effect of Increasing Dose of MOD-5014 and NovoSeven on PT Values in Warfarin Treated Rats.

Figure 39:
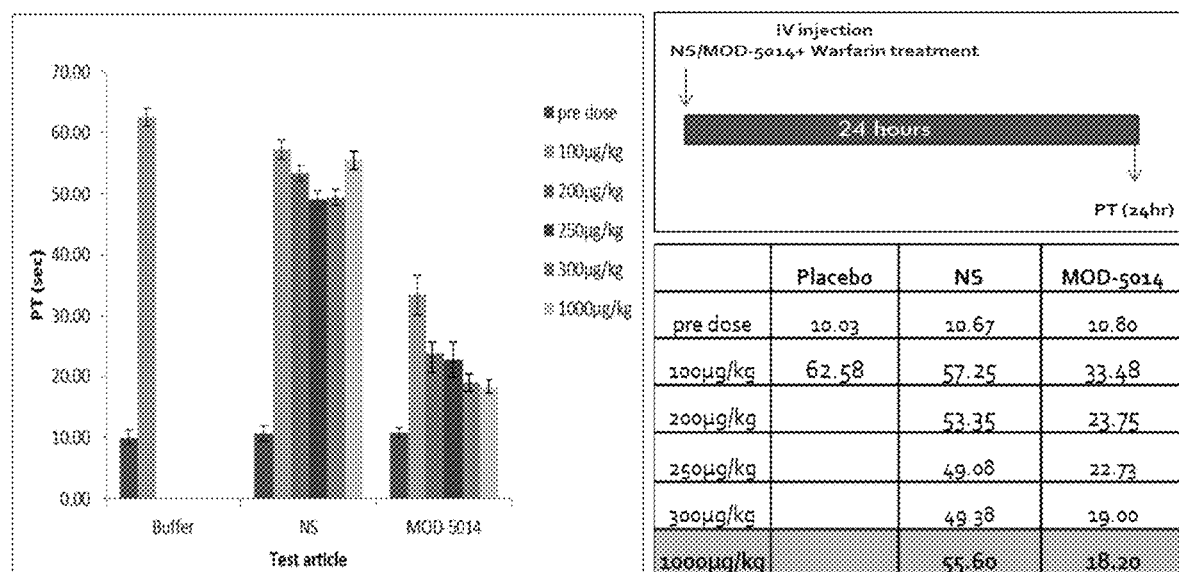
FIG. 39. Shows the response of Warfarin treated rats to a wide range of MOD-5014 and NovoSeven doses, 24 hours post injection.

SD-rats were treated with 10 mg/Kg warfarin in parallel to 100-1000 μg/Kg MOD-5014 or NovoSeven IV injection. 24 hours post treatment, PT was determined in plasma samples. NovoSeven injected 24 hours before PT determination, did not have any significant effect on PT values in all the doses tested. In contrast, MOD-5014 shows a dose-response behavior 24 hours after administration (FIG. 39).

Figure 40:
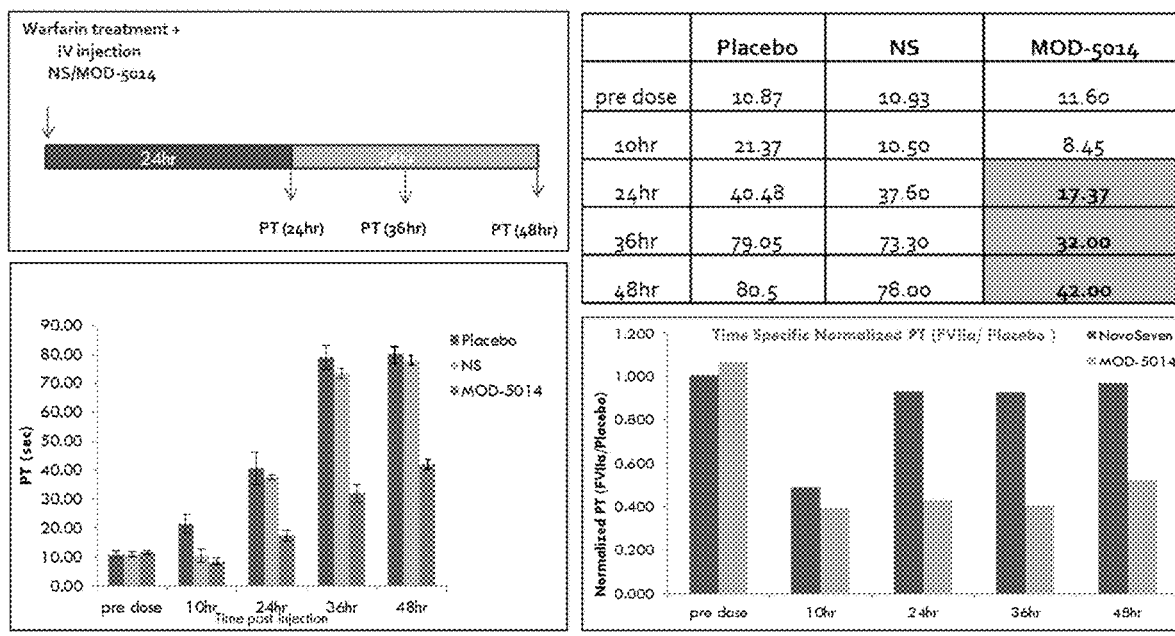
FIG. 40. Shows that MOD-5014 restored PT values to normal up to 48 hours post dosing, while the effect of NovoSeven no longer exists after 24 hours.

SD-rats were treated with 10 mg/Kg warfarin in parallel to 1000 μg/Kg MOD-5014 or NovoSeven IV injection. PT was determined in plasma samples 10, 24, 36 and 48 hours post treatment. MOD-5014 restored PT values to normal up to 48 hours post dosing, while the effect of NovoSeven no longer exists after 24 hours (FIG. 40).

MOD-5014's Long Lasting Effect can be Demonstrated by Tail Clip Assay in Warfarin Injected Rats SD-rats were treated with Warfarin 24 hours before tail clip. Rats were anesthetized and placed on a warm pad, the tail tip was placed in 37° C. saline and a complete amputation of the tail was performed 0.5 cm from tail tip. Blood was collected for 30 minutes and blood loss was determined by weight.

Figure 41:
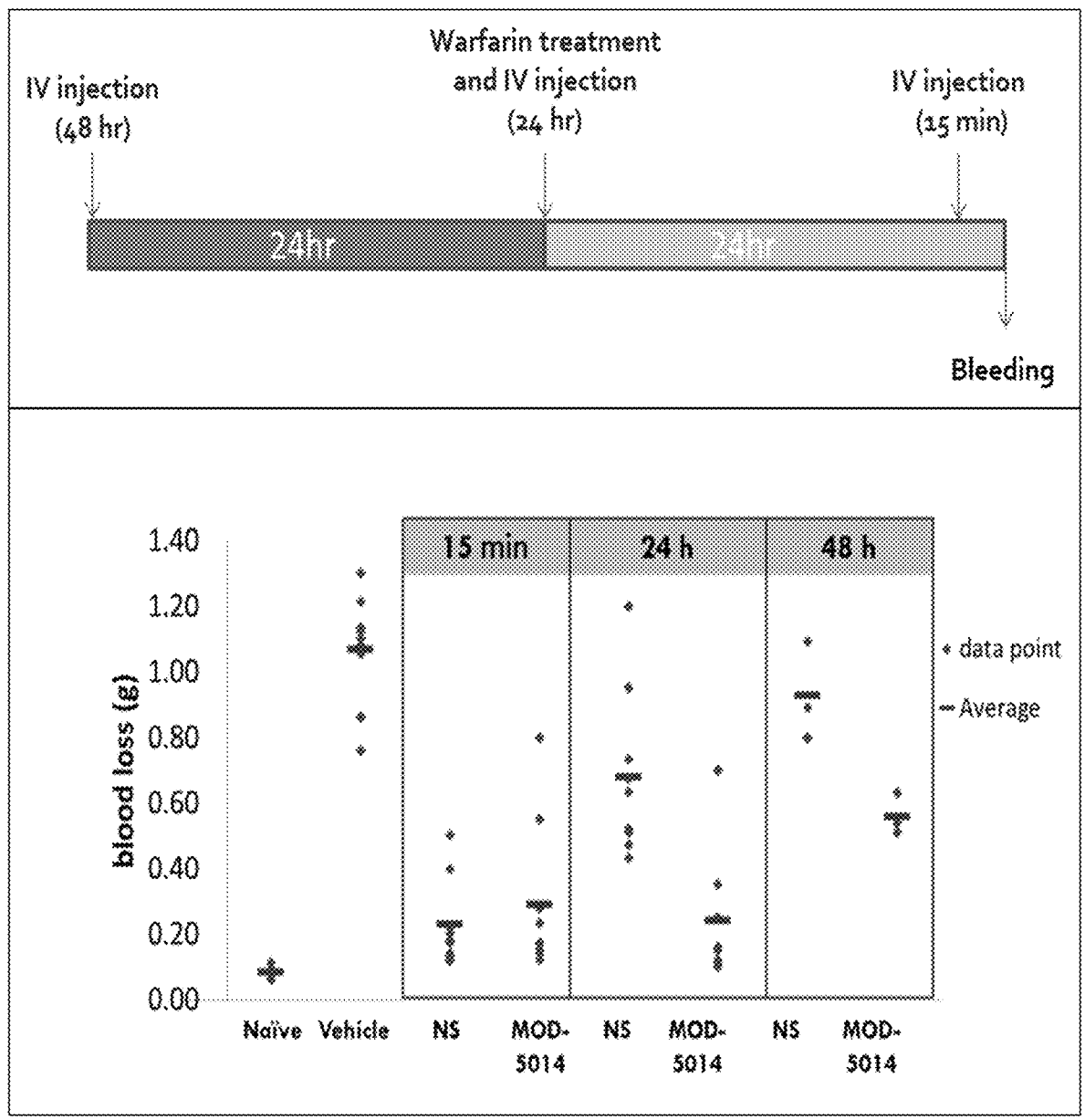
FIG. 41. Shows IV injection of MOD-5014 reduce bleeding time in warfarin treated rats as compared to NovoSeven 24 and 48 hours post injection.

Vehicle or 500 μg/Kg MOD-5014 or NovoSeven was administered 15 min, 24 or 48 hours before tail clip. Results are presented in FIG. 41. Rats treated with warfarin lost 5 fold more blood than naïve rats. 15 min post injection, tail clip of MOD-5014 and NovoSeven treated rats resulted in reduced bleeding which is comparable to naïve rats. The effect of MOD-5014 is completely preserved 24 hours post injection, and partially preserved after 48 hours.

Sub-Cutaneous Injection of MOD-5014 is Also Demonstrating a Long Lasting Effect.

SD-rats were treated with 10 mg/Kg warfarin in parallel to 2000 μg/Kg MOD-5014 or NovoSeven SC injection. PT was determined in plasma samples 10, 24, 36 and 48 hours post treatment.

Figure 42:
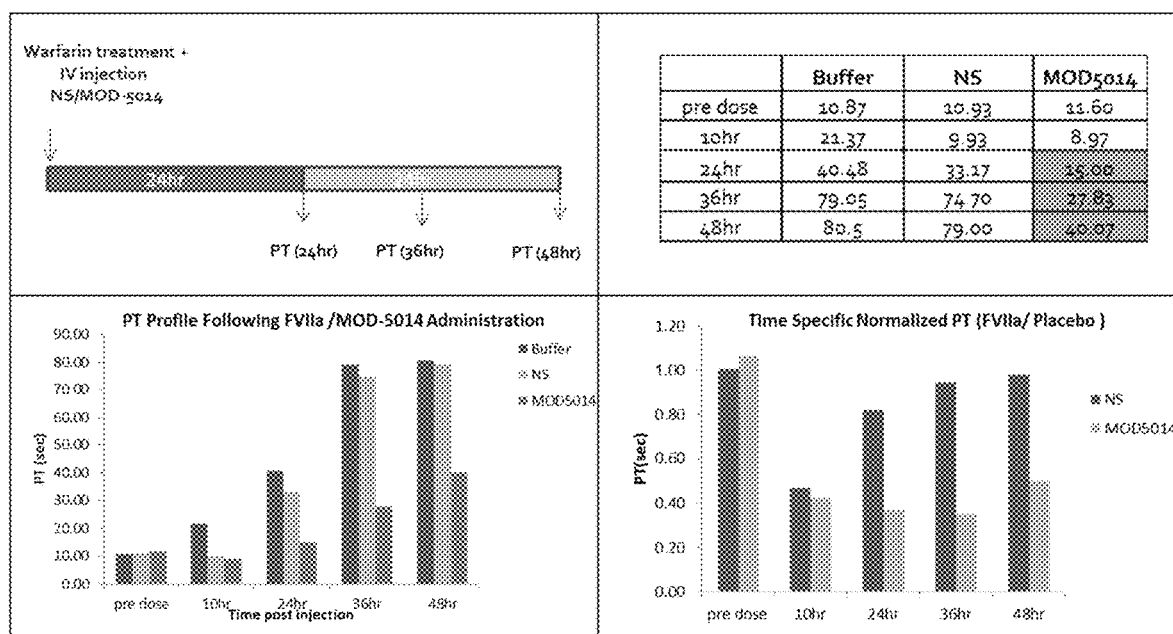
FIG. 42. Shows that MOD-5014 is able to restore PT values to normal up to 48 hours post dosing, while the effect of NovoSeven no longer exists after 24 hours FIG. 43. Shows superiority over NovoSeven by keeping the blood loss at low level for 48 hours after administration.

MOD-5014 is able to restore PT values to normal up to 48 hours post dosing, while the effect of NovoSeven no longer exists after 24 hours (FIG. 42).

SC Injection of MOD-5014 Reduces Blood Loss for at 48 Hours.

SD-rats were treated with Warfarin 24 hours before tail clip. Rats were anesthetized and placed on a warm pad, the tail tip was placed in 37° C. saline and a complete amputation of the tail was performed 0.5 cm from tail tip. Blood was collected for 30 minutes and blood loss was determined by weight.

Figure 43:
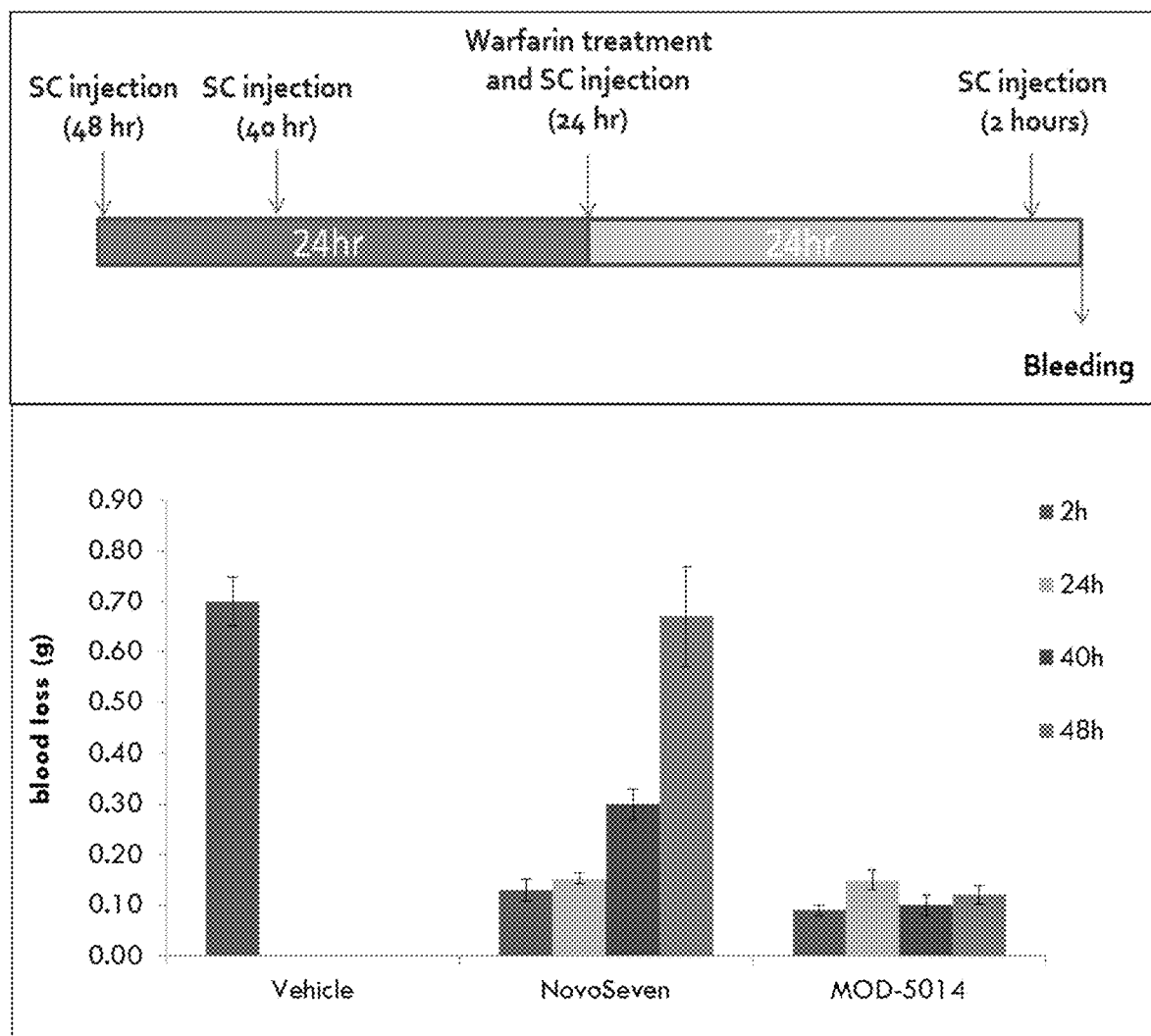

Vehicle or 1000 μg/Kg MOD-5014 or NovoSeven was SC administrated 15 min, 24 or 48 hours before tail clip. Results are presented in FIG. 43.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of increasing patient compliance in the use of a coagulation factor therapy in a human subject, comprising administering to a subject in need thereof a chorionic gonadotropin carboxy terminal peptide (CTP)-modified coagulation Factor VII (FVII) polypeptide selected from;
   a. a CTP-modified coagulation FVII polypeptide having an amino acid sequence selected from the group consisting of SEQ ID NO: 25 and amino acids 39-528 of SEQ ID NO: 25, or
   b. an activated CTP-modified Factor VII (FVIIa) polypeptide having an amino acid sequence selected from the group consisting of SEQ ID NO: 25 and amino acids 39-528 of SEQ ID NO: 25,
   wherein said increasing patient compliance is achieved by reducing the frequency of administration of said coagulation factor polypeptide in a coagulation factor therapy, as compared to an unmodified coagulation factor.

2. The method of claim 1, wherein said coagulation factor therapy is for treating Hemophilia or Hemophilia A.

3. The method of claim 1, wherein at least one CTP consists of an amino acid sequence selected from the group consisting of: SEQ ID NO: 1 and SEQ ID NO: 2.

4. The method of claim 1, wherein at least one CTP is glycosylated.

5. The method of claim 1, wherein at least one CTP is truncated.

6. The method of claim 1, wherein at least one CTP is attached to said coagulation Factor VII polypeptide via a linker, wherein said linker is a peptide bond.

7. The method of claim 1, wherein the sequence of said CTP-modified Factor VII (FVII) is selected from the group consisting of SEQ ID NO: 25 and SEQ ID NO: 46.

8. The method of claim 1, wherein said CTP-modified coagulation Factor VII as a signal peptide.

9. The method of claim 8, wherein said signal peptide is set forth in SEQ ID NO: 47.

10. The method of claim 1, wherein said coagulation FVII polypeptide is an activated coagulation Factor VII (FVIIa) polypeptide.

11. The method of claim 10, wherein the sequence of said CTP-modified activated coagulation Factor VII is set forth in SEQ ID NO: 46.

12. The method of claim 10, wherein said activated coagulation FVII polypeptide is in the form of a disulfide-linked two chain heterodimer.

13. The method of claim 12, wherein said two chains comprise a light chain consisting of amino acids 1-152 and a heavy chain consisting of amino acids 153-490 of SEQ ID NO: 46.

14. The method of claim 12, wherein, wherein said heavy and the light chain domains are separated and migrate as separated bands of molecular weights 55 kDa and 25 kDa.

15. The method of claim 1, wherein CTP-modified coagulation FVII is administered to said subject in the form of a pharmaceutical composition comprising a pharmaceutically acceptable carrier.

16. The method of claim 15, wherein said administration is once a week.

17. The method of claim 15, wherein said administration is subcutaneous or intravenous.

18. The method of claim 15, wherein said subject is a hemophilic subject or is a subject suffering from a vitamin K deficiency or a liver disease.

19. The method of claim 15, wherein said subject is a child.

* * * * *